United States Patent
Kallewaard-Lelay et al.

(10) Patent No.: US 11,926,657 B2
(45) Date of Patent: *Mar. 12, 2024

(54) NEUTRALIZING ANTI-INFLUENZA BINDING MOLECULES AND USES THEREOF

(71) Applicant: MEDIMMUNE, LLC, Gaithersburg, MD (US)

(72) Inventors: Nicole Kallewaard-Lelay, Gaithersburg, MD (US); Qing Zhu, Gaithersburg, MD (US); Godfrey Jonah Rainey, Gaithersburg, MD (US); Cuihua Gao, Gaithersburg, MD (US); Srinath Kasturirangan, Gaithersburg, MD (US); Changshou Gao, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,757

(22) Filed: Nov. 11, 2022

(65) Prior Publication Data
US 2023/0112916 A1 Apr. 13, 2023

Related U.S. Application Data

(63) Continuation of application No. 17/108,608, filed on Dec. 1, 2020, now Pat. No. 11,524,993, which is a
(Continued)

(51) Int. Cl.
*A61P 31/16* (2006.01)
*C07K 16/10* (2006.01)
*A61K 39/00* (2006.01)

(52) U.S. Cl.
CPC .......... *C07K 16/1018* (2013.01); *A61P 31/16* (2018.01); *A61K 2039/505* (2013.01);
(Continued)

(58) Field of Classification Search
None
See application file for complete search history.

(56) References Cited

U.S. PATENT DOCUMENTS

| | | |
|---|---|---|
| 3,766,162 A | 10/1973 | Spector |
| 3,791,932 A | 2/1974 | Schuurs et al. |

(Continued)

FOREIGN PATENT DOCUMENTS

| | | |
|---|---|---|
| CN | 1671741 A | 9/2005 |
| CN | 102124028 B | 5/2015 |

(Continued)

OTHER PUBLICATIONS

Any references not provided herewith were previously cited and submitted in U.S. Appl. No. 16/560,040, filed Sep. 4, 2019 to which this application claims priority.
(Continued)

*Primary Examiner* — Shanon A. Foley
(74) *Attorney, Agent, or Firm* — MEDLER FERRO WOODHOUSE & MILLS PLLC

(57) ABSTRACT

Binding molecules, including bispecific antibodies that include at least two anti-influenza binding domains are disclosed, including binding molecules having a first binding domain that specifically binds influenza A virus and a second binding domain that specifically binds influenza B virus.

13 Claims, 6 Drawing Sheets

Specification includes a Sequence Listing.

Related U.S. Application Data continuation of application No. 16/560,040, filed on Sep. 4, 2019, now Pat. No. 10,882,897, which is a continuation of application No. 15/577,799, filed as application No. PCT/US2016/035026 on May 31, 2016, now Pat. No. 10,442,854.

(60) Provisional application No. 62/169,272, filed on Jun. 1, 2015.

(52) U.S. Cl.
CPC .... *A61K 2039/545* (2013.01); *C07K 2317/24* (2013.01); *C07K 2317/31* (2013.01); *C07K 2317/33* (2013.01); *C07K 2317/56* (2013.01); *C07K 2317/565* (2013.01); *C07K 2317/567* (2013.01); *C07K 2317/622* (2013.01); *C07K 2317/66* (2013.01); *C07K 2317/72* (2013.01); *C07K 2317/74* (2013.01); *C07K 2317/76* (2013.01); *C07K 2317/92* (2013.01)

(56) References Cited

U.S. PATENT DOCUMENTS

| | | | |
|---|---|---|---|
| 3,817,837 | A | 6/1974 | Rubenstein et al. |
| 4,179,337 | A | 12/1979 | Davis et al. |
| 4,233,402 | A | 11/1980 | Maggio et al. |
| 4,495,285 | A | 1/1985 | Shimizu et al. |
| 4,609,546 | A | 9/1986 | Hiratani |
| 4,676,980 | A | 6/1987 | Segal et al. |
| 4,766,106 | A | 8/1988 | Katre et al. |
| 4,831,175 | A | 5/1989 | Gasnow et al. |
| 5,595,721 | A | 1/1997 | Kaminski et al. |
| 5,807,715 | A | 9/1998 | Morrison et al. |
| 6,300,064 | B1 | 10/2001 | Knappik et al. |
| 6,300,104 | B1 | 10/2001 | Morrison et al. |
| 8,101,553 | B1 | 1/2012 | Kurosawa et al. |
| 8,871,207 | B2 | 10/2014 | Lanzavecchia |
| 9,243,054 | B2 | 1/2016 | Burioni et al. |
| 9,340,603 | B2 | 5/2016 | Lanzavecchia |
| 10,442,854 | B2 * | 10/2019 | Kallewaard-Lelay ...... A61P 31/16 |
| 10,494,419 | B2 | 12/2019 | Benjamin et al. |
| 10,519,221 | B2 | 12/2019 | Kallewaard-Lelay et al. |
| 10,882,897 | B2 * | 1/2021 | Kallewaard-Lelay ...... A61P 31/16 |
| 11,174,304 | B2 * | 11/2021 | Kallewaard-Lelay ...... A61P 31/16 |
| 2007/0219149 | A1 | 9/2007 | Hasegawa et al. |
| 2010/0080813 | A1 | 4/2010 | Lanzavecchia |
| 2011/0014187 | A1 | 1/2011 | Burioni et al. |
| 2012/0128684 | A1 | 5/2012 | Marasco et al. |
| 2016/0257732 | A1 | 9/2016 | Benjamin et al. |
| 2017/0218054 | A1 | 8/2017 | Kallewaard-Lelay et al. |
| 2018/0155413 | A1 | 6/2018 | Kallewaard-Lelay et al. |
| 2019/0015509 | A1 | 1/2019 | Kallewaard-Lelay et al. |
| 2020/0109187 | A1 | 4/2020 | Kallewaard-Lelay et al. |
| 2021/0079069 | A1 | 3/2021 | Kallewaard-Lelay et al. |
| 2023/0112916 | A1 * | 4/2023 | Kallewaard-Lelay ...... A61P 31/16 424/206.1 |

FOREIGN PATENT DOCUMENTS

| | | |
|---|---|---|
| CN | 103906763 A | 10/2016 |
| EP | 1167382 A1 | 1/2002 |
| EP | 2919813 B1 | 10/2018 |
| JP | A 2014-527403 A | 10/2014 |
| JP | A 2015-501815 A | 1/2015 |
| RU | 2366662 C2 | 9/2009 |
| RU | 2536956 C1 | 12/2014 |
| WO | WO00/52031 A2 | 9/2000 |
| WO | WO00/52473 A2 | 9/2000 |
| WO | WO2004/001007 A1 | 12/2003 |
| WO | WO2004/007667 A2 | 1/2004 |
| WO | 2005/007697 A1 | 1/2005 |
| WO | WO2006/124269 A2 | 11/2006 |
| WO | WO2007/045477 A2 | 4/2007 |
| WO | WO2007/109742 A2 | 9/2007 |
| WO | WO2007/117577 A2 | 10/2007 |
| WO | WO2007/134327 A2 | 11/2007 |
| WO | WO2008/028946 A2 | 3/2008 |
| WO | WO2008/054606 A2 | 5/2008 |
| WO | WO2008/066691 A2 | 6/2008 |
| WO | WO2008/076379 A2 | 6/2008 |
| WO | WO2008/084410 A2 | 7/2008 |
| WO | WO2008/110937 A2 | 9/2008 |
| WO | WO2009/115972 A1 | 9/2009 |
| WO | WO2010/010466 A2 | 1/2010 |
| WO | WO2010/010467 A2 | 1/2010 |
| WO | WO2010/054007 A1 | 5/2010 |
| WO | WO2012/082634 A1 | 6/2012 |
| WO | WO2013/007770 A1 | 1/2013 |
| WO | WO2013/011347 A1 | 1/2013 |
| WO | WO2013/043729 A1 | 3/2013 |
| WO | WO2013/044203 A2 | 3/2013 |
| WO | WO2013/086052 A2 | 6/2013 |
| WO | WO2013/132007 A1 | 9/2013 |
| WO | WO2014/078268 A1 | 5/2014 |
| WO | WO2014/158001 A1 | 10/2014 |
| WO | WO2015/051010 A1 | 4/2015 |
| WO | WO2016/011035 A2 | 1/2016 |
| WO | WO2016/196470 A1 | 12/2016 |
| WO | WO2017/123685 A1 | 7/2017 |
| WO | WO2017/147248 A1 | 8/2017 |

OTHER PUBLICATIONS

Abed et al., "A Review of Clinical Influenza A and B Infections with Reduced Susceptibility to Both Oseltamivir and Zanamivir," Open Forum Infectious Diseases 4(3): ofx105 (2017).

Ali et al., "Evaluation of MEDI8852, an Anti-Influenza A Monoclonal Antibody, in Treating Acute Uncomplicated Influenza," Antimicrobial Agents and Chemotherapy 62(11): e00694-18 (2018).

Benjamin et al., "A Broadly Neutralizing Human Monoclonal Antibody Directed against a Novel Conserved Epitope on the Influenza Virus H3 Hemagglutinin Globular Head," J Virol 88(12):6743-6750 (2014).

Biere et al., "Differentiation of Influenza B Virus Lineages Yamagata and Victoria by Real-Time PCR," J Clin Microbiol 48:1425-1427 (2010).

Bouvier, "The Future of Influenza Vaccines: A Historical and Clinical Perspective," Vaccines 6:58 (2018).

Chai et al., "A broadly protective therapeutic antibody against influenza B virus with two mechanisms of action," Nature Comm 8:14234 (2017).

Corti et al., "Heterosubtypic neutralizing antibodies are produced by individuals immunized with a seasonal influenza vaccine," J Clin Invest 120:1663-1673 (2010).

Corti et al., "A Neutralizing Antibody Selected from Plasma Cells That Binds to Group 1 and Group 2 Influenza A Hemagglutinins," Science 333(6044):850-856 (2011).

Corti et al., "Cross-neutralization of four paramyxoviruses by a human monoclonal antibody," Nature 501(7467):439-443 (2013).

Corti et al., "Tackling influenza with broadly neutralizing antibodies," Curr Opin Virol 24:60-69 (2017).

Deyev and Lebedenko. "Modern Technologies for Creating Synthetic Antibodies for Clinical Application." Acta Naturae 1:32-50 (2009).

Dreyfus et al., "Highly Conserved Protective Epitopes on Influenza B Viruses," Science 337(6100):1343-1348 (2012).

Ekiert et al., "Antibody recognition of a highly conserved influenza virus epitope: implications for universal prevention and therapy," Science 324(5924):246-251 (2009).

Ekiert et al., "A Highly Conserved Neutralizing Epitope on Group 2 Influenza A Viruses," Science 333(6044):843-850 (2011).

Ekiert et al., "Cross-neutralization of influenza A viruses mediated by a single antibody loop," Nature 489(7417):526-532 (2012).

(56) References Cited

OTHER PUBLICATIONS

Friesen et al., "A common solution to group 2 influenza virus neutralization," Proc Natl Acad Sci USA 111(1):445-450 (2014).
GENBANK Accession ID AAK94805.1, immunoglobulin light chain variable region, partial [*Homo sapiens*], published Dec. 31, 2001.
GENBANK Accession ID ACS95408.1, immunoglobulin heavy chain variable region, partial [*Homo sapiens*], published Dec. 31, 2001.
Gerhard et al., "Prospects for Universal Influenza Virus Vaccine," Emerg Infect Dis 12(4):569-574 (2006).
Gioia et al., "Cross-subtype Immunity against Avian Infl uenza in Persons Recently Vaccinated for Influenza," Emerg Infect Dis 14(1):121-128 (2008).
Greenspan et al., "Defining epitopes: It's not as easy as it seems," Nature Biotechnol 17:936-937 (1999).
Hassantoufighi et al., "A practical influenza neutralization assay to simultaneously quantify hemagglutinin and neuraminidase-inhibiting antibody responses," Vaccine 28:790-797 (2010).
Ignatiev, Anna Viktorovna, "Features of the antigenic structure of hemagglutinin recognized by antibodies against modern influenza A viruses of subtypes H5 and H1." Virology (2012).
Kallewaard et al., "Structure and Function Analysis of an Antibody Recognizing All Influenza A Subtypes," Cell 166: 596-608 (2016).
Kashyap et al., "Combinatorial antibody libraries from survivors of the Turkish H5N1 avian influenza outbreak reveal virus neutralization strategies," Proc Natl Acad Sci USA 105(16):5986-5991 (2008).
Kaverin et al., "Epitope Mapping of the Hemagglutinin Molecule of a Highly Pathogenic H5N1 Influenza Virus by Using Monoclonal Antibodies," J Virol 81(23):12911-12917 (2007).
Kozbor et al., "The production of monoclonal antibodies from human lymphocytes," Immunol Today 4(3):72-79 (1983).
Krause et al., "A Broadly Neutralizing Human Monoclonal Antibody That Recognizes a Conserved, Novel Epitope on the Globular Head of the Influenza H1N1 Virus Hemagglutinin," J Virol 85(20):10905-10908 (2011).
Lee et al., "Heterosubtypic antibody recognition of the influenza virus hemagglutinin receptor binding site enhanced by avidity," Proc Natl Acad Sci USA 109(42):17040-17045 (2012).
Li et al., "Pandemic H1N1 influenza vaccine induces a recall response in humans that favors broadly cross-reactive memory B cells," Proc Natl Acad Sci USA 109(23):9047-9052 (2012).
Lin et al., "Recent changes among human influenza viruses." Virus Res. 103:47-52 (2004).
Nakamura et al., "An In Vivo Human-Plasmablast Enrichment Technique Allows Rapid Identification of Therapeutic Influenza A Antibodies," Cell Host Microbe 14:93-103 (2013).
Nguyen et al., "Heterosubtypic Immunity to Influenza A Virus Infection Requires B Cells but Not CD8+ Cytotoxic T Lymphocytes," J Virol 183:368-376 (2001).
Okuno et al., "A Common Neutralizing Epitope Conserved between the Hemagglutinins of Influenza A Virus H1 and H2 Strains," J Virol 67(5):2552-2558 (1993).
Pakula and Sauer, "Genetic Analysis of Protein Stability and Function," Annu. Rev. Genet. 23:289-310 (1989).
Pan et al., "Weight-based Dosing in Medication Use: What Should We Know?" Patient Preference and Adherence 10: 549-560 (2016).
Pappas et al., "Rapid development of broadly influenza neutralizing antibodies through redundant mutations," Nature 516(7531):418-422 (2014).
Paul et al., eds. Fundamental Immunology $3^{rd}$ Edition (1993), pp. 292-295.
Prabhu et al., "Monoclonal Antibodies against the Fusion Peptide of Hemagglutinin Protect Mice from Lethal Influenza A Virus H5N1 Infection," J Virol 83(6):2553-2562 (2009).
Ren et al., "Epitope-focused vaccine design against influenza A and B viruses," Curr Opin Immunol 42:83-90 (2016).
Roit, Ivan M. (1991) *Essential Immunology* ($7^{th}$ Ed.) Blackwell Science, Inc.
Rowe et al., "Detection of Antibody to Avian Influenza A (H5N1) Virus in Human Serum by Using a Combination of Serologic Assays," J Clin Microbiol 37(4):937-943 (1999).
Rudikoff et al., "Single amino acid substitution altering antigen-binding specificity," Proc Natl Acad Sci USA 79(6):1979-1983 (1982).
Simmons et al., "Prophylactic and Therapeutic Efficacy of Human Monoclonal Antibodies against H5N1 Influenza," PLOS Med 4(5):e178 (2007).
Smirnov et al., "Prevention and treatment of bronchopneumonia in mice caused by mouse-adapted variant of avian H5N2 influenza A virus using monoclonal antibody against conserved epitope in the HA stem region," Arch Virol 145:1733-1741 (2000).
Sui et al., "Structural and functional bases for broad-spectrum neutralization of avian and human influenza A viruses," Nature Struct Mol Biol 16(3):265-273 (2009).
Temperton et al., "Longitudinally Profiling Neutralizing Antibody Response to SARS Coronavirus with Pseudotypes," Emerg Infect Dis 11(3):411-416 (2005).
Thompson et al., "Influenza-Associated Hospitalizations in the United States," JAMA 292:1333-1340 (2004).
Throsby et al., "Heterosubtypic Neutralizing Monoclonal Antibodies Cross-Protective against H5N1 and H1N1 Recovered from Human IgM+ Memory B Cells," PLOS One 3(12):e3942 (2008).
Traggiai et al., "An efficient method to make human monoclonal antibodies from memory B cells: potent neutralization of SARS coronavirus," Nature Med 10:871-875 (2004).
Vareckova et al., "HA2-specific monoclonal antibodies as tools for differential recognition of influenza A virus antigenic subtypes," Virus Res 132(1-2):181-186 (2008).
Wagner et al., "Bispecific antibody generated with sortase and click chemistry has broad antiinfluenza activity," Proc Natl Acad Sci USA 111(47):16820-16825 (2014).
Wang, Qinghua et al., "Crystal Structure of Unliganded Influenza B Virus Hemagglutinin," J Virol 82(6):3011-3020 (2008).
Wang, Taia T. et al., "Broadly Protective Monoclonal Antibodies against H3 Influenza Viruses following Sequential Immunization with Different Hemagglutinins," PLOS Pathog 6(2):e1000796 (2010).
Whittle et al., "Broadly neutralizing human antibody that recognizes the receptor-binding pocket of influenza virus hemagglutinin," Proc Natl Acad Sci USA 108(34):14216-14221 (2011).
Wilson et al., "Structure of the hemagglutinin membrane glycoprotein of influenza virus at 3 Å resolution," Nature 289:366-373 (1981).
Wrammert et al., "Rapid Cloning of High Affinity Human Monoclonal Antibodies Against Influenza Virus," Nature 453(7195):667-671 (2008).
Wrammert et al., "Broadly cross-reactive antibodies dominate the human B cell response against 2009 pandemic H1N1 influenza virus infection," J Exp Med 208(1):181-193 (2011).
Xiang et al., "Framework Residues 71 and 93 of the Chimeric B72.3 Antibody are Major Determinants of the Conformation of Heavy-chain Hypervariable Loops," J Mol Biol 253:385-390 (1995).
Yasugi et al., "Human Monoclonal Antibodies Broadly Neutralizing against Influenza B Virus," PLOS Pathog 9(2):e1003150 (2013).
Yoshida et al., "Cross-Protective Potential of a Novel Monoclonal Antibody Directed against Antigenic Site B of the Hemagglutinin of Influenza A Viruses," PLOS Pathog 5(3):e1000350 (2009).
Zabetakis et al., "Contributions of the Complementarity Determining Regions to the Thermal Stability of a Single-Domain Antibody," PLoS ONE 8(10):e77678 (2013).
Zhou et al., "Hospitalizations Associated With Influenza and Respiratory Syncytial Virus in the United States, 1993-2008," Clin Infect Dis 54(10):1427-1436.
Non-final Office Action issued in U.S. Appl. No. 15/026,276, dated Apr. 6, 2018.
Non-final Office Action issued in U.S. Appl. No. 15/026,276, dated Oct. 19, 2018.
Non-final Office Action issued in U.S. Appl. No. 15/026,276, dated Apr. 17, 2019.
Non-final Office Action issued in U.S. Appl. No. 15/325,603, dated Jun. 27, 2017.
Final Office Action issued in U.S. Appl. No. 15/325,603, dated Mar. 8, 2018.

(56) References Cited

OTHER PUBLICATIONS

Non-final Office Action issued in U.S. Appl. No. 15/325,603, dated Sep. 7, 2018.
Non-final Office Action issued in U.S. Appl. No. 16/068,941, dated Oct. 21, 2019.
Office Action in Chinese Application No. 201580038244.1 dated Jan. 17, 2020.
Office Action in Chinese Application No. 201480053969.3 dated Feb. 3, 2020.
Office Action in European Application No. 15821645.7 dated Jul. 9, 2020.
Office Action in Japanese Application No. 2017-561892 dated Jun. 2, 2020.
Search Report in Russian Application No. 2020100073 dated May 28, 2020.
Office Action in Russian Application No. 2020100073 dated Jun. 10, 2020.
Office Action in U.S. Appl. No. 16/068,941 dated Feb. 5, 2020.
Centers for Disease Control and Prevention. "Influenza (Flu): Antiviral drugs for seasonal influenza: additional links and resources." Jan. 7, 2021.
Davies and Riechmann. "Affinity improvement of single antibody VH domains: residues in all three hypervariable regions affect antigen binding." Immunotechnology. 2:169-179 (1996).
Deyde et al. "Surveillance of resistance to adamantanes among influenza A(H3N2) and A(H1N1) viruses isolated worldwide." JID 196:249 (2007).
Duwe, S. "Influenza viruses—antiviral therapy and resistance." GMS Infect Dis 5:ISSN 2195-8831 (2017).
Fan et al. "Bispecific antibodies and their applications." J. Hematol. Oncol. 8:130 (2015).
Holliger et al. "'Diabodies': small bivalent and bispecific antibody fragments." 90:6444-6448 (1993).
Holt et al. "Domain antibodies: proteins for therapy." TRENDS Biotech. 21(11):484 (2003).
Lamepjo, T. "Influenza and antiviral resistance: an overview." Eur. J. Clin. Microbiol. Infect. Dis. (2020) doi.org/10.1007/s10096-020-03840-9.
Coleman, P.M. "Effects of amino acid sequence changes on antibody-antigen interactions." Research in Immunology, 145:33-36 (1994).
Paul, Fundamental Immunology, $3^{rd}$ Edition, pp. 292-295 (1993).
Rudikoff, S. et al. "Single amino acid substitution altering antigen-binding specificity." Proc. Natl. Acad. Sci. USA, 79:1979-1983 (1982).

* cited by examiner

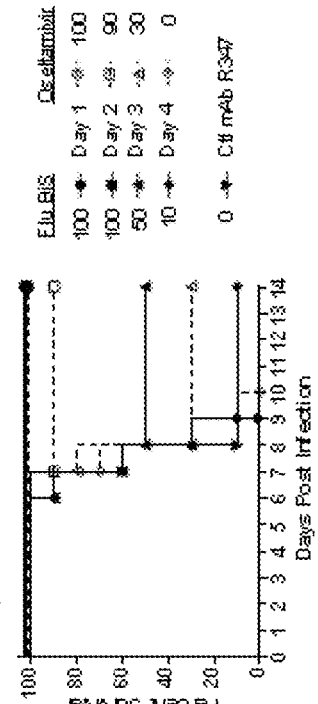
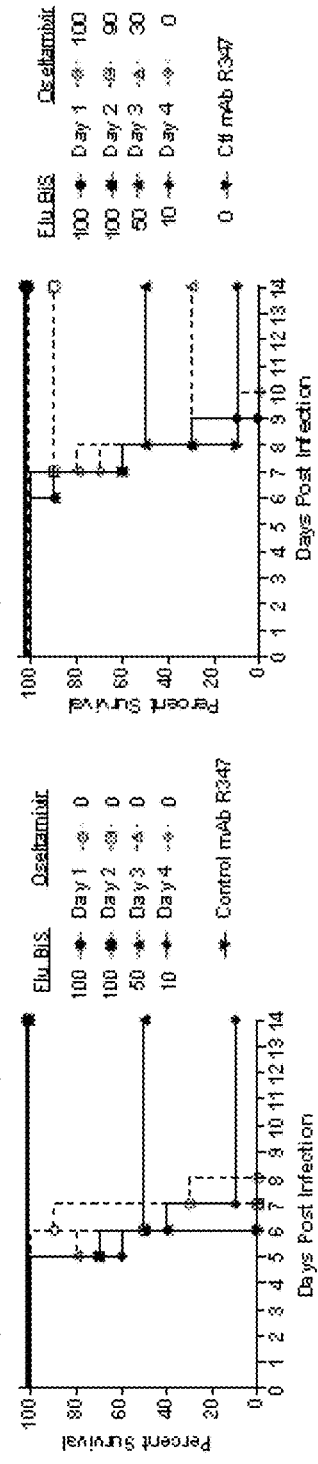
FIG. 6A
FIG. 6B
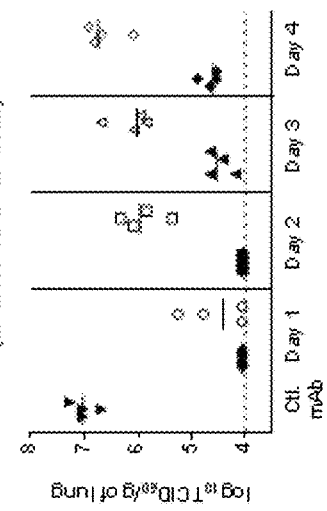
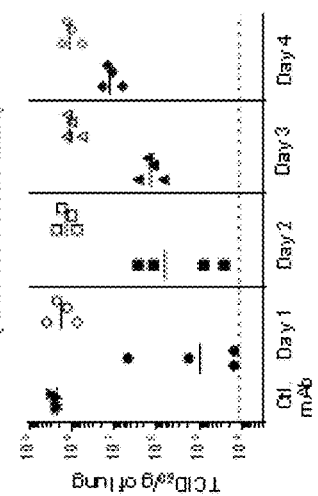
FIG. 6C
FIG. 6D
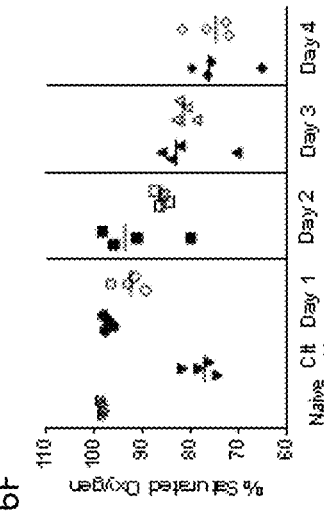
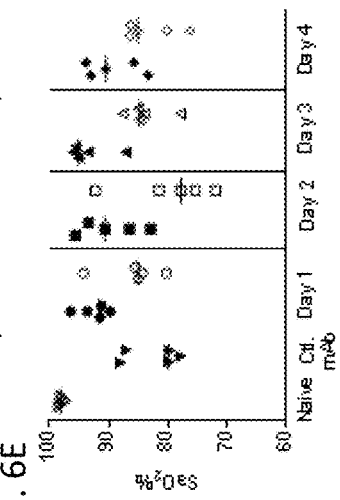
FIG. 6E
FIG. 6F

SEQUENCE LISTING

```
Sequence total quantity: 131
SEQ ID NO: 1               moltype = DNA   length = 309
FEATURE                    Location/Qualifiers
misc_feature               1..309
                           note = Description of Artificial Sequence: Synthetic
                            polynucleotide
source                     1..309
                           mol_type = other DNA
                           organism = synthetic construct
SEQUENCE: 1
gacatccaga tgacccagtc gccatcctcc ctgtctgcat ctgtaggaga cagagtaacc    60
atcacttgcc ggacaagtca gagccttagt agctatttac attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagtag tctgcaacct   240
gaagattttg caacttacta ctgtcaacag agtcggacgt tcggccaagg gaccaaggtg   300
gaaatcaaa                                                           309

SEQ ID NO: 2               moltype = AA   length = 103
FEATURE                    Location/Qualifiers
REGION                     1..103
                           note = Description of Artificial Sequence: Synthetic
                            polypeptide
source                     1..103
                           mol_type = protein
                           organism = synthetic construct
SEQUENCE: 2
DIQMTQSPSS LSASVGDRVT ITCRTSQSLS SYLHWYQQKP GKAPKLLIYA ASSLQSGVPS    60
RFSGSGSGTD FTLTISSLQP EDFATYYCQQ SRTFGQGTKV EIK                     103

SEQ ID NO: 3               moltype = AA   length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 3
RTSQSLSSYL H                                                        11

SEQ ID NO: 4               moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 4
AASSLQS                                                             7

SEQ ID NO: 5               moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 5
QQSRT                                                               5

SEQ ID NO: 6               moltype = DNA   length = 385
FEATURE                    Location/Qualifiers
misc_feature               1..385
                           note = Description of Artificial Sequence: Synthetic
                            polynucleotide
source                     1..385
                           mol_type = other DNA
                           organism = synthetic construct
SEQUENCE: 6
caggtacagc tgcaggagtc gggtccagga ctggtgaagc cctcgcagac cctctcactc    60
acctgtgcca tctccgggga cagtgtctct agcaacaatg ctgtttggaa ctggatcagg   120
cagtccccat cgagaggcct tgagtggctg ggaaggacat actacaggtc caagtggtat   180
aatgattatg cagaatctgt gaaaagtcga ataccgtca atccagacac atccaagaac   240
cagttctccc tgcacctgaa gtctgtgact cccgaggaca cggctgtgtt ttactgtgta   300
cgatctggcc acattacggt tttggagtg aatgttgacg cttttgatat gtggggccaa   360
gggacaatgg tcaccgtctc ttcag                                        385

SEQ ID NO: 7               moltype = AA   length = 128
FEATURE                    Location/Qualifiers
```

| | | |
|---|---|---|
| REGION | 1..128<br>note = Description of Artificial Sequence: Synthetic polypeptide | |
| source | 1..128<br>mol_type = protein<br>organism = synthetic construct | |

SEQUENCE: 7
```
QVQLQESGPG LVKPSQTLSL TCAISGDSVS SNNAVWNWIR QSPSRGLEWL GRTYYRSKWY    60
NDYAESVKSR ITVNPDTSKN QFSLHLKSVT PEDTAVFYCV RSGHITVFGV NVDAFDMWGQ   120
GTMVTVSS                                                           128
```

| | | |
|---|---|---|
| SEQ ID NO: 8<br>FEATURE<br>REGION | moltype = AA  length = 7<br>Location/Qualifiers<br>1..7<br>note = Description of Artificial Sequence: Synthetic peptide | |
| source | 1..7<br>mol_type = protein<br>organism = synthetic construct | |

SEQUENCE: 8
```
SNNAVWN                                                              7
```

| | | |
|---|---|---|
| SEQ ID NO: 9<br>FEATURE<br>REGION | moltype = AA  length = 18<br>Location/Qualifiers<br>1..18<br>note = Description of Artificial Sequence: Synthetic peptide | |
| source | 1..18<br>mol_type = protein<br>organism = synthetic construct | |

SEQUENCE: 9
```
RTYYRSKWYN DYAESVKS                                                 18
```

| | | |
|---|---|---|
| SEQ ID NO: 10<br>FEATURE<br>REGION | moltype = AA  length = 16<br>Location/Qualifiers<br>1..16<br>note = Description of Artificial Sequence: Synthetic peptide | |
| source | 1..16<br>mol_type = protein<br>organism = synthetic construct | |

SEQUENCE: 10
```
SGHITVFGVN VDAFDM                                                   16
```

| | | |
|---|---|---|
| SEQ ID NO: 11<br>FEATURE<br>misc_feature | moltype = DNA  length = 309<br>Location/Qualifiers<br>1..309<br>note = Description of Artificial Sequence: Synthetic polynucleotide | |
| source | 1..309<br>mol_type = other DNA<br>organism = synthetic construct | |

SEQUENCE: 11
```
gatattcaga tgacccagag ccccttccagc ctgtccgctt cagtggggga tcgagtgacc    60
attacctgcc gaaccagcca gagcctgagc tcctacacgc actggtatca gcagaagccc   120
ggcaaagccc ctaagctgct gatctacgcc gcttctagtc gggggtccgg agtgccaagc   180
cggttctccg gatctgggag tggaaccgac tttaccctga caatttcaag cctgcagccc   240
gaggatttcg ctacatacta ctgtcagcag agcagaactt cgggcaggg cactaaggtg   300
gagatcaaa                                                           309
```

| | | |
|---|---|---|
| SEQ ID NO: 12<br>FEATURE<br>REGION | moltype = AA  length = 103<br>Location/Qualifiers<br>1..103<br>note = Description of Artificial Sequence: Synthetic polypeptide | |
| source | 1..103<br>mol_type = protein<br>organism = synthetic construct | |

SEQUENCE: 12
```
DIQMTQSPSS LSASVGDRVT ITCRTSQSLS SYTHWYQQKP GKAPKLLIYA ASSRGSGVPS    60
RFSGSGSGTD FTLTISSLQP EDFATYYCQQ SRTFGQGTKV EIK                     103
```

| | | |
|---|---|---|
| SEQ ID NO: 13<br>FEATURE<br>REGION | moltype = AA  length = 11<br>Location/Qualifiers<br>1..11<br>note = Description of Artificial Sequence: Synthetic peptide | |
| source | 1..11<br>mol_type = protein<br>organism = synthetic construct | |

SEQUENCE: 13
```
RTSQSLSSYT H                                                        11
```

```
SEQ ID NO: 14              moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 14
AASSRGS                                                                             7

SEQ ID NO: 15              moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 15
QQSRT                                                                               5

SEQ ID NO: 16              moltype = DNA  length = 384
FEATURE                    Location/Qualifiers
misc_feature               1..384
                           note = Description of Artificial Sequence: Synthetic
                            polynucleotide
source                     1..384
                           mol_type = other DNA
                           organism = synthetic construct
SEQUENCE: 16
caggtccagc tgcagcagag cggcccccgga ctggtcaagc cttcacagac actgagcctg               60
acatgcgcca ttagcggaga tagcgtgagc tcctacaatg ccgtgtggaa ctggatcagg              120
cagtctccaa gtcgaggact ggagtggctg ggacgaacat actatagatc cgggtggtac              180
aatgactatg ctgaatcagt gaaaagccga attactatca accccgatac ctccaagaat              240
cagttctctc tgcagctgaa cagtgtgacc cctgaggaca cagccgtgta ctactgcgcc              300
agaagcggcc atatcaccgt ctttggcgtc aatgtggatg ctttcgatat gtgggggcag              360
gggactatgg tcaccgtgtc aagc                                                     384

SEQ ID NO: 17              moltype = AA   length = 128
FEATURE                    Location/Qualifiers
REGION                     1..128
                           note = Description of Artificial Sequence: Synthetic
                            polypeptide
source                     1..128
                           mol_type = protein
                           organism = synthetic construct
SEQUENCE: 17
QVQLQQSGPG LVKPSQTLSL TCAISGDSVS SYNAVWNWIR QSPSRGLEWL GRTYYRSGWY               60
NDYAESVKSR ITINPDTSKN QFSLQLNSVT PEDTAVYYCA RSGHITVFGV NVDAFDMWGQ              120
GTMVTVSS                                                                       128

SEQ ID NO: 18              moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 18
SYNAVWN                                                                             7

SEQ ID NO: 19              moltype = AA   length = 18
FEATURE                    Location/Qualifiers
REGION                     1..18
                           note = Description of Artificial Sequence: Synthetic peptide
source                     1..18
                           mol_type = protein
                           organism = synthetic construct
SEQUENCE: 19
RTYYRSGWYN DYAESVKS                                                                18

SEQ ID NO: 20              moltype = AA   length = 16
FEATURE                    Location/Qualifiers
REGION                     1..16
                           note = Description of Artificial Sequence: Synthetic peptide
source                     1..16
                           mol_type = protein
                           organism = synthetic construct
SEQUENCE: 20
SGHITVFGVN VDAFDM                                                                  16
```

```
SEQ ID NO: 21            moltype = DNA  length = 322
FEATURE                  Location/Qualifiers
misc_feature             1..322
                         note = Description of Artificial Sequence: Synthetic
                          polynucleotide
source                   1..322
                         mol_type = other DNA
                         organism = synthetic construct
SEQUENCE: 21
gacatccaga tgacccagtc tccatcttcc gtgtctgcat ctgtgggaga cagagtcacc   60
atcacttgtc gggcgagtca ggatattagc acctggttag cctggtatca gcagaaacca  120
gggaaagccc ctaagctcct gatctatgct gcatccagtt tgcaaagtgg ggtcccatca  180
agattcagcg gcagtggatc tgggacagat ttcactctca ccatcagcag cctgcagcct  240
gaagattttg caacttactt ttgtcagcag gctaacagtt tccctccgac ttttggccag  300
gggaccaagc tggagatcaa ac                                           322

SEQ ID NO: 22            moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 22
DIQMTQSPSS VSASVGDRVT ITCRASQDIS TWLAWYQQKP GKAPKLLIYA ASSLQSGVPS   60
RFSGSGSGTD FTLTISSLQP EDFATYFCQQ ANSFPPTFGQ GTKLEIK                107

SEQ ID NO: 23            moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 23
RASQDISTWL A                                                        11

SEQ ID NO: 24            moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 24
AASSLQS                                                             7

SEQ ID NO: 25            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 25
QQANSFPPT                                                           9

SEQ ID NO: 26            moltype = DNA  length = 403
FEATURE                  Location/Qualifiers
misc_feature             1..403
                         note = Description of Artificial Sequence: Synthetic
                          polynucleotide
source                   1..403
                         mol_type = other DNA
                         organism = synthetic construct
SEQUENCE: 26
gaggtgcagc tggtggtgtc tgggggaggc ttggtaaagc ctgggggggtc ccttagactc   60
tcctgtgcag cctctggact cagtttcctt aacgcctgga tgagctgggt ccgccaggct  120
ccagggaagg ggctggagtg ggttggccgt attaaaagta atactgatgg tgggacaaca  180
gactacgccg cacccgtgaa aggcagattc agcatctcaa gagacgattc aaagaacatg  240
ctgtttctgc atatgagcag cctgagaacc gaggacacag ccgtctatta ctgcgccaca  300
gatggacctt actctgacga ttttagaagt ggttatgccg cacgctaccg ttatttcgga  360
atggacgtct ggggccaagg gaccacggtc accgtctcct cag                    403

SEQ ID NO: 27            moltype = AA  length = 134
FEATURE                  Location/Qualifiers
REGION                   1..134
```

```
                            note = Description of Artificial Sequence: Synthetic
                                   polypeptide
source                      1..134
                            mol_type = protein
                            organism = synthetic construct
SEQUENCE: 27
EVQLVVSGGG LVKPGGSLRL SCAASGLSFL NAWMSWVRQA PGKGLEWVGR IKSNTDGGTT    60
DYAAPVKGRF SISRDDSKNM LFLHMSSLRT EDTAVYYCAT DGPYSDDFRS GYAARYRYFG   120
MDVWGQGTTV TVSS                                                     134

SEQ ID NO: 28               moltype = AA   length = 5
FEATURE                     Location/Qualifiers
REGION                      1..5
                            note = Description of Artificial Sequence: Synthetic peptide
source                      1..5
                            mol_type = protein
                            organism = synthetic construct
SEQUENCE: 28
NAWMS                                                                 5

SEQ ID NO: 29               moltype = AA   length = 19
FEATURE                     Location/Qualifiers
REGION                      1..19
                            note = Description of Artificial Sequence: Synthetic peptide
source                      1..19
                            mol_type = protein
                            organism = synthetic construct
SEQUENCE: 29
RIKSNTDGGT TDYAAPVKG                                                 19

SEQ ID NO: 30               moltype = AA   length = 23
FEATURE                     Location/Qualifiers
REGION                      1..23
                            note = Description of Artificial Sequence: Synthetic peptide
source                      1..23
                            mol_type = protein
                            organism = synthetic construct
SEQUENCE: 30
DGPYSDDFRS GYAARYRYFG MDV                                            23

SEQ ID NO: 31               moltype = AA   length = 261
FEATURE                     Location/Qualifiers
REGION                      1..261
                            note = Description of Artificial Sequence: Synthetic
                                   polypeptide
source                      1..261
                            mol_type = protein
                            organism = synthetic construct
SEQUENCE: 31
DIQMTQSPSS VSASVGDRVT ITCRASQDIS TWLAWYQQKP GKAPKLLIYA ASSLQSGVPS    60
RFSGSGSGTD FTLTISSLQP EDFATYFCQQ ANSFPPTFGC GTKLEIKGGG GSGGGGSGGG   120
GSGGGGSEVQ LVVSGGGLVK PGGSLRLSCA ASGLSFLNAW MSWVRQAPGK CLEWVGRIKS   180
NTDGGTTDYA APVKGRFSIS RDDSKNMLFL HMSSLRTEDT AVYYCATDGP YSDDFRSGYA   240
ARYRYFGMDV WGQGTTVTVS S                                             261

SEQ ID NO: 32               moltype = AA   length = 107
FEATURE                     Location/Qualifiers
REGION                      1..107
                            note = Description of Artificial Sequence: Synthetic
                                   polypeptide
source                      1..107
                            mol_type = protein
                            organism = synthetic construct
SEQUENCE: 32
DIQMTQSPSS VSASVGDRVT ITCRASQDIS TWLAWYQQKP GKAPKLLIYA ASSLQSGVPS    60
RFSGSGSGTD FTLTISSLQP EDFATYFCQQ ANSFPPTFGC GTKLEIK                 107

SEQ ID NO: 33               moltype = AA   length = 134
FEATURE                     Location/Qualifiers
REGION                      1..134
                            note = Description of Artificial Sequence: Synthetic
                                   polypeptide
source                      1..134
                            mol_type = protein
                            organism = synthetic construct
SEQUENCE: 33
EVQLVVSGGG LVKPGGSLRL SCAASGLSFL NAWMSWVRQA PGKCLEWVGR IKSNTDGGTT    60
DYAAPVKGRF SISRDDSKNM LFLHMSSLRT EDTAVYYCAT DGPYSDDFRS GYAARYRYFG   120
MDVWGQGTTV TVSS                                                     134
```

```
SEQ ID NO: 34          moltype = AA  length = 261
FEATURE                Location/Qualifiers
REGION                 1..261
                       note = Description of Artificial Sequence: Synthetic
                        polypeptide
source                 1..261
                       mol_type = protein
                       organism = synthetic construct
SEQUENCE: 34
DIQMTQSPSS VSASVGDRVT ITCRASQDIS TWLAWYQQKP GKCPKLLIYA ASSLQSGVPS   60
RFSGSGSGTD FTLTISSLQP EDFATYFCQQ ANSFPPTFGQ GTKLEIKGGG GSGGGGSGGG  120
GSGGGGSEVQ LVVSGGGLVK PGGSLRLSCA ASGLSFLNAW MSWVRQAPGK GLEWVGRIKS  180
NTDGGTTDYA APVKGRFSIS RDDSKNMLFL HMSSLRTEDT AVYYCATDGP YSDDFRSGYA  240
ARYRYFGMDV WGCGTTVTVS S                                            261

SEQ ID NO: 35          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 35
DIQMTQSPSS VSASVGDRVT ITCRASQDIS TWLAWYQQKP GKCPKLLIYA ASSLQSGVPS   60
RFSGSGSGTD FTLTISSLQP EDFATYFCQQ ANSFPPTFGQ GTKLEIK                107

SEQ ID NO: 36          moltype = AA  length = 134
FEATURE                Location/Qualifiers
REGION                 1..134
                       note = Description of Artificial Sequence: Synthetic
                        polypeptide
source                 1..134
                       mol_type = protein
                       organism = synthetic construct
SEQUENCE: 36
EVQLVVSGGG LVKPGGSLRL SCAASGLSFL NAWMSWVRQA PGKGLEWVGR IKSNTDGGTT   60
DYAAPVKGRF SISRDDSKNM LFLHMSSLRT EDTAVYYCAT DGPYSDDFRS GYAARYRYFG  120
MDVWGCGTTV TVSS                                                    134

SEQ ID NO: 37          moltype = DNA  length = 322
FEATURE                Location/Qualifiers
misc_feature           1..322
                       note = Description of Artificial Sequence: Synthetic
                        polynucleotide
source                 1..322
                       mol_type = other DNA
                       organism = synthetic construct
SEQUENCE: 37
gacatccaga tgacccagtc tccatcttcc gtgtctgcat ctgtgggaga cagagtcacc   60
atcacttgtc gggcgagtca ggatattagc acctggttag cctggtatca gcagaaacca  120
gggaaagccc ctaagctcct gatctatgct gcatccagtt tgcaaagtgg ggtcccatca  180
agattcagcg gcagtggatc tgggacagat ttcactctca ccatcagcag cctgcagcct  240
gaagattttg caacttacta ttgtcagcag gctaacagtt ccctccgac ttttggccag  300
gggaccaagc tggagatcaa ac                                           322

SEQ ID NO: 38          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 38
DIQMTQSPSS VSASVGDRVT ITCRASQDIS TWLAWYQQKP GKAPKLLIYA ASSLQSGVPS   60
RFSGSGSGTD FTLTISSLQP EDFATYYCQQ ANSFPPTFGQ GTKLEIK                107

SEQ ID NO: 39          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 39
RASQDISTWL A                                                        11
```

```
SEQ ID NO: 40               moltype = AA   length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 40
AASSLQS                                                                   7

SEQ ID NO: 41               moltype = AA   length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 41
QQANSFPPT                                                                 9

SEQ ID NO: 42               moltype = DNA   length = 402
FEATURE                     Location/Qualifiers
misc_feature                1..402
                            note = Description of Artificial Sequence: Synthetic
                            polynucleotide
source                      1..402
                            mol_type = other DNA
                            organism = synthetic construct
SEQUENCE: 42
gaggtgcagc tggtggagtc tgggggaggc ttggtaaagc ctggggggtc ccttagactc          60
tcctgtgcag cctctggatt cactttcctt aacgcctgga tgagctgggt ccgccaggct         120
ccagggaagg gcctggagtg ggttggccgt attaaaagta atactgatgg tgggacaaca         180
gactacgccg cacccgtgaa aggcagattc accatctcaa gagacgattc aaagaacacg         240
ctgtatctgc aaatgagcag cctgaaaacc gaggacacag ccgtctatta ctgcaccaca         300
gatggacctt actctgacga ttttagaagt ggttatgccg cacgctaccg ttatttcgga         360
atggacgtct ggggccaagg gaccacggtc accgtctcct ca                           402

SEQ ID NO: 43               moltype = AA   length = 134
FEATURE                     Location/Qualifiers
REGION                      1..134
                            note = Description of Artificial Sequence: Synthetic
                            polypeptide
source                      1..134
                            mol_type = protein
                            organism = synthetic construct
SEQUENCE: 43
EVQLVESGGG LVKPGGSLRL SCAASGFTFL NAWMSWVRQA PGKGLEWVGR IKSNTDGGTT          60
DYAAPVKGRF TISRDDSKNT LYLQMSSLKT EDTAVYYCTT DGPYSDDFRS GYAARYRYFG         120
MDVWGQGTTV TVSS                                                          134

SEQ ID NO: 44               moltype = AA   length = 5
FEATURE                     Location/Qualifiers
REGION                      1..5
                            note = Description of Artificial Sequence: Synthetic peptide
source                      1..5
                            mol_type = protein
                            organism = synthetic construct
SEQUENCE: 44
NAWMS                                                                     5

SEQ ID NO: 45               moltype = AA   length = 19
FEATURE                     Location/Qualifiers
REGION                      1..19
                            note = Description of Artificial Sequence: Synthetic peptide
source                      1..19
                            mol_type = protein
                            organism = synthetic construct
SEQUENCE: 45
RIKSNTDGGT TDYAAPVKG                                                      19

SEQ ID NO: 46               moltype = AA   length = 23
FEATURE                     Location/Qualifiers
REGION                      1..23
                            note = Description of Artificial Sequence: Synthetic peptide
source                      1..23
                            mol_type = protein
                            organism = synthetic construct
SEQUENCE: 46
DGPYSDDFRS GYAARYRYFG MDV                                                 23
```

```
SEQ ID NO: 47          moltype = AA   length = 261
FEATURE                Location/Qualifiers
REGION                 1..261
                       note = Description of Artificial Sequence: Synthetic
                        polypeptide
source                 1..261
                       mol_type = protein
                       organism = synthetic construct
SEQUENCE: 47
DIQMTQSPSS VSASVGDRVT ITCRASQDIS TWLAWYQQKP GKAPKLLIYA ASSLQSGVPS    60
RFSGSGSGTD FTLTISSLQP EDFATYYCQQ ANSFPPTFGC GTKLEIKGGG GSGGGGSGGG   120
GSGGGGSEVQ LVESGGGLVK PGGSLRLSCA ASGFTFLNAW MSWVRQAPGK CLEWVGRIKS   180
NTDGGTTDYA APVKGRFTIS RDDSKNTLYL QMSSLKTEDT AVYYCTTDGP YSDDFRSGYA   240
ARYRYFGMDV WGQGTTVTVS S                                            261

SEQ ID NO: 48          moltype = AA   length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 48
DIQMTQSPSS VSASVGDRVT ITCRASQDIS TWLAWYQQKP GKAPKLLIYA ASSLQSGVPS    60
RFSGSGSGTD FTLTISSLQP EDFATYYCQQ ANSFPPTFGC GTKLEIK                 107

SEQ ID NO: 49          moltype = AA   length = 134
FEATURE                Location/Qualifiers
REGION                 1..134
                       note = Description of Artificial Sequence: Synthetic
                        polypeptide
source                 1..134
                       mol_type = protein
                       organism = synthetic construct
SEQUENCE: 49
EVQLVESGGG LVKPGGSLRL SCAASGFTFL NAWMSWVRQA PGKCLEWVGR IKSNTDGGTT    60
DYAAPVKGRF TISRDDSKNT LYLQMSSLKT EDTAVYYCTT DGPYSDDFRS GYAARYRYFG   120
MDVWGQGTTV TVSS                                                    134

SEQ ID NO: 50          moltype = AA   length = 261
FEATURE                Location/Qualifiers
REGION                 1..261
                       note = Description of Artificial Sequence: Synthetic
                        polypeptide
source                 1..261
                       mol_type = protein
                       organism = synthetic construct
SEQUENCE: 50
DIQMTQSPSS VSASVGDRVT ITCRASQDIS TWLAWYQQKP GKCPKLLIYA ASSLQSGVPS    60
RFSGSGSGTD FTLTISSLQP EDFATYYCQQ ANSFPPTFGQ GTKLEIKGGG GSGGGGSGGG   120
GSGGGGSEVQ LVESGGGLVK PGGSLRLSCA ASGFTFLNAW MSWVRQAPGK GLEWVGRIKS   180
NTDGGTTDYA APVKGRFTIS RDDSKNTLYL QMSSLKTEDT AVYYCTTDGP YSDDFRSGYA   240
ARYRYFGMDV WGCGTTVTVS S                                            261

SEQ ID NO: 51          moltype = AA   length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 51
DIQMTQSPSS VSASVGDRVT ITCRASQDIS TWLAWYQQKP GKCPKLLIYA ASSLQSGVPS    60
RFSGSGSGTD FTLTISSLQP EDFATYYCQQ ANSFPPTFGQ GTKLEIK                 107

SEQ ID NO: 52          moltype = AA   length = 134
FEATURE                Location/Qualifiers
REGION                 1..134
                       note = Description of Artificial Sequence: Synthetic
                        polypeptide
source                 1..134
                       mol_type = protein
                       organism = synthetic construct
SEQUENCE: 52
EVQLVESGGG LVKPGGSLRL SCAASGFTFL NAWMSWVRQA PGKGLEWVGR IKSNTDGGTT    60
DYAAPVKGRF TISRDDSKNT LYLQMSSLKT EDTAVYYCTT DGPYSDDFRS GYAARYRYFG   120
```

MDVWGCGTTV TVSS                                                              134

```
SEQ ID NO: 53              moltype = DNA   length = 322
FEATURE                    Location/Qualifiers
misc_feature               1..322
                           note = Description of Artificial Sequence: Synthetic
                            polynucleotide
source                     1..322
                           mol_type = other DNA
                           organism = synthetic construct
SEQUENCE: 53
gaaattgtgt tgacacagtc tccagccact ctgtctttgt ctccagggga aagagccacc   60
ctctcctgca gggccagtcg gagtattacc accttcttag cctggtacca acaaaaacct  120
ggccaggctc ccaggctcct catctacgat gcatccaaca gggccactgg cgtcccagcc  180
aggttcagtg gcagtgggtc tgggacagac ttcactctca ccatcaacag cctagagcct  240
gacgattttg caatttatta ctgtcagcag cgtgaccact ggcctccgat cttcggccaa  300
gggacacgac tggagattaa ac                                           322

SEQ ID NO: 54              moltype = AA    length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 54
EIVLTQSPAT LSLSPGERAT LSCRASRSIT TFLAWYQQKP GQAPRLLIYD ASNRATGVPA   60
RFSGSGSGTD FTLTINSLEP DDFAIYYCQQ RDHWPPIFGQ GTRLEIK                107

SEQ ID NO: 55              moltype = AA    length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 55
RASRSITTFL A                                                        11

SEQ ID NO: 56              moltype = AA    length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 56
DASNRAT                                                             7

SEQ ID NO: 57              moltype = AA    length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 57
QQRDHWPPI                                                           9

SEQ ID NO: 58              moltype = DNA   length = 391
FEATURE                    Location/Qualifiers
misc_feature               1..391
                           note = Description of Artificial Sequence: Synthetic
                            polynucleotide
source                     1..391
                           mol_type = other DNA
                           organism = synthetic construct
SEQUENCE: 58
gaagtgcagc tggtggagtc tgggggaggc ttggtgcaac ctggcaggtc cctgagactc   60
tcctgtgcag tttctggatt catctttgaa gattatgcca taaactgggt ccggcaagct  120
ccagggaagg gcctggagtg ggtctcaatt attagttggg acagtggtag atagcgctac  180
gcggactctg tgaggggccg attcaccatc tccagagaca cgccaagaa ctcctcgttt   240
ctgcaaatga acagtctgag acccgaagac acggccgtgt attattgtgt aaaagatatg  300
ttggcgtatt attatgatgg tagcggcatc aggtacaacc tctacggtat ggacgtctgg  360
ggccaaggga ccacggtcac cgtctcctca g                                 391

SEQ ID NO: 59              moltype = AA    length = 130
FEATURE                    Location/Qualifiers
```

```
REGION                  1..130
                        note = Description of Artificial Sequence: Synthetic
                         polypeptide
source                  1..130
                        mol_type = protein
                        organism = synthetic construct
SEQUENCE: 59
EVQLVESGGG LVQPGRSLRL SCAVSGFIFE DYAINWVRQA PGKGLEWVSI ISWDSGRIGY   60
ADSVRGRFTI SRDNAKNSSF LQMNSLRPED TAVYYCVKDM LAYYYDGSGI RYNLYGMDVW  120
GQGTTVTVSS                                                         130

SEQ ID NO: 60           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 60
DYAIN                                                                5

SEQ ID NO: 61           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 61
IISWDSGRIG YADSVRG                                                  17

SEQ ID NO: 62           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 62
DMLAYYYDGS GIRYNLYGMD V                                             21

SEQ ID NO: 63           moltype = AA  length = 257
FEATURE                 Location/Qualifiers
REGION                  1..257
                        note = Description of Artificial Sequence: Synthetic
                         polypeptide
source                  1..257
                        mol_type = protein
                        organism = synthetic construct
SEQUENCE: 63
EIVLTQSPAT LSLSPGERAT LSCRASRSIT TFLAWYQQKP GQAPRLLIYD ASNRATGVPA   60
RFSGSGSGTD FTLTINSLEP DDFAIYYCQQ RDHWPPIFGC GTRLEIKGGG GSGGGGSGGG  120
GSGGGGSEVQ LVESGGGLVQ PGRSLRLSCA VSGFIFEDYA INWVRQAPGK CLEWVSIISW  180
DSGRIGYADS VRGRFTISRD NAKNSSFLQM NSLRPEDTAV YYCVKDMLAY YYDGSGIRYN  240
LYGMDVWGQG TTVTVSS                                                 257

SEQ ID NO: 64           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 64
EIVLTQSPAT LSLSPGERAT LSCRASRSIT TFLAWYQQKP GQAPRLLIYD ASNRATGVPA   60
RFSGSGSGTD FTLTINSLEP DDFAIYYCQQ RDHWPPIFGC GTRLEIK                107

SEQ ID NO: 65           moltype = AA  length = 130
FEATURE                 Location/Qualifiers
REGION                  1..130
                        note = Description of Artificial Sequence: Synthetic
                         polypeptide
source                  1..130
                        mol_type = protein
                        organism = synthetic construct
SEQUENCE: 65
EVQLVESGGG LVQPGRSLRL SCAVSGFIFE DYAINWVRQA PGKCLEWVSI ISWDSGRIGY   60
ADSVRGRFTI SRDNAKNSSF LQMNSLRPED TAVYYCVKDM LAYYYDGSGI RYNLYGMDVW  120
```

```
GQGTTVTVSS                                                                   130

SEQ ID NO: 66            moltype = AA  length = 210
FEATURE                  Location/Qualifiers
REGION                   1..210
                         note = Description of Artificial Sequence: Synthetic
                         polypeptide
source                   1..210
                         mol_type = protein
                         organism = synthetic construct
SEQUENCE: 66
DIQMTQSPSS LSASVGDRVT ITCRTSQSLS SYTHWYQQKP GKAPKLLIYA ASSRGSGVPS  60
RFSGSGSGTD FTLTISSLQP EDFATYYCQQ SRTFGQGTKV EIKRTVAAPS VFIFPPSDEQ 120
LKSGTASVVC LLNNFYPREA KVQWKVDNAL QSGNSQESVT EQDSKDSTYS LSSTLTLSKA 180
DYEKHKVYAC EVTHQGLSSP VTKSFNRGEC                                   210

SEQ ID NO: 67            moltype = AA  length = 739
FEATURE                  Location/Qualifiers
REGION                   1..739
                         note = Description of Artificial Sequence: Synthetic
                         polypeptide
source                   1..739
                         mol_type = protein
                         organism = synthetic construct
SEQUENCE: 67
QVQLQQSGPG LVKPSQTLSL TCAISGDSVS SYNAVWNWIR QSPSRGLEWL GRTYYRSGWY  60
NDYAESVKSR ITINPDTSKN QFSLQLNSVT PEDTAVYYCA RSGHITVFGV NVDAFDMWGQ 120
GTMVTVSSAS TKGPSVFPLA PSSKSTSGGT AALGCLVKDY FPEPVTVSWN SGALTSGVHT 180
FPAVLQSSGL YSLSSVVTVP SSSLGTQTYI CNVNHKPSNT KVDKRVEPKS CGGGGSGGGG 240
SDIQMTQSPS SVSASVGDRV TITCRASQDI STWLAWYQQK PGKAPKLLIY AASSLQSGVP 300
SRFSGSGSGT DFTLTISSLQ PEDFATYFCQ QANSFPPTFG CGTKLEIKGG GGSGGGGSGG 360
GGSGGGGSEV QLVVSGGGLV KPGGSLRLSC AASGLSFLNA WMSWVRQAPG KCLEWVGRIK 420
SNTDGGTTDY AAPVKGRFSI SRDDSKNMLF LHMSSLRTED TAVYYCATDG PYSDDFRSGY 480
AARYRYFGMD VWGQGTTVTV SSGGGGSGGG GSDKTHTCPP CPAPELLGGP SVFLFPPKPK 540
DTLMISRTPE VTCVVVDVSH EDPEVKFNWY VDGVEVHNAK TKPREEQYNS TYRVVSVLTV 600
LHQDWLNGKE YKCKVSNKAL PAPIEKTISK AKGQPREPQV YTLPPSREEM TKNQVSLTCL 660
VKGFYPSDIA VEWESNGQPE NNYKTTPPVL DSDGSFFLYS KLTVDKSRWQ QGNVFSCSVM 720
HEALHNHYTQ KSLSLSPGK                                              739

SEQ ID NO: 68            moltype = AA  length = 210
FEATURE                  Location/Qualifiers
REGION                   1..210
                         note = Description of Artificial Sequence: Synthetic
                         polypeptide
source                   1..210
                         mol_type = protein
                         organism = synthetic construct
SEQUENCE: 68
DIQMTQSPSS LSASVGDRVT ITCRTSQSLS SYTHWYQQKP GKAPKLLIYA ASSRGSGVPS  60
RFSGSGSGTD FTLTISSLQP EDFATYYCQQ SRTFGQGTKV EIKRTVAAPS VFIFPPSDEQ 120
LKSGTASVVC LLNNFYPREA KVQWKVDNAL QSGNSQESVT EQDSKDSTYS LSSTLTLSKA 180
DYEKHKVYAC EVTHQGLSSP VTKSFNRGEC                                   210

SEQ ID NO: 69            moltype = AA  length = 739
FEATURE                  Location/Qualifiers
REGION                   1..739
                         note = Description of Artificial Sequence: Synthetic
                         polypeptide
source                   1..739
                         mol_type = protein
                         organism = synthetic construct
SEQUENCE: 69
QVQLQQSGPG LVKPSQTLSL TCAISGDSVS SYNAVWNWIR QSPSRGLEWL GRTYYRSGWY  60
NDYAESVKSR ITINPDTSKN QFSLQLNSVT PEDTAVYYCA RSGHITVFGV NVDAFDMWGQ 120
GTMVTVSSAS TKGPSVFPLA PSSKSTSGGT AALGCLVKDY FPEPVTVSWN SGALTSGVHT 180
FPAVLQSSGL YSLSSVVTVP SSSLGTQTYI CNVNHKPSNT KVDKRVEPKS CGGGGSGGGG 240
SDIQMTQSPS SVSASVGDRV TITCRASQDI STWLAWYQQK PGKCPKLLIY AASSLQSGVP 300
SRFSGSGSGT DFTLTISSLQ PEDFATYFCQ QANSFPPTFG QGTKLEIKGG GGSGGGGSGG 360
GGSGGGGSEV QLVVSGGGLV KPGGSLRLSC AASGLSFLNA WMSWVRQAPG KGLEWVGRIK 420
SNTDGGTTDY AAPVKGRFSI SRDDSKNMLF LHMSSLRTED TAVYYCATDG PYSDDFRSGY 480
AARYRYFGMD VWGCGTTVTV SSGGGGSGGG GSDKTHTCPP CPAPELLGGP SVFLFPPKPK 540
DTLMISRTPE VTCVVVDVSH EDPEVKFNWY VDGVEVHNAK TKPREEQYNS TYRVVSVLTV 600
LHQDWLNGKE YKCKVSNKAL PAPIEKTISK AKGQPREPQV YTLPPSREEM TKNQVSLTCL 660
VKGFYPSDIA VEWESNGQPE NNYKTTPPVL DSDGSFFLYS KLTVDKSRWQ QGNVFSCSVM 720
HEALHNHYTQ KSLSLSPGK                                              739

SEQ ID NO: 70            moltype = DNA  length = 45
FEATURE                  Location/Qualifiers
misc_feature             1..45
```

```
                        note = Description of Artificial Sequence: Synthetic primer
source                  1..45
                        mol_type = other DNA
                        organism = synthetic construct
SEQUENCE: 70
ttctctccac aggtgtacac tccgacatcc agatgaccca gtctc            45

SEQ ID NO: 71           moltype = DNA  length = 43
FEATURE                 Location/Qualifiers
misc_feature            1..43
                        note = Description of Artificial Sequence: Synthetic primer
source                  1..43
                        mol_type = other DNA
                        organism = synthetic construct
SEQUENCE: 71
ggatgggccc ttggtcgacg cgcttgacac ggtgaccata gtc              43

SEQ ID NO: 72           moltype = DNA  length = 41
FEATURE                 Location/Qualifiers
misc_feature            1..41
                        note = Description of Artificial Sequence: Synthetic primer
source                  1..41
                        mol_type = other DNA
                        organism = synthetic construct
SEQUENCE: 72
ctctggcgga gggggatccg acatccagat gacccagtct c                41

SEQ ID NO: 73           moltype = DNA  length = 62
FEATURE                 Location/Qualifiers
misc_feature            1..62
                        note = Description of Artificial Sequence: Synthetic primer
source                  1..62
                        mol_type = other DNA
                        organism = synthetic construct
SEQUENCE: 73
gtgagttttg tcggatcccc ctccgccaga gccacctccg cctgaggaga cggtgaccgt  60
gg                                                                62

SEQ ID NO: 74           moltype = DNA  length = 45
FEATURE                 Location/Qualifiers
misc_feature            1..45
                        note = Description of Artificial Sequence: Synthetic primer
source                  1..45
                        mol_type = other DNA
                        organism = synthetic construct
SEQUENCE: 74
ctggctcccc ggggcgcgct gtgacatcca gatgacccag tctcc            45

SEQ ID NO: 75           moltype = DNA  length = 47
FEATURE                 Location/Qualifiers
misc_feature            1..47
                        note = Description of Artificial Sequence: Synthetic primer
source                  1..47
                        mol_type = other DNA
                        organism = synthetic construct
SEQUENCE: 75
cccctccgcc ggatcccccct ccgcctgagg agacggtgac cgtggtc         47

SEQ ID NO: 76           moltype = DNA  length = 48
FEATURE                 Location/Qualifiers
misc_feature            1..48
                        note = Description of Artificial Sequence: Synthetic primer
source                  1..48
                        mol_type = other DNA
                        organism = synthetic construct
SEQUENCE: 76
aggggggatcc ggcggagggg gctctgatat tcagatgacc cagagccc        48

SEQ ID NO: 77           moltype = DNA  length = 40
FEATURE                 Location/Qualifiers
misc_feature            1..40
                        note = Description of Artificial Sequence: Synthetic primer
source                  1..40
                        mol_type = other DNA
                        organism = synthetic construct
SEQUENCE: 77
tggtgcagcc accgtacgtt tgatctccac cttagtgccc                  40

SEQ ID NO: 78           moltype = DNA  length = 55
```

```
FEATURE                 Location/Qualifiers
misc_feature            1..55
                        note = Description of Artificial Sequence: Synthetic primer
source                  1..55
                        mol_type = other DNA
                        organism = synthetic construct
SEQUENCE: 78
aaagcggag ggggatccgg cggaggggc tctgacatcc agatgaccca gtctc          55

SEQ ID NO: 79           moltype = DNA  length = 44
FEATURE                 Location/Qualifiers
misc_feature            1..44
                        note = Description of Artificial Sequence: Synthetic primer
source                  1..44
                        mol_type = other DNA
                        organism = synthetic construct
SEQUENCE: 79
tcaatgaatt cgcggccgct catgaggaga cggtgaccgt ggtc                    44

SEQ ID NO: 80           moltype = DNA  length = 45
FEATURE                 Location/Qualifiers
misc_feature            1..45
                        note = Description of Artificial Sequence: Synthetic primer
source                  1..45
                        mol_type = other DNA
                        organism = synthetic construct
SEQUENCE: 80
ttctctccac aggtgtacac tccgaaattg tgttgacaca gtctc                   45

SEQ ID NO: 81           moltype = DNA  length = 47
FEATURE                 Location/Qualifiers
misc_feature            1..47
                        note = Description of Artificial Sequence: Synthetic primer
source                  1..47
                        mol_type = other DNA
                        organism = synthetic construct
SEQUENCE: 81
cccctccgcc ggatccccct ccgcctgagg agacggtgac cgtggtc                 47

SEQ ID NO: 82           moltype = DNA  length = 46
FEATURE                 Location/Qualifiers
misc_feature            1..46
                        note = Description of Artificial Sequence: Synthetic primer
source                  1..46
                        mol_type = other DNA
                        organism = synthetic construct
SEQUENCE: 82
aggggatcc ggcggagggg gctctcaggt ccagctgcag gagagc                   46

SEQ ID NO: 83           moltype = DNA  length = 43
FEATURE                 Location/Qualifiers
misc_feature            1..43
                        note = Description of Artificial Sequence: Synthetic primer
source                  1..43
                        mol_type = other DNA
                        organism = synthetic construct
SEQUENCE: 83
ggatgggccc ttggtcgacg cgcttgacac ggtgaccata gtc                     43

SEQ ID NO: 84           moltype = DNA  length = 41
FEATURE                 Location/Qualifiers
misc_feature            1..41
                        note = Description of Artificial Sequence: Synthetic primer
source                  1..41
                        mol_type = other DNA
                        organism = synthetic construct
SEQUENCE: 84
ctctggcgga ggggatccg aaattgtgtt gacacagtct c                        41

SEQ ID NO: 85           moltype = DNA  length = 62
FEATURE                 Location/Qualifiers
misc_feature            1..62
                        note = Description of Artificial Sequence: Synthetic primer
source                  1..62
                        mol_type = other DNA
                        organism = synthetic construct
SEQUENCE: 85
gtgagttttg tcggatcccc ctccgccaga gccacctccg cctgaggaga cggtgaccgt   60
gg                                                                  62
```

```
SEQ ID NO: 86              moltype = DNA   length = 41
FEATURE                    Location/Qualifiers
misc_feature               1..41
                           note = Description of Artificial Sequence: Synthetic primer
source                     1..41
                           mol_type = other DNA
                           organism = synthetic construct
SEQUENCE: 86
ctctggcgga gggggatccg acatccagat gacccagtct c                         41

SEQ ID NO: 87              moltype = DNA   length = 62
FEATURE                    Location/Qualifiers
misc_feature               1..62
                           note = Description of Artificial Sequence: Synthetic primer
source                     1..62
                           mol_type = other DNA
                           organism = synthetic construct
SEQUENCE: 87
gtgagttttg tcggatcccc ctccgccaga gccacctccg cctgaggaga cggtgaccgt     60
gg                                                                    62

SEQ ID NO: 88              moltype = DNA   length = 41
FEATURE                    Location/Qualifiers
misc_feature               1..41
                           note = Description of Artificial Sequence: Synthetic primer
source                     1..41
                           mol_type = other DNA
                           organism = synthetic construct
SEQUENCE: 88
ctctggcgga gggggatccg acatccagat gacccagtct c                         41

SEQ ID NO: 89              moltype = DNA   length = 62
FEATURE                    Location/Qualifiers
misc_feature               1..62
                           note = Description of Artificial Sequence: Synthetic primer
source                     1..62
                           mol_type = other DNA
                           organism = synthetic construct
SEQUENCE: 89
gtgagttttg tcggatcccc ctccgccaga gccacctccg cctgaggaga cggtgaccgt     60
gg                                                                    62

SEQ ID NO: 90              moltype = DNA   length = 41
FEATURE                    Location/Qualifiers
misc_feature               1..41
                           note = Description of Artificial Sequence: Synthetic primer
source                     1..41
                           mol_type = other DNA
                           organism = synthetic construct
SEQUENCE: 90
ctctggcgga gggggatccg acatccagat gacccagtct c                         41

SEQ ID NO: 91              moltype = DNA   length = 62
FEATURE                    Location/Qualifiers
misc_feature               1..62
                           note = Description of Artificial Sequence: Synthetic primer
source                     1..62
                           mol_type = other DNA
                           organism = synthetic construct
SEQUENCE: 91
gtgagttttg tcggatcccc ctccgccaga gccacctccg cctgaggaga cggtgaccgt     60
gg                                                                    62

SEQ ID NO: 92              moltype = AA    length = 20
FEATURE                    Location/Qualifiers
REGION                     1..20
                           note = Description of Artificial Sequence: Synthetic peptide
source                     1..20
                           mol_type = protein
                           organism = synthetic construct
SEQUENCE: 92
GGGGSGGGGS GGGGSGGGGS                                                 20

SEQ ID NO: 93              moltype = AA    length = 25
FEATURE                    Location/Qualifiers
REGION                     1..25
                           note = Description of Artificial Sequence: Synthetic peptide
REGION                     1..25
```

```
                    note = misc_feature - This sequence may encompass 0, 1, 2,
                    3, 4, or 5 "Gly Gly Gly Gly Ser" repeating units, wherein
                    some positions may be absent
source              1..25
                    mol_type = protein
                    organism = synthetic construct
SEQUENCE: 93
GGGGSGGGGS GGGGSGGGGS GGGGS                                              25

SEQ ID NO: 94       moltype = AA  length = 6
FEATURE             Location/Qualifiers
REGION              1..6
                    note = Description of Artificial Sequence: Synthetic peptide
source              1..6
                    mol_type = protein
                    organism = synthetic construct
SEQUENCE: 94
QDISTW                                                                    6

SEQ ID NO: 95       moltype =   length =
SEQUENCE: 95
000

SEQ ID NO: 96       moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 96
QQANSFPPT                                                                 9

SEQ ID NO: 97       moltype = AA  length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 97
GLSFLNAW                                                                  8

SEQ ID NO: 98       moltype = AA  length = 10
FEATURE             Location/Qualifiers
REGION              1..10
                    note = Description of Artificial Sequence: Synthetic peptide
source              1..10
                    mol_type = protein
                    organism = synthetic construct
SEQUENCE: 98
IKSNTDGGTT                                                               10

SEQ ID NO: 99       moltype = AA  length = 25
FEATURE             Location/Qualifiers
REGION              1..25
                    note = Description of Artificial Sequence: Synthetic peptide
source              1..25
                    mol_type = protein
                    organism = synthetic construct
SEQUENCE: 99
TDGPYSDDFR SGYAARYRYF GMDVW                                              25

SEQ ID NO: 100      moltype = AA  length = 6
FEATURE             Location/Qualifiers
REGION              1..6
                    note = Description of Artificial Sequence: Synthetic peptide
source              1..6
                    mol_type = protein
                    organism = synthetic construct
SEQUENCE: 100
QDISTW                                                                    6

SEQ ID NO: 101      moltype =   length =
SEQUENCE: 101
000

SEQ ID NO: 102      moltype = AA  length = 9
FEATURE             Location/Qualifiers
```

```
REGION                    1..9
                          note = Description of Artificial Sequence: Synthetic peptide
source                    1..9
                          mol_type = protein
                          organism = synthetic construct
SEQUENCE: 102
QQANSFPPT                                                                      9

SEQ ID NO: 103            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 103
GFTFLNAW                                                                       8

SEQ ID NO: 104            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 104
IKSNTDGGTT                                                                    10

SEQ ID NO: 105            moltype = AA  length = 25
FEATURE                   Location/Qualifiers
REGION                    1..25
                          note = Description of Artificial Sequence: Synthetic peptide
source                    1..25
                          mol_type = protein
                          organism = synthetic construct
SEQUENCE: 105
TTDGPYSDDF RSGYAARYRY FGMDV                                                   25

SEQ ID NO: 106            moltype = AA  length = 20
FEATURE                   Location/Qualifiers
REGION                    1..20
                          note = Description of Artificial Sequence: Synthetic peptide
REGION                    1..20
                          note = MISC_FEATURE - This sequence may encompass 0, 1, 2,
                          3, 4, or 5 'Gly Gly Gly Gly' repeating units
source                    1..20
                          mol_type = protein
                          organism = synthetic construct
SEQUENCE: 106
GGGGGGGGGG GGGGGGGGGG                                                         20

SEQ ID NO: 107            moltype = AA  length = 210
FEATURE                   Location/Qualifiers
REGION                    1..210
                          note = Description of Artificial Sequence: Synthetic
                          polypeptide
source                    1..210
                          mol_type = protein
                          organism = synthetic construct
SEQUENCE: 107
DIQMTQSPSS LSASVGDRVT ITCRTSQSLS SYLHWYQQKP GKAPKLLIYA ASSLQSGVPS              60
RFSGSGSGTD FTLTISSLQP EDFATYYCQQ SRTFGQGTKV EIKRTVAAPS VFIFPPSDEQ             120
LKSGTASVVC LLNNFYPREA KVQWKVDNAL QSGNSQESVT EQDSKDSTYS LSSTLTLSKA             180
DYEKHKVYAC EVTHQGLSSP VTKSFNRGEC                                              210

SEQ ID NO: 108            moltype = AA  length = 729
FEATURE                   Location/Qualifiers
REGION                    1..729
                          note = Description of Artificial Sequence: Synthetic
                          polypeptide
source                    1..729
                          mol_type = protein
                          organism = synthetic construct
SEQUENCE: 108
DIQMTQSPSS VSASVGDRVT ITCRASQDIS TWLAWYQQKP GKAPKLLIYA ASSLQSGVPS              60
RFSGSGSGTD FTLTISSLQP EDFATYFCQQ ANSFPPTFGC GTKLEIKGGG GSGGGGSGGG             120
GSGGGGSEVQ LVVSGGGLVK PGGSLRLSCA ASGLSFLNAW MSWVRQAPGK CLEWVGRIKS             180
NTDGGTTDYA APVKGRFSIS RDDSKNMLFL HMSSLRTEDT AVYYCATDGP YSDDFRSGYA             240
ARYRYFGMDV WGQGTTVTVS SGGGGSGGGG SQVQLQESGP GLVKPSQTLS LTCAISGDSV             300
```

```
SSNNAVWNWI RQSPSRGLEW LGRTYYRSKW YNDYAESVKS RITVNPDTSK NQFSLHLKSV    360
TPEDTAVFYC VRSGHITVFG VNVDAFDMWG QGTMVTVSSA STKGPSVFPL APSSKSTSGG    420
TAALGCLVKD YFPEPVTVSW NSGALTSGVH TFPAVLQSSG LYSLSSVVTV PSSSLGTQTY    480
ICNVNHKPSN TKVDKRVEPK SCDKTHTCPP CPAPELLGGP SVFLFPPKPK DTLMISRTPE    540
VTCVVVDVSH EDPEVKFNWY VDGVEVHNAK TKPREEQYNS TYRVVSVLTV LHQDWLNGKE    600
YKCKVSNKAL PAPIEKTISK AKGQPREPQV YTLPPSREEM TKNQVSLTCL VKGFYPSDIA    660
VEWESNGQPE NNYKTTPPVL DSDGSFFLYS KLTVDKSRWQ QGNVFSCSVM HEALHNHYTQ    720
KSLSLSPGK                                                          729

SEQ ID NO: 109           moltype = AA  length = 210
FEATURE                  Location/Qualifiers
REGION                   1..210
                         note = Description of Artificial Sequence: Synthetic
                          polypeptide
source                   1..210
                         mol_type = protein
                         organism = synthetic construct
SEQUENCE: 109
DIQMTQSPSS LSASVGDRVT ITCRTSQSLS SYLHWYQQKP GKAPKLLIYA ASSLQSGVPS     60
RFSGSGSGTD FTLTISSLQP EDFATYYCQQ SRTFGQGTKV EIKRTVAAPS VFIFPPSDEQ    120
LKSGTASVVC LLNNFYPREA KVQWKVDNAL QSGNSQESVT EQDSKDSTYS LSSTLTLSKA    180
DYEKHKVYAC EVTHQGLSSP VTKSFNRGEC                                    210

SEQ ID NO: 110           moltype = AA  length = 739
FEATURE                  Location/Qualifiers
REGION                   1..739
                         note = Description of Artificial Sequence: Synthetic
                          polypeptide
source                   1..739
                         mol_type = protein
                         organism = synthetic construct
SEQUENCE: 110
QVQLQESGPG LVKPSQTLSL TCAISGDSVS SNNAVWNWIR QSPSRGLEWL GRTYYRSKWY     60
NDYAESVKSR ITVNPDTSKN QFSLHLKSVT PEDTAVFYCV RSGHITVFGV NVDAFDMWGQ    120
GTMVTVSSAS TKGPSVFPLA PSSKSTSGGT AALGCLVKDY FPEPVTVSWN SGALTSGVHT    180
FPPAVLQSSGL YSLSSVVTVP SSSLGTQTYI CNVNHKPSNT KVDKRVEPKS CGGGGSGGGG    240
SDIQMTQSPS SVSASVGDRV TITCRASQDI STWLAWYQQK PGKAPKLLIY AASSLQSGVP    300
SRFSGSGSGT DFTLTISSLQ PEDFATYFCQ QANSFPPTFG CGTKLEIKGG GGSGGGGSGG    360
GGSGGGGSEV QLVVSGGGLV KPGGSLRLSC AASGLSFLNA WMSWVRQAPG KCLEWVGRIK    420
SNTDGGTTDY AAPVKGRFSI SRDDSKNMLF LHMSSLRTED TAVYYCATDG PYSDDFRSGY    480
AARYRYFGMD VWGQGTTVTV SSGGGGSGGG GSDKTHTCPP CPAPELLGGP SVFLFPPKPK    540
DTLMISRTPE VTCVVVDVSH EDPEVKFNWY VDGVEVHNAK TKPREEQYNS TYRVVSVLTV    600
LHQDWLNGKE YKCKVSNKAL PAPIEKTISK AKGQPREPQV YTLPPSREEM TKNQVSLTCL    660
VKGFYPSDIA VEWESNGQPE NNYKTTPPVL DSDGSFFLYS KLTVDKSRWQ QGNVFSCSVM    720
HEALHNHYTQ KSLSLSPGK                                                739

SEQ ID NO: 111           moltype = DNA  length = 1197
FEATURE                  Location/Qualifiers
misc_feature             1..1197
                         note = Description of Artificial Sequence: Synthetic
                          polynucleotide
source                   1..1197
                         mol_type = other DNA
                         organism = synthetic construct
SEQUENCE: 111
gacatccaga tgacccagtc tccatcttcc gtgtctgcat ctgtgggaga cagagtcacc     60
atcacttgtc gggcgagtca ggatattagc acctggttag cctggtatca gcagaaacca    120
gggaaagccc ctaagctcct gatctatgct gcatccagtt tgcaaagtgg ggtcccatca    180
agattcagcg gcagtggatc tgggacagat ttcactctca ccatcagcag cctgcagcct    240
gaagattttg caacttactt ttgtcagcag gctaacagtt tccctccgac ttttggctgc    300
gggaccaagc tggagatcaa aggcggaggg ggctctgggg gaggggggcag cggcggcgga    360
ggatctgggg gaggggggcag cgaggtgcag ctggtggtgt ctgggggagg cttggtaaag    420
cctggggggt ccttagact ctcctgtgca gcctctggac tcagtttcct taacgcctgg    480
atgagctggg tccgccaggc tccagggaag tgcctggagt gggttggccg tattaaaagt    540
aatactgatg gtgggacaac agactacgcc gcacccgtga aaggcagatt cagcatctca    600
agagacgatt caaagaacat gctgtttctg catatgagca gcctgagaac cgaggacaca    660
gccgtctatt actgcgccac agatggacct tactctgacg atttagaag tggttatgcc    720
gcacgctacc gttatttcgg aatggacgtc tggggccaag gaccacggt caccgtctct    780
tcaggcggag ggggatccgg cggaggggc tctcaggtcc agctcggaga gagcggcccc    840
ggactggtca agccttcaca gacactgagc ctgacatgcg ccattagcgg agatagcgtg    900
agctccaaca atgccgtgtg gaactggatc aggcagtctc caagtcgagg actggagtgg    960
ctgggacgaa catactatag atccaagtgg tacaatgact atgctgaatc agtgaaaagc   1020
cgaattactg tcaaccccga tacctccaag aatcagttct ctctgcacct gaaaagtgtg   1080
accccggagg acacagccgt gttctactgc gtcagaagcg gccatatcac cgtctttggc   1140
gtcaatgtgg atgctttcga tatgtggggg caggggacta tggtcaccgt gtcaagc      1197

SEQ ID NO: 112           moltype = DNA  length = 783
FEATURE                  Location/Qualifiers
misc_feature             1..783
```

```
                        note = Description of Artificial Sequence: Synthetic
                               polynucleotide
source                  1..783
                        mol_type = other DNA
                        organism = synthetic construct
SEQUENCE: 112
gacatccaga tgacccagtc tccatcttcc gtgtctgcat ctgtgggaga cagagtcacc    60
atcacttgtc gggcgagtca ggatattagc acctggttag cctggtatca gcagaaacca   120
gggaaagccc ctaagctcct gatctatgct gcatccagtt tgcaaagtgg ggtcccatca   180
agattcagcg gcagtggatc tgggacagat ttcactctca ccatcagcag cctgcagcct   240
gaagattttg caacttactt ttgtcagcag gctaacagtt ccctccgac  ttttggctgc   300
gggaccaagc tggagatcaa aggcggaggg ggctctgggg gaggggcag  cggcggcgga   360
ggatctgggg gaggggcag  cgaggtgcag ctggtggtgt ctggggagg  cttggtaaag   420
cctgggggt  cccttagact ctcctgtgca gcctctggat tcagtttcct taacgcctgg   480
atgagctggg tccgccaggc tccagggaag tgcctggagt gggttggccg tattaaaagt   540
aatactgatg gtgggacaac agactacgcc gcacccgtga aagcagatt  cagcatctca   600
agagacgatt caaagaacat gctgtttctg catatgagca gcctgagaac cgaggacaca   660
gccgtctatt actgcgccac agatggacct tactctgacg attttagaag tggttatgcc   720
gcacgctacc gttatttcgg aatggacgtc tggggccaag gaccacggt  caccgtctcc   780
tca                                                                 783

SEQ ID NO: 113          moltype = AA  length = 481
FEATURE                 Location/Qualifiers
REGION                  1..481
                        note = Description of Artificial Sequence: Synthetic
                               polypeptide
source                  1..481
                        mol_type = protein
                        organism = synthetic construct
SEQUENCE: 113
DIQMTQSPSS VSASVGDRVT ITCRASQDIS TWLAWYQQKP GKAPKLLIYA ASSLQSGVPS    60
RFSGSGSGTD FTLTISSLQP EDFATYFCQQ ANSFPPTFGC GTKLEIKGGG GSGGGGSGGG   120
GSGGGGSEVQ LVVSGGGLVK PGGSLRLSCA ASGLSFLNAW MSWVRQAPGK CLEWVGRIKS   180
NTDGGTTDYA APVKGRFSIS RDDSKNMLFL HMSSLRTEDT AVYYCATDGP YSDDFRSGYA   240
ARYRYFGMDV WGQGTTVTVS SGGGGSGGGG SDIQMTQSPS SLSASVGDRV TITCRTSQSL   300
SSYLHWYQQK PGKAPKLLIY AASSLQSGVP SRFSGSGSGT DFTLTISSLQ PEDFATYYCQ   360
QSRTFGQGTK VEIKRTVAAP SVFIFPPSDE QLKSGTASVV CLLNNFYPRE AKVQWKVDNA   420
LQSGNSQESV TEQDSKDSTY SLSSTLTLSK ADYEKHKVYA CEVTHQGLSS PVTKSFNRGE   480
C                                                                  481

SEQ ID NO: 114          moltype = AA  length = 458
FEATURE                 Location/Qualifiers
REGION                  1..458
                        note = Description of Artificial Sequence: Synthetic
                               polypeptide
source                  1..458
                        mol_type = protein
                        organism = synthetic construct
SEQUENCE: 114
QVQLQESGPG LVKPSQTLSL TCAISGDSVS SNNAVWNWIR QSPSRGLEWL GRTYYRSKWY    60
NDYAESVKSR ITVNPDTSKN QFSLHLKSVT PEDTAVFYCV RSGHITVFGV NVDAFDMWGQ   120
GTMVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLGGPS VFLFPPKPKD TLMISRTPEV TCVVVDVSHE DPEVKFNWYV DGVEVHNAKT   300
KPREEQYNST YRVVSVLTVL HQDWLNGKEY KCKVSNKALP APIEKTISKA KGQPREPQVY   360
TLPPSREEMT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                          458

SEQ ID NO: 115          moltype = AA  length = 210
FEATURE                 Location/Qualifiers
REGION                  1..210
                        note = Description of Artificial Sequence: Synthetic
                               polypeptide
source                  1..210
                        mol_type = protein
                        organism = synthetic construct
SEQUENCE: 115
DIQMTQSPSS LSASVGDRVT ITCRTSQSLS SYLHWYQQKP GKAPKLLIYA ASSLQSGVPS    60
RFSGSGSGTD FTLTISSLQP EDFATYYCQQ SRTFGQGTKV EIKRTVAAPS VFIFPPSDEQ   120
LKSGTASVVC LLNNFYPREA KVQWKVDNAL QSGNSQESVT EQDSKDSTYS LSSTLTLSKA   180
DYEKHKVYAC EVTHQGLSSP VTKSFNRGEC                                   210

SEQ ID NO: 116          moltype = AA  length = 729
FEATURE                 Location/Qualifiers
REGION                  1..729
                        note = Description of Artificial Sequence: Synthetic
                               polypeptide
source                  1..729
                        mol_type = protein
```

```
                        organism = synthetic construct
SEQUENCE: 116
QVQLQESGPG LVKPSQTLSL TCAISGDSVS SNNAVWNWIR QSPSRGLEWL GRTYYRSKWY     60
NDYAESVKSR ITVNPDTSKN QFSLHLKSVT PEDTAVFYCV RSGHITVFGV NVDAFDMWGQ    120
GTMVTVSSAS TKGPSVFPLA PSSKSTSGGT AALGCLVKDY FPEPVTVSWN SGALTSGVHT    180
FPAVLQSSGL YSLSSVVTVP SSSLGTQTYI CNVNHKPSNT KVDKRVEPKS CDKTHTCPPC    240
PAPELLGGPS VFLFPPKPKD TLMISRTPEV TCVVVDVSHE DPEVKFNWYV DGVEVHNAKT    300
KPREEQYNST YRVVSVLTVL HQDWLNGKEY KCKVSNKALP APIEKTISKA KGQPREPQVY    360
TLPPSREEMT KNQVSLTCLV KGFYPSDIAV EWESNGQPEN NYKTTPPVLD SDGSFFLYSK    420
LTVDKSRWQQ GNVFSCSVMH EALHNHYTQK SLSLSPGKGG GGSGGGGSDI QMTQSPSSVS    480
ASVGDRVTIT CRASQDISTW LAWYQQKPGK APKLLIYAAS SLQSGVPSRF SGSGSGTDFT    540
LTISSLQPED FATYFCQQAN SFPPTFGCGT KLEIKGGGGS GGGGSGGGGS GGGGSEVQLV    600
VSGGGLVKPG GSLRLSCAAS GLSFLNAWMS WVRQAPGKCL EWVGRIKSNT DGGTTDYAAP    660
VKGRFSISRD DSKNMLFLHM SSLRTEDTAV YYCATDGPYS DDFRSGYAAR YRYFGMDVWG    720
QGTTVTVSS                                                            729

SEQ ID NO: 117          moltype = AA  length = 210
FEATURE                 Location/Qualifiers
REGION                  1..210
                        note = Description of Artificial Sequence: Synthetic
                         polypeptide
source                  1..210
                        mol_type = protein
                        organism = synthetic construct
SEQUENCE: 117
DIQMTQSPSS LSASVGDRVT ITCRTSQSLS SYLHWYQQKP GKAPKLLIYA ASSLQSGVPS     60
RFSGSGSGTD FTLTISSLQP EDFATYYCQQ SRTFGQGTKV EIKRTVAAPS VFIFPPSDEQ    120
LKSGTASVVC LLNNFYPREA KVQWKVDNAL QSGNSQESVT EQDSKDSTYS LSSTLTLSKA    180
DYEKHKVYAC EVTHQGLSSP VTKSFNRGEC                                     210

SEQ ID NO: 118          moltype = AA  length = 725
FEATURE                 Location/Qualifiers
REGION                  1..725
                        note = Description of Artificial Sequence: Synthetic
                         polypeptide
source                  1..725
                        mol_type = protein
                        organism = synthetic construct
SEQUENCE: 118
EIVLTQSPAT LSLSPGERAT LSCRASRSIT TFLAWYQQKP GQAPRLLIYD ASNRATGVPA     60
RFSGSGSGTD FTLTINSLEP DDFAIYYCQQ RDHWPPIFGC GTRLEIKGGG GSGGGGSGGG    120
GSGGGGSEVQ LVESGGGLVQ PGRSLRLSCA VSGFIFEDYA INWVRQAPGK CLEWVSIISW    180
DSGRIGYADS VRGRFTISRD NAKNSSFLQM NSLRPEDTAV YYCVCDMLAY YYDGSGIRYN    240
LYGMDVWGQG TTVTVSSGGG GSGGGGSQVQ LQESGPGLVK PSQTLSLTCA ISGDSVSSNN    300
AVWNWIRQSP SRGLEWLGRT YYRSKWYNDY AESVKSRITV NPDTSKNQFS LHLKSVTPED    360
TAVFYCVRSG HITVFGVNVD AFDMWGQGTM VTVSSASTKG PSVFPLAPSS KSTSGGTAAL    420
GCLVKDYFPE PVTVSWNSGA LTSGVHTFPA VLQSSGLYSL SSVVTVPSSS LGTQTYICNV    480
NHKPSNTKVD KRVEPKSCDK THTCPPCPAP ELLGGPSVFL FPPKPKDTLM ISRTPEVTCV    540
VVDVSHEDPE VKFNWYVDGV EVHNAKTKPR EEQYNSTYRV VSVLTVLHQD WLNGKEYKCK    600
VSNKALPAPI EKTISKAKGQ PREPQVYTLP PSREEMTKNQ VSLTCLVKGF YPSDIAVEWE    660
SNGQPENNYK TTPPVLDSDG SFFLYSKLTV DKSRWQQGNV FSCSVMHEAL HNHYTQKSLS    720
LSPGK                                                                725

SEQ ID NO: 119          moltype = DNA  length = 771
FEATURE                 Location/Qualifiers
misc_feature            1..771
                        note = Description of Artificial Sequence: Synthetic
                         polynucleotide
source                  1..771
                        mol_type = other DNA
                        organism = synthetic construct
SEQUENCE: 119
gaaattgtgt tgacacagtc tccagccact ctgtctttgt ctccagggga aagagccacc     60
ctctcctgca gggccagtcg gagtattacc accttcttag cctggtacca acaaaaacct    120
ggccaggctc ccaggctcct catctacgat gcatccaaca gggccactgg cgtcccagcc    180
aggttcagtg gcagtgggtc tgggacagac ttcactctca ccatcaacag cctagagcct    240
gacgattttg caatttatta ctgtcagcag cgtgaccact ggcctccgat cttcggctgt    300
gggacacgac tggagattaa aggaggcgga ggatctggtg gtggtggatc tggcggcgga    360
ggaagtgcag gcggaggctc tgaagtgcag ctggtggaat ctgggggagg cttggtgcaa    420
cctggcaggt ccctgagact ctcctgtgca gtttctggat tcatctttga agattatgcc    480
ataaactggg tccggcaagc tccagggaag tgcctggagt gggtctcaat tattagttgg    540
gacagtggta ggataggcta cgcggactct gtgaggggcc gattccacat ctccagagac    600
aacgccaaga actcctcgtt tctgcaaatg aacagtctga cccccgaaga caccgccgtg    660
tattgtaaag atat gttggcgtat tattatgatg gtagcggcat caggtacaac    720
ctctacggta tggacgtctg gggccaaggg accacggtca ccgtctcctc a             771

SEQ ID NO: 120          moltype = AA  length = 210
FEATURE                 Location/Qualifiers
REGION                  1..210
```

```
                        note = Description of Artificial Sequence: Synthetic
                             polypeptide
source                  1..210
                        mol_type = protein
                        organism = synthetic construct
SEQUENCE: 120
DIQMTQSPSS LSASVGDRVT ITCRTSQSLS SYLHWYQQKP GKAPKLLIYA ASSLQSGVPS    60
RFSGSGSGTD FTLTISSLQP EDFATYYCQQ SRTFGQGTKV EIKRTVAAPS VFIFPPSDEQ   120
LKSGTASVVC LLNNFYPREA KVQWKVDNAL QSGNSQESVT EQDSKDSTYS LSSTLTLSKA   180
DYEKHKVYAC EVTHQGLSSP VTKSFNRGEC                                    210

SEQ ID NO: 121          moltype = AA   length = 739
FEATURE                 Location/Qualifiers
REGION                  1..739
                        note = Description of Artificial Sequence: Synthetic
                             polypeptide
source                  1..739
                        mol_type = protein
                        organism = synthetic construct
SEQUENCE: 121
QVQLQESGPG LVKPSQTLSL TCAISGDSVS SNNAVWNWIR QSPSRGLEWL GRTYYRSKWY    60
NDYAESVKSR ITVNPDTSKN QFSLHLKSVT PEDTAVFYCV RSGHITVFGV NVDAFDMWGQ   120
GTMVTVSSAS TKGPSVFPLA PSSKSTSGGT AALGCLVKDY FPEPVTVSWN SGALTSGVHT   180
FPPAVLQSSG LYSLSSVVTVP SSSLGTQTYI CNVNHKPSNT KVDKRVEPKS CGGGGSGGGG   240
SDIQMTQSPS SVSASVGDRV TITCRASQDI STWLAWYQQK PGKCPKLLIY AASSLQSGVP   300
SRFSGSGSGT DFTLTISSLQ PEDFATYFCQ QANSFPPTFG QGTKLEIKGG GGSGGGGSGG   360
GGSGGGGSEV QLVVSGGGLV KPGGSLRLSC AASGLSFLNA WMSWVRQAPG KGLEWVGRIK   420
SNTDGGTTDY AAPVKGRFSI SRDDSKNMLF LHMSSLRTED TAVYYCATDG PYSDDFRSGY   480
AARYRYFGMD VWGCGTTVTV SSGGGGSGGG GSDKTHTCPP CPAPELLGGP SVFLFPPKPK   540
DTLMISRTPE VTCVVVDVSH EDPEVKFNWY VDGVEVHNAK TKPREEQYNS TYRVVSVLTV   600
LHQDWLNGKE YKCKVSNKAL PAPIEKTISK AKGQPREPQV YTLPPSREEM TKNQVSLTCL   660
VKGFYPSDIA VEWESNGQPE NNYKTTPPVL DSDGSFFLYS KLTVDKSRWQ QGNVFSCSVM   720
HEALHNHYTQ KSLSLSPGK                                                739

SEQ ID NO: 122          moltype = DNA   length = 783
FEATURE                 Location/Qualifiers
misc_feature            1..783
                        note = Description of Artificial Sequence: Synthetic
                             polynucleotide
source                  1..783
                        mol_type = other DNA
                        organism = synthetic construct
SEQUENCE: 122
gacatccaga tgacccagtc tccatcttcc gtgtctgcat ctgtgggaga cagagtcacc    60
atcacttgtc gggcgagtca ggatattagc acctggttag cctggtatca gcagaaacca   120
gggaaatgcc ctaagctcct gatctatgct gcatccagtt tgcaaagtgg ggtcccatca   180
agattcagcg gcagtggatc tgggacagat ttcactctca ccatcagcag cctgcagcct   240
gaagattttg caacttactt ttgtcagcag gctaacagtt tccctccgac ttttggccaa   300
gggaccaagc tggagatcaa aggaggcgga ggatctggtg gtggtggatc tggcggcgga   360
ggaagtggtg gcggaggctc tgaggtgcag ctggtggtgt ctgggggagg cttggtaaag   420
cctggggggt cccttagact ctcctgtgca gcctctggat tcagtttcct taacgcctat   480
atgagctggg tccgccaggc tccagggaag gggctggagt gggttggccg tattaaaagt   540
aatactgatg gtgggacaac agactacgcc gcaccgtgaa aggcagatt cagcatctca   600
agagacgatt caaagaacat gctgtttctg catatgagca gctgagaaac cgaggacaca   660
gccgtctatt actgcgccac agatggacct tactctgacg attttagaag tggttatgcc   720
gcacgctacc gttatttcgg aatggacgtc tggggctgcg gaccacggt caccgtctcc   780
tca                                                                 783

SEQ ID NO: 123          moltype = DNA   length = 2526
FEATURE                 Location/Qualifiers
misc_feature            1..2526
                        note = Description of Artificial Sequence: Synthetic
                             polynucleotide
source                  1..2526
                        mol_type = other DNA
                        organism = synthetic construct
SEQUENCE: 123
gatattcaga tgacccagag cccttccagc ctgtccgctt cagtggggga tcgagtgacc    60
attacctgcc gaaccagcca gagcctgagc tcctacacgc actggtatca gcagaagccc   120
ggcaaagccc ctaagctgct gatctacgcg gcttctagtc gggggtccgg agtgccaagc   180
cggttctccg gatctgggag tggaaccgac tttaccctga caatttcaag cctgcagccc   240
gaggatttcg ctacatacta ctgtcagcag agcagaactt cgggcagggg cactaaggtg   300
gagatcaaac gtacggtggc tgcaccatct gtcttcatct tcccgccatc tgatgagcag   360
ttgaaatctg gaactgcctc tgttgtgtgc ctgctgaata acttctatcc cagagaggcc   420
aaagtacagt ggaaggtgga taacgccctc caatcgggta actcccagga gagtgtcaca   480
gagcaggaca gcaaggacag cacctacagc ctcagcagca cctgacgct gagcaaagca   540
gactacgaga aacacaaagt ctacgcctgc gaagtcaccc atcagggcct gagctcgccc   600
gtcacaaaga gcttcaacag gggagagtgt tagtgagcta gcgatgataa tcagccatac   660
cacatttgta gaggttttac ttgctttaaa aaacctccca cacctccccc tgaacctgaa   720
```

```
acataaaatg aatgcaattg ttgttgttaa cttgtttatt gcagcttata atggttacaa  780
ataaagcaat agcatcacaa atttcacaaa taaagcattt ttttcactgc attctagttg  840
tggtttgtcc aaactcatca atgtatctta tcatgtctgg atgggcccgt ttaaacccgc  900
tgatcagcct cgactgtgcc ttctagttgc cagccatctg ttgtttgccc ctcccccgtg  960
ccttccttga ccctggaagg tgccactccc actgtccttt cctaataaaa tgaggaaatt 1020
gcatcgcatt gtctgagtag gtgtcattct attctggggg gtggggtggg gcaggacagc 1080
aaggggggagg attgggaaga caatagcagg catgctgggg atgcgtggg ctctatggct 1140
tctgaggcgg aaagaaccag ctggggctct agctagttat taatagtaat caattacggg 1200
gtcattagtt catagcccat atatggagtt ccgcgttaca taacttacgg taaatggccc 1260
gcctggctga ccgcccaacg accccgcc attgacgtca ataatgacgt atgttcccat 1320
agtaacgcca atagggactt tccattgacg tcaatgggtg gagtatttac ggtaaactgc 1380
ccacttggca gtacatcaag tgtatcatat gccaagtacg cccctattg acgtcaatga 1440
cggtaaatgg cccgcctggc attatgccca gtacatgacc ttatgggact ttcctacttg 1500
gcagtacatc tacgtattag tcatcgctat taccatggtg atgcggtttt ggcagtacat 1560
caatgggcgt ggatagcggt ttgactcacg gggatttcca agtctccacc ccattgacgt 1620
caatgggagt ttgttttggc accaaaatca acgggacttt ccaaaatgtc gtaacaactc 1680
cgccccattg acgcaaatgg gcggtaggcg tgtacggtgg gaggtctata taagcagagc 1740
tcgtttagtg aaccgtcaga tcgcctggag acgccatcca cgctgttttg acctccatag 1800
aagacaccgg gaccgatcca gcctccgcgg ccgggaacgg tgcattggaa cgcggattcc 1860
ccgtgccaag agtgacgtaa gtaccgccta tagactctat aggcacaccc ctttggctct 1920
tatgcatgaa ttaatacgac tcactatagg gagacagact gttcctttcc tgggtctttt 1980
ctgcaggcac cgtcgccgcc accatggcat ggagctgta catcctcttc ttggtagcaa 2040
cagctacagg taaggggctc acagtagcag gcttgaggtc tagacatata tatgggtgac 2100
aatgacatcc actttgcctt tctctccaca ggtgtacact cccaggtcca gctgcagcag 2160
agcggcccg gactggtcaa gccttacag acactgagcc tgacatgcgc cattagcgga 2220
gatagcgtga gctcctacaa tgccgtgtgg aactggatca agcagcccga gagcgagga 2280
ctggagtggc tgggacgaac atactataga tccgggtggt acaatgacta tgctgaatca 2340
gtgaaaagcc gaattactat caaccccgat acctccaaga atcagttctc tctgcagctg 2400
aacagtgtga cccctgagga cacagccgtg tactactgcg ccagaagcgg ccatatcacc 2460
gtctttggcg tcaatgtgga tgctttcgat atgtgggggc aggggactat ggtcaccgtg 2520
tcaagc                                                            2526

SEQ ID NO: 124          moltype = DNA  length = 783
FEATURE                 Location/Qualifiers
misc_feature            1..783
                        note = Description of Artificial Sequence: Synthetic
                        polynucleotide
source                  1..783
                        mol_type = other DNA
                        organism = synthetic construct
SEQUENCE: 124
gacatccaga tgacccagtc tccatcttcc gtgtctgcat ctgtgggaga cagagtcacc   60
atcacttgtc gggcgagtca ggatattagc acctggttag cctggtatca gcagaaacca  120
gggaaagccc ctaagctcct gatctatgct gcatccagtt tgcaaagtgg ggtcccatca  180
agattcagcg gcagtggatc tgggacagat ttcactctca ccatcagcag cctgcagcct  240
gaagattttg caacttacta ttgtcagcag gctaacagtt ccctccgac ttttggctgc  300
gggaccaagc tggagatcaa aggaggcgga ggatctggcg gtggtggatc tggcggcgga  360
ggaagtggtg gcggaggctc tgaggtcag ctggtggagt ctgggggagg cttggtaaag  420
cctggggggt cccttagact ctcctgtgca gcctctggat tcacttttcct taacgcctgg  480
atgagctggg tccgccaggc tccagggaag tgcctggagt gggttggccg tattaaaagt  540
aatactgatg gtgggacaac agactacgcc gcacccgtga aagcagatt caccatctca  600
agagacgatt caaagaacac gctgtatctg caaatgagca gcctgaaaac cgaggacaca  660
gccgtctatt actgcaccac agatggacct tactctgacg attttagaag tggttatgcc  720
gcacgctacc gttatttcgg aatggacgtc tggggccaag ggaccacggt caccgtctcc  780
tca                                                                783

SEQ ID NO: 125          moltype = AA  length = 210
FEATURE                 Location/Qualifiers
REGION                  1..210
                        note = Description of Artificial Sequence: Synthetic
                        polypeptide
source                  1..210
                        mol_type = protein
                        organism = synthetic construct
SEQUENCE: 125
DIQMTQSPSS LSASVGDRVT ITCRTSQSLS SYTHWYQQKP GKAPKLLIYA ASSRGSGVPS   60
RFSGSGSGTD FTLTISSLQP EDFATYYCQQ SRTFGQGTKV EIKRTVAAPS VFIFPPSDEQ  120
LKSGTASVVC LLNNFYPREA KVQWKVDNAL QSGNSQESVT EQDSKDSTYS LSSTLTLSKA  180
DYEKHKVYAC EVTHQGLSSP VTKSFNRGEC                                   210

SEQ ID NO: 126          moltype = AA  length = 739
FEATURE                 Location/Qualifiers
REGION                  1..739
                        note = Description of Artificial Sequence: Synthetic
                        polypeptide
source                  1..739
                        mol_type = protein
                        organism = synthetic construct
SEQUENCE: 126
```

```
QVQLQQSGPG LVKPSQTLSL TCAISGDSVS SYNAVWNWIR QSPSRGLEWL GRTYYRSGWY    60
NDYAESVKSR ITINPDTSKN QFSLQLNSVT PEDTAVYYCA RSGHITVFGV NVDAFDMWGQ   120
GTMVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CGGGGSGGGG   240
SDIQMTQSPS SVSASVGDRV TITCRASQDI STWLAWYQQK PGKCPKLLIY AASSLQSGVP   300
SRFSGSGSGT DFTLTISSLQ PEDFATYYCQ QANSFPPTFG QGTKLEIKGG GSGGGGSGG    360
GGSGGGGSEV QLVESGGGLV KPGGSLRLSC AASGFTFLNA WMSWVRQAPG KGLEWVGRIK   420
SNTDGGTTDY AAPVKGRFTI SRDDSKNTLY LQMSSLKTED TAVYYCTTDG PYSDDFRSGY   480
AARYRYFGMD VWGCGTTVTV SSGGGGSGGG GSDKTHTCPP CPAPELLGGP SVFLFPPKPK   540
DTLMISRTPE VTCVVVDVSH EDPEVKFNWY VDGVEVHNAK TKPREEQYNS TYRVVSVLTV   600
LHQDWLNGKE YKCKVSNKAL PAPIEKTISK AKGQPREPQV YTLPPSREEM TKNQVSLTCL   660
VKGFYPSDIA VEWESNGQPE NNYKTTPPVL DSDGSFFLYS KLTVDKSRWQ QGNVFSCSVM   720
HEALHNHYTQ KSLSLSPGK                                               739

SEQ ID NO: 127         moltype = DNA  length = 783
FEATURE                Location/Qualifiers
misc_feature           1..783
                       note = Description of Artificial Sequence: Synthetic
                       polynucleotide
source                 1..783
                       mol_type = other DNA
                       organism = synthetic construct
SEQUENCE: 127
gacatccaga tgacccagtc tccatcttcc gtgtctgcat ctgtgggaga cagagtcacc    60
atcacttgtc gggcgagtca ggatattagc acctggttag cctggtatca gcagaaacca   120
gggaaatgcc ctaagctcct gatctatgct gcatccagtt tgcaaagtgg ggtcccatca   180
agattcagcg gcagtggatc tgggacagat ttcactctca ccatcagcag cctgcagcct   240
gaagattttg caacttacta ttgtcagcag gctaacagtt tccctccgac ttttggccag   300
gggaccaagc tggagatcaa aggaggcgga ggatctggtg gtggtggatc tggcggcgga   360
ggaagtggtg gcggaggctc tgaggtgcag ctggtggagt ctgggggagg cttggtaaag   420
cctggggggt cccttagact ctcctgtgca gcctctggat tcactttcct taacgcctgg   480
atgagctggg tccgccaggc tccagggaag gggctggagt gggttggccg tattaaaagt   540
aatactgatg gtgggacaac agactacgcc gcacccgtga aaggcagatt caccatctca   600
agagacgatt caaagaacac gctgtatctg caaatgagca gcctgaaaac cgaggacaca   660
gccgtctatt actgcaccac agatggacct tactctgacg attttagaag tggttatgcc   720
gcacgctacc gttatttcgg aatggacgtc tggggctgcg ggaccacggt caccgtctcc   780
tca                                                                 783

SEQ ID NO: 128         moltype = AA  length = 210
FEATURE                Location/Qualifiers
REGION                 1..210
                       note = Synthetic polypeptide
source                 1..210
                       mol_type = protein
                       organism = synthetic construct
SEQUENCE: 128
DIQMTQSPSS LSASVGDRVT ITCRTSQSLS SYTHWYQQKP GKAPKLLIYA ASSRGSGVPS    60
RFSGSGSGTD FTLTISSLQP EDFATYYCQQ SRTFGQGTKV EIKRTVAAPS VFIFPPSDEQ   120
LKSGTASVVC LLNNFYPREA KVQWKVDNAL QSGNSQESVT EQDSKDSTYS LSSTLTLSKA   180
DYEKHKVYAC EVTHQGLSSP VTKSFNRGEC                                    210

SEQ ID NO: 129         moltype = AA  length = 739
FEATURE                Location/Qualifiers
REGION                 1..739
                       note = Synthetic polypeptide
source                 1..739
                       mol_type = protein
                       organism = synthetic construct
SEQUENCE: 129
QVQLQQSGPG LVKPSQTLSL TCAISGDSVS SYNAVWNWIR QSPSRGLEWL GRTYYRSGWY    60
NDYAESVKSR ITINPDTSKN QFSLQLNSVT PEDTAVYYCA RSGHITVFGV NVDAFDMWGQ   120
GTMVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLGGPS VFLFPPKPKD TLMISRTPEV TCVVVDVSHE DPEVKFNWYV DGVEVHNAKT   300
KPREEQYNST YRVVSVLTVL HQDWLNGKEY KCKVSNKALP APIEKTISKA KGQPREPQVY   360
TLPPSREEMT KNQVSLTCLV KGFYPSDIAV EWESNGGGGS GGGGSDIQMT QSPSSVSASV   420
GDRVTITCRA SQDISTWLAW YQQKPGKAPK LLIYAASSLQ SGVPSRFSGS GSGTDFTLTI   480
SSLQPEDFAT YFCQQANSFP PTFGCGTKLE IKGGGGSGGG GSGGGGSGGG GSEVQLVVSG   540
GGLVKPGGSL RLSCAASGLS FLNAWMSWVR QAPGKGLEWV GRIKSNTDGG TTDYAAPVKG   600
RFSISRDDSK NMLFLHMSSL RTEDTAVYYC ATDGPYSDDF RSGYAARYRY FGMDVWGQGT   660
TVTVSSGGGG SGGGGSGQPE NNYKTTPPVL DSDGSFFLYS KLTVDKSRWQ QGNVFSCSVM   720
HEALHNHYTQ KSLSLSPGK                                               739

SEQ ID NO: 130         moltype = AA  length = 210
FEATURE                Location/Qualifiers
REGION                 1..210
                       note = Synthetic polypeptide
source                 1..210
                       mol_type = protein
```

```
                        organism = synthetic construct
SEQUENCE: 130
DIQMTQSPSS LSASVGDRVT ITCRTSQSLS SYTHWYQQKP GKAPKLLIYA ASSRGSGVPS   60
RFSGSGSGTD FTLTISSLQP EDFATYYCQQ SRTFGQGTKV EIKRTVAAPS VFIFPPSDEQ  120
LKSGTASVVC LLNNFYPREA KVQWKVDNAL QSGNSQESVT EQDSKDSTYS LSSTLTLSKA  180
DYEKHKVYAC EVTHQGLSSP VTKSFNRGEC                                   210

SEQ ID NO: 131          moltype = AA  length = 739
FEATURE                 Location/Qualifiers
REGION                  1..739
                        note = Synthetic polypeptide
source                  1..739
                        mol_type = protein
                        organism = synthetic construct
SEQUENCE: 131
QVQLQQSGPG LVKPSQTLSL TCAISGDSVS SYNAVWNWIR QSPSRGLEWL GRTYYRSGWY   60
NDYAESVKSR ITINPDTSKN QFSLQLNSVT PEDTAVYYCA RSGHITVFGV NVDAFDMWGQ  120
GTMVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKRVEPKS CDKTHTCPPC  240
PAPELLGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSREEMT KNQVSLTCLV KGFYPSDIAV EWESNGGGGS GGGGSDIQMT QSPSSVSASV  420
GDRVTITCRA SQDISTWLAW YQQKPGKCPK LLIYAASSLQ SGVPSRFSGS GSGTDFTLTI  480
SSLQPEDFAT YFCQQANSFP PTFGQGTKLE IKGGGGSGGG GSGGGGSGGG GSEVQLVVSG  540
GGLVKPGGSL RLSCAASGLS FLNAWMSWVR QAPGKGLEWV GRIKSNTDGG TTDYAAPVKG  600
RFSISRDDSK NMLFLHMSSL RTEDTAVYYC ATDGPYSDDF RSGYAARYRY FGMDVWGCGT  660
TVTVSSGGGG SGGGGSGQPE NNYKTTPPVL DSDGSFFLYS KLTVDKSRWQ QGNVFSCSVM  720
HEALHNHYTQ KSLSLSPGK                                               739
```

NEUTRALIZING ANTI-INFLUENZA BINDING MOLECULES AND USES THEREOF

REFERENCE TO SEQUENCE LISTING SUBMITTED ELECTRONICALLY

The content of the electronically submitted sequence listing in ASCII text file entitled 0098-0032US4_SL created on Nov. 10, 2022 and having a size of 196,608 bytes filed with the application is incorporated herein by reference in its entirety.

FIELD OF THE INVENTION

The invention relates to bispecific antibodies that have broad neutralizing activity against influenza A and B virus and to uses of such antibodies.

BACKGROUND TO THE INVENTION

Influenza viruses cause annual influenza epidemics and occasional pandemics, which pose a significant threat to public health worldwide. Seasonal influenza infection is associated with 200,000-500,000 deaths each year, particularly in young children, immunocompromised patients and the elderly. Mortality rates typically increase further during seasons with pandemic influenza outbreaks. There remains a significant unmet medical need for potent anti-viral therapeutics for preventing and treating influenza infections, particularly in under-served populations.

There are three types of influenza viruses: types A, B and C. The majority of influenza disease is caused by influenza A and B viruses (Thompson et al. (2004) JAMA. 292:1333-1340; and Zhou et al. (2012) Clin Infect. Dis. 54:1427-1436). The overall structure of influenza viruses A, B and C is similar, and includes a viral envelope which surrounds a central core. The viral envelope includes two surface glycoproteins, Hemagglutinin (HA) and neuraminidase (NA); HA mediates binding of the virus to target cells and entry into target cells, whereas NA is involved in the release of progeny virus from infected cells.

The HA protein is responsible for the binding to the host cell receptor as well as fusion of viral and host cell membranes and is the primary target of protective humoral immune responses. The HA protein is trimeric in structure and includes three identical copies of a single polypeptide precursor, HA0, which, upon proteolytic maturation, is cleaved into a metastable intermediate containing a globular head (HA1) and stalk region (HA2) (Wilson et al. (1981) Nature. 289:366-373). The membrane distal "globular head" constitutes the majority of the HA1 structure and contains the sialic acid binding pocket for viral entry and major antigenic domains. The membrane proximal "stalk" structure, assembled from HA2 and HA1 residues, contains the fusion machinery, which undergoes a conformational change in the low pH environment of late endosomes to trigger membrane fusion and penetration into cells. The degree of sequence homology between influenza A subtypes is smaller in the HA1 (34%-59% homology between subtypes) than in the HA2 region (51%-80% homology).

Influenza A viruses can be classified into subtypes based on genetic variations in hemagglutinin (HA) and neuraminidase (NA) genes. Serologically, influenza A can be divided into 18 HA subtypes which are further divided into two distinct phylogenetic groups: group 1 (subtypes H1, H2, H5, H6, H8, H9, H11, H12, H13, H16, H17 and H18) and group 2 (subtypes H3, H4, H7, H10, H14, and H15). Currently, in seasonal epidemics, influenza A H1 and H3 HA subtypes are primarily associated with human disease, whereas viruses encoding H5, H7, H9 and H10 caused sporadic human outbreaks due to direct transmission from animals. In contrast to influenza A viruses, influenza B viruses are restricted to human infection and influenza B viruses are not divided into subtypes based on the two surface glycoproteins. In fact, until the 1970s, influenza B viruses were classified as one homogenous group. However, through the 1970s, the influenza B viruses started to diverge into two antigenically distinguishable lineages which were named the Victoria and Yamagata lineages after their first representatives, B/Victoria/2/87 and B/Yamagata/16/88, respectively. (Biere et al. (2010) J Clin Microbiol. 48(4):1425-7; doi: 10.1128/JCM.02116-09. Epub 2010 Jan. 27). Both Yamagata and Victoria lineages contribute to annual epidemics. Although the morbidity caused by influenza B viruses is lower than that associated with influenza A H3N2, it is higher than that associated with influenza A H1N1 (Zhou et al. (2012) Clin Infect. Dis. 54:1427-1436).

Neutralizing antibodies elicited by influenza virus infection are normally targeted to the variable HA1 globular head to prevent viral receptor binding and are usually strain-specific. Broadly cross-reactive antibodies that neutralize one or more subtype or lineage are rare. Recently, a few antibodies have been discovered that can neutralize multiple subtypes of influenza A viruses in both group 1 and 2 (Corti et al. (2011) Science 333(6044):850-856, Li et al. (2012) PNAS 109(46):18897-18902, Dreyfus et al. (2012) Science 337(6100):1343-1348, and Nakamura et al. (2013) Cell Host and Microbe 14:93-103), or influenza B viruses of both lineages (Dreyfus et al. (2012) Science 337(6100):1343-1348 and Yasugi et al. (2013) PLoS Path 9(2): e1003150. doi: 10.1371/journal.ppat.1003150), although most have limitations in breadth of coverage, resistance profile, or potency. Only one antibody has been described to bind to both influenza A and B HA proteins, although this antibody does not functionally neutralize influenza B viruses or attenuate disease when given therapeutically (Dreyfus et al. (2012) Science 337(6100):1343-1348). To date, there are no available antibodies that broadly neutralize or inhibit a broad spectrum of influenza A and B virus infections or attenuate diseases caused by influenza A and B virus. Therefore, there is a need to identify new antibodies that protect against multiple influenza viruses.

SUMMARY OF THE INVENTION

In one embodiment, an isolated binding molecule which specifically binds to influenza A virus and influenza B virus is provided. In one embodiment, the isolated binding molecule includes a first binding domain that is capable of binding to influenza A virus hemagglutinin (HA) and neutralizing at least one group 1 subtype and at least 1 group 2 subtype of influenza A virus; and a second binding domain that is capable of binding to influenza B virus hemagglutinin (HA) and neutralizing influenza B virus in at least two phylogenetically distinct lineages. In one embodiment, the first binding domain is capable of neutralizing one or more influenza A virus group 1 subtypes selected from: H1, H2, H5, H6, H8, H9, H11, H12, H13, H16, H17, H18 and variants thereof; and one or more influenza A virus group 2 subtypes selected from: H3, H4, H7, H10, H14 and H15 and variants thereof. In one embodiment, the second binding domain is capable of neutralizing influenza B virus in both Yamagata and Victoria lineages.

In one embodiment, the first binding domain of the binding molecule includes an anti-influenza A virus antibody or antigen-binding fragment thereof. In one embodiment, the second binding domain of the binding molecule includes an anti-influenza B virus antibody or antigen-binding fragment thereof. In one embodiment, the binding molecule includes at least one VH of an antibody heavy chain and at least one VL of an antibody light chain. In a more particular embodiment, the first binding domain includes at least one VH of an antibody heavy chain and at least one VL of an antibody light chain. In one embodiment, the second binding domain includes at least one VH of an antibody heavy chain and at least one VL of an antibody light chain.

In one embodiment, the first binding domain of the binding molecule includes a set of six CDRs: HCDR1, HCDR2, HCDR3, LCDR1, LCDR2, LCDR3 in which the set of six CDRs has an amino acid sequence selected from:
- (a) an amino acid sequence that is at least 75% identical to: HCDR1 of SEQ ID NO.: 8, HCDR2 of SEQ ID NO.: 9, HCDR3 of SEQ ID NO.: 10, LCDR1 of SEQ ID NO.: 3, LCDR2 of SEQ ID NO.: 4 and LCDR3 of SEQ ID NO.: 5;
- (b) an amino acid sequence of: HCDR1 of SEQ ID NO.: 8, HCDR2 of SEQ ID NO.: 9, HCDR3 of SEQ ID NO.: 10, LCDR1 of SEQ ID NO.: 3, LCDR2 of SEQ ID NO.: 4 and LCDR3 of SEQ ID NO.: 5;
- (c) an amino acid sequence that is at least 75% identical to: HCDR1 of SEQ ID NO.: 18, HCDR2 of SEQ ID NO.: 19, HCDR3 of SEQ ID NO.: 20, LCDR1 of SEQ ID NO.: 13, LCDR2 of SEQ ID NO.: 14, LCDR3 of SEQ ID NO.: 15; and
- (d) an amino acid sequence of: HCDR1 of SEQ ID NO.: 18, HCDR2 of SEQ ID NO.: 19, HCDR3 of SEQ ID NO.: 20, LCDR1 of SEQ ID NO.: 13, LCDR2 of SEQ ID NO.: 14, LCDR3 of SEQ ID NO.: 15.

In one embodiment, the first binding domain of the binding molecule includes a VH having an amino acid sequence that is at least 75% identical to an amino acid sequence selected from SEQ ID NO.: 7; and SEQ ID NO.: 17. In one embodiment, the first binding domain of the binding molecule includes a VL having an amino acid sequence that is at least 75% identical to an amino acid sequence selected from SEQ ID NO.: 2; and a VL of SEQ ID NO.: 12. In a more particular embodiment, the first binding domain of the binding molecule includes a VH and a VL that is at least 75% identical to an amino acid sequence of a VH and a VL, respectively, selected from a VH of SEQ ID NO.: 7 and a VL of SEQ ID NO.: 2; and a VH of SEQ ID NO.: 17 and a VL of SEQ ID NO.: 12. In one embodiment, the first binding domain includes a VH and a VL selected from: a VH of SEQ ID NO.: 7 and a VL of SEQ ID NO.: 2; and a VH of SEQ ID NO.: 17 and a VL of SEQ ID NO.: 12.

In one embodiment, the second binding domain includes a set of six CDRs: HCDR1, HCDR2, HCDR3, LCDR1, LCDR2, LCDR3 in which the set of six CDRs has an amino acid sequence selected from:
- (a) an amino acid sequence that is at least 75% identical to: HCDR1 of SEQ ID NO.: 28, HCDR2 of SEQ ID NO.: 29, HCDR3 of SEQ ID NO.: 30, LCDR1 of SEQ ID NO.: 23, LCDR2 of SEQ ID NO.: 24 and LCDR3 of SEQ ID NO.: 25;
- (b) an amino acid sequence of: HCDR1 of SEQ ID NO.: 28, HCDR2 of SEQ ID NO.: 29, HCDR3 of SEQ ID NO.: 30, LCDR1 of SEQ ID NO.: 23, LCDR2 of SEQ ID NO.: 24 and LCDR3 of SEQ ID NO.: 25;
- (c) an amino acid sequence that is at least 75% identical to an amino acid sequence of: HCDR1 of SEQ ID NO.: 44, HCDR2 of SEQ ID NO.: 45, HCDR3 of SEQ ID NO.: 46, LCDR1 of SEQ ID NO.: 39, LCDR2 of SEQ ID NO.: 40 and LCDR3 of SEQ ID NO.: 41;
- (d) an amino acid sequence of: HCDR1 of SEQ ID NO.: 44, HCDR2 of SEQ ID NO.: 45, HCDR3 of SEQ ID NO.: 46, LCDR1 of SEQ ID NO.: 39, LCDR2 of SEQ ID NO.: 40 and LCDR3 of SEQ ID NO.: 41;
- (e) an amino acid sequence that is at least 75% identical to: HCDR1 of SEQ ID NO.: 60, HCDR2 of SEQ ID NO.: 61, HCDR3 of SEQ ID NO.: 62, LCDR1 of SEQ ID NO.: 55, LCDR2 of SEQ ID NO.: 56, LCDR3 of SEQ ID NO.: 57; and
- (f) an amino acid sequence of: HCDR1 of SEQ ID NO.: 60, HCDR2 of SEQ ID NO.: 61, HCDR3 of SEQ ID NO.: 62, LCDR1 of SEQ ID NO.: 55, LCDR2 of SEQ ID NO.: 56, LCDR3 of SEQ ID NO.: 57.

In one embodiment, the second binding domain of the binding molecule includes a VH having an amino acid sequence that is at least 75% identical to an amino acid sequence of a VH selected from:
- (a) a VH of SEQ ID NO.: 27;
- (b) a VH of SEQ ID NO.: 33;
- (c) a VH of SEQ ID NO.: 36;
- (d) a VH of SEQ ID NO.: 43;
- (e) a VH of SEQ ID NO.: 49;
- (f) a VH of SEQ ID NO.: 52;
- (g) a VH of SEQ ID NO.: 59; and
- (h) a VH of SEQ ID NO.: 65.

In one embodiment, the second binding domain of the binding molecule includes a VL having an amino acid sequence that is at least 75% identical to an amino acid sequence of a VL selected from:
- (a) a VL of SEQ ID NO.: 22;
- (b) a VL of SEQ ID NO.: 32;
- (c) a VL of SEQ ID NO.: 35;
- (d) a VL of SEQ ID NO.: 38;
- (e) a VL of SEQ ID NO.: 48;
- (f) a VL of SEQ ID NO.: 51;
- (g) a VL of SEQ ID NO.: 54; and
- (h) a VL of SEQ ID NO.: 64.

In one embodiment, the second binding domain of the binding molecule includes a VH and a VL that is at least 75% identical to the amino acid sequence of a VH and a VL, respectively, selected from:
- (a) a VH of SEQ ID NO.: 27 and a VL of SEQ ID NO.: 22;
- (b) a VH of SEQ ID NO.: 33 and a VL of SEQ ID NO.: 32;
- (c) a VH of SEQ ID NO.: 36 and a VL of SEQ ID NO.: 35;
- (d) a VH of SEQ ID NO.: 43 and a VL of SEQ ID NO.: 38;
- (e) a VH of SEQ ID NO.: 49 and a VL of SEQ ID NO.: 48;
- (f) a VH of SEQ ID NO.: 52 and a VL of SEQ ID NO.: 51;
- (g) a VH of SEQ ID NO.: 59 and a VL of SEQ ID NO.: 54; and
- (h) a VH of SEQ ID NO.: 65 and a VL of SEQ ID NO.: 64.

In one embodiment, the second binding domain of the binding molecule includes a VH and a VL selected from:
- (a) a VH of SEQ ID NO.: 27 and a VL of SEQ ID NO.: 22;

(b) a VH of SEQ ID NO.: 33 and a VL of SEQ ID NO.: 32;

(c) a VH of SEQ ID NO.: 36 and a VL of SEQ ID NO.: 35;

(d) a VH of SEQ ID NO.: 43 and a VL of SEQ ID NO.: 38;

(e) a VH of SEQ ID NO.: 49 and a VL of SEQ ID NO.: 48;

(f) a VH of SEQ ID NO.: 52 and a VL of SEQ ID NO.: 51;

(g) a VH of SEQ ID NO.: 59 and a VL of SEQ ID NO.: 54; and (h) a VH of SEQ ID NO.: 65 and a VL of SEQ ID NO.: 64.

In one embodiment, the binding molecule includes at least two antibody heavy chains and at least two antibody light chains. In one embodiment, the binding molecule includes a bispecific antibody. In one embodiment, one or more binding domains of the binding molecule include a variable fragment (Fv) domain. In one embodiment, one or more binding domains of the binding molecule include an scFv molecule. In one embodiment, one or more binding domains of the binding molecule include an Fv domain and one or more binding domains include an scFv molecule. In a more particular embodiment, the first binding domain of the binding molecule includes an anti-influenza A virus Fv domain. In one embodiment, the binding molecule includes an Fv domain including an antibody heavy chain variable domain and an antibody light chain variable domain, and specifically binds anti-influenza A virus. In one embodiment, the second binding domain of the binding molecule includes an anti-influenza B virus scFv molecule.

In one embodiment, the first binding domain includes an anti-influenza A virus Fv domain and the second binding domain includes an anti-influenza B virus scFv molecule. In one embodiment, the the Fv domain of the first binding domain has a heavy chain (HC) with a polypeptide chain having an amino terminus and a carboxy terminus and a light chain (LC) with a polypeptide chain having an amino terminus and a carboxy terminus, and (a) the second binding domain is covalently linked to the carboxy-terminus of the HC of the first binding domain;

(b) the second binding domain is covalently linked to the amino-terminus of the HC of the first binding domain;

(c) the second binding domain is covalently linked to the amino-terminus of the LC of the first binding domain; or (d) the second binding domain is covalently intercalated in the polypeptide chain of the HC of the first binding domain.

In one embodiment, the binding molecule includes an antibody or fragment thereof having one or more N-terminal domains wherein one or more scFv molecules are covalently attached to one or more N-terminal domains of the antibody or fragment thereof. In one embodiment, the N-terminal domain of the antibody or fragment thereof includes one or more Fv domains and one or more scFv molecules are covalently attached to one or more Fv domains of the antibody or fragment thereof. In one embodiment, the N-terminal domain includes an Fv domain including a variable heavy chain domain (VH) and a variable light chain domain (VL). In one embodiment, one or more scFv molecules are covalently attached to one or more light chain variable domains (VL) of the antibody or fragment thereof. In one embodiment, the binding molecule includes an antibody or fragment thereof including an antibody light chain having a formula scFv-L1-VL-CL, wherein scFv is an scFv molecule, L1 is a linker, VL is a light chain variable domain, CL is a light chain constant domain and VL is a light chain variable domain. In one embodiment, one or more scFv molecules are covalently attached to one or more heavy chain variable domains (VH) of the antibody or fragment thereof. In one embodiment, the heavy chain includes a formula scFv-L1-VH-CH1-CH2-CH3, wherein scFv is an scFv molecule, L1 is a linker, VH is a heavy chain variable domain, CH1 is a heavy chain constant domain domain-1, CH2 is a heavy chain constant domain domain-2, and CH3 is a heavy chain constant domain domain-3.

In one embodiment, the binding molecule includes a variable heavy chain domain (VH) with an amino acid sequence that is at least 75% identical to an amino acid VH domain sequence selected from SEQ ID NO: 7 and SEQ ID NO: 17. In one embodiment, the binding molecule includes a variable light chain domain (VL) with an amino acid sequence that is at least 75% identical to an amino acid VL domain sequence selected from SEQ ID NO: 2 and SEQ ID NO: 12.

In one embodiment, the binding molecule includes an antibody or fragment thereof having a C-terminal domain wherein one or more scFv molecules are covalently attached to the C-terminal domain of the antibody or fragment thereof. In one embodiment, the binding molecule includes a first and a second heavy chain with first and second C-terminal domains, respectively, wherein one or more scFv molecules are covalently attached to the C-terminal domain of the first heavy chain, the second heavy chain, or combinations thereof. In one embodiment, the binding molecule includes an antibody or fragment thereof including one or more heavy chain constant domains wherein one or more scFv molecules are inserted into the heavy chain between one or more heavy chain constant domains of one or more heavy chains. In one embodiment, one or more heavy chains include a formula VH-CH1-CH2-CH3, wherein VH is a heavy chain variable domain, CH1 is a heavy chain constant domain domain-1, CH2 is a heavy chain constant domain domain-2, and CH3 is a heavy chain constant domain domain-3. In one embodiment, one or more heavy chains include a formula VH-CH1-L1-scFv-L2-CH2-CH3, wherein L1 and L2 independently are a linker and scFv is an scFv molecule. In one embodiment, one or more heavy chains include a formula VH-CH1-CH2-L1-scFv-L2-CH3, wherein L1 and L2 independently are a linker and scFv is an scFv molecule. In one embodiment, L1 and L2 independently include (a) [GGGGS]n, wherein n is 0, 1, 2, 3, 4, or 5, (SEQ ID NO:93) (b) [GGGG]n, wherein n is 0, 1, 2, 3, 4, or 5 (SEQ ID NO:106), or a combination of (a) and (b).

In one embodiment, the scFv includes a formula: VH-LS-VL, and wherein VH is a heavy chain variable domain, LS is a linker, and VL is a light chain variable domain. In one embodiment, LS includes (a) [GGGGS]n, wherein n is 0, 1, 2, 3, 4, or 5 (SEQ ID NO:93), (b) [GGGG]n, wherein n is 0, 1, 2, 3, 4, or 5 (SEQ ID NO:106), or a combination of (a) and (b).

In one embodiment, the heavy chain and the light chain of the first binding domain are linked by one or more disulfide bonds. In a more particular embodiment, the scFv of the second binding domain includes a heavy chain variable domain (VH) and a light chain variable domain (VL) and the VH of the scFv includes a cysteine residue at a position selected from position 43, 44, 100, 101, 105, and combinations thereof and the VL of the scFv includes a cysteine residue at a position selected from position 43, 44, 46, 49, 50, 100, and combinations thereof. In one embodiment, the VL and VH of the scFv are linked by a disulfide bond selected from: VL100-VH44, VL43-VH105, VL46-VH101, VL49-VH100, VL50-VH100, and combinations thereof. In one embodiment, the VH and VL of the scFv are linked by a disulfide bond selected from: VH44-VL100, VH100-VL49, VH100-VL50, VH101-VL46, VH105-VL43, and combinations thereof.

In one embodiment, VH includes a set of three CDRs: HCDR1, HCDR2, HCDR3, in which the set of three CDRs is selected from:
(a) an amino acid sequence that is at least 75% identical to: HCDR1 of SEQ ID NO.: 28, HCDR2 of SEQ ID NO.: 29, HCDR3 of SEQ ID NO.: 30;
(b) an amino acid sequence of: HCDR1 of SEQ ID NO.: 28, HCDR2 of SEQ ID NO.: 29, HCDR3 of SEQ ID NO.: 30;
(c) an amino acid sequence that is at least 75% identical to: HCDR1 of SEQ ID NO.: 44, HCDR2 of SEQ ID NO.: 45, HCDR3 of SEQ ID NO.: 46;
(d) an amino acid sequence of: HCDR1 of SEQ ID NO.: 44, HCDR2 of SEQ ID NO.: 45, HCDR3 of SEQ ID NO.: 46;
(e) an amino acid sequence that is at least 75% identical to: HCDR1 of SEQ ID NO.: 60, HCDR2 of SEQ ID NO.: 61, HCDR3 of SEQ ID NO.: 62; and
(f) an amino acid sequence of: HCDR1 of SEQ ID NO.: 60, HCDR2 of SEQ ID NO.: 61, HCDR3 of SEQ ID NO.: 62.

In one embodiment, VL includes a set of three CDRs: LCDR1, LCDR2, LCDR3 in which the set of three CDRs is selected from:
(a) an amino acid sequence that is at least 75% identical to: LCDR1 of SEQ ID NO.: 23, LCDR2 of SEQ ID NO.: 24 and LCDR3 of SEQ ID NO.: 25;
(b) an amino acid sequence of: LCDR1 of SEQ ID NO.: 23, LCDR2 of SEQ ID NO.: 24 and LCDR3 of SEQ ID NO.: 25;
(c) an amino acid sequence that is at least 75% identical to: LCDR1 of SEQ ID NO.: 39, LCDR2 of SEQ ID NO.: 40 and LCDR3 of SEQ ID NO.: 41;
(d) an amino acid sequence of: LCDR1 of SEQ ID NO.: 39, LCDR2 of SEQ ID NO.: 40 and LCDR3 of SEQ ID NO.: 41;
(e) an amino acid sequence that is at least 75% identical to: LCDR1 of SEQ ID NO.: 55, LCDR2 of SEQ ID NO.: 56, LCDR3 of SEQ ID NO.: 57; and
(f) an amino acid sequence of: LCDR1 of SEQ ID NO.: 55, LCDR2 of SEQ ID NO.: 56, LCDR3 of SEQ ID NO.: 57.

In one embodiment, the scFv has an amino acid sequence that is at least 75% identical to an amino acid sequence selected from: SEQ ID NO:31, SEQ ID NO:34, SEQ ID NO:47, SEQ ID NO:50, SEQ ID NO:63.

In one embodiment, the binding molecule is a bispecific antibody which specifically binds to influenza A virus and influenza B virus, including a light chain with an amino acid sequence that is at least 75% identical to an amino acid sequence of SEQ ID NO:66 or SEQ ID NO:68. In one embodiment, the bispecific antibody includes a light chain with an amino acid sequence of SEQ ID NO:66 or SEQ ID NO:68. In one embodiment, the binding molecule is a bispecific antibody which specifically binds to influenza A virus and influenza B virus, and includes a heavy chain with an amino acid sequence that is at least 75% identical to an amino acid sequence of SEQ ID NO:67 or SEQ ID NO:69. In one embodiment, the heavy chain has an amino acid sequence of SEQ ID NO:67 or SEQ ID NO:69. In one embodiment, the binding molecule is a bispecific antibody which specifically binds to influenza A virus and influenza B virus, and includes a light chain with an amino acid sequence that is at least 75% identical to an amino acid sequence of SEQ ID NO:66 or SEQ ID NO:68 and a heavy chain with an amino acid sequence that is at least 75% identical to an amino acid sequence of SEQ ID NO:67 or SEQ ID NO:69.

In one embodiment, the bispecific antibody includes:
(a) a light chain with an amino acid sequence including SEQ ID NO:66 and a heavy chain with an amino acid sequence including SEQ ID NO:67; or
(b) a light chain with an amino acid sequence including SEQ ID NO:68 and a heavy chain with an amino acid sequence including SEQ ID NO:69

Also provided is a cell that includes or produces a binding molecule or bispecific antibody or fragment described herein.

Also provided is an isolated polynucleotide which encodes a binding molecule or bispecific antibody described herein. In one embodiment, a vector is provided that includes a polynucleotide which encodes a binding molecule or bispecific antibody described herein.

In another embodiment, a host cell is provided that includes a polynucleotide which encodes a binding molecule or bispecific antibody described herein.

Also provided herein is a composition that includes a binding molecule or bispecific antibody or fragment thereof as described herein, and a pharmaceutically acceptable carrier. Also provided is a kit that includes such a composition. In another embodiment, a method of preventing or treating an influenza A virus or influenza B virus infection in a subject is provided in which the method includes administering to a subject an effective amount of such a composition.

Also provided herein is a method for manufacturing a binding molecule or bispecific antibody or fragment thereof as described herein. In one embodiment, the method includes culturing a host cell under conditions suitable for expression of the binding molecule or bispecific antibody or fragment thereof. In one embodiment, the method further includes isolating the binding molecule from the host cell culture.

Also provided are methods of using a binding molecule or bispecific antibody or fragment thereof described herein. In one embodiment, the binding molecule or bispecific antibody or fragment thereof is used in the prophylaxis or treatment of influenza A infection, influenza B infection, or a combination thereof in a subject.

In another embodiment, a binding molecule or bispecific antibody or fragment thereof described herein is suitable for use in the manufacture of a medicament for the prophylaxis or treatment of influenza A infection, influenza B infection, or a combination thereof in a subject. In one embodiment, a binding molecule or bispecific antibody or fragment thereof described herein is used in the manufacture of a medicament for the prophylaxis or treatment of influenza A and influenza B infection in a subject. In one embodiment, a method for prophylaxis or treatment of influenza A infection, influenza B infection, or a combination thereof in a subject is provided, which includes administering an effective amount of a binding molecule or bispecific antibody or fragment thereof described herein to the subject.

In one embodiment, a method for prophylaxis or treatment of influenza A and influenza B infection in a subject is provided, which includes administering an effective amount of a binding molecule or bispecific antibody or fragment thereof described herein to the subject.

In one embodiment, a binding molecule or bispecific antibody or fragment thereof described herein are suitable for in vitro diagnosis of influenza A infection, influenza B infection, or a combination thereof in a subject.

BRIEF DESCRIPTION OF THE FIGURES

FIGS. 6A-F show the survival rate (A and B), lung viral titers at day 5 post-infection (C and D), and lung function measured by pulse oximetry on Day 6 post-infection (E and F) in each group of a study in which mice were infected with a lethal dose of A/Wilson Smith N/33 H1N1 influenza virus (A, C, E) or B/Florida/4/2006 yamagata lineage virus (B, D, F). Treatment of 25 mg/kg twice daily (BID) oseltamivir for 5 days, 10 mg/kg of GL20/39 BiS4 43/105 (Flu BiS), or 10 mg/kg of non-relevant control antibody (Ctl. mAb) was initiated at different time points (Day 1, Day 2, Day 3, Day 4 post infection).

DETAILED DESCRIPTION

Introduction

Figure 1:
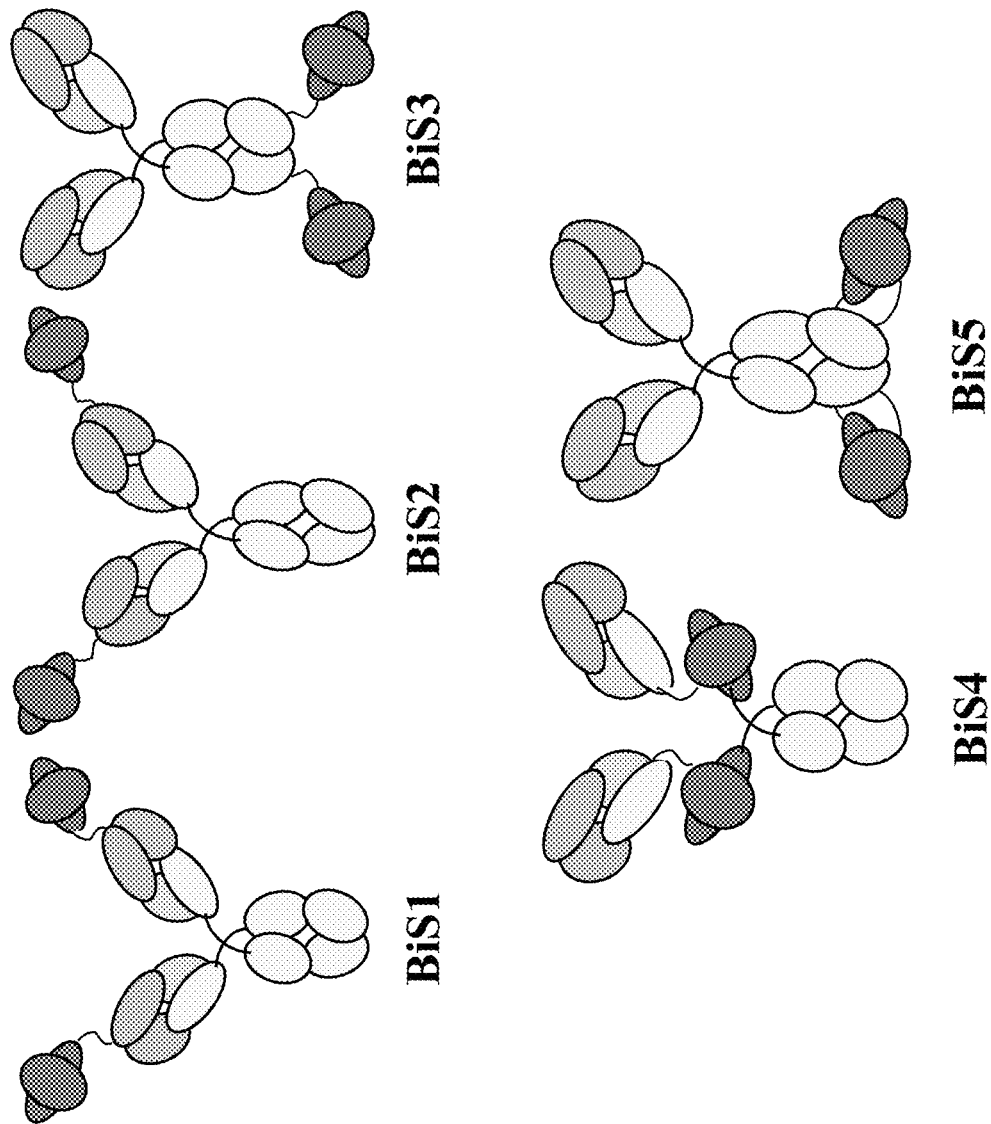
FIG. 1 depicts the general structural format of five different bispecific antibody (BiS) backbones, BiS1, BiS2, BiS3, BiS4, and BiS5. The scFv is depicted in dark grey and the IgG Fv is depicted in light grey.
Figure 2B:
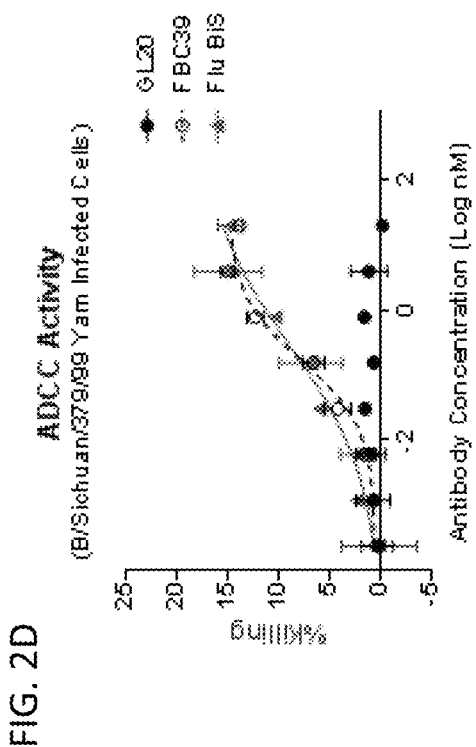
FIGS. 2A-D show the ADCC activity of primary human natural killer (NK) cells incubated in the presence of increasing amounts of GL20/39 BiS4 43/105 (Flu BiS), GL20, or FBC39. Infected cell killing of (A) A/California/07/2009 H1N1 (B) A/Hong Kong/8/68 H3N2 (C) B/Malaysia/2506/2004 victoria lineage and (D) B/Sichuan/379/99 yamagata lineage infected A549 cells were measured by lactate dehydrogenase (LDH) release.
Figure 2D:
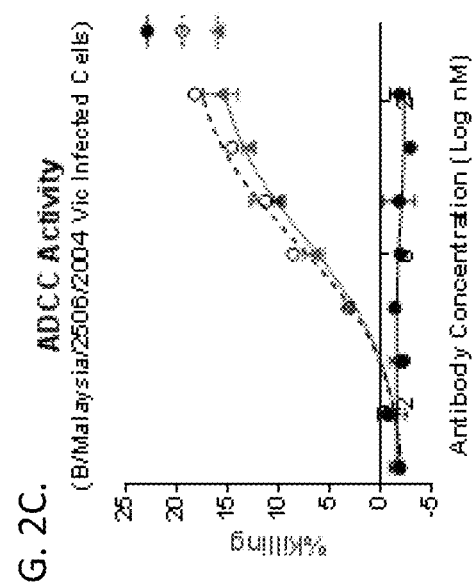
Figure 2A:
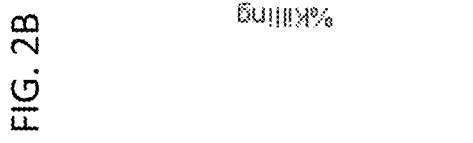
Figure 2C:
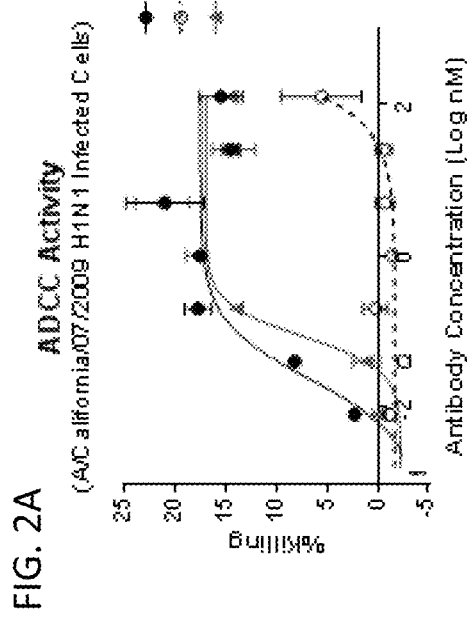
Figure 3A:
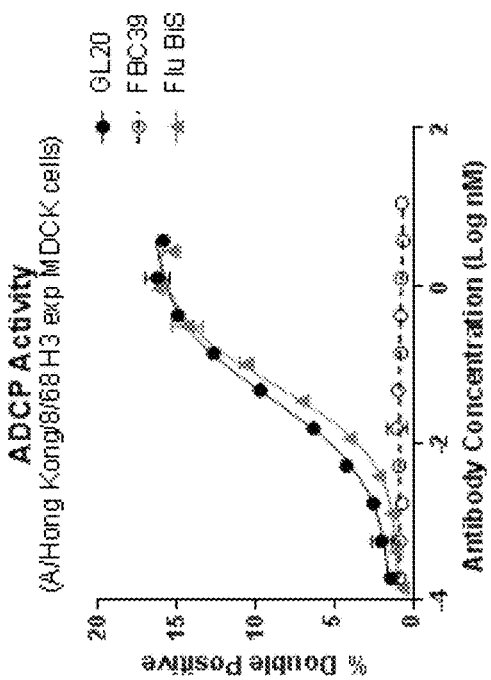
FIGS. 3A-C show the ADCP and CDC activity of GL20/39 BiS4 43/105 (Flu BiS), GL20, or FBC39 anti-HA antibodies. ADCP activity is represented by the percentage of human macrophages that phagocytosed MDCK target cells expressing the HA protein of (A) A/South Dakota/6/2007 H1N1 and (B) A/Hong Kong/8/68 H3N2. (C) CDC mediated cell killing was measured by the LDH release from A/Puerto Rico/8/34 infected MDCK cells in the presence of rabbit baby complement.
Figure 3B:
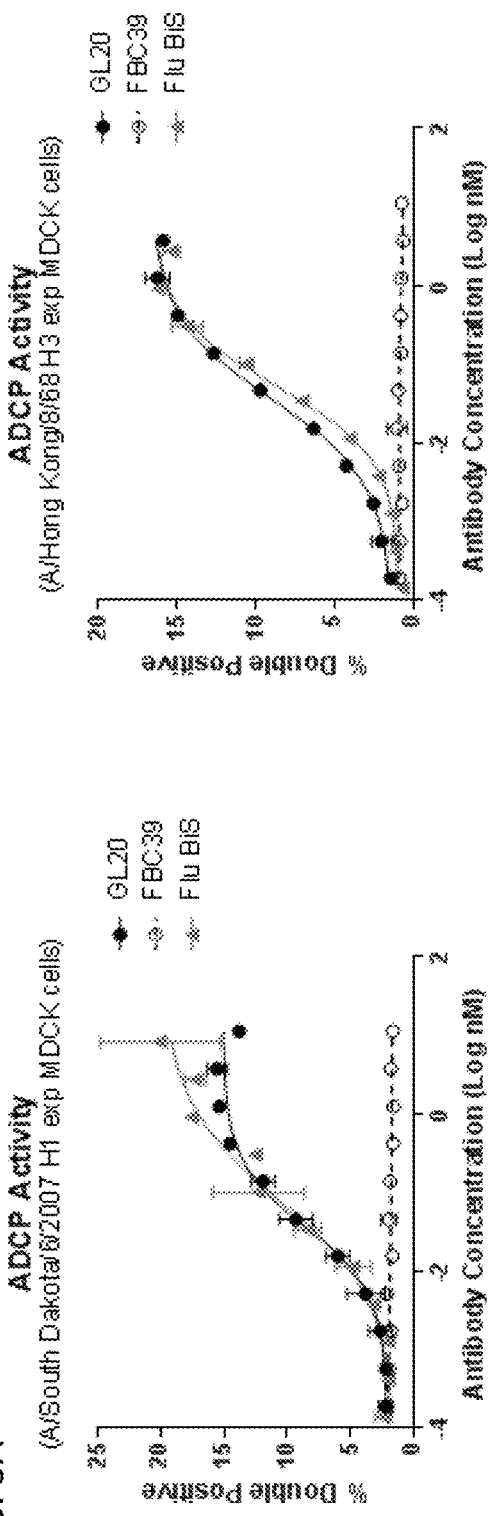
Figure 3C:
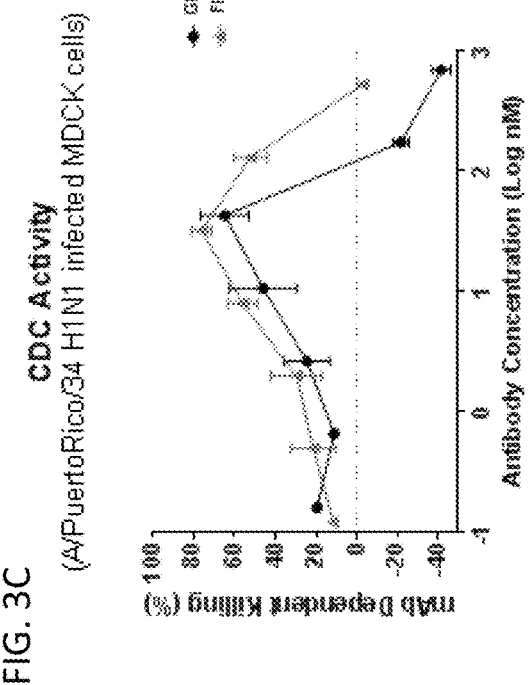
Figure 4B:
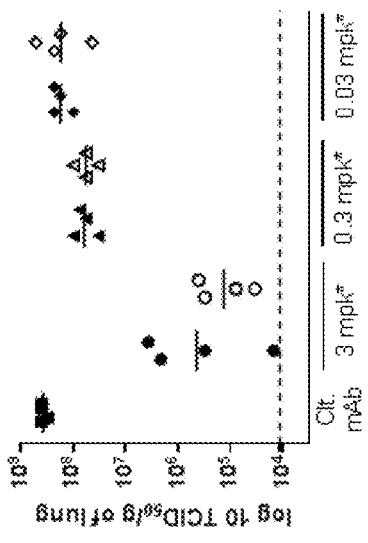
FIGS. 4A-D show the survival rate (A and C) and lung viral titers at day 5 post-infection (B and D) in each group of a study when different concentrations of GL20/39 BiS4 43/105 (Flu BiS), GL20, and a non-relevant control antibody (Ctl. mAb) were administered to mice 4 hours before infection with a lethal dose of A/Wilson Smith N/33 H1N1 (A and B), rA/HK/68 H3N2 (C and D) influenza viruses.
Figure 4A:
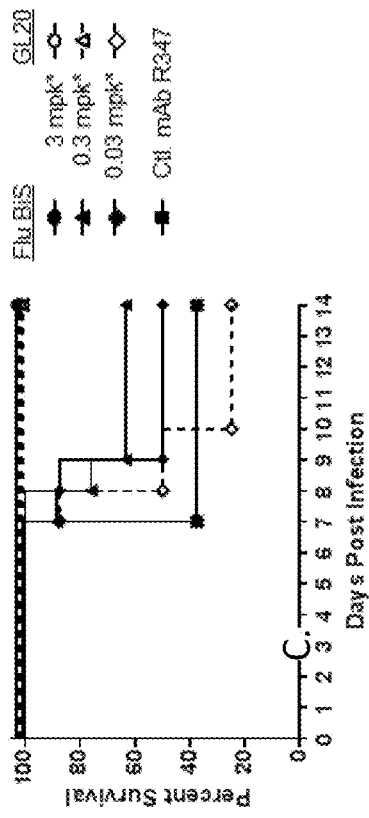
Figure 4D:
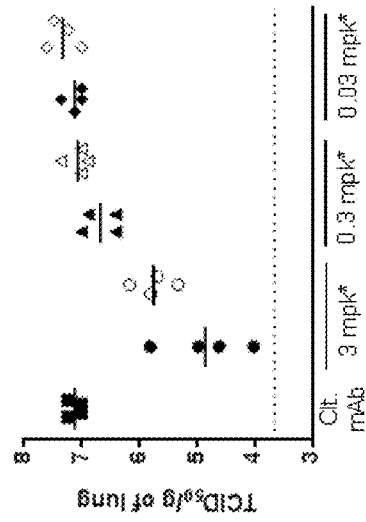
Figure 4C:
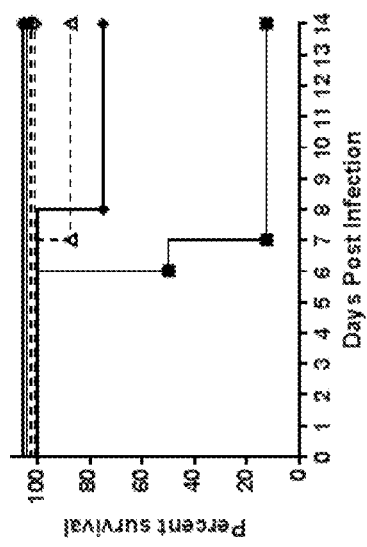

Described herein are binding molecules, for example, antibodies, including, but not limited to, bispecific antibodies, human antibodies, antigen binding fragments, derivatives or conjugates thereof that include at least two anti-influenza binding domains. In one embodiment, the binding molecule includes a first binding domain that specifically binds influenza A virus and a second binding domain that specifically binds influenza B virus. Antibodies that specifically bind influenza A virus are described in U.S. Provisional Application Nos. 61/885,808, filed Oct. 2, 2013 and 62/002,414, filed May 23, 2014, and antibodies that specifically bind influenza B virus are described in U.S. Provisional Application No. 62/024,804, filed Jul. 15, 2014, wherein the disclosures of each is hereby incorporated by reference herein in its entirety.

In one embodiment, the first binding domain specifically binds influenza A virus hemagglutinin (HA) stalk. In a more particular embodiment, the first binding domain specifically binds influenza A virus hemagglutinin (HA) stalk and neutralizes at least one group 1 subtype and at least one group 2 subtype of influenza A virus.

In one embodiment, the second binding domain specifically binds influenza B virus hemagglutinin (HA). In a more particular embodiment, the second binding domain specifically binds influenza B virus hemagglutinin (HA) and neutralizes influenza B virus in two phylogenetically distinct lineages. In one embodiment, the second binding domain specifically binds influenza B virus hemagglutinin (HA) and neutralizes influenza B virus in both Yamagata and Victoria lineages. In another embodiment, the second binding domain specifically binds influenza B virus hemagglutinin (HA) and influenza A virus hemagglutinin (HA) and neutralizes at least one Yamagata lineage influenza B virus; at least one Victoria lineage influenza B virus; at least one influenza A virus subtype, and combinations thereof.

In one embodiment, the binding molecule is a bispecific antibody with enhanced neutralization activity against one or more influenza A virus and/or influenza B virus strains as compared to either parental antibody. In one embodiment, the binding molecule is a bispecific antibody with enhanced neutralization activity against one or more influenza A group 1 or group 2 strains. In a more particular embodiment, the binding molecule is a bispecific antibody with enhanced neutralization activity against an influenza A virus group 1 strain selected from subtypes H1, H2, H5, H6, H8, H9, H11, H12, H13, H16, H17 and H18. In a more particular embodiment, the binding molecule is a bispecific antibody with enhanced neutralization activity against an influenza A virus group 2 strain selected from subtypes H3, H4, H7, H10, H14, and H15. In one embodiment, the binding molecule is a bispecific antibody with enhanced neutralization activity against H9 subtype of influenza A virus.

As used herein, the term "neutralize" refers to the ability of a binding molecule, such as an antibody, or antigen binding fragment thereof, to bind to an infectious agent, for example, influenza A and/or B virus, and reduce the biological activity of the infectious agent, for example, virulence. In one embodiment, the binding molecule immunospecifically binds at least one specified epitope or antigenic determinant of the influenza A virus; influenza B virus, or combinations thereof. A binding molecule can neutralize the activity of an infectious agent, such as influenza A and/or influenza B virus at various points during the lifecycle of the virus. For example, an antibody may interfere with viral attachment to a target cell by interfering with the interaction of the virus and one or more cell surface receptors. Alternately, an antibody may interfere with one or more post-attachment interactions of the virus with its receptors, for example, by interfering with viral internalization by receptor-mediated endocytosis.

Terminology

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise.

The term "about" refers to variation in the numerical quantity that can occur, for example, through typical measuring and handling procedures used for making compounds, compositions, concentrates or formulations; through inadvertent error in these procedures; through differences in the manufacture, source, or purity of starting materials or ingredients used to carry out the methods, and similar considerations. The term "about" also encompasses amounts that differ due to aging of compounds, compositions, concentrates or formulations with a particular initial concentration or mixture, and amounts that differ due to mixing or processing compounds, compositions, concentrates or formulations with a particular initial concentration or mixture. Where modified by the term "about" the claims appended hereto include equivalents to these quantities.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show (2002) 2nd ed. CRC Press; The Dictionary of Cell and Molecular Biology, 3rd ed. (1999) Academic Press; and the Oxford Dictionary Of Biochemistry And Molecular Biology, Revised (2000) Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.
Definitions The term "nucleic acid" or "polynucleotide" encompasses any physical string of monomer units that correspond to a string of nucleotides, including, but not limited to, a polymer of nucleotides, including DNA and RNA polymers, and modified oligonucleotides, for example, oligonucleotides having bases that are not typical to biological RNA or DNA in solution, such as 2'-O-methylated oligonucleotides. A polynucleotide can include conventional phosphodiester bonds or non-conventional bonds, for example, an amide bond, such as found in peptide nucleic acids (PNA). A nucleic acid can be single-stranded or double-stranded. Unless otherwise indicated, a nucleic acid sequence encompasses complementary sequences, in addition to the sequence explicitly indicated.

The term "gene" is used broadly to refer to a nucleic acid associated with a biological function. Thus, genes include coding sequences and/or regulatory sequences required for their expression. The term "gene" applies to a specific genomic sequence, as well as to a cDNA or an mRNA encoded by that genomic sequence. Genes also include non-expressed nucleic acid sequences that, for example, form recognition sequences for other proteins. Non-expressed regulatory sequences include "promoters" and "enhancers," to which regulatory proteins such as transcription factors bind, resulting in transcription of adjacent or nearby sequences. For example, a polynucleotide which encodes a polypeptide can include a promoter and/or other transcription or translation control elements operably associated with one or more coding regions. "Operably associated" refers to a coding region for a gene product that is associated with one or more regulatory sequences in such a way as to place expression of the gene product under the influence or control of the regulatory sequence(s). "Expression of a gene" or "expression of a nucleic acid" refers to transcription of DNA into RNA, translation of RNA into a polypeptide, or both transcription and translation, as indicated by the context.

As used herein, the term "coding region" refers to a portion of nucleic acid which includes codons that can be translated amino acids. Although a "stop codon" (TAG, TGA, or TAA) is not translated into an amino acid, it is generally considered to be part of a coding region. However, flanking sequences, for example promoters, ribosome binding sites, transcriptional terminators, and introns, are not considered part of a coding region. A vector can contain a single coding region, or can include two or more coding regions. Additionally, a vector, polynucleotide, or nucleic acid can encode heterologous coding regions, either fused or unfused to a nucleic acid encoding a gene product of interest, for example, an antibody, or antigen-binding fragment, variant, or derivative thereof. Heterologous coding regions include, but are not limited to, specialized elements or motifs, such as a secretory signal peptide or a heterologous functional domain.

The term "vector" refers to the means by which a nucleic acid can be propagated and/or transferred between organisms, cells, or cellular components. Vectors include, but are not limited to, plasmids, viruses, bacteriophage, pro-viruses, phagemids, transposons, and artificial chromosomes, which are capable of replicating autonomously or integrating into a chromosome of a host cell. Vectors also include, but are not limited to: a naked RNA polynucleotide, a naked DNA polynucleotide, a polynucleotide that includes both DNA and RNA within the same strand, a poly-lysine-conjugated DNA or RNA, a peptide-conjugated DNA or RNA, a liposome-conjugated DNA, which are not autonomously replicating. An "expression vector" is a vector, such as a plasmid, which is capable of promoting expression as well as replication of a nucleic acid incorporated therein. Typically, the nucleic acid to be expressed is "operably linked" to a promoter and/or enhancer, and is subject to transcription regulatory control by the promoter and/or enhancer.

The term "host cell" refers to a cell which contains a heterologous nucleic acid, such as a vector, and supports the replication and/or expression of the nucleic acid. Host cells can be prokaryotic cells such as *E. coli*, or eukaryotic cells such as yeast, insect, amphibian, avian or mammalian cells, including human cells, for example, HEp-2 cells and Vero cells.

The term "introduced" when referring to a heterologous or isolated nucleic acid refers to the transfer of a nucleic acid into a eukaryotic or prokaryotic cell where the nucleic acid can be incorporated into the genome of the cell, converted into an autonomous replicon, or transiently expressed. The term includes such methods as "infection," "transfection," "transformation" and "transduction." A variety of methods can be employed to introduce nucleic acids into host cells, including, but not limited to, electroporation, calcium phosphate precipitation, lipid mediated transfection, and lipofection.

The term "expression" refers to the process by which information from a gene is used in the synthesis of a functional gene product. Gene products are often proteins, but can also be functional RNA. Gene expression can be detected by determining the presence of corresponding rRNA, tRNA, mRNA, snRNA and/or gene products at the protein level.

A "polypeptide" refers to a molecule that includes two or more amino acid residues linearly linked by amide bonds (also known as peptide bonds), such as a peptide or a protein. The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, and is not necessarily translated from a designated nucleic acid sequence. It can be generated in any manner, including by chemical synthesis. The amino acid residues of the polypeptide can be natural or non-natural and can be unsubstituted, unmodified, substituted or modified. An "amino acid sequence" is a polymer of amino acid residues, for example, a protein or polypeptide, or a character string representing an amino acid polymer, depending on context.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, with two pairs of polypeptide chains, each pair having one "light" and one "heavy" chain, wherein the variable regions of each light/heavy chain pair form an antibody binding site. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Typically, each heavy chain has at one end a variable domain (VH) followed by a number of constant domains (CH) and each light chain has a variable domain at one end (VL) and a constant domain (CL) at its other end in which the constant domain of the light chain is aligned with the first constant domain of the heavy chain, and the light chain variable domain is aligned with the variable domain of the heavy chain.

The terms "antibody," "antibodies" and "immunoglobulins" as used herein encompass monoclonal antibodies (including full-length monoclonal antibodies), polyclonal antibodies, multispecific antibodies formed from at least two different epitope binding fragments (e.g., bispecific antibodies), CDR-grafted, human antibodies, humanized antibodies, camelised antibodies, chimeric antibodies, single-chain Fvs (scFv), single-chain antibodies, single domain antibodies, Fab fragments, Fab' fragments, F(ab')$_2$ fragments, antibody fragments that exhibit a desired biological activity (e.g. the antigen binding portion), disulfide-linked Fvs (dsFv), and anti-idiotypic (anti-Id) antibodies, intrabodies, and epitope-binding fragments or derivatives of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammalian species, including, but not limited to, humans, monkeys, pigs, horses, rabbits, dogs, cats, mice, etc., or other animals such as birds (e.g. chickens). Antibodies may be fused to a heterologous polypeptide sequence, for example, a tag to facilitate purification.

The term "specifically binds," refers to the binding of a binding molecule, such as an antibody or fragment, variant, or derivative thereof to an epitope via its antigen binding domain more readily than it would bind to a random, unrelated epitope. The term "specificity" is used herein to qualify the relative affinity by which a certain binding molecule binds to a certain epitope.

As used herein, the term "affinity" refers to a measure of the strength of the binding of an individual epitope with the binding domain of an immunoglobulin molecule.

The term "epitope" as used herein refers to a protein determinant capable of binding to an antibody binding domain. Epitopes usually include chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "isolated" refers to a biological material, such as a nucleic acid or a protein, which is substantially free from components that normally accompany or interact with it in its naturally occurring environment. On the other hand, the isolated material may include material not found with the material in its natural environment. For example, if the material is in its natural environment, such as a cell, the material may have been placed at a location in the cell not native to material found in that environment. For example, a naturally occurring nucleic acid can be considered isolated if it is introduced by non-naturally occurring means to a locus of the genome not native to that nucleic acid. Such nucleic acids are also referred to as "heterologous" nucleic acids.

The term "recombinant" refers to a material that has been artificially or synthetically altered by human intervention. The alteration can be performed on the material within or removed from, its natural environment or state. For example, a "recombinant nucleic acid" may refer to a nucleic acid that is made by recombining nucleic acids, for example, during cloning, DNA shuffling or other procedures, or by chemical or other mutagenesis; and a "recombinant polypeptide" or "recombinant protein" can refer to a polypeptide or protein which is produced by expression of a recombinant nucleic acid.

As used herein the term "engineered" includes manipulation of nucleic acid or polypeptide molecules by synthetic means, including, for example, recombinant techniques, in vitro peptide synthesis, enzymatic or chemical coupling of peptides or combinations thereof.

As used herein, the term "effective amount" or "therapeutically effective amount" refers to an amount of a therapeutic composition necessary or sufficient to realize a desired clinical outcome for a given condition and administration regimen, for example, an amount sufficient to achieve a concentration of a compound which is capable of preventing or treating influenza infection in a subject. Such amounts and concentrations can be determined by those skilled in the art. The amount of the therapeutic composition actually administered will typically be determined by a physician, in the light of the relevant circumstances, including, but not limited to, the condition to be treated, the chosen route of administration, the actual compound administered, the age, weight, and response of the individual patient, and the severity of the patient's symptoms.

As used herein, the term "therapeutic composition" refers to a compound or composition with a therapeutic use and includes, but is not limited to, biological compounds, such as antibodies, proteins and nucleic acids, as well as small organic molecule compounds that are chemically synthesized.

As used herein, the term "pharmaceutical composition" refers to a composition that includes a therapeutically effective amount of a therapeutic agent together with a pharmaceutically acceptable carrier and, if desired, one or more diluents or excipients. As used herein, the term "pharmaceutically acceptable" means that it is approved by a regulatory agency of a Federal or a state government or listed in the U.S. Pharmacopia, European Pharmacopia or other generally recognized pharmacopia for use in mammals, and more particularly in humans.

The term "synergistic effect" as used herein refers to a greater-than-additive therapeutic effect produced by a combination of compounds wherein the therapeutic effect obtained with the combination exceeds the additive effects that would otherwise result from individual administration the compounds alone. Certain embodiments include methods of producing a synergistic effect in the treatment of influenza A virus and/or influenza B virus infections, wherein said effect is at least 5%, at least 10%, at least 20%, at least 30%, at least 40%, at least 50%, at least 60%, at least 70%, at least 80%, at least 90%, at least 100%, at least 200%, at least 500%, or at least 1000% greater than the corresponding additive effect.

As used herein, the terms "treatment" or "treating" refer to both therapeutic treatment and prophylactic or preventative measures, wherein the object is to stabilize, prevent, alleviate or reduce one or more symptoms of influenza infection, or to delay, prevent, or inhibit progression of influenza infection. Treatment can also refer to clearance or reduction of an infectious agent such as influenza A and/or influenza B in a subject, "Treatment" can also mean prolonging survival as compared to expected survival if not receiving treatment. Treatment need not mean that the infection is completely cured.

As use herein, the term "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn mammals are intended to be covered.

Binding Molecules

Described herein are binding molecules which specifically bind to influenza A virus and/or influenza B virus. As used herein, the term "binding molecule" refers to a molecule that is capable of binding to a target molecule or antigen in a manner similar to that of an antibody binding to an antigen. Examples of binding molecules include intact antibodies as well as antigen-binding fragments, variants, analogs, or derivatives of such antibodies, for example, naturally occurring antibody or immunoglobulin molecules or engineered antibody molecules or fragments, including bispecific antibodies. A binding molecule can include one or more binding domains. While a binding molecule can include the canonical antibody structure, binding molecules can have other structures that include one or more binding domains. In one embodiment, the binding molecule includes at least two binding domains and at least two binding specificities.

As used herein, a "binding domain" refers to the portion, region, or site of a binding molecule that is responsible for specific binding to a target molecule or antigen. In one embodiment, the binding domain includes a variable fragment (Fv) of an antibody. In one embodiment, the binding domain includes a variable heavy (VH) chain sequence and variable light (VL) chain sequence of an antibody. In one embodiment, the binding domain includes one or more, two, three, four, five or six complementarity determining regions (CDRs) from an antibody positioned with suitable framework (FR) regions. A binding domain may be derived from a single species or a binding domain may include CDRs from one species and framework sequences from another species, for example, as in a humanized antibody.

Binding molecules can be from any animal origin, including, but not limited to, birds and mammals. Antibodies or fragments thereof of the binding molecule can be human, murine, donkey, rabbit, goat, guinea pig, camel, llama, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins.

In one embodiment, the binding molecule includes at least one binding domain that is capable of binding to and/or neutralizing influenza A virus. In another embodiment, the binding molecule includes at least one binding domain that is capable of binding to and/or neutralizing influenza B virus. In one embodiment, the binding molecule includes a first binding domain that is capable of binding to and/or neutralizing influenza A virus and a second binding domain that is capable of binding to and/or neutralizing influenza B virus. In a more particular embodiment, the binding molecule includes a first binding domain that is capable of binding to influenza A virus hemagglutinin (HA) and neutralizing at least one group 1 subtype and at least one group 2 subtype of influenza A virus; and a second binding domain that is capable of binding to influenza B virus hemagglutinin (HA) and neutralizing influenza B virus in at least two phylogenetically distinct lineages. In one embodiment, the first binding domain is capable of neutralizing one or more influenza A virus group 1 subtypes selected from: H1, H2, H5, H6, H8, H9, H11, H12, H13, H16, H17, H18 and variants thereof; and one or more influenza A virus group 2 subtypes selected from: H3, H4, H7, H10, H14 and H15 and variants thereof. In one embodiment, the second binding domain is capable of neutralizing influenza B virus in both Yamagata and Victoria lineages.

Antibodies

The binding molecule can include a full length or intact antibody, an antibody fragment, including an antigen binding fragment, a human, humanized, post-translationally modified, chimeric or fusion antibody, immunoconjugate, or a functional fragment thereof. In one embodiment, the binding molecule includes one or more binding domains that include a full length or intact antibody, or one or more antibody fragments, including antigen binding fragments.

Examples "antigen-binding fragments" of an antibody include (i) a Fab fragment, a monovalent fragment that includes a VL, VH, CL and CH1 domain of an antibody; (ii)

a F(ab')2 fragment, a bivalent fragment that includes two Fab fragments linked by a disulfide bridge at a hinge region; (iii) a Fd fragment that includes the VH and CH1 domains; (iv) a Fv fragment that includes VL and VH domains of a single arm of an antibody, (v) a dAb fragment (Ward et al., (1989) Nature 341:544-546), which includes a VH domain; and (vi) an isolated complementarity determining region (CDR). Antigen-binding fragments can be produced by recombinant DNA techniques, or by enzymatic or chemical cleavage of intact immunoglobulins.

In one embodiment, the antigen-binding fragment includes a single chain antibody, including, for example, a "single-chain variable fragment" or "scFv." The term "single-chain variable fragment" or "scFv" refers to a fusion protein that includes at least one variable region of a heavy chain (VH) and at least one variable region of a light chain (VL) of an immunoglobulin. These single chain antibody fragments can be obtained using conventional techniques known to those with skill in the art. For example, the VH and VL domains of a Fv fragment, which are encoded by separate genes, can be joined, using recombinant methods, by a synthetic linker that enables them to be made as a single polypeptide chain in which the VL and VH regions pair to form a monovalent molecule (See, Bird et al. (1988) Science 242:423-426; and Huston et al. (1988) Proc. Natl. Acad. Sci. USA 85:5879-5883). In one embodiment, the VH and VL regions of the scFv are connected with a short linker peptide of at least about 5, 10, 15 or 20 and up to about 10, 15, 20, 25 or 30 amino acids. ScFv linkers are known and include linkers that are rich in glycine (for flexibility), as well linkers that include serine or threonine (for solubility). In one embodiment, the linker connects the N-terminus of a VH with the C-terminus of a VL. In other embodiments, the linker connects the C-terminus of a VH with the N-terminus of a VL. In one embodiment, the scFv retains the specificity of the original immunoglobulin, despite removal of the constant regions and the introduction of the linker. Methods for producing single-chain Fvs include those described in U.S. Pat. Nos. 4,946,778 and 5,258,498; Huston et al., (1991) Methods in Enzymology 203:46-88; Shu et al., (1993) PNAS 90:7995-7999; and Skerra et al., (1988) Science 240:1038-1040.

In one embodiment, the binding molecule includes at least one binding domain that includes an anti-influenza A virus antibody or antigen-binding fragment thereof. In another embodiment, the binding molecule includes at least one binding domain that includes an anti-influenza B virus antibody or antigen-binding fragment thereof. In a more particular embodiment, the binding molecule includes at least one binding domain that includes an anti-influenza A virus antibody or antigen-binding fragment thereof and at least one binding domain that includes an anti-influenza B virus antibody or antigen-binding fragment thereof.

As used herein, the terms "antibody" and "antibodies", also known as immunoglobulins, encompass monoclonal antibodies, including full-length monoclonal antibodies, human antibodies, humanized antibodies, camelid antibodies, chimeric antibodies, single-chain antibodies, single-chain Fvs (scFv), single domain antibodies, domain antibodies, Fab fragments, F(ab')2 fragments, antibody fragments with a desired biological activity, for example, antigen binding fragments, disulfide-linked Fvs (dsFv), and anti-idiotypic (anti-Id) antibodies, intrabodies, and antigen binding fragments thereof.

Suitable immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Immunoglobulin molecules can include light chains classified as either lambda chains or kappa chains based on the amino acid sequence of the light chain constant region.

A typical immunoglobulin (antibody) structural unit is a tetramer of about 150 kD, which includes two pairs of polypeptide chains, each pair having one "light" chain (about 25 kD) and one "heavy" chain (about 50-70 kD). Typically, each light chain is linked to a heavy chain by one covalent disulfide bond, although the number of disulfide linkages between the heavy chains of different immunoglobulin isotypes can vary. Each heavy and light chain also has regularly spaced intrachain disulfide bridges. In most naturally occurring antibodies, the two pairs of polypeptide chains are identical. However, in engineered antibodies the two pairs of polypeptide chains are not necessarily identical, for example, as in trifunctional antibodies.

Both the light and heavy chains of an antibody can be divided into "constant" and "variable" domains. The C-terminal portion of the heavy and light chains is referred to as a constant domain. "CH1 domain" refers to the heavy chain immunoglobulin constant domain located between the variable heavy (VH) domain and the hinge region. "CH2 domain" refers to the heavy chain immunoglobulin constant domain that is located between the hinge region and the CH3 domain. "CH3 domain" refers to the heavy chain immunoglobulin constant domain that is located C-terminally of the CH2 domain. "CH4 domain" refers to the heavy chain immunoglobulin constant domain that is located C-terminally of the CH3 domain in IgM and IgE antibodies. The term "hinge region" refers to the portion of a heavy chain molecule that joins the CH1 domain to the CH2 domain. "CL domain" refers to the light chain immunoglobulin constant domain that is located C-terminally to the variable light (VL) domain.

The N-terminus of each heavy and light chain defines a three dimensional antigen binding site variable region referred to as a variable domain. The variable domains of both the light (VL) and the heavy (VH) chain include about 100 to 110 or more amino acids and are primarily responsible for antigen recognition and specificity. The constant domains of the light chain (CL) and the heavy chain (CH1, CH2 or CH3) confer biological properties such as secretion, transplacental mobility, Fc receptor binding, and complement binding. By convention, the numbering of the constant region domains increases for the domains more distal from the antigen binding site or N-terminus of the antibody.

As used herein, the term "heavy chain portion" refers to amino acid sequences derived from an immunoglobulin heavy chain that include at least one of: a VH, CH1 domain, a hinge region, a CH2 domain, a CH3 domain, or a variant or fragment thereof. As used herein, the term "light chain portion" refers to amino acid sequences derived from an immunoglobulin light chain that include at least one of a VL or CL domain.

Antibody Variable Regions

In one embodiment, the binding molecule includes at least one antigen binding domain that includes a variable fragment (Fv) domain. In one embodiment, the binding molecule includes at least one binding domain that includes at least one VH of an antibody heavy chain and at least one VL of an antibody light chain. In a more particular embodiment, the binding molecule includes a first binding domain that includes at least one VH of an antibody heavy chain and at least one VL of an antibody light chain and a second binding domain that includes at least one VH of an antibody heavy chain and at least one VL of an antibody light chain. In one embodiment, the binding molecule includes a first binding domain that binds to influenza A virus and includes at least one VH of an antibody heavy chain and at least one VL of an antibody light chain and a second binding domain that binds to influenza B virus and includes at least one VH of an antibody heavy chain and at least one VL of an antibody light chain. Exemplary VH and VL domains of an antibody that bind to influenza A virus and influenza B virus are shown in Tables 1 and 2, respectively.

TABLE 1

Anti-influenza A virus

| Antibody | VL nucleic acid SEQ ID NO: | VL amino acid SEQ ID NO: | VH nucleic acid SEQ ID NO: | VH amino acid SEQ ID NO: |
|---|---|---|---|---|
| FY1 | 1 | 2 | 6 | 7 |
| GL20 | 11 | 12 | 16 | 17 |

TABLE 2

Anti-influenza B virus

| Antibody | VL nucleic acid SEQ ID NO: | VL amino acid SEQ ID NO: | VH nucleic acid SEQ ID NO: | VH amino acid SEQ ID NO: |
|---|---|---|---|---|
| FBC39 | 21 | 22 | 26 | 27 |
| FBC39-FTL | 37 | 38 | 42 | 43 |
| FBD94 | 53 | 54 | 58 | 59 |

In one embodiment, the binding molecule includes one or more VH and/or VL domains having at least a specified percent identify to one or more of the VH and/or VL sequences disclosed in Tables 1 and 2 As used herein, the term "percent (%) sequence identity", or "homology" refers to the percentage of amino acid residues or nucleotides in a candidate sequence that are identical with the amino acid residues or nucleotides in a reference sequence, such as parent antibody sequence, after aligning the sequences and introducing gaps, if necessary, to achieve the maximum percent sequence identity, and not considering any conservative substitutions as part of the sequence identity. Sequence alignments may be produced manually or using the homology algorithm of Smith and Waterman, (1981) Ads App. Math. 2, 482 or Neddleman and Wunsch, (1970) J. Mol. Biol. 48, 443, using the similarity search method of Pearson and Lipman, (1988) Proc. Natl Acad. Sci. USA 85, 2444, or using computer programs based on one or more of these algorithms (GAP, BESTFIT, FASTA, BLAST P, BLAST N and TFASTA in Wisconsin Genetics Software Package, Genetics Computer Group, 575 Science Drive, Madison, Wisconsin).

In one embodiment, the binding molecule includes one or more binding domains having a VH amino acid sequence having at least 65%, 70%, 75%, 80%, 85%, 90%, 95% or 100% identity to a VH amino acid sequence described herein, including, for example, those shown in Table 1 or 2. In one embodiment, the binding molecule includes one or more binding domains having a VH amino acid sequence having at least, 90%, 91%, 92%, 93%, 94%, 95%, 96%, 97%, 98%, 99% or 100% identity to a VH amino acid sequence described herein, including, for example, those shown in Table 1 or 2.

In one embodiment, the binding molecule includes one or more binding domains having a VL amino acid sequence having at least 65%, 70%, 75%, 80%, 85%, 90%, 95% or having 100% identity to a VL amino acid sequence described herein, including, for example, those shown in Table 1 or 2. In one embodiment, the binding molecule includes one or more binding domains having a VL amino acid sequence having at least, 90%, 91%, 92%, 93%, 94%, 95%, 96%, 97%, 98%, 99% or 100% identity to a VL amino acid sequence described herein, including, for example, those shown in Table 1 or 2.

In one embodiment, the binding molecule includes one or more binding domains having a VH and a VL amino acid sequence having at least 65%, 70%, 75%, 80%, 85%, 90%, 95% or 100% identity to a VH and a VL amino acid sequence, respectively, described herein, including, for example, those shown in Table 1 or 2. In one embodiment, the binding molecule includes one or more binding domains having a VH and a VL amino acid sequence having at least, 90%, 91%, 92%, 93%, 94%, 95%, 96%, 97%, 98%, 99% or 100% identity to a VH and a VL amino acid sequence, respectively, described herein, including, for example, those shown in Table 1 or 2.

In one embodiment, the binding molecule includes one or more binding domains having a VH and a VL amino acid sequence having at least 65%, 70%, 75%, 80%, 85%, 90%, 95% or 100% identity to a VH and a VL amino acid sequence, respectively, shown in Table 1. In one embodiment, the binding molecule includes one or more binding domains having a VH and a VL amino acid sequence having at least, 90%, 91%, 92%, 93%, 94%, 95%, 96%, 97%, 98%, 99% or 100% identity to a VH and a VL amino acid sequence, respectively, shown in Table 1.

In one embodiment, the binding molecule includes one or more binding domains having a VH and a VL amino acid sequence having at least 65%, 70%, 75%, 80%, 85%, 90%, 95% or 100% identity to a VH and a VL amino acid sequence, respectively, shown in Table 2. In one embodiment, the binding molecule includes one or more binding domains having a VH and a VL amino acid sequence having at least, 90%, 91%, 92%, 93%, 94%, 95%, 96%, 97%, 98%, 99% or 100% identity to a VH and a VL amino acid sequence, respectively, shown in Table 2.

In one embodiment, the binding molecule includes a first binding domain having a VH and a VL amino acid sequence having at least 65%, 70%, 75%, 80%, 85%, 90%, 95% or 100% identity to a VH and a VL amino acid sequence, respectively, shown in Table 1 and a second binding domain having a VH and a VL amino acid sequence having at least 65%, 70%, 75%, 80%, 85%, 90%, 95% or 100% identity to a VH and a VL amino acid sequence, respectively, shown in Table 2. In one embodiment, the binding molecule includes a first binding domains having a VH and a VL amino acid sequence having at least, 90%, 91%, 92%, 93%, 94%, 95%, 96%, 97%, 98%, 99% or 100% identity to a VH and a VL amino acid sequence, respectively, shown in Table 1 and a second binding domain having a VH and a VL amino acid sequence having at least, 90%, 91%, 92%, 93%, 94%, 95%, 96%, 97%, 98%, 99% or 100% identity to a VH and a VL amino acid sequence, respectively, shown in Table 2.

In one embodiment, the first binding domain of the binding molecule includes a VH having an amino acid sequence that is at least 75% identical to an amino acid sequence selected from SEQ ID NO.: 7; and SEQ ID NO.: 17. In one embodiment, the first binding domain of the binding molecule includes a VL having an amino acid sequence that is at least 75% identical to an amino acid sequence selected from SEQ ID NO.: 2; and a VL of SEQ ID NO.: 12. In a more particular embodiment, the first binding domain of the binding molecule includes a VH and a VL that is at least 75% identical to an amino acid sequence of a VH and a VL, respectively, selected from a VH of SEQ ID NO.: 7 and a VL of SEQ ID NO.: 2; and a VH of SEQ ID NO.: 17 and a VL of SEQ ID NO.: 12. In one embodiment, the first binding domain includes a VH and a VL selected from: a VH of SEQ ID NO.: 7 and a VL of SEQ ID NO.: 2; and a VH of SEQ ID NO.: 17 and a VL of SEQ ID NO.: 12.

Complementarity Determining Regions (CDRs)

In naturally occurring antibodies, six short, non-contiguous sequences of amino acids, referred to as "complementarity determining regions" or "CDRs" are present in each antigen binding domain. The remainder of the amino acids in the antigen binding domains are referred to as "framework" regions. The framework regions function as a scaffold that positions the CDRs in correct orientation by inter-chain, non-covalent interactions. The three CDRs of the heavy chain are designated CDRH1, CDRH2, and CDRH3, and the three CDRs of the light chain are designated CDRL1, CDRL2, and CDRL3.

The amino acids that make up the CDRs and the framework regions can be readily identified by one of ordinary skill in the art and have been described by Kabat et al., (1983) U.S. Dept. of Health and Human Services, "Sequences of Proteins of Immunological Interest" and by Chothia et al., (1987) J. Mol. Biol. 196:901-917. The definitions of Kabat et al. and Chothia et al. include overlapping amino acid residues. The amino acid residues which encompass the CDRs as defined by Kabat et al. and Chothia et al. are set forth below in Table 3. The exact residue numbers which encompass a particular CDR can vary depending on the sequence and size of the CDR. Those skilled in the art can routinely determine which residues are in a particular CDR given the variable region amino acid sequence of the antibody.

TABLE 3

Example CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of the CDR is according to the convention set forth by Kabat et al.

Application of either definition is intended to be within the scope of the term "CDR" as defined and used herein. However, unless otherwise specified, references to the numbering of specific amino acid residue positions in a binding molecule, antibody, antigen-binding fragment, variant, or derivative thereof herein are according to the numbering system of Kabat et al.

In one embodiment, the amino acids in the variable domain, complementarity determining region (CDRs) and framework regions (FR) of an antibody are identified following Kabat et al. The Kabat numbering of residues may be determined for a given antibody by alignment at regions of homology of the sequence of the antibody with a "standard" Kabat numbered sequence. Maximal alignment of framework residues may require insertion of "spacer" residues in the numbering system. In addition, the identity of certain individual residues at any given Kabat site number may vary from antibody chain to antibody chain due to interspecies or allelic divergence.

According to the Kabat et al. numbering system, HCDR1 begins at approximately amino acid 31 (i.e., approximately 9 residues after the first cysteine residue), includes approximately 5-7 amino acids, and ends at the next tyrosine residue. HCDR2 begins at the fifteenth residue after the end of CDRH1, includes approximately 16-19 amino acids, and ends at the next arginine or lysine residue. HCDR3 begins at approximately the thirty third amino acid residue after the end of HCDR2; includes 3-25 amino acids; and ends at the sequence W-G-X-G, where X is any amino acid. LCDR1 begins at approximately residue 24 (i.e., following a cysteine residue); includes approximately 10-17 residues; and ends at the next tyrosine residue. LCDR2 begins at approximately the sixteenth residue after the end of LCDR1 and includes approximately 7 residues. LCDR3 begins at approximately the thirty third residue after the end of LCDR2; includes approximately 7-11 residues and ends at the sequence F-G-X-G, where X is any amino acid. CDRs vary considerably from antibody to antibody (and by definition will not exhibit homology with the Kabat consensus sequences). CDR heavy chain and light chain sequences of antibodies of the invention, numbered using the Kabat system are shown in Tables 4 and 5, below.

In one embodiment, the binding molecule includes at least one, two, three, four, five or six CDRs. In one embodiment, the binding molecule includes at least one, two, three, four, five or six heavy chain CDRs (HCDR) shown in Tables 4 and 5. In one embodiment, the binding molecule includes at least one, two, three, four, five or six light chain CDRs (LCDR) shown in Tables 4 and 5. In one embodiment, the binding molecule includes at least one, two, three, four, five or six HCDRs shown in Tables 4 and 5 and at least one, two, three, four, five or six LCDRs shown in Tables 4 and 5.

TABLE 4

Anti-influenza A Antibody CDRs as identified by Kabat et al.

| Antibody | LCDR1 SEQ ID: | LCDR2 SEQ ID: | LCDR3 SEQ ID: | HCDR1 SEQ ID: | HCDR2 SEQ ID: | HCDR3 SEQ ID: |
|---|---|---|---|---|---|---|
| FY1 | 3 | 4 | 5 | 8 | 9 | 10 |
| GL20 | 13 | 14 | 15 | 18 | 19 | 20 |

TABLE 5

Anti-influenza B Antibody CDRs as identified by Kabat et al.

| Antibody | LCDR1 SEQ ID: | LCDR2 SEQ ID: | LCDR3 SEQ ID: | HCDR1 SEQ ID: | HCDR2 SEQ ID: | HCDR3 SEQ ID: |
|---|---|---|---|---|---|---|
| FBC39 | 23 | 24 | 25 | 28 | 29 | 30 |
| FBC39-FTL | 39 | 40 | 41 | 44 | 45 | 46 |
| FBD94 | 55 | 56 | 57 | 60 | 61 | 62 |

In another embodiment, the amino acids in the variable domain, complementarity determining regions (CDRs) and framework regions (FR) of an antibody can be identified using the Immunogenetics (IMGT) database (imgt.cines.fr). Lefranc et al. (2003) Dev Comp Immunol. 27(1):55-77. The IMGT database was developed using sequence information for immunoglobulins (IgGs), T-cell receptors (TcR) and Major Histocompatibility Complex (MHC) molecules and unifies numbering across antibody lambda and kappa light chains, heavy chains and T-cell receptor chains and avoids the use of insertion codes for all but uncommonly long insertions. IMGT also takes into account and combines the definition of the framework (FR) and complementarity determining regions (CDR) from Kabat et al., the characterization of the hypervariable loops from Chothia et al., as well as structural data from X-ray diffraction studies. CDR heavy chain and light chain sequences numbered using the IMGT system, are shown in Table 6, below.

TABLE 6

Anti-influenza B antibody CDRs as identified by IMGT

| | LCDR1 SEQ ID NO: | LCDR2 SEQ ID NO: | LCDR3 SEQ ID NO: | HCDR1 SEQ ID NO: | HCDR2 SEQ ID NO: | HCDR3 SEQ ID NO: |
|---|---|---|---|---|---|---|
| FBC-39 | 94 | 95 | 96 | 97 | 98 | 99 |
| FBC-39 FTL | 100 | 101 | 102 | 103 | 104 | 105 |

In one embodiment, the binding molecule includes one or more binding domains that include one or more, including, one, two, three, four, five, or six CDRs selected from HCDR1, HCDR2, HCDR3, LCDR1, LCDR2, LCDR3. In one embodiment, the binding molecule includes one or more binding domains that include a set of six CDRs: HCDR1, HCDR2, HCDR3, LCDR1, LCDR2, LCDR3, wherein CDRs are selected from the HCDRs and LCDRs shown in Tables 4 through 6. In another embodiment, the binding molecule includes one or more binding domains that include a set of six CDRs: HCDR1, HCDR2, HCDR3, LCDR1, LCDR2, LCDR3, wherein CDRs include an amino acids sequence that is at least 75%, 80%, 85%, 90%, 95% or 100% identical to an amino acid sequence of the HCDRs and LCDRs shown in Tables 4 through 6. In another embodiment, the binding molecule includes one or more binding domains that include a set of six CDRs: HCDR1, HCDR2, HCDR3, LCDR1, LCDR2, LCDR3, wherein CDRs include an amino acid sequence that is at least 95%, 96%, 97%, 98%, 99% or 100% identical to an amino acid sequence of the HCDRs and LCDRs shown in Tables 4 through 6.

In one embodiment, the binding molecule includes one or more binding domains that include a set of six CDRs: HCDR1, HCDR2, HCDR3, LCDR1, LCDR2, LCDR3, wherein CDRs are selected from the HCDRs and LCDRs shown in Table 4. In another embodiment, the binding molecule includes one or more binding domains that include a set of six CDRs: HCDR1, HCDR2, HCDR3, LCDR1, LCDR2, LCDR3, wherein CDRs include an amino acids sequence that is at least 75%, 80%, 85%, 90%, 95% or 100% identical to an amino acid sequence of the HCDRs and LCDRs shown in Table 4. In another embodiment, the binding molecule includes one or more binding domains that include a set of six CDRs: HCDR1, HCDR2, HCDR3, LCDR1, LCDR2, LCDR3, wherein CDRs include an amino acid sequence that is at least 95%, 96%, 97%, 98%, 99% or 100% identical to an amino acid sequence of the HCDRs and LCDRs shown in Table 4.

In one embodiment, the binding molecule includes one or more binding domains that include a set of six CDRs: HCDR1, HCDR2, HCDR3, LCDR1, LCDR2, LCDR3, wherein CDRs are selected from the HCDRs and LCDRs shown in Tables 5 and 6. In another embodiment, the binding molecule includes one or more binding domains that include a set of six CDRs: HCDR1, HCDR2, HCDR3, LCDR1, LCDR2, LCDR3, wherein CDRs include an amino acids sequence that is at least 75%, 80%, 85%, 90%, 95% or 100% identical to an amino acid sequence of the HCDRs and LCDRs shown in Tables 5 and 6. In another embodiment, the binding molecule includes one or more binding domains that include a set of six CDRs: HCDR1, HCDR2, HCDR3, LCDR1, LCDR2, LCDR3, wherein CDRs include an amino acid sequence that is at least 95%, 96%, 97%, 98%, 99% or 100% identical to an amino acid sequence of the HCDRs and LCDRs shown in Tables 5 and 6.

In one embodiment, the binding molecule includes a first binding domain that include a set of six CDRs: HCDR1, HCDR2, HCDR3, LCDR1, LCDR2, LCDR3 shown in Table 4 and a second binding domain that includes a set of six CDRs: HCDR1, HCDR2, HCDR3, LCDR1, LCDR2, LCDR3, selected from the HCDRs and LCDRs shown in Tables 5 and 6. In another embodiment, the binding molecule includes a first binding domain that includes a set of six CDRs: HCDR1, HCDR2, HCDR3, LCDR1, LCDR2, LCDR3, wherein CDRs include an amino acids sequence that is at least 75%, 80%, 85%, 90%, 95% or 100% identical to an amino acid sequence of the HCDRs and LCDRs shown in Table 4 and a second binding domain that includes a set of six CDRs: HCDR1, HCDR2, HCDR3, LCDR1, LCDR2, LCDR3, wherein CDRs include an amino acids sequence that is at least 75%, 80%, 85%, 90%, 95% or 100% identical to an amino acid sequence of the HCDRs and LCDRs shown in Tables 5 and 6. In another embodiment, the binding molecule includes a first binding domain that includes a set of six CDRs: HCDR1, HCDR2, HCDR3, LCDR1, LCDR2, LCDR3, wherein CDRs include an amino acid sequence that is at least 95%, 96%, 97%, 98%, 99% or 100% identical to an amino acid sequence of the HCDRs and LCDRs shown in Table 4 and a second binding domain that includes a set of six CDRs: HCDR1, HCDR2, HCDR3, LCDR1, LCDR2, LCDR3, wherein CDRs include an amino acid sequence that is at least 95%, 96%, 97%, 98%, 99% or 100% identical to an amino acid sequence of the HCDRs and LCDRs shown in Tables 5 and 6.

In one embodiment, the first binding domain of the binding molecule includes a set of six CDRs: HCDR1, HCDR2, HCDR3, LCDR1, LCDR2, LCDR3 in which the CDRs individually have an amino acid sequence that is at least 75%, 80%, 85%, 90%, 95% or 100% identical to an amino acid sequence of:
(a) HCDR1 of SEQ ID NO.: 8, HCDR2 of SEQ ID NO.: 9, HCDR3 of SEQ ID NO.: 10, LCDR1 of SEQ ID NO.: 3, LCDR2 of SEQ ID NO.: 4 and LCDR3 of SEQ ID NO.: 5, respectively; or
(b) HCDR1 of SEQ ID NO.: 18, HCDR2 of SEQ ID NO.: 19, HCDR3 of SEQ ID NO.: 20, LCDR1 of SEQ ID NO.: 13, LCDR2 of SEQ ID NO.: 14, LCDR3 of SEQ ID NO.: 15, respectively.

In one embodiment, the first binding domain of the binding molecule includes a set of six CDRs: HCDR1, HCDR2, HCDR3, LCDR1, LCDR2, LCDR3 in which the CDRs individually have an amino acid sequence that is at least 95%, 96%, 97%, 98%, 99% or 100% identical to an amino acid sequence of:
(a) HCDR1 of SEQ ID NO.: 8, HCDR2 of SEQ ID NO.: 9, HCDR3 of SEQ ID NO.: 10, LCDR1 of SEQ ID NO.: 3, LCDR2 of SEQ ID NO.: 4 and LCDR3 of SEQ ID NO.: 5, respectively; or
(b) HCDR1 of SEQ ID NO.: 18, HCDR2 of SEQ ID NO.: 19, HCDR3 of SEQ ID NO.: 20, LCDR1 of SEQ ID NO.: 13, LCDR2 of SEQ ID NO.: 14, LCDR3 of SEQ ID NO.: 15; respectively.

In one embodiment, the second binding domain includes a set of six CDRs: HCDR1, HCDR2, HCDR3, LCDR1, LCDR2, LCDR3 in which the CDRs individually have an amino acid sequence that is at least 75%, 80%, 85%, 90%, 95% or 100% identical to an amino acid sequence of:
(a) HCDR1 of SEQ ID NO.: 28, HCDR2 of SEQ ID NO.: 29, HCDR3 of SEQ ID NO.: 30, LCDR1 of SEQ ID NO.: 23, LCDR2 of SEQ ID NO.: 24 and LCDR3 of SEQ ID NO.: 25, respectively;
(b) HCDR1 of SEQ ID NO.: 44, HCDR2 of SEQ ID NO.: 45, HCDR3 of SEQ ID NO.: 46, LCDR1 of SEQ ID NO.: 39, LCDR2 of SEQ ID NO.: 40 and LCDR3 of SEQ ID NO.: 41, respectively; or
(c) HCDR1 of SEQ ID NO.: 60, HCDR2 of SEQ ID NO.: 61, HCDR3 of SEQ ID NO.: 62, LCDR1 of SEQ ID NO.: 55, LCDR2 of SEQ ID NO.: 56, LCDR3 of SEQ ID NO.: 57, respectively.

In one embodiment, the second binding domain includes a set of six CDRs: HCDR1, HCDR2, HCDR3, LCDR1, LCDR2, LCDR3 in which the CDRs individually have an amino acid sequence that is at least 95%, 96%, 97%, 98%, 99% or 100% identical to an amino acid sequence of:
(a) HCDR1 of SEQ ID NO.: 28, HCDR2 of SEQ ID NO.: 29, HCDR3 of SEQ ID NO.: 30, LCDR1 of SEQ ID NO.: 23, LCDR2 of SEQ ID NO.: 24 and LCDR3 of SEQ ID NO.: 25, respectively;
(b) HCDR1 of SEQ ID NO.: 44, HCDR2 of SEQ ID NO.: 45, HCDR3 of SEQ ID NO.: 46, LCDR1 of SEQ ID NO.: 39, LCDR2 of SEQ ID NO.: 40 and LCDR3 of SEQ ID NO.: 41, respectively; or
(c) HCDR1 of SEQ ID NO.: 60, HCDR2 of SEQ ID NO.: 61, HCDR3 of SEQ ID NO.: 62, LCDR1 of SEQ ID NO.: 55, LCDR2 of SEQ ID NO.: 56, LCDR3 of SEQ ID NO.: 57, respectively.

Framework Regions

The variable domains of the heavy and light chains each include four framework regions (FR1, FR2, FR3, FR4), which are the more highly conserved portions of the variable domains. The four FRs of the heavy chain are designated FRH1, FRH2, FRH3 and FRH4, and the four FRs of the light chain are designated FRL1, FRL2, FRL3 and FRL4. Using the Kabat numbering system, FRH1 begins at position 1 and ends at approximately amino acid 30; FRH2 is approximately from amino acid 36 to 49; FRH3 is approximately from amino acid 66 to 94; and FRH4 is approximately amino acid 103 to 113. In one embodiment, one or more modifications, such as substitutions, deletions or insertions of one or more FR residues may be introduced, for example, to improve or optimize the binding affinity of one or more binding domains of the binding molecule for Influenza A virus and/or influenza B virus. Examples of framework region residues that can be modified include those which non-covalently bind antigen directly (Amit et al., *Science,* 233:747-753 (1986)); interact with/effect the conformation of a CDR (Chothia et al., *J. Mol. Biol.,* 196:901-917 (1987)); and/or participate in the VL-VH interface (U.S. Pat. No. 5,225,539).

In one embodiment, the FR of one or more binding domains of the binding molecule includes one or more amino acid changes for the purposes of "germlining". In germlining, the amino acid sequences of an antibody heavy chain and/or light chain are compared to germline heavy and light chain amino acid sequences. Where certain framework residues of the heavy chain and/or light chain differ from the germline configuration, for example, as a result of somatic mutation of the immunoglobulin genes used to prepare the phage library, it may be desirable to "back-mutate" the altered framework residues to the germline configuration (i.e., change the framework amino acid sequences so that they are the same as the germline framework amino acid sequences). Such "back-mutation" (or "germ lining") of framework residues can be accomplished by standard molecular biology methods for introducing specific mutations (e.g., site-directed mutagenesis; PCR-mediated mutagenesis, and the like).

Disulfide Bonds

As used herein the term "disulfide bond" refers to a covalent bond formed between two sulfur atoms. The amino acid cysteine includes a thiol group that can form a disulfide bond or bridge with a second thiol group. In most naturally occurring IgG molecules, the CH1 and CL regions are linked by a disulfide bond and the two heavy chains are linked by two disulfide bonds in the flexible region of the heavy chain known as the hinge region (typically at positions corresponding to 239 and 242 using the Kabat numbering system).

In one embodiment, one or more amino acid substitutions can be made within a framework region, for example, to improve binding of the antibody to its antigen. In one embodiment, the amino acid sequence of a framework region can be modified to make an amino acid substitution or deletion of one or more cysteine residues participating in an intrachain disulfide bond, for example, to generate a binding molecule lacking one or more intrachain disulfide bonds; to generate a binding molecule having one or more additional intrachain disulfide bonds; or to change the location of one or more intrachain disulfide bonds.

In one embodiment, the binding molecule includes one or more scFv. In one embodiment, the scFv includes a VH and a VL, in which the C-terminus of a first variable region domain is connected to the N-terminus of a second variable region domain by means of a flexible peptide linker. In one embodiment, the C-terminus of a Variable Heavy (VH) domain is connected to the N-terminus of a Variable Light (VL) domain. This can be referred to as a "VH-VL" or "HL" orientation. In other embodiments, the C-terminus of a Variable Light (VL) domain is connected to the N-terminus of a Variable Heavy (VH) domain. This can be referred to as a "VL-VH" or "LH" orientation. The length of the linker (LS) joining the VH and the VL of the scFv can be varied. In one embodiment, the linker (LS) has an amino acid sequence of [GGGGS]n, wherein n is 0, 1, 2, 3, 4, or 5 (SEQ ID NO: 93). In another embodiment, the linker (LS) has an amino acid sequence of [GGGG]n, wherein n is 0, 1, 2, 3, 4, or 5, (SEQ ID NO: 106). In other embodiments, the linker includes a combination of the two sequences. In a more particular embodiment, the linker includes an amino acid sequence of GGGGSGGGGSGGGGSGGGGS (SEQ ID NO:92).

In other embodiments, the position of the disulfide bond between the VH and VL of the scFv can be varied by adding, removing, or changing the location of one or more cysteine residues in the scFv. In one embodiment, the VH of the scFv includes a cysteine residue at position 43, 44, 100, 101, 105, and combinations thereof (as numbered by Kabat). In one embodiment, the VL of the scFv includes a cysteine residue at position 43, 44, 46, 49, 50, 100, and combinations thereof (as numbered by Kabat). In one embodiment, the scFv has a VL-VH orientation in which the VL and VH are linked by a disulfide bond at VL100-VH44, VL43-VH105, VL46-VH101, VL49-VH100, VL50-VH100, or combinations thereof. In another embodiment, the scFv has a VH-VL orientation in which the VH and VL are linked by a disulfide bond at VH44-VL100, VH100-VL49, VH100-VL50, VH101-VL46, VH105-VL43, or combinations thereof.

Bispecific Antibodies In one embodiment, the binding molecule includes a "bispecific antibody." As used herein, the term "bispecific antibody" refers to an antibody or antigen binding fragment thereof that has two or more binding domains that can specifically bind two different target molecules or antigens. In general, bispecific antibodies incorporate the specificities and properties of one or more, often at least two, and typically two distinct monoclonal antibodies, referred to as "parental antibodies," into a single molecule. Some bispecific antibodies demonstrate synergistic activities. In one embodiment, the bispecific antibody demonstrates enhanced neutralization activity against one or more influenza A and/or B strains as compared to a parental antibody.

In one embodiment, the bispecific antibodies described herein have an extended breadth of coverage as compared to a single mAb, and may also show enhanced neutralization of one or more strains of influenza A virus. In one embodiment, the binding molecule is a bispecific antibody with enhanced neutralization activity against one or more influenza A group 1 or group 2 strains. In a more particular embodiment, the binding molecule is a bispecific antibody with enhanced neutralization activity against an influenza A virus group 1 strain selected from subtypes H1, H2, H5, H6, H8, H9, H11, H12, H13, H16, H17 and H18). In a more particular embodiment, the binding molecule is a bispecific antibody with enhanced neutralization activity against an influenza A virus group 2 strain selected from subtypes H3, H4, H7, H10, H14, and H15. In one embodiment, the binding molecule is a bispecific antibody with enhanced neutralization activity against H9 subtype of influenza A virus.

In one embodiment, the binding molecule includes a bispecific antibody having more than two valencies. For example, in one embodiment, the binding molecule includes a trispecific antibody. Trispecific antibodies are known and can be prepared using methods known to one of skill in the art (Tutt et al., (1991) J. Immunol., 147:60).

Bispecific antibodies can be expressed by cell lines such as triomas and hybrid hybridomas or can be constructed by recombinant means. (Ströhlein and Heiss, *Future Oncol.* 6:1387-94 (2010); Mabry and Snavely, *IDrugs.* 13:543-9 (2010)).

In one embodiment, the binding molecule includes a bispecific antibody that includes at least two pairs of heavy and light chains, or binding fragments thereof, wherein a first pair is derived from a first "parental" antibody and has a first binding specificity and the second pair is derived from a second "parental" antibody and has a second binding specificity. In one embodiment, the binding molecule includes a first heavy and light chain pair, or fragments thereof, that specifically bind influenza A virus and a second heavy and light chain pair, or fragments thereof, that specifically bind influenza B virus. In one embodiment, the binding molecule includes a bispecific antibody that includes two or more chemically linked Fab regions that are directed against two different target molecules or antigens. In a more particular embodiment, the binding molecule includes one or more Fab regions that specifically bind influenza A virus. In another embodiment, the binding molecule includes one or more Fab regions that specifically bind influenza B virus. In another embodiment, the binding molecule includes a bispecific antibody that includes one or more single chain variable fragments (scFvs). In one embodiment, the binding molecule includes at least one scFv that specifically binds influenza A virus. In another embodiment, the binding molecule includes at least one scFv that specifically binds influenza B virus.

In one embodiment, the binding molecule is a bispecific antibody formed by fusing an IgG antibody and one or more single chain binding domains. In one embodiment, the binding molecule retains an antibody core structure (IgA, IgD, IgE, IgG or IgM). In other embodiment, the antibody core structure (IgA, IgD, IgE, IgG or IgM) is not retained, for example, in dia-, tria- or tetrabodies, minibodies and single chain formats (scFv, Bis-scFv). In another embodiment, the bispecific antibody can include an F(ab)$_2$ fusion wherein two or more Fab fragments are fused with a chemical crosslinker. Many bispecific antibody formats use one or more linkers, for example, to fuse an antibody core (IgA, IgD, IgE, IgG or IgM) to a binding domain (e.g. scFv) or to fuse two or more Fab fragments or scFvs. In some embodiments, the Fc domain, and hence Fc effector functions, are retained. In other embodiments, the Fc domain is not retained.

In one embodiment, the binding molecule includes an asymmetric IgG-like structure with two heavy and two light chains that form a "Y" shaped molecule, wherein a first "arm" of the antibody specifically binds a first antigen and the second "arm" of the antibody binds a second antigen.

In one embodiment, the binding molecule includes one or more antibody fragments, such as single-chain antibodies, that include one or more heavy chain variable regions (VH) alone or in combination with none, some or all of the following: hinge region (H), CH1, CH2, and CH3 domains and/or one or more light chain variable regions (VL) alone or in combination with a CL domain.

In one embodiment, the bispecific antibody includes one or more single chain Fv (scFv). In one embodiment, the bispecific antibody includes two or more scFvs. In another embodiment, the bispecific antibody includes part or all of an immunoglobulin "base" structure, for example, an IgA, IgD, IgE, IgG or IgM structure that includes one or more Fv domains, for example, one or more heavy chains and one or more light chains, wherein one or more scFv are fused to the immunoglobulin "base" structure. In a more particular embodiment, the binding molecule includes an IgG structure that includes two heavy chains and two light chains, wherein one or more scFv are fused thereto.

In one embodiment, the format of the antibody may be any format disclosed herein. In another embodiment, the format is any one of Bis1, Bis2, Bis3, Bis4, or Bis5. In one embodiment, the Fv domain of the first binding domain includes a heavy chain (HC) having an amino terminus and a carboxy terminus and a light chain (LC) having an amino terminus and a carboxy terminus, and the second binding domain is covalently linked to the carboxy-terminus of the HC of the first binding domain using one or two linkers. In one embodiment, the Fv domain of the first binding domain includes a heavy chain (HC) having an amino terminus and a carboxy terminus and a light chain (LC) having an amino terminus and a carboxy terminus, and the second binding domain is covalently linked to the carboxy-terminus of the HC of the first binding domain using one linker. In one embodiment, the Fv domain of the first binding domain includes a heavy chain (HC) having an amino terminus and a carboxy terminus and a light chain (LC) having an amino terminus and a carboxy terminus, and the second binding domain is covalently linked to the carboxy-terminus of the HC of the first binding domain using two linkers. In one embodiment, the Fv domain of the first binding domain includes a heavy chain (HC) having an amino terminus and a carboxy terminus and a light chain (LC) having an amino terminus and a carboxy terminus, and the second binding domain is covalently linked to the amino-terminus of the HC of the first binding domain. In one embodiment, the Fv domain of the first binding domain includes a heavy chain (HC) having an amino terminus and a carboxy terminus and a light chain (LC) having an amino terminus and a carboxy terminus, and the second binding domain is covalently linked to the amino-terminus of the LC of the first binding domain. In another embodiment, the Fv domain of the first binding domain includes a heavy chain (HC) having an amino terminus and a carboxy terminus and a light chain (LC) having an amino terminus and a carboxy terminus, and the second binding domain is covalently intercalated along the polypeptide chain of the HC of the first binding domain.

In one embodiment, the binding molecule includes a bispecific antibody that includes an antibody heavy chain having the formula VH-CH1-H-CH2-CH3, wherein VH is a heavy chain variable domain, CH1 is a heavy chain constant region domain-1, H is a hinge region, CH2 is a heavy chain constant region domain-2, and CH3 is a heavy chain constant region domain-3. In one embodiment, the binding molecule is a bispecific antibody that includes an antibody light chain having the formula VL-CL, wherein VL is a variable light chain domain and CL is a light chain constant domain.

In one embodiment, the binding molecule includes an antibody heavy chain with an N-terminal domain, wherein the antibody heavy chain has the formula VH-CH1-H-CH2-CH3, wherein VH is a heavy chain variable domain, CH1 is a heavy chain constant region domain-1, H is a hinge region, CH2 is a heavy chain constant region domain-2, and CH3 is a heavy chain constant region domain-3 and an antibody light chain with an N-terminal domain, wherein the antibody light chain has the formula VL-CL, wherein VL is a variable light chain domain and CL is a light chain constant domain, and wherein one or more scFv molecules are covalently attached to one or more N-terminal domains of the antibody heavy chain or antibody light chain (FIG. 1).

In a more particular embodiment, the N-terminal domain of the antibody or fragment thereof includes one or more Fv domains and one or more scFv molecules are covalently attached to one or more Fv domains of the antibody or fragment thereof (FIG. 1). In a more particular embodiment, one or more scFv molecules are covalently attached to the N-terminal domain of one or more light chain variable domains (VL) of the antibody or fragment thereof. (FIG. 1) In a more particular embodiment, the binding molecule includes an antibody light chain having a formula scFv-L1-VL-CL, wherein scFv is an scFv molecule, L1 is a linker, VL is a light chain variable domain, VL is a light chain variable domain and CL is a light chain constant domain (FIG. 1).

In one embodiment, one or more scFv molecules are covalently attached to the N-terminal domain of one or more heavy chain variable domains (VH) of the antibody or fragment thereof (FIG. 1). In one embodiment, the heavy chain has a formula scFv-L1-VH-CH1-CH2-CH3, wherein scFv is an scFv molecule, L1 is a linker, VH is a heavy chain variable domain, CH1 is a heavy chain constant domain domain-1, CH2 is a heavy chain constant domain domain-2, and CH3 is a heavy chain constant domain domain-3 (FIG. 1).

In another embodiment, the binding molecule includes an antibody or fragment thereof having a C-terminal domain, wherein one or more scFv molecules are covalently attached to the C-terminal domain of the antibody or fragment thereof (FIG. 1). In one embodiment, the binding molecule includes a first and a second heavy chain with first and second C-terminal domains, respectively, wherein one or more scFv molecules are covalently attached to the C-terminal domain of the first heavy chain, the second heavy chain, or combinations thereof (FIG. 1). In one embodiment, one or more heavy chains have a formula VH-CH1-CH2-CH3, wherein VH is a heavy chain variable domain, CH1 is a heavy chain constant domain domain-1, CH2 is a heavy chain constant domain domain-2, and CH3 is a heavy chain constant domain domain-3 (FIG. 1). In one embodiment, one or more heavy chains have a formula VH-CH1-CH2-CH3-L1-scFv, wherein L1 is a linker and scFv is an scFv molecule (FIG. 1).

In another embodiment, the binding molecule includes an antibody or fragment thereof having a C-terminal domain, wherein one or more scFv molecules are covalently attached to the C-terminal domain of the antibody or fragment thereof (FIG. 1). In one embodiment, the binding molecule includes a first and a second heavy chain with first and second C-terminal domains, respectively, wherein one or more scFv molecules are covalently attached to the C-terminal domain of the first heavy chain, the second heavy chain, or combinations thereof (FIG. 1). In one embodiment, one or more heavy chains have a formula VH-CH1-CH2-CH3, wherein VH is a heavy chain variable domain, CH1 is a heavy chain constant domain domain-1, CH2 is a heavy chain constant domain domain-2, and CH3 is a heavy chain constant domain domain-3 (FIG. 1). In one embodiment, one or more heavy chains have a formula VH-CH1-CH2-CH3-L1-scFvL2, wherein L1 and L2 independently are linkers and scFv is an scFv molecule (FIG. 1).

In one embodiment, the binding molecule includes an antibody or fragment thereof having one or more heavy chain constant domains, wherein one or more scFv molecules are inserted between one or more heavy chain constant domains of one or more heavy chains (FIG. 1). In one embodiment, one or more heavy chains have a formula VH-CH1-CH2-CH3, wherein VH is a heavy chain variable domain, CH1 is a heavy chain constant domain domain-1, CH2 is a heavy chain constant domain domain-2, and CH3 is a heavy chain constant domain domain-3 (FIG. 1). In one embodiment, one or more heavy chains have a formula VH-CH1-L1-scFv-L2-CH2-CH3, wherein L1 and L2 independently are a linker and scFv is an scFv molecule (FIG. 1). In one embodiment, one or more heavy chains have a formula VH-CH1-CH2-L1-scFv-L2-CH3, wherein L1 and L2 independently are linkers and scFv is an scFv molecule.

In one embodiment, the binding molecule includes an immunoglobulin structure, for example, an IgG structure having one or more Fv domains. In one embodiment, the Fv domain includes a VH and a VL sequence having an amino acid sequence having at least 65%, 70%, 75%, 80%, 85%, 90%, 95% or 100% identity to a VH or VL sequence shown in Table 1. In another embodiment, the Fv domain includes a VH and a VL sequence having at least, 90%, 91%, 92%, 93%, 94%, 95%, 96%, 97%, 98%, 99% or 100% identity to a VH or VL sequence shown in Table 1. In one embodiment, the Fv domain includes a VH and a VL sequence having an amino acid sequence having at least 65%, 70%, 75%, 80%, 85%, 90%, 95% or 100% identity to a VH or VL sequence shown in Table 2. In another embodiment, the Fv domain includes a VH and a VL sequence having at least, 90%, 91%, 92%, 93%, 94%, 95%, 96%, 97%, 98%, 99% or 100% identity to a VH or VL sequence shown in Table 2.

In one embodiment, the binding molecule includes an immunoglobulin structure having one or more binding domains that include one or more, including, one, two, three, four, five, or six CDRs selected from HCDR1, HCDR2, HCDR3, LCDR1, LCDR2, LCDR3. In one embodiment, the binding molecule includes an immunoglobulin structure having one or more binding domains that include a set of six CDRs: HCDR1, HCDR2, HCDR3, LCDR1, LCDR2, LCDR3, wherein CDRs are selected from the HCDRs and LCDRs shown in Tables 4 through 6. In another embodiment, the binding molecule includes an immunoglobulin structure having one or more binding domains that include a set of six CDRs: HCDR1, HCDR2, HCDR3, LCDR1, LCDR2, LCDR3, wherein CDRs include an amino acids sequence that is at least 75%, 80%, 85%, 90%, 95% or 100% identical to an amino acid sequence of the HCDRs and LCDRs shown in Tables 4 through 6. In another embodiment, the binding molecule includes an immunoglobulin structure having one or more binding domains that include a set of six CDRs: HCDR1, HCDR2, HCDR3, LCDR1, LCDR2, LCDR3, wherein CDRs include an amino acid sequence that is at least 95%, 96%, 97%, 98%, 99% or 100% identical to an amino acid sequence of the HCDRs and LCDRs shown in Tables 4 through 6.

In one embodiment, the binding molecule includes one or more scFv having the formula VH-LS-VL or alternatively VL-LS-VH, where LS is a linker sequence. In one embodiment, the scFv includes a VH and a VL sequence having an amino acid sequence having at least 65%, 70%, 75%, 80%, 85%, 90%, 95% or 100% identity to a VH or VL sequence shown in Table 1. In another embodiment, the scFv includes a VH and a VL sequence having at least, 90%, 91%, 92%, 93%, 94%, 95%, 96%, 97%, 98%, 99% or 100% identity to a VH or VL sequence shown in Table 1. In one embodiment, the scFv includes a VH and a VL sequence having an amino acid sequence having at least 65%, 70%, 75%, 80%, 85%, 90%, 95% or 100% identity to a VH or VL sequence shown in Table 2. In another embodiment, the scFv includes a VH and a VL sequence having at least, 90%, 91%, 92%, 93%, 94%, 95%, 96%, 97%, 98%, 99% or 100% identity to a VH or VL sequence shown in Table 2.

In one embodiment, the binding molecule includes one or more scFv with one or more, including, one, two, three, four, five, or six CDRs selected from HCDR1, HCDR2, HCDR3, LCDR1, LCDR2, LCDR3. In one embodiment, the binding molecule includes one or more scFv with a set of six CDRs: HCDR1, HCDR2, HCDR3, LCDR1, LCDR2, LCDR3, wherein CDRs are selected from the HCDRs and LCDRs shown in Tables 4 through 6. In another embodiment, the binding molecule includes one or more scFv with a set of six CDRs: HCDR1, HCDR2, HCDR3, LCDR1, LCDR2, LCDR3, wherein CDRs include an amino acids sequence that is at least 75%, 80%, 85%, 90%, 95% or 100% identical to an amino acid sequence of the HCDRs and LCDRs shown in Tables 4 through 6. In another embodiment, the binding molecule includes one or more scFv with a set of six CDRs: HCDR1, HCDR2, HCDR3, LCDR1, LCDR2, LCDR3, wherein CDRs include an amino acid sequence that is at least 95%, 96%, 97%, 98%, 99% or 100% identical to an amino acid sequence of the HCDRs and LCDRs shown in Tables 4 through 6.

In one embodiment, the linker LS has an amino acid sequence of: (a) [GGGGS]n, wherein n is 0, 1, 2, 3, 4, or 5 (SEQ ID NO: 93), (b) [GGGG]n, wherein n is 0, 1, 2, 3, 4, or 5, (SEQ ID NO: 106) or a combination of (a) and (b). For example, an exemplary linker includes: GGGGSGGGGSGGGGSGGGGS (SEQ ID NO:92). In one embodiment, the scFv is fused to an immunoglobulin structure, for example, an IgG structure via a linker (L1 or L2) having an amino acid sequence of: (a) [GGGGS]n, wherein n is 0, 1, 2, 3, 4, or 5 (SEQ ID NO: 93), (b) [GGGG]n, wherein n is 0, 1, 2, 3, 4, or 5, (SEQ ID NO: 106) or a combination of (a) and (b), including for example, an amino acid sequence of GGGGSGGGGSGGGGSGGGGS (SEQ ID NO:92).

In a more particular embodiment, the binding molecule includes an immunoglobulin structure, for example, an IgG structure having one or more Fv domains that include a VH and a VL sequence having an amino acid sequence having at least 65%, 70%, 75%, 80%, 85%, 90%, 95% or 100% identity to a VH or VL sequence shown in Table 1 or a VH and a VL sequence having at least, 90%, 91%, 92%, 93%, 94%, 95%, 96%, 97%, 98%, 99% or 100% identity to a VH or VL sequence shown in Table 1. In one embodiment, one or more scFv having the formula VH-LS-VL or alternatively VL-LS-VH, where LS is a linker sequence are fused to the immunoglobulin structure and the scFv includes a VH and a VL sequence having an amino acid sequence having at least 65%, 70%, 75%, 80%, 85%, 90%, 95% or 100% identity to a VH or VL sequence shown in Table 2. In another embodiment, the scFv includes a VH and a VL sequence having at least, 90%, 91%, 92%, 93%, 94%, 95%, 96%, 97%, 98%, 99% or 100% identity to a VH or VL sequence shown in Table 2. In one embodiment, the linker LS has an amino acid sequence of: (a) [GGGGS]n, wherein n is 0, 1, 2, 3, 4, or 5 (SEQ ID NO: 93), (b) [GGGG]n, wherein n is 0, 1, 2, 3, 4, or 5, (SEQ ID NO: 106) or a combination of (a) and (b). For example, an exemplary linker includes: GGGGSGGGGSGGGGSGGGGS (SEQ ID NO:92). In one embodiment, the scFv is fused to an immunoglobulin structure, for example, an IgG structure via a linker (L1 or L2) having an amino acid sequence of: (a) [GGGGS]n, wherein n is 0, 1, 2, 3, 4, or 5 (SEQ ID NO: 93), (b) [GGGG]n, wherein n is 0, 1, 2, 3, 4, or 5, (SEQ ID NO: 106) or a combination of (a) and (b), including for example, an amino acid sequence of GGGGSGGGGSGGGGSGGGGS (SEQ ID NO:92).

In one embodiment, the first binding domain of the binding molecule includes an anti-influenza A virus antibody or antigen-binding fragment thereof. In one embodiment, the second binding domain of the binding molecule includes an anti-influenza B virus antibody or antigen-binding fragment thereof. In one embodiment, the first binding domain includes an anti-influenza A virus Fv domain. In a more particular embodiment, the binding molecule includes a variable fragment (Fv) domain having an antibody heavy chain variable domain and an antibody light chain variable domain, wherein the Fv specifically binds anti-influenza A virus. In one embodiment, the binding molecule includes one or more binding domains that include an anti-influenza B virus scFv molecule. In one embodiment, the binding molecule includes a first binding domain that includes an anti-influenza A virus Fv domain and a second binding domain that includes an anti-influenza B virus scFv molecule.

In one embodiment, the binding molecule includes a light chain with an amino acid sequence that is at least 75%, 80%, 85%, 90%, 95%, 96%, 97%, 98% or 99% identical to an amino acid sequence of SEQ ID NO:66 or SEQ ID NO:68. In one embodiment, the binding molecule includes a light chain with an amino acid sequence of SEQ ID NO:66 or SEQ ID NO:68.

In one embodiment, the binding molecule is a bispecific antibody which specifically binds to influenza A virus and influenza B virus, having a heavy chain with an amino acid sequence that is at least 75%, 80%, 85%, 90%, 95%, 96%, 97%, 98% or 99% identical to an amino acid sequence of SEQ ID NO:67 or SEQ ID NO:69. In one embodiment, the binding molecule is a bispecific antibody which specifically binds to influenza A virus and influenza B virus, having a heavy chain with an amino acid sequence of SEQ ID NO:67 or SEQ ID NO:69.

In one embodiment, the binding molecule includes a light chain with an amino acid sequence that is at least 75%, 80%, 85%, 90%, 95%, 96%, 97%, 98% or 99% identical to an amino acid sequence of SEQ ID NO:66 or SEQ ID NO:68. In one embodiment, the binding molecule includes a heavy chain with an amino acid sequence that is at least 75%, 80%, 85%, 90%, 95%, 96%, 97%, 98% or 99% identical to an amino acid sequence of SEQ ID NO:67 or SEQ ID NO:69. In one embodiment, the binding molecule is a bispecific antibody which specifically binds to influenza A virus and influenza B virus, which includes a light chain with an amino acid sequence that is at least 75%, 80%, 85%, 90%, 95%, 96%, 97%, 98% or 99% identical to an amino acid sequence of SEQ ID NO:66 or SEQ ID NO:68 and a heavy chain with an amino acid sequence that is at least 75%, 80%, 85%, 90%, 95%, 96%, 97%, 98% or 99% identical to an amino acid sequence of SEQ ID NO:67 or SEQ ID NO:69.

In one embodiment, the binding molecule is a bispecific antibody which specifically binds to influenza A virus and influenza B virus, which includes a light chain with an amino acid sequence of SEQ ID NO:66 or SEQ ID NO:68 and a heavy chain with an amino acid sequence of SEQ ID NO:67 or SEQ ID NO:69. In one embodiment, the binding molecule is a bispecific antibody having a light chain with an amino acid sequence of SEQ ID NO:66 and a heavy chain with an amino acid sequence of SEQ ID NO:67. In one embodiment, the binding molecule is a bispecific antibody having a light chain with an amino acid sequence of SEQ ID NO:68 and a heavy chain with an amino acid sequence of SEQ ID NO:69

In one embodiment, the scFv molecule includes a VH domain having a set of three CDRs: HCDR1, HCDR2, HCDR3, in which the set of three CDRs include an amino acid sequence that is at least 75%, 80%, 85%, 90%, 95% or 100% identical to an amino acid sequence of the HCDRs shown in Tables 5 and 6. In another embodiment, the binding molecule includes a VH domain having a set of three CDRs: HCDR1, HCDR2, HCDR3, wherein the set of three CDRs include an amino acid sequence that is at least 95%, 96%, 97%, 98%, 99% or 100% identical to an amino acid sequence of the HCDRs shown in Tables 5 and 6.

In one embodiment, the scFv molecule includes a VL domain having a set of three CDRs: LCDR1, LCDR2, LCDR3, in which the set of three CDRs include an amino acid sequence that is at least 75%, 80%, 85%, 90%, 95% or 100% identical to an amino acid sequence of the LCDRs shown in Tables 5 and 6. In another embodiment, the binding molecule includes a VL domain having a set of three CDRs: LCDR1, LCDR2, LCDR3, wherein the set of three CDRs include an amino acid sequence that is at least 95%, 96%, 97%, 98%, 99% or 100% identical to an amino acid sequence of the LCDRs shown in Tables 5 and 6.

In a more particular embodiment, the binding molecule includes one or more scFv having an amino acid sequence that is at least 75%, 80%, 85%, 90%, 95%, 96%, 97%, 98%, or 99% identical to an amino acid sequence shown in SEQ ID NO:31, SEQ ID NO:34, SEQ ID NO:47, SEQ ID NO:50, and SEQ ID NO:63. In one embodiment, the binding molecule includes one or more scFv having an amino acid sequence shown in SEQ ID NO:31, SEQ ID NO:34, SEQ ID NO:47, SEQ ID NO:50, and SEQ ID NO:63.

Influenza A Binding Domain

In one embodiment, the binding molecule includes one or more binding domains that immunospecifically bind at least one specified epitope of the influenza A virus. As used herein, the terms "binding domain" or "antigen binding domain" includes a site that specifically binds an epitope on an antigen. The antigen binding domain of an antibody typically includes at least a portion of an immunoglobulin heavy chain variable region and at least a portion of an immunoglobulin light chain variable region, wherein the binding site formed by these variable regions determines the specificity of the antibody.

In a more particular embodiment, the binding molecule includes one or more binding domains that immunospecifically bind at least one specified epitope of the influenza A virus HA protein. The term "epitope" as used herein refers to a protein determinant capable of binding to an antibody. Epitopes usually include chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In one embodiment, the antibody or antigen binding fragment thereof binds to an epitope that is conserved among at least 1, 2, 3, 4, 5, 6, 7, 8, 9, 10, 11, 12, 13, 14, 15, 16, 17 or all influenza A subtypes. In another embodiment, the antibody or antigen binding fragment thereof binds to an epitope that is conserved among one or more, or at least 1, 2, 3, 4, 5, 6, 7, 8, 9, or 10 influenza A virus group 1 subtypes selected from H1, H2, H5, H6, H8, H9, H11, H12, H13, H16, H17, and H18 and one or more, or at least 1, 2, 3, 4, 5, or 6 group 2 subtypes selected from H3, H4, H7, H10, H14 and H15.

In one embodiment, the antibody or antigen binding fragment thereof binds at least 1, 2, 3, 4, 5, 6, 7, 8, 9, 10, 11, 12, 13, 14, 15, 16, or 17 or all influenza A subtypes with an $EC_{50}$ of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml. In another embodiment, the antibody or antigen binding fragment thereof binds one or more, or at least 1, 2, 3, 4, 5, 6, 7, 8, 9, or 10 influenza A virus group 1 subtypes selected from H1, H2, H5, H6, H8, H9, H11, H12, H13, H16, H17, and H18 and one or more, or at least 1, 2, 3, 4, 5, or 6 group 2 subtypes selected from H3, H4, H7, H10, H14 and H15 with an $EC_{50}$ of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml.

In one embodiment, the antibody or antigen binding fragment thereof recognizes an epitope that is either a linear epitope, or continuous epitope. In another embodiment, the antibody or antigen binding fragment thereof recognizes a non-linear or conformational epitope. In one embodiment, the epitope is located in the highly conserved stalk region of HA2. In a more particular embodiment, the antibody or antigen binding fragment binds to a conformational epitope in the highly conserved stalk region of HA2. (Wilson et al. (1981) Nature. 289:366-373). In one embodiment, the epitope includes one or more amino acids selected from: 18, 19, 42, 45, 156, and 196 in the stalk region of HA2 as contact residues. In a more particular embodiment, the epitope includes one or more amino acids selected from 18, 19, 42 and 45 in the stalk region of HA2 as contact residues. In a further embodiment, the epitope includes amino acids 18, 19, 42 and 45 in the stalk region of HA2 as contact residues.

In yet a further embodiment, the epitope includes amino acids 18, 19, and 42 in the stalk region of HA2 as contact residues.

Influenza B Binding Domain

In one embodiment, the binding molecule includes one or more binding domains that immunospecifically bind at least one specified epitope of the influenza B virus. In a more particular embodiment, the binding molecule includes one or more binding domains that immunospecifically bind at least one specified epitope of the influenza B virus HA protein. In one embodiment, the binding molecule includes one or more binding domains that specifically bind to an epitope present on at least two phylogenetically distinct influenza B lineages. In a more particular embodiment, the binding molecule includes one or more binding domains that bind to an epitope present in at least one influenza B Yamagata strain and at least one influenza B Victoria strain. In one embodiment, the binding molecule includes one or more binding domains that bind to an epitope that is present in influenza B virus of both Yamagata lineage and Victoria lineage. In one embodiment, the binding member includes one or more binding domains that bind to an epitope that is conserved among influenza B of both Yamagata lineage and Victoria lineage.

In one embodiment, the binding molecule includes one or more binding domains that bind to at least one influenza B Yamagata strain and at least one influenza B Victoria strain with a half maximal effective concentration ($EC_{50}$) of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml, 50 ng/ml, 40 ng/ml, 30 ng/ml, 20 ng/ml, or 15 pg/ml. In another embodiment, the binding molecule includes one or more binding domains that bind to influenza B virus of Yamagata and Victoria lineage with an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml, 50 ng/ml, 40 ng/ml, 30 ng/ml, 20 ng/ml, or 15 µg/ml. In one embodiment, the binding molecule includes one or more binding domains that bind to an epitope present in influenza B virus of both Yamagata lineage and Victoria lineage with an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml, 50 ng/ml, 40 ng/ml, 30 ng/ml, 20 ng/ml, or 15 µg/ml.

In one embodiment, the binding molecule includes one or more binding domains that bind to: an epitope present on influenza B Yamagata lineage at an $EC_{50}$ of between about 1 ng/ml and about 100 ng/ml, 1 ng/ml and about 50 ng/ml, or between about 1 ng/ml and about 25 ng/ml, or less than about 50 ng/ml or 25 ng/ml; and an epitope present on influenza B Victoria lineage at an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml or 50 ng/ml.

In another embodiment, the binding molecule includes one or more binding domains that bind to: an epitope present on influenza B Yamamoto lineage at an $EC_{50}$ of between about 1 ng/ml and about 100 ng/ml, 1 ng/ml and about 50 ng/ml, or between about 1 ng/ml and about 25 ng/ml, or less than about 50 ng/ml or 25 ng/ml; an epitope present on influenza B Victoria lineage at an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml or 100 ng/ml; and an epitope on influenza A HA with an $EC_{50}$ of between about 1 µg/ml and about 50 µg/ml, or less than about 50 µg/ml, 25 µg/ml, 15 µg/ml or 10 µg/ml. In another embodiment, the binding molecule includes one or more binding domains that bind to: an epitope present on influenza B Yamagata lineage at an $EC_{50}$ of between about 1 ng/ml and about 100 ng/ml, 1 ng/ml and about 50 ng/ml, or between about 1 ng/ml and about 25 ng/ml, or less than about 50 ng/ml or 25 ng/ml; an epitope present on influenza B Victoria lineage at an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml or 100 ng/ml; and an epitope on influenza A H9 HA with an $EC_{50}$ of between about 1 µg/ml and about 50 µg/ml, or less than about 50 µg/ml, 25 µg/ml, 15 µg/ml or 10 µg/ml.

In one embodiment, the binding molecule includes one or more binding domains that recognize an epitope that is either a linear epitope, or continuous epitope. In another embodiment, the binding molecule includes one or more binding domains that recognize a non-linear or conformational epitope. In one embodiment, the epitope is located on the hemagglutinin (HA) glycoprotein of influenza B. In a more particular embodiment, the epitope is located on the head region of the HA glycoprotein of influenza B. In one embodiment, the epitope includes one or more amino acids at positions 128, 141, 150 or 235 in the head region of influenza B HA as contact residues, which are numbered according to the H3 numbering system as described in Wang et al. (2008) J. Virol. 82(6):3011-20. In one embodiment, the epitope includes amino acid 128 of the sequence of the head region of influenza B HA as a contact residue. In another embodiment, the epitope includes amino acids 141, 150 and 235 of the sequence of the head region of influenza B HA as contact residues.

Cross Reactivity

In one embodiment, the binding molecule can be described or specified in terms of the epitope(s) or portion(s) of an antigen that the binding molecule recognizes or specifically binds. The portion of a target molecule which specifically interacts with the antigen binding domain of an antibody is referred to as an "epitope," or an "antigenic determinant." A target antigen can include any number of epitopes, depending on the size, conformation, and type of antigen. In one embodiment, the binding molecule specifically binds to the same epitope as one or more of the antibodies described herein, and/or will competitively inhibit an antibody described herein from binding to the epitope.

In one embodiment, one or more binding domains of the binding molecule display cross-reactivity with influenza A virus and influenza B virus. As used herein, the term "cross-reactivity" refers to the ability of a binding domain of a binding molecule that is specific for one antigen, to react with a second antigen. Thus, a binding molecule is cross reactive if it binds to an epitope other than the one that induced its formation.

Fc Region

In one embodiment, the binding molecule is an antibody that is modified in the Fc region to provide desired effector functions or serum half-life. In one embodiment, the Fc region can induce cytotoxicity, for example, via antibody-dependent cellular cytotoxicity (ADCC) or by recruiting complement in complement dependent cytotoxicity (CDC), or by recruiting nonspecific cytotoxic cells that express one or more effector ligands that recognize bound antibody on the influenza A and/or influenza B virus and subsequently cause phagocytosis of the cell in antibody dependent cell-mediated phagocytosis (ADCP), or some other mechanism. In other embodiments, it may be desirable to eliminate or reduce effector function, so as to minimize side effects or therapeutic complications. Methods for enhancing as well as reducing or eliminating Fc-effector function are known. In other embodiments, the Fc region can be modified to increase the binding affinity for FcRn and thus increase serum half-life. In still other embodiments, the Fc region can be conjugated to PEG or albumin to increase the serum half-life. Fc variants are described more fully in U.S. Provisional Application Nos. 61/885,808, filed Oct. 2, 2013, 62/002,414, filed May 23, 2014, and 62/024,804, filed Jul. 15, 2014, the disclosures of which are hereby incorporated by reference herein in their entirety Binding Characteristics As described above, the binding molecules described herein immunospecifically bind at least one specified epitope or antigenic determinant of influenza A virus and/or influenza B virus protein, peptide, subunit, fragment, portion or any combination thereof either exclusively or preferentially with respect to other polypeptides. The term "epitope" or "antigenic determinant" as used herein refers to a protein determinant capable of binding to an antibody. In one embodiment, the term "binding" herein relates to specific binding. These protein determinants or epitopes usually include chemically active surface groupings of molecules such as amino acids or sugar side chains and usually have a specific three dimensional structural characteristics, as well as specific charge characteristics. Conformational and non-conformational epitopes are distinguished in that the binding to the former but not the latter is lost in the presence of denaturing solvents. The term "discontinuous epitope" as used herein, refers to a conformational epitope on a protein antigen which is formed from at least two separate regions in the primary sequence of the protein.

The interactions between antigens and antibodies are the same as for other non-covalent protein-protein interactions. In general, four types of binding interactions exist between antigens and antibodies: (i) hydrogen bonds, (ii) dispersion forces, (iii) electrostatic forces between Lewis acids and Lewis bases, and (iv) hydrophobic interactions. Hydrophobic interactions are a major driving force for the antibody-antigen interaction, and are based on repulsion of water by non-polar groups rather than attraction of molecules (Tanford, (1978) Science. 200:1012-8). However, certain physical forces also contribute to antigen-antibody binding, for example, the fit or complimentary of epitope shapes with different antibody binding sites. Moreover, other materials and antigens may cross-react with an antibody, thereby competing for available free antibody.

Measurement of the affinity constant and specificity of binding between antigen and antibody can assist in determining the efficacy of prophylactic, therapeutic, diagnostic and research methods using binding molecules described herein. "Binding affinity" generally refers to the strength of the sum total of the noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant (Kd), which is calculated as the ratio $k_{off}/k_{on}$. See, e.g., Chen et al. (1999) J. Mol Biol. 293:865-881. Low-affinity antibodies generally bind antigen slowly and tend to dissociate readily, whereas high-affinity antibodies generally bind antigen faster and tend to remain bound longer. A variety of methods of measuring binding affinity are known in the art.

In one embodiment, a binding molecule includes one or more amino acid alterations, for example, one or more substitutions, deletion and/or additions, introduced in one or more of the variable regions of the antibody. In another embodiment, the amino acid alterations are introduced in the framework regions. One or more alterations of framework region residues may result in an improvement in the binding affinity of the binding molecule for the antigen. In one embodiment, from about one to about five framework residues may be altered.

One method for determining binding affinity includes measuring the disassociation constant "Kd" by a radiolabeled antigen binding assay (RIA) performed with the Fab version of an antibody of interest and its antigen as described by Chen et al. (1999) J. Mol Biol. 293:865-881. Alternately, the Kd value may be measured by using surface plasmon resonance assays using a BIAcore™-2000 or a BIAcore™-3000 (BIAcore, Inc., Piscataway, New Jersey). If the on-rate exceeds $10^6 M^{-1} S^{-1}$ by the surface plasmon resonance assay, then the on-rate can be determined by using a fluorescent quenching technique that measures the increase or decrease in fluorescence emission intensity in the presence of increasing concentrations of antigen. An "on-rate" or "rate of association" or "association rate" or "$k_{on}$" can also be determined with the same surface plasmon resonance technique described above.

Methods and reagents suitable for determination of binding characteristics of a binding molecule are known in the art and/or are commercially available (U.S. Pat. Nos. 6,849,425; 6,632,926; 6,294,391; 6,143,574). Moreover, equipment and software designed for such kinetic analyses are commercially available (e.g. Biacore® A100, and Biacore® 2000 instruments; Biacore International AB, Uppsala, Sweden).

In one embodiment, binding molecules, including antigen binding fragments or variants thereof, may be described or specified in terms of their binding affinity for influenza A virus; influenza B virus; or a combination thereof. Typically, antibodies with high affinity have Kd of less than $10^{-7}$ M. In one embodiment, the binding molecule or antigen binding fragments thereof bind influenza A virus; influenza B virus; fragments or variants thereof; or a combination thereof, with a dissociation constant or Kd of less than or equal to $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M or $10^{-15}$ M. In a more particular embodiment, the binding molecule or antigen binding fragments thereof bind influenza A virus; influenza B virus, fragments or variants thereof; or combinations thereof, with a dissociation constant or Kd of less than or equal to $5 \times 10^{-10}$ M, $10^{-10}$ M, $5 \times 10^{-11}$ M, $10^{-11}$ M, $5 \times 10^{-12}$ M or $10^{-12}$ M. The invention encompasses binding molecules or antigen binding fragments thereof that bind influenza A virus; influenza B virus; or a combination thereof, with a dissociation constant or Kd that is within a range between any of the individual recited values.

In another embodiment, the binding molecule or antigen binding fragments thereof bind influenza A virus; influenza B virus; fragments or variants thereof; or combinations thereof, with an off rate ($k_{off}$) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$, $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, 5×10$^{-7}$ secs or 10$^{-7}$ sec$^{-1}$. In a more particular embodiment, the binding molecule or antigen binding fragments thereof bind influenza A polypeptides or fragments or variants thereof with an off rate (k$_{off}$) less than or equal to 5×10$^{-4}$ sec$^{-1}$, 10$^{-4}$ sec$^{-1}$, 5×10$^{-5}$ sec$^{-1}$, or 10$^{-5}$ sec$^{-1}$, 5×10$^{-6}$ sec$^{-1}$, 10$^{-6}$ sec$^{-1}$, 5×10$^{-7}$ sec$^{-1}$ or 10$^{-7}$ sec$^{-1}$. The invention also encompasses binding molecules or antigen binding fragments thereof that bind influenza A virus; influenza B virus; or combinations thereof, with an off rate (k$_{off}$) that is within a range between any of the individual recited values.

In another embodiment, the binding molecule or antigen binding fragment thereof bind influenza A virus; influenza B virus; fragments or variants thereof; or combinations thereof, with an on rate (k$_{on}$) of greater than or equal to 10$^3$ M$^{-1}$ sec$^{-1}$, 5×10$^3$ M$^{-1}$ sec$^{-1}$, 10$^4$ M$^{-1}$ sec$^{-1}$, 5×10$^4$ M$^{-1}$ sec$^{-1}$, 10$^5$ M$^{-1}$ sec$^{-1}$, 5×10$^5$ M$^{-1}$ sec$^{-1}$, 10$^6$ M$^{-1}$ sec-1, 5×10$^6$ M$^{-1}$ sec$^{-1}$, 10$^7$ M$^{-1}$ sec-1, or 5×10$^7$ M$^{-1}$ sec$^{-1}$. In a more particular embodiment, the binding molecule or antigen binding fragments thereof bind influenza A virus; influenza B virus; fragments or variants thereof; or combinations thereof, with an on rate (k$_{on}$) greater than or equal to 10$^5$ M$^{-1}$ sec$^{-1}$, 5×10$^5$ M$^{-1}$ sec$^{-1}$, 10$^6$ M$^{-1}$ sec-1, 5×10$^6$ M$^{-1}$ sec$^{-1}$, 10$^7$ M$^{-1}$ sec$^{-1}$ or 5×10$^7$ M$^{-1}$ sec$^{-1}$. The invention encompasses antibodies that bind influenza A virus; influenza B virus; or combinations thereof, with on rate (k$_{on}$) that is within a range between any of the individual recited values.

In one embodiment, a binding assay may be performed either as a direct binding assay or as a competition-binding assay. Binding can be detected using standard ELISA or standard Flow Cytometry assays. In a direct binding assay, a candidate binding molecule or antibody is tested for binding to its cognate antigen. A competition-binding assay, on the other hand, assess the ability of a candidate binding molecule or antibody to compete with a known antibody or other compound that binds to a particular antigen, for example, influenza A virus HA or influenza B virus HA. In general any method that permits the binding of the binding molecule with influenza A virus HA and/or influenza B virus HA that can be detected can be used to detect and measure binding characteristics of the binding molecules disclosed herein.

In one embodiment, the binding molecule is capable of immunospecifically binding to influenza A virus HA and/or influenza B virus HA and is capable of neutralizing influenza A virus and/or influenza B virus infection.

In one embodiment, at least one binding domain of the binding molecule is capable of immunospecifically binding to influenza A virus HA and is capable of neutralizing influenza A virus infection. The hemagglutinin subtypes of influenza A viruses fall into two major phylogenetic groupings, identified as group 1, which includes subtypes H1, H2, H5, H6, H8, H9, H11, H12, H13, H16 H17, and H18 and group 2, which includes subtypes H3, H4, H7, H10, H14, and H15. In one embodiment, at least one binding domain of the binding molecule or binding fragment thereof is capable of binding to and/or neutralizing one or more influenza A virus group 1 subtypes selected from H1, H2, H5, H6, H8, H9, H11, H12, H13, H16, H17, and H18 and variants thereof. In another embodiment, at least one binding domain of the binding molecule or binding fragment thereof is capable of binding to and/or neutralizing one or more influenza A virus group 2 subtypes selected from H3, H4, H7, H10, H14 and H15 and variants thereof. In one embodiment, the binding molecule includes one or more binding domains that are capable of immunospecifically binding to influenza A virus group 1 subtype H9. In one embodiment, the binding molecule includes one or more binding domains that are capable of immunospecifically binding to and neutralizing influenza A virus group 1 subtype H9.

In one embodiment, at least one binding domain of the binding molecule is capable of immunospecifically binding to and neutralizing at least one Yamagata lineage influenza B virus and at least one Victoria lineage influenza B virus. In another embodiment, at least one binding domain of the binding molecule immunospecifically binds and neutralizes both Yamagata lineage and Victoria lineage influenza B virus.

In one embodiment, at least one binding domain of the binding molecule or antigen binding fragment thereof is capable of immunospecifically binding to both influenza A virus HA and influenza B virus HA and neutralizing both influenza A virus infection and influenza B virus infection. Neutralization assays can be performed using methods known in the art. The term "inhibitory concentration 50%" (abbreviated as "IC$_{50}$") represents the concentration of an inhibitor (e.g., an binding molecule describe herein) that is required for 50% neutralization of influenza A virus and/or influenza B virus. It will be understood by one of ordinary skill in the art that a lower IC$_{50}$ value corresponds to a more potent inhibitor.

In one embodiment, the binding molecule or binding fragment thereof has an IC$_{50}$ for neutralizing influenza A virus and/or influenza B virus in the range of from about 0.001 μg/ml to about 5 μg/ml, or in the range of from about 0.001 μg/ml to about 1 μg/ml of antibody, or less than 5 μg/ml, less than 2 μg/ml, less than 1 μg/ml, less than 0.5 μg/ml, less than 0.1 μg/ml, less than 0.05 μg/ml or less than 0.01 μg/ml in a microneutralization assay.

In one embodiment, the binding molecule or binding fragment thereof has a first binding domain with an IC$_{50}$ for neutralizing influenza A virus in the range of from about 0.001 μg/ml to about 5 μg/ml, or in the range of from about 0.001 μg/ml to about 1 μg/ml of antibody, or less than 5 μg/ml, less than 2 μg/ml, less than 1 μg/ml, less than 0.5 μg/ml, less than 0.1 μg/ml, less than 0.05 μg/ml or less than 0.01 μg/ml in a microneutralization assay. In one embodiment, the binding molecule or binding fragment thereof has a second binding domain with an IC$_{50}$ for neutralizing influenza B virus in the range of from about 0.001 μg/ml to about 50 μg/ml, or in the range of from about 0.001 μg/ml to about 5 μg/ml of antibody, or in the range of from about 0.001 μg/ml to about 1 μg/ml of antibody, or less than 10 μg/ml, less than 5 μg/ml, less than 1 μg/ml, less than 0.5 μg/ml, less than 0.1 μg/ml, less than 0.05 μg/ml or less than 0.01 μg/ml in a microneutralization assay.

In one embodiment, the binding molecule has a binding domain or binding fragment thereof with an IC$_{50}$ for neutralizing influenza B virus in the range of from about 0.001 μg/ml to about 5 μg/ml, or in the range of from about 0.001 μg/ml to about 1 μg/ml of antibody, or less than 5 μg/ml, less than 2 μg/ml, less than 1 μg/ml, less than 0.5 μg/ml, less than 0.1 μg/ml, less than 0.05 μg/ml or less than 0.01 μg/ml in a microneutralization assay; and an IC$_{50}$ for neutralizing influenza A virus in the range of from about 0.1 μg/ml to about 5 μg/ml, or in the range of from about 0.1 μg/ml to about 2 μg/ml of antibody, or less than 5 μg/ml, less than 2 μg/ml, less than 1 μg/ml, or less than 0.5 μg/ml for neutralization of influenza A virus in a microneutralization assay.

In certain embodiments, the binding molecules described herein may induce cell death. An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue (see, Moore et al. (1995) Cytotechnology 17:1-11), 7AAD or other methods well known in the art can be assessed relative to untreated cells.

In one embodiment, the binding molecule may induce cell death via apoptosis. A binding molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. In one embodiment, the antibody which induces apoptosis is one which results in about 2 to 50 fold, in one embodiment about 5 to 50 fold, and in one embodiment about 10 to 50 fold, induction of annexin binding relative to untreated cell in an annexin binding assay.

In another embodiment, the binding molecules described herein may induce cell death via antibody-dependent cellular cytotoxicity (ADCC) and/or complement-dependent cell-mediated cytotoxicity (CDC) and/or antibody dependent cell-mediated phagocytosis (ADCP). Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (Greenwood et al. (1993) Eur. J. Immunol. 23(5):1098-104; Morgan et al. (1995) Immunology. 86(2):319-324; Clark, M. (1997) Chemical Immunology. 65:88-110) and that a sugar chain in the Cγ2 domain (Clark, M. (1997) Chemical Immunology. 65:88-110) is also important.

To assess ADCC activity, an in vitro ADCC assay can be used, such as that described in U.S. Pat. No. 5,500,362. The assay may also be performed using a commercially available kit, e.g. CytoTox 96 ® (Promega). Useful effector cells for such assays include, but are not limited to peripheral blood mononuclear cells (PBMC), Natural Killer (NK) cells, and NK cell lines. NK cell lines expressing a transgenic Fc receptor (e.g. CD16) and associated signaling polypeptide (e.g. FC$_\varepsilon$RI-γ) may also serve as effector cells (WO 2006/023148). In one embodiment, the NK cell line includes CD16 and has luciferase under the NFAT promoter and can be used to measure NK cell activation, rather than cell lysis or cell death. A similar technology is sold by Promega, which uses Jurkat cells instead of NK cells (Promega ADCC reporter bioassay #G7010). For example, the ability of any particular antibody to mediate lysis by complement activation and/or ADCC can be assayed. The cells of interest are grown and labeled in vitro; the binding molecule is added to the cell culture in combination with immune cells which may be activated by the antigen antibody complexes; i.e., effector cells involved in the ADCC response. The binding molecule can also be tested for complement activation. In either case, cytolysis is detected by the release of label from the lysed cells. The extent of cell lysis may also be determined by detecting the release of cytoplasmic proteins (e.g. LDH) into the supernatant. In fact, antibodies can be screened using the patient's own serum as a source of complement and/or immune cells. Binding molecules that are capable of mediating human ADCC in the in vitro test can then be used therapeutically in that particular patient. ADCC activity of the binding molecule may also be assessed in vivo, e.g., in an animal model such as that disclosed in Clynes et al. (1998) Proc. Natl. Acad. Sci. USA 95:652-656. Moreover, techniques for modulating (i.e., increasing or decreasing) the level of ADCC, and optionally CDC activity, of an antibody are well-known in the art (e.g., U.S. Pat. Nos. 5,624,821; 6,194,551; 7,317,091). Binding molecules described herein may be capable or may have been modified to have the ability of inducing ADCC and/or CDC. Assays to determine ADCC function can be practiced using human effector cells to assess human ADCC function. Such assays may also include those intended to screen for antibodies that induce, mediate, enhance, block cell death by necrotic and/or apoptotic mechanisms. Such methods including assays utilizing viable dyes, methods of detecting and analyzing caspases, and assays measuring DNA breaks can be used to assess the apoptotic activity of cells cultured in vitro with an antibody of interest.

Polynucleotides

Also provided herein are nucleotide sequences corresponding to the amino acid sequences and encoding the binding molecules described herein. In one embodiment, the invention provides polynucleotides that include a nucleotide sequence encoding a binding molecule described herein or fragments thereof, including, for example, polynucleotide sequences encoding VH and VL regions including CDRs and FRs as well as expression vectors for efficient expression in cells (e.g. mammalian cells). Methods of making the binding molecules using polynucleotides are known and are described briefly below.

Also included are polynucleotides that hybridize under stringent or lower stringency hybridization conditions, e.g., as defined herein, to polynucleotides that encode a binding molecule described herein or fragment thereof. The term "stringency" as used herein refers to experimental conditions (e.g. temperature and salt concentration) of a hybridization experiment to denote the degree of homology between the probe and the filter bound nucleic acid; the higher the stringency, the higher percent homology between the probe and filter bound nucleic acid.

Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 65° C., or any other stringent hybridization conditions known to those skilled in the art (see, for example, Ausubel et al., eds. (1989) Current Protocols in Molecular Biology, vol. 1, Green Publishing Associates, Inc. and John Wiley and Sons, Inc., NY at pages 6.3.1 to 6.3.6 and 2.10.3).

Substantially identical sequences include polymorphic sequences, i.e., alternative sequences or alleles in a population. An allelic difference may be as small as one base pair. Substantially identical sequences may also include mutagenized sequences, including sequences having silent mutations. A mutation may include one or more residue changes, a deletion of one or more residues, or an insertion of one or more additional residues.

The polynucleotides may be obtained, and the nucleotide sequence of the polynucleotides determined, by any method known in the art. For example, if the nucleotide sequence of the binding molecule is known, a polynucleotide encoding the binding molecule may be assembled from chemically synthesized oligonucleotides (e.g., as described in Kutmeier et al. (1994) BioTechniques. 17:242), which, briefly, involves the synthesis of overlapping oligonucleotides containing portions of the sequence encoding the binding molecule, annealing and ligating of those oligonucleotides, and then amplification of the ligated oligonucleotides by PCR.

A polynucleotide encoding a binding molecule may also be generated from nucleic acid from a suitable source. If a clone containing a nucleic acid encoding a particular binding molecule is not available, but the sequence of the binding molecule is known, a nucleic acid encoding the immunoglobulin may be chemically synthesized or obtained from a suitable source (e.g., an antibody cDNA library, or a cDNA library generated from, or nucleic acid, in one embodiment polyA+RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the binding molecule is determined, the nucleotide sequence of the binding molecule may be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual, 2d Ed., Cold Spring Harbor Laboratory, Cold Spring Harbor, New York and Ausubel et al. eds. (1998) Current Protocols in Molecular Biology, John Wiley & Sons, NY), to generate binding molecules having a different amino acid sequence, for example to create amino acid substitutions, deletions, and/or insertions.

Production of Binding Molecules

Recombinant DNA methods for producing and screening for polypeptides, such as the binding molecules described herein, are routine and well known in the art (e.g. U.S. Pat. No. 4,816,567). DNA encoding the binding molecules or fragments thereof, for example, DNA encoding a VH domain, a VL domain, an scFv, or combinations thereof can inserted into a suitable expression vector, which is then transfected into a suitable host cell, such as E. coli cells, simian COS cells, Chinese Hamster Ovary (CHO) cells, or myeloma cells that do not otherwise produce antibody protein, to obtain the binding molecule.

In one embodiment, an expression vector containing a polynucleotide that encodes a binding molecule, a heavy or light chain of the binding molecule or a binding domain thereof, a heavy or light chain variable domain of a binding domain, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

The expression vector can be transferred to a host cell by conventional techniques and the transfected cells can be cultured by conventional techniques to produce the binding molecule. In one embodiment, host cells containing a polynucleotide encoding the binding molecule or fragments thereof, or a heavy or light chain thereof, or portion thereof, or a single-chain antibody, operably linked to a heterologous promoter are provided.

Mammalian cell lines suitable as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. Human cell lines developed by immortalizing human lymphocytes can be used to recombinantly produce monoclonal antibodies. The human cell line PER.C6®. (Crucell, Netherlands) can be used to recombinantly produce monoclonal antibodies.

Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681; etc.), plants cells (US20080066200); and chicken cells (WO2008142124).

In one embodiment, the binding molecule is stably expressed in a cell line. Stable expression can be used for long-term, high-yield production of recombinant proteins. For stable expression, host cells can be transformed with an appropriately engineered vector that includes expression control elements (e.g., promoter, enhancer, transcription terminators, polyadenylation sites, etc.), and a selectable marker gene. Following the introduction of the foreign DNA, cells are allowed to grow for 1-2 days in an enriched media, and are then switched to a selective media. The selectable marker in the recombinant plasmid confers resistance to the selection and allows cells that have stably integrated the plasmid into their chromosomes to grow and form foci which in turn can be cloned and expanded into cell lines. Methods for producing stable cell lines with a high yield are well known in the art and reagents are generally available commercially.

In other embodiments, the binding molecules are transiently expressed in a cell line. Transient transfection is a process in which the nucleic acid introduced into a cell does not integrate into the genome or chromosomal DNA of that cell and is maintained as an extra-chromosomal element, e.g. as an episome, in the cell.

The cell line, either stable or transiently transfected, is maintained in cell culture medium and conditions well known in the art resulting in the expression and production of the binding molecule. In certain embodiments, the mammalian cell culture media is based on commercially available media formulations, including, for example, DMEM or Ham's F12. In other embodiments, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

In one embodiment, the cell lines are maintained using a fed batch method. As used herein, "fed batch method," refers to a method by which a cell culture is supplied with additional nutrients after first being incubated with a basal medium. For example, a fed batch method may include adding supplemental media according to a determined feeding schedule within a given time period. Thus, a "fed batch cell culture" refers to a cell culture wherein the cells, typically mammalian, and culture medium are supplied to the culturing vessel initially and additional culture nutrients are fed, continuously or in discrete increments, to the culture during culturing, with or without periodic cell and/or product harvest before termination of culture.

Cell culture media and the nutrients contained therein are known to one of skill in the art. In one embodiment, the cell culture medium includes a basal medium and at least one hydrolysate, e.g., soy-based hydrolysate, a yeast-based hydrolysate, or a combination of the two types of hydrolysates resulting in a modified basal medium. In another embodiment, the additional nutrients may include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the invention include BME Basal Medium (Gibco-Invitrogen; see also Eagle, H (1965) Proc. Soc. Exp. Biol. Med. 89, 36); Dulbecco's Modified Eagle Medium (DMEM, powder) (Gibco-Invitrogen (#31600); see also Dulbecco and Freeman (1959) Virology. 8:396; Smith et al. (1960) Virology. 12:185. Tissue Culture Standards Committee, In Vitro 6:2, 93); CMRL 1066 Medium (Gibco-Invitrogen (#11530); see also Parker et al. (1957) Special Publications, New York Academy of Sciences, 5:303).

The basal medium may be serum-free, meaning that the medium contains no serum (e.g., fetal bovine serum (FBS), horse serum, goat serum, or any other animal-derived serum known to one skilled in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. In certain embodiments, the cell culture medium contains a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. In another embodiment, the modified basal medium further contains glutamine, e.g, L-glutamine, and/or methotrexate.

Purification and Isolation

Once an binding molecule has been produced, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") to facilitate purification. In one embodiment, a substantially purified/isolated binding molecule is provided.

In one embodiment, these isolated/purified recombinantly expressed binding molecules may be administered to a patient to mediate a prophylactic or therapeutic effect. A prophylactic is a medication or a treatment designed and used to prevent a disease, disorder or infection from occurring. A therapeutic is concerned specifically with the treatment of a particular disease, disorder or infection. A therapeutic dose is the amount needed to treat a particular disease, disorder or infection. In another embodiment these isolated/purified antibodies may be used to diagnose influenza virus infection, for example, influenza A virus infection, influenza B virus infection, or combinations thereof.

Glycosylation

In addition to the ability of glycosylation to alter the effector function of antibodies, modified glycosylation in the variable region can alter the affinity of the antibody for antigen. In one embodiment, the glycosylation pattern in the variable region of the present antibodies is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated antibodies may be produced in bacterial cells which lack the necessary glycosylation machinery.

Variants and Conjugates

In one embodiment, the binding molecule includes one or more binding domains that include one or more amino acid residues and/or polypeptide substitutions, additions and/or deletions in the variable light (VL) domain and/or variable heavy (VH) domain and/or Fc region and post translational modifications. In one embodiment, the binding molecule includes one or more conservative amino acid substitutions. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In one embodiment, one or more cysteine residues may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

In one embodiment, one or more mutations are introduced in one or more framework regions of an antibody molecule. In another embodiment, one or more mutations are introduced in one or more CDR regions of an antibody molecule.

In one embodiment, the binding molecule is conjugated or covalently attached to a heterologous amino acid sequence or other moiety or substance using methods known in the art. In one embodiment, the attached substance is a therapeutic agent, a detectable label (also referred to herein as a reporter molecule) or a solid support. Suitable substances for attachment to antibodies include, but are not limited to, an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a virus, a fluorophore, a chromophore, a dye, a toxin, an enzyme, an antibody, an antibody fragment, a radioisotope, solid matrixes, semi-solid matrixes and combinations thereof. Methods for conjugation or covalently attaching another substance to an antibody are known.

In one embodiment, the binding molecule is conjugated to a solid support. Binding molecules may be conjugated to a solid support as part of the screening and/or purification and/or manufacturing process. Alternatively binding molecules may be conjugated to a solid support as part of a diagnostic method or composition. A solid support is typically substantially insoluble in liquid phases. A large number of supports are available and are known to one of ordinary skill in the art.

In one embodiment, the binding molecule is conjugated to a label for purposes of diagnostics and other assays wherein the binding molecules and/or its associated ligand may be detected. A label includes any chemical moiety, organic or inorganic, that exhibits an absorption maximum at wavelengths greater than 280 nm, and retains its spectral properties when covalently attached to the binding molecule. Labels include, without limitation, a chromophore, a fluorophore, a fluorescent protein, a phosphorescent dye, a tandem dye, a particle, a hapten, an enzyme and a radioisotope.

In certain embodiments, the label is an enzyme. Enzymes may be desirable as labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art.

In another embodiment, the label is a hapten such as biotin. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal. Haptens also include hormones, naturally occurring and synthetic drugs, pollutants, allergens, affector molecules, growth factors, chemokines, cytokines, lymphokines, amino acids, peptides, chemical intermediates, nucleotides and the like.

In certain embodiments, fluorescent proteins may be used as a label. Examples of fluorescent proteins include green fluorescent protein (GFP) and the phycobiliproteins and the derivatives thereof.

In certain embodiments, the label is a radioactive isotope. Examples of suitable radioactive materials include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Medical Treatments and Uses

The binding molecules and antigen binding fragments thereof described herein may be used for the treatment of influenza A virus infection and/or influenza B virus infection, for the prevention of influenza A virus infection and/or influenza B virus infection; for the detection, diagnosis and/or prognosis of influenza A virus infection and/or influenza B virus infection; or combinations thereof.

Methods of diagnosis may include contacting binding molecule or fragment thereof with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of detection, diagnosis, and/or prognosis may also include the detection of an antigen/antibody complex.

In one embodiment, a method of treating a subject is provided, which includes administering to the subject an effective amount of binding molecule or binding fragment thereof, or a pharmaceutical composition that includes the binding molecule or binding fragment thereof. In one embodiment, the binding molecule or binding fragment thereof is substantially purified (i.e., substantially free from substances that limit its effect or produce undesired side-effects). In one embodiment, the binding molecule or binding fragment thereof is administered post-exposure, or after the subject has been exposed to influenza A virus and/or influenza B virus or is infected with influenza A virus and/or influenza B virus. In another embodiment, the binding molecule or binding fragment thereof is administered pre-exposure, or to a subject that has not yet been exposed to influenza A virus and/or influenza B virus or is not yet infected with influenza A virus and/or influenza B virus.

In one embodiment, the binding molecule or binding fragment thereof is administered to a subject that is sero-negative for one or more influenza A virus subtypes and/or influenza B virus strains. In another embodiment, the binding molecule or antigen binding fragment thereof is administered to a subject that is sero-positive for one or more influenza A virus subtypes and/or influenza B virus strains. In one embodiment, the binding molecule or binding fragment thereof is administered to a subject within 1, 2, 3, 4, 5 days of infection or symptom onset. In another embodiment, the binding molecule or binding fragment thereof is administered to a subject after 1, 2, 3, 4, 5, 6, or 7 days, and within 2, 3, 4, 5, 6, 7, 8, 9 or 10 days after infection or symptom onset.

In one embodiment, the method reduces influenza A virus and/or influenza B virus infection in a subject. In another embodiment, the method prevents, reduces the risk or delays influenza A virus and/or influenza B virus infection in a subject. In one embodiment, the subject is an animal. In one embodiment, the subject is a member of subphylum cordata, including, for example, humans and other primates, including non-human primates such as chimpanzees and other apes and monkey species. In another embodiment, the subject is a farm animals such as cattle, sheep, pigs, goats and horses; a domestic animal, such as dogs and cats; a laboratory animals, including rodents such as mice, rats and guinea pigs; a bird, including domestic, wild and game birds such as chickens, turkeys and other gallinaceous birds, ducks, geese. In one embodiment, the subject includes, but is not limited to, one who is particularly at risk of or susceptible to influenza A virus and/or influenza B virus infection, including, for example, an immunocompromised subject.

Treatment can be a single dose schedule or a multiple dose schedule and the binding molecule or binding fragment thereof can be used in passive immunization or active vaccination.

In one embodiment, the binding molecule or binding fragment thereof is administered to a subject in combination with one or more antiviral medications. In one embodiment, the binding molecule or binding fragment thereof is administered to a subject in combination with one or more small molecule antiviral medications, including, but not limited to, neuraminidase inhibitors such as oseltamivir (TAMIFLU®), zanamivir (RELENZA®) and adamantanes such as Amantadine and rimantadine.

In another embodiment, a composition for use as a medicament for the prevention or treatment of influenza A virus and/or influenza B virus infection is provided. In another embodiment, a binding molecule or binding fragment thereof and/or a protein having an epitope to which the binding molecule or antigen binding fragment thereof binds is used in the manufacture of a medicament for treatment of a subject and/or diagnosis in a subject.

Binding molecules and fragments thereof as described herein may also be used in a kit for the diagnosis of influenza A virus infection; influenza B virus infection; or combinations thereof. Binding molecules, antibody fragment, or variants and derivatives thereof, as described herein, may also be used in a kit for monitoring vaccine immunogenicity.

In one embodiment, a method of preparing a pharmaceutical composition, which includes the step of admixing a binding molecule described herein with one or more pharmaceutically-acceptable carriers is provided.

Various delivery systems are known and can be used to administer the binding molecule or binding fragment thereof described herein, including, but not limited to, encapsulation in liposomes, microparticles, microcapsules, recombinant cells capable of expressing the binding molecule or fragment, receptor-mediated endocytosis, electroportation, construction of a nucleic acid as part of a retroviral or other vector, etc. Methods of introduction include, but are not limited to, intradermal, intramuscular, intraperitoneal, intravenous, subcutaneous, intranasal, epidural, and oral routes. In one embodiment, the binding molecule can be administered as a plasmid with DNA or RNA encoding the binding molecule, for example, by electroporation. The compositions may be administered together with other biologically active agents, including, but not limited to small molecule antiviral compositions. Administration can be systemic or local. Pulmonary administration can also be employed, e.g., by use of an inhaler or nebulizer, and formulation with an aerosolizing agent. In yet another embodiment, the composition can be delivered in a controlled release system.

Also provided herein are pharmaceutical compositions that include a therapeutically effective amount of a binding molecule or binding fragment thereof, and a pharmaceutically acceptable carrier. The term "pharmaceutically acceptable" as used herein, means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. In one embodiment, the pharmaceutical composition contains a therapeutically effective amount of the antibody or antigen binding fragment thereof, preferably in purified form, together with a suitable amount of carrier so as to provide the form for proper administration to the patient. The formulation should suit the mode of administration. Typically, for antibody therapeutics, the dosage administered to a patient is between about 0.1 mg/kg to 100 mg/kg of the patient's body weight.

Kits

In one embodiment, articles of manufacture are provided that include at least a binding molecule as described herein, such as sterile dosage forms and kits. Kits can be provided which contain the binding molecules for detection and quantitation of influenza virus in vitro, e.g. in an ELISA or a Western blot. Binding molecules useful for detection may be provided with a label such as a fluorescent or radiolabel.

Exemplary Embodiments

1. An isolated binding molecule which specifically binds to influenza A virus and influenza B virus, comprising:

(a) a first binding domain that is capable of binding to influenza A virus hemagglutinin (HA) and neutralizing at least one group 1 subtype and at least 1 group 2 subtype of influenza A virus; and (b) a second binding domain that is capable of binding to influenza B virus hemagglutinin (HA) and neutralizing influenza B virus in at least two phylogenetically distinct lineages.

2. The isolated binding molecule according to claim 1, wherein the first binding domain is capable of neutralizing one or more influenza A virus group 1 subtypes selected from: H1, H2, H5, H6, H8, H9, H11, H12, H13, H16, H17, H18 and variants thereof; and one or more influenza A virus group 2 subtypes selected from: H3, H4, H7, H10, H14 and H15 and variants thereof.

3. The isolated binding molecule according to claim 1, wherein the second binding domain is capable of neutralizing influenza B virus in both Yamagata and Victoria lineages.

4. The binding molecule according to any one of the preceding claims, wherein the first binding domain comprises an anti-influenza A virus antibody or antigen-binding fragment thereof.

5. The binding molecule according to any one of the preceding claims, wherein the second binding domain comprises an anti-influenza B virus antibody or antigen-binding fragment thereof.

6. The binding molecule according to any of the preceding claims, comprising at least one VH of an antibody heavy chain and at least one VL of an antibody light chain.

7. The binding molecule according to any of the preceding claims, wherein the first binding domain comprises at least one VH of an antibody heavy chain and at least one VL of an antibody light chain.

8. The binding molecule according to any of the preceding claims, wherein the second binding domain comprises at least one VH of an antibody heavy chain and at least one VL of an antibody light chain.

9. The isolated binding molecule according to any one of the preceding claims, wherein the first binding domain includes a set of six CDRs: HCDR1, HCDR2, HCDR3, LCDR1, LCDR2, LCDR3 in which the set of six CDRs has an amino acid sequence selected from:

(a) an amino acid sequence that is at least 75% identical to: HCDR1 of SEQ ID NO.: 8, HCDR2 of SEQ ID NO.: 9, HCDR3 of SEQ ID NO.: 10, LCDR1 of SEQ ID NO.: 3, LCDR2 of SEQ ID NO.: 4 and LCDR3 of SEQ ID NO.: 5;

(b) an amino acid sequence of: HCDR1 of SEQ ID NO.: 8, HCDR2 of SEQ ID NO.: 9, HCDR3 of SEQ ID NO.: 10, LCDR1 of SEQ ID NO.: 3, LCDR2 of SEQ ID NO.: 4 and LCDR3 of SEQ ID NO.: 5;

(c) an amino acid sequence that is at least 75% identical to: HCDR1 of SEQ ID NO.: 18, HCDR2 of SEQ ID NO.: 19, HCDR3 of SEQ ID NO.: 20, LCDR1 of SEQ ID NO.: 13, LCDR2 of SEQ ID NO.: 14, LCDR3 of SEQ ID NO.: 15; and (d) an amino acid sequence of: HCDR1 of SEQ ID NO.: 18, HCDR2 of SEQ ID NO.: 19, HCDR3 of SEQ ID NO.: 20, LCDR1 of SEQ ID NO.: 13, LCDR2 of SEQ ID NO.: 14, LCDR3 of SEQ ID NO.: 15.

10. The isolated binding molecule according to any one of the preceding claims wherein the first binding domain comprises a VH having an amino acid sequence that is at least 75% identical to an amino acid sequence of a VH selected from:

(a) a VH of SEQ ID NO.: 7; and (b) a VH of SEQ ID NO.: 17.

11. The isolated binding molecule according to any one of the preceding claims wherein the first binding domain comprises a VL having an amino acid sequence that is at least 75% identical to an amino acid sequence of a VL selected from:

(a) a VL of SEQ ID NO.: 2; and (b) a VL of SEQ ID NO.: 12.

12. The isolated binding molecule according to any one of the preceding claims wherein the first binding domain comprises a VH and a VL that is at least 75% identical to an amino acid sequence of a VH and a VL, respectively, selected from:

(a) a VH of SEQ ID NO.: 7 and a VL of SEQ ID NO.: 2; and (b) a VH of SEQ ID NO.: 17 and a VL of SEQ ID NO.: 12.

13. The isolated binding molecule according to any one of the preceding claims wherein the first binding domain comprises a VH and a VL selected from:

(a) a VH of SEQ ID NO.: 7 and a VL of SEQ ID NO.: 2; and (b) a VH of SEQ ID NO.: 17 and a VL of SEQ ID NO.: 12.

14. The isolated binding molecule according to any one of the preceding claims, wherein the second binding domain includes a set of six CDRs: HCDR1, HCDR2, HCDR3, LCDR1, LCDR2, LCDR3 in which the set of six CDRs has an amino acid sequence selected from:

(a) an amino acid sequence that is at least 75% identical to: HCDR1 of SEQ ID NO.: 28, HCDR2 of SEQ ID NO.: 29, HCDR3 of SEQ ID NO.: 30, LCDR1 of SEQ ID NO.: 23, LCDR2 of SEQ ID NO.: 24 and LCDR3 of SEQ ID NO.: 25;

(b) an amino acid sequence of: HCDR1 of SEQ ID NO.: 28, HCDR2 of SEQ ID NO.: 29, HCDR3 of SEQ ID NO.: 30, LCDR1 of SEQ ID NO.: 23, LCDR2 of SEQ ID NO.: 24 and LCDR3 of SEQ ID NO.: 25;

(c) an amino acid sequence that is at least 75% identical to an amino acid sequence of: HCDR1 of SEQ ID NO.: 44, HCDR2 of SEQ ID NO.: 45, HCDR3 of SEQ ID NO.: 46, LCDR1 of SEQ ID NO.: 39, LCDR2 of SEQ ID NO.: 40 and LCDR3 of SEQ ID NO.: 41;

(d) an amino acid sequence of: HCDR1 of SEQ ID NO.: 44, HCDR2 of SEQ ID NO.: 45, HCDR3 of SEQ ID NO.: 46, LCDR1 of SEQ ID NO.: 39, LCDR2 of SEQ ID NO.: 40 and LCDR3 of SEQ ID NO.: 41;

(e) an amino acid sequence that is at least 75% identical to: HCDR1 of SEQ ID NO.: 60, HCDR2 of SEQ ID NO.: 61, HCDR3 of SEQ ID NO.: 62, LCDR1 of SEQ ID NO.: 55, LCDR2 of SEQ ID NO.: 56, LCDR3 of SEQ ID NO.: 57; and (f) an amino acid sequence of: HCDR1 of SEQ ID NO.: 60, HCDR2 of SEQ ID NO.: 61, HCDR3 of SEQ ID NO.: 62, LCDR1 of SEQ ID NO.: 55, LCDR2 of SEQ ID NO.: 56, LCDR3 of SEQ ID NO.: 57.

15. The isolated binding molecule according to any one of the preceding claims wherein the second binding domain comprises a VH having an amino acid sequence that is at least 75% identical to an amino acid sequence of a VH selected from:
(a) a VH of SEQ ID NO.: 27;
(b) a VH of SEQ ID NO.: 33;
(c) a VH of SEQ ID NO.: 36;
(d) a VH of SEQ ID NO.: 43;
(e) a VH of SEQ ID NO.: 49;
(f) a VH of SEQ ID NO.: 52;
(g) a VH of SEQ ID NO.: 59; and
(h) a VH of SEQ ID NO.: 65.

16. The isolated binding molecule according to any one of the preceding claims wherein the second binding domain comprises a VL having an amino acid sequence that is at least 75% identical to an amino acid sequence of a VL selected from:
(a) a VL of SEQ ID NO.: 22;
(b) a VL of SEQ ID NO.: 32;
(c) a VL of SEQ ID NO.: 35;
(d) a VL of SEQ ID NO.: 38;
(e) a VL of SEQ ID NO.: 48;
(f) a VL of SEQ ID NO.: 51;
(g) a VL of SEQ ID NO.: 54; and
(h) a VL of SEQ ID NO.: 64.

17. The isolated binding molecule according to any one of the preceding claims wherein the second binding domain comprises a VH and a VL that is at least 75% identical to the amino acid sequence of a VH and a VL, respectively, selected from:
(a) a VH of SEQ ID NO.: 27 and a VL of SEQ ID NO.: 22;
(b) a VH of SEQ ID NO.: 33 and a VL of SEQ ID NO.: 32;
(c) a VH of SEQ ID NO.: 36 and a VL of SEQ ID NO.: 35;
(d) a VH of SEQ ID NO.: 43 and a VL of SEQ ID NO.: 38;
(e) a VH of SEQ ID NO.: 49 and a VL of SEQ ID NO.: 48;
(f) a VH of SEQ ID NO.: 52 and a VL of SEQ ID NO.: 51;
(g) a VH of SEQ ID NO.: 59 and a VL of SEQ ID NO.: 54; and
(h) a VH of SEQ ID NO.: 65 and a VL of SEQ ID NO.: 64.

18. The isolated binding molecule according to any one of the preceding claims wherein the second binding domain comprises a VH and a VL selected from:
(a) a VH of SEQ ID NO.: 27 and a VL of SEQ ID NO.: 22;
(b) a VH of SEQ ID NO.: 33 and a VL of SEQ ID NO.: 32;
(c) a VH of SEQ ID NO.: 36 and a VL of SEQ ID NO.: 35;
(d) a VH of SEQ ID NO.: 43 and a VL of SEQ ID NO.: 38;
(e) a VH of SEQ ID NO.: 49 and a VL of SEQ ID NO.: 48;
(f) a VH of SEQ ID NO.: 52 and a VL of SEQ ID NO.: 51;
(g) a VH of SEQ ID NO.: 59 and a VL of SEQ ID NO.: 54; and
(h) a VH of SEQ ID NO.: 65 and a VL of SEQ ID NO.: 64.

19. The binding molecule according to any one of the preceding claims, comprising a bispecific antibody.

20. The binding molecule according to any one of the preceding claims, wherein one or more binding domains comprise a variable fragment (Fv) domain.

21. The binding molecule according to any one of the preceding claims, wherein one or more binding domains comprise an scFv molecule.

22. The binding molecule according to any one of the preceding claims, wherein one or more binding domains comprise an Fv domain and one or more binding domains comprise an scFv molecule.

23. The binding molecule according to any one of the preceding claims, wherein the first binding domain comprises an anti-influenza A virus Fv domain.

24. The binding molecule according to any of the preceding claims, comprising two antibody heavy chains and two antibody light chains.

25. The binding molecule according to any of the preceding claims, comprising an Fv domain comprising an antibody heavy chain variable domain and an antibody light chain variable domain, wherein the Fv specifically binds anti-influenza A virus.

26. The binding molecule according to any one of the preceding claims, wherein the second binding domain comprises an anti-influenza B virus scFv molecule.

27. The binding molecule according to any one of the preceding claims, wherein the first binding domain comprises an anti-influenza A virus Fv domain and the second binding domain comprises an anti-influenza B virus scFv molecule.

28. The binding molecule according to claim 27, wherein the Fv domain of the first binding domain comprises a heavy chain (HC) comprising a polypeptide chain having an amino terminus and a carboxy terminus and a light chain (LC) comprising a polypeptide chain having an amino terminus and a carboxy terminus, and
(a) the second binding domain is covalently linked to the carboxy-terminus of the HC of the first binding domain;
(b) the second binding domain is covalently linked to the amino-terminus of the HC of the first binding domain;
(c) the second binding domain is covalently linked to the amino-terminus of the LC of the first binding domain; or
(d) the second binding domain is covalently intercalated in the polypeptide chain of the HC of the first binding domain.

29. The binding molecule according to claim 28, wherein the binding molecule comprises an antibody or fragment thereof comprising an antibody light chain having a formula scFv-L1-VL-CL, wherein scFv is an scFv molecule, L1 is a linker, VL is a light chain variable domain, CL is a light chain constant domain and VL is a light chain variable domain.

30. The binding molecule according to claim 28, wherein the heavy chain comprises a formula scFv-L1-VH-CH1-CH2-CH3, wherein scFv is an scFv molecule, L1 is a linker, VH is a heavy chain variable domain, CH1 is a heavy chain constant domain domain-1, CH2 is a heavy chain constant domain domain-2, and CH3 is a heavy chain constant domain domain-3.

31. The binding molecule according to any one of claims 28-30, comprising a variable heavy chain domain (VH) with an amino acid sequence that is at least 75% identical to an amino acid VH domain sequence selected from SEQ ID NO: 7 and SEQ ID NO: 17.

32. The binding molecule according to any one of claims 28-31, comprising a variable light chain domain (VL) with an amino acid sequence that is at least 75% identical to an amino acid VL domain sequence selected from SEQ ID NO: 2 and SEQ ID NO: 12.

33. The binding molecule according to claim 28, wherein the binding molecule comprises a first and a second heavy chain with first and second C-terminal domains, respectively, wherein one or more scFv molecules are covalently attached to the C-terminal domain of the first heavy chain, the second heavy chain, or combinations thereof.

34. The binding molecule according to claim 28, wherein one or more heavy chains comprise a formula VH-CH1-CH2-CH3, wherein VH is a heavy chain variable domain, CH1 is a heavy chain constant domain domain-1, CH2 is a heavy chain constant domain domain-2, and CH3 is a heavy chain constant domain-3.

35. The binding molecule according to claim 34, wherein one or more heavy chains comprise a formula VH-CH1-L1-scFv-L2-CH2-CH3, wherein L1 and L2 independently are a linker and scFv is an scFv molecule.

36. The binding molecule according to claim 34, wherein one or more heavy chains comprise a formula VH-CH1-CH2-L1-scFV-L2-CH3, wherein L1 and L2 independently are a linker and scFv is an scFv molecule.

37. The binding molecule according to claim 34, wherein one or more heavy chains comprise a formula VH-CH1-CH2-CH3-L1-scFV-L2-CH3, wherein L1 and L2 independently are a linker and scFv is an scFv molecule.

38. The binding molecule according to claim 35, 36, or 37 wherein L1 and L2 independently comprise (a) [GGGGS]n, wherein n is 0, 1, 2, 3, 4, or 5, (b) [GGGG]n, wherein n is 0, 1, 2, 3, 4, or 5, or a combination of (a) and (b).

39. The binding molecule according to claims 21-38, wherein the scFv comprises a formula: VH-LS-VL, and wherein VH is a heavy chain variable domain, LS is a linker, and VL is a light chain variable domain.

40. The binding molecule according to claim 39, wherein LS comprises (a) [GGGGS]n, wherein n is 0, 1, 2, 3, 4, or 5, (b) [GGGG]n, wherein n is 0, 1, 2, 3, 4, or 5, or a combination of (a) and (b).

41. The binding molecule according to claim 28, wherein the heavy chain and the light chain of the second binding domain are linked by one or more disulfide bonds.

42. The binding molecule according to claim 41, wherein the scFv of the second binding domain comprises a heavy chain variable domain (VH) and a light chain variable domain (VL) and the VH of the scFv includes a cysteine residue at a position selected from position 43, 44, 100, 101, 105, and combinations thereof and the VL of the scFv includes a cysteine residue at a position selected from position 43, 44, 46, 49, 50, 100, and combinations thereof.

43. The binding molecule according to claim 42, wherein the VL and VH of the scFv are linked by a disulfide bond selected from: VL100-VH44, VL43-VH105, VL46-VH101, VL49-VH100, VL50-VH100, and combinations thereof.

44. The binding molecule according to claim 42, wherein the VH and VL of the scFv are linked by a disulfide bond selected from: VH44-VL100, VH100-VL49, VH100-VL50, VH101-VL46, VH105-VL43, and combinations thereof.

45. The binding molecule according to claim 39, wherein VH comprises a set of three CDRs: HCDR1, HCDR2, HCDR3, in which the set of three CDRs is selected from:
(a) an amino acid sequence that is at least 75% identical to: HCDR1 of SEQ ID NO.: 28, HCDR2 of SEQ ID NO.: 29, HCDR3 of SEQ ID NO.: 30;
(b) an amino acid sequence of: HCDR1 of SEQ ID NO.: 28, HCDR2 of SEQ ID NO.: 29, HCDR3 of SEQ ID NO.: 30;
(c) an amino acid sequence that is at least 75% identical to: HCDR1 of SEQ ID NO.: 44, HCDR2 of SEQ ID NO.: 45, HCDR3 of SEQ ID NO.: 46;
(d) an amino acid sequence of: HCDR1 of SEQ ID NO.: 44, HCDR2 of SEQ ID NO.: 45, HCDR3 of SEQ ID NO.: 46;
(e) an amino acid sequence that is at least 75% identical to: HCDR1 of SEQ ID NO.: 60, HCDR2 of SEQ ID NO.: 61, HCDR3 of SEQ ID NO.: 62; and
(f) an amino acid sequence of: HCDR1 of SEQ ID NO.: 60, HCDR2 of SEQ ID NO.: 61, HCDR3 of SEQ ID NO.: 62.

46. The binding molecule according to claim 39, wherein VL comprises a set of three CDRs: LCDR1, LCDR2, LCDR3 in which the set of three CDRs is selected:
(a) an amino acid sequence that is at least 75% identical to: LCDR1 of SEQ ID NO.: 23, LCDR2 of SEQ ID NO.: 24 and LCDR3 of SEQ ID NO.: 25;
(b) an amino acid sequence of: LCDR1 of SEQ ID NO.: 23, LCDR2 of SEQ ID NO.: 24 and LCDR3 of SEQ ID NO.: 25;
(c) an amino acid sequence that is at least 75% identical to: LCDR1 of SEQ ID NO.: 39, LCDR2 of SEQ ID NO.: 40 and LCDR3 of SEQ ID NO.: 41;
(d) an amino acid sequence of: LCDR1 of SEQ ID NO.: 39, LCDR2 of SEQ ID NO.: 40 and LCDR3 of SEQ ID NO.: 41;
(e) an amino acid sequence that is at least 75% identical to: LCDR1 of SEQ ID NO.: 55, LCDR2 of SEQ ID NO.: 56, LCDR3 of SEQ ID NO.: 57; and
(f) an amino acid sequence of: LCDR1 of SEQ ID NO.: 55, LCDR2 of SEQ ID NO.: 56, LCDR3 of SEQ ID NO.: 57.

47. The binding molecule according to any one of claims 21-46, wherein the scFv has an amino acid sequence selected from SEQ ID NO:31, SEQ ID NO:34, SEQ ID NO:47, SEQ ID NO:50, SEQ ID NO:63.

48. A bispecific antibody which specifically binds to influenza A virus and influenza B virus, comprising at least one light chain with an amino acid sequence that is at least 75% identical to an amino acid sequence of SEQ ID NO:66 or SEQ ID NO:68.

49. A bispecific antibody according to claim 48, comprising at least one light chain with an amino acid sequence comprising SEQ ID NO:66 or SEQ ID NO:68.

50. A bispecific antibody which specifically binds to influenza A virus and influenza B virus, comprising at least one heavy chain with an amino acid sequence that is at least 75% identical to an amino acid sequence of SEQ ID NO:67 or SEQ ID NO:69.

51. A bispecific antibody according to claim 50, comprising at least one heavy chain with an amino acid sequence comprising SEQ ID NO:67 or SEQ ID NO:69.

52. A bispecific antibody which specifically binds to influenza A virus and influenza B virus, comprising at least one light chain with an amino acid sequence that is at least 75% identical to an amino acid sequence of SEQ ID NO:66 or SEQ ID NO:68 and at least one heavy chain with an amino acid sequence that is at least 75% identical to an amino acid sequence of SEQ ID NO:67 or SEQ ID NO:69.

53. A bispecific antibody according to claim 52, comprising: (a) at least one light chain with an amino acid sequence comprising SEQ ID NO:66 and at least one heavy chain with an amino acid sequence comprising SEQ ID NO:67; or
(b) at least one light chain with an amino acid sequence comprising SEQ ID NO:68 and at least one heavy chain with an amino acid sequence comprising SEQ ID NO:69

54. A cell comprising or producing the binding molecule according to any one of claims 1-47, the bispecific antibody or fragment thereof of claims 48-53, or any combination thereof.

55. An isolated polynucleotide comprising a nucleic acid which encodes the binding molecule according to any one of claims 1-47 or the bispecific antibody or fragment thereof of claims 48-53.

56. A vector comprising the polynucleotide of claim 55.

57. A host cell comprising the polynucleotide of claim 55 or the vector of claim 56.

58. A composition comprising the binding molecule according to any one of claims 1-47, the bispecific antibody or fragment thereof of claims 48-53, and a pharmaceutically acceptable carrier.

59. A kit comprising the composition of claim 58.

60. A method of preventing or treating an influenza A virus or influenza B virus infection in a subject in need thereof, comprising administering to a subject an effective amount of the composition of claim 58.

61. A method for manufacturing a binding molecule according to any one of claims 1-47 or the bispecific antibody or fragment thereof of claims 48-53, comprising culturing a host cell according to claim 57 under conditions suitable for expression of the binding molecule or bispecific antibody or fragment thereof.

62. A method according to claim 61, further comprising isolating the binding molecule from the host cell culture.

63. A binding molecule according to any one of claims 1-47 or the bispecific antibody or fragment thereof of claims 48-53 for use in the prophylaxis or treatment of influenza A infection, influenza B infection, or a combination thereof in a subject.

64. Use of a binding molecule according to any one of claims 1-47 or the bispecific antibody or fragment thereof of claims 48-53 in the manufacture of a medicament for the prophylaxis or treatment of influenza A infection, influenza B infection, or a combination thereof in a subject.

65. Use of a binding molecule according to any one of claims 1-47 or the bispecific antibody or fragment thereof of claims 48-53 in the manufacture of a medicament for the prophylaxis or treatment of influenza A and influenza B infection in a subject.

66. A method for prophylaxis or treatment of influenza A infection, influenza B infection, or a combination thereof in a subject comprising administering an effective amount of a binding molecule according to any one of claims 1-47 or the bispecific antibody or fragment thereof of claims 48-53 to the subject.

67. A method for prophylaxis or treatment of influenza A and influenza B infection in a subject comprising administering an effective amount of a binding molecule according to any one of claims 1-47 or the bispecific antibody or fragment thereof of claims 48-53 to the subject.

68. Use of a binding molecule according to any one of claims 1-47 or the bispecific antibody or fragment thereof of claims 48-53 for in vitro diagnosis of influenza A infection, influenza B infection, or a combination thereof in a subject.

EXAMPLES

Example 1. Preparation of Bispecific Antibody Constructs

Anti-HA IgG antibodies that specifically bind influenza A virus are described in U.S. Provisional Application Nos. 61/885,808, filed Oct. 2, 2013 and 62/002,414, filed May 23, 2014, and anti-HA IgG antibodies that specifically bind influenza B virus are described in U.S. Provisional Application No. 62/024,804, filed Jul. 15, 2014. In brief, these antibodies are broadly cross-reactive antibodies that recognize influenza A virus (FY1 and GL20) and influenza B virus (FBD94, FBC39, and FBC39 FTL). A series of bispecific (BiS) antibodies were constructed using the IgG VH and VL gene sequences of these antibodies. The resultant bispecific antibodies combine the complementary activities of the distinct anti-influenza A or B HA mAbs to create single antibody like molecules capable of neutralizing all influenza A and B strains.

FIG. 1 shows a schematic of the orientation of five different BiS backbones. In for example Bis-Flu A+B antibodies generated, the anti-Flu A antibody (FY1 or its optimized form GL20) was used as an IgG, and the anti-Flu B antibody (FBD94, FBC39 or its optimized form FBC39FTL) was used as an scFv, wherein the scFv was inserted at different positions along the IgG structure in the different Bis formats. The BiS constructs were named using an abbreviation of the two IgGs from which the Bis antibody was derived, followed by the BiS format used, and then followed by the amino acid position of two cysteine residues used to form a stabilizing disulfide bond in the scFv.

A. FY1/39 BiS2 100/44

The following method was used to generate the FY1/39 BiS2 100/44 construct, which includes FY1/39 Bis2 100/44 Light Chain (SEQ ID NO:107) and FY1/39 Bis2 100/44 Heavy Chain (SEQ ID NO:108). Briefly, a vector containing FY1 VH and VL sequences (pOE-FY1 vector) was digested with BssHII/BsiWI to obtain FY1 VL DNA (SEQ ID NO:1). The FY1 VL DNA (SEQ ID NO:1) was then gel purified and cloned into a vector containing light chain, scFv and heavy chain sequences (BiS2 vector), which had been digested with BssHII/BsiWI, to form a FY1 LC-BiS2 vector.

FBC39 scFv-FY1 VH DNA (SEQ ID NO:111) was synthesized by Geneart and PCR amplified using the following primers, which contain recognition sequences for BsrGI/SalI at the 5' and 3' ends.

```
Forward primer:
                                         (SEQ ID NO: 70)
TTCTCTCCACAGGTGTACACTCCGACATCCAGATGACCCAGTCTC Reverse primer:
                                         (SEQ ID NO: 71)
GGATGGGCCCTTGGTCGACGCGCTTGACACGGTGACCATAGTC
```

Amplification of the FBC39 scFv-FY1 VH DNA (SEQ ID NO:111) was verified and the DNA was gel purified.

The FY1-LC-BiS2 vector was then digested with BsrGI/SalI and the vector band was gel purified. The purified FY1-LC-BiS2 vector was infused with FBC39 scFv-FY1 VH (SEQ ID NO:111) PCR product by using the In-Fusion system (Clontech®) to generate a FY1/39 BiS2 100/44 construct. Stellar competent cells were transformed with the FY1/39 BiS2 100/44 construct and colonies were sequenced for correct FY1 VL, VH and FBC39 scFv sequences.

B. FY1/39 BiS4 100/44

A similar method was used to generate the FY1/39 BiS4 100/44 construct, which includes FY1/39 Bis4 100/44 Light Chain (SEQ ID NO: 109) and FY1/39 Bis4 100/44 Heavy Chain (SEQ ID NO: 110). Briefly, pOE-FY1-VL vector was digested with BssHII/BsiWI to obtain FY1 VL DNA (SEQ ID NO:1). The FY1 VL DNA (SEQ ID NO:1) was then gel purified and cloned into a vector containing light chain, VH, CH1, scFv, CH2 and CH3 sequences (BiS4 vector), which had been digested with BssHII/BsiWI to generate a FY1-LC BiS4 vector.

FBC39 scFv DNA (SEQ ID NO:112) was amplified from FBC39 scFv-FY1 VH DNA (SEQ ID NO:111), which was synthesized by Geneart, using the following primers:

```
Forward primer:
                                        (SEQ ID NO: 72)
CTCTGGCGGAGGGGGATCCGACATCCAGATGACCCAGTCTC Reverse primer:
                                        (SEQ ID NO: 73)
GTGAGTTTTGTCGGATCCCCCTCCGCCAGAGCCACCTCCGCCTGAGGAGA

CGGTGACCGTGG
```

The FY1-LC-BiS4 vector was then digested with BsrGI/SalI and the vector band was gel purified. A vector containing FY1 VL and VH sequences (pOE-FY1) was digested with BsrGI/SalI to obtain FY1 VH (SEQ ID NO:6).

FY1-LC-Bis4 vector (digested with BsrGI/SalI, described in line 5 and 6) was then ligated with FY1 VH (SEQ ID NO:6) to obtain vector BiS4-FY1, which was digested with BamHI and gel purified. Purified BiS4-FY1 vector was then infused with the FBC39 scFv PCR product obtained above using the In-Fusion system (Clontech®) to obtain the FY1/39 BiS4 100/44 construct. Stellar competent cells were transformed with the FY1/39 BiS4 100/44 construct and colonies were sequenced for correct FY1 VL, VH and FBC39 scFv sequences.

C. FY1/39 BiS1 100/44

A similar method was used to create the FY1/39 BiS1 100/44 construct, which includes FY1/39 Bis1 100/44 light chain (SEQ ID NO:113) and FY1/39 Bis1 100/44 heavy chain (SEQ ID NO:114).

FY1 VL was amplified from FY1/FBC39 BiS4 100/44 (SEQ ID NO:109), described above, using the following primers:

```
BiS1 FY1-VL forward primer:
                                        (SEQ ID NO: 76)
AGGGGGATCCGGCGGAGGGGGCTCTGATATTCAGATGACCCAGAGCCC BiS1 FY1-VL reverse primer:
                                        (SEQ ID NO: 77)
TGGTGCAGCCACCGTACGTTTGATCTCCACCTTAGTGCCC
```

FBC39 scFv was amplified from FBC39 scFv-FY1 VH DNA (SEQ ID NO:111) which was synthesized by Geneart, using the following primers:

```
BiS1 FBC39 forward primer:
                                        (SEQ ID NO: 74)
CTGGCTCCCCGGGGCGCGCTGTGACATCCAGATGACCCAGTCTCC BiS1 FBC39 reverse primer:
                                        (SEQ ID NO: 75)
CCCCTCCGCCGGATCCCCCTCCGCCTGAGGAGACGGTGACCGTGGTC
```

FBC39 scFv and FY1-VL PCR bands were gel purified.

FY1/FBC39 BiS4 100/44 was digested with BsrGI/SalI to obtain FY1 VH, FY1 VH band was gel purified. FY1 VH (SEQ ID NO:6) was ligated with a vector containing scFv, LC and HC sequences (BiS1 vector), which had also been digested with BsrGI/SalI.

The resulting vector FY1 HC BiS1 was then digested with BssHII/BsiWI, the vector band was gel purified, and infused with FBC39 scFv and FY1 VL PCR products using the In-Fusion system (Clontech®) to form the FY1/39 BiS1 100/44 construct. Stellar competent cells were transformed with the FY1/39 BiS1 100/44 construct and colonies were sequenced for correct FY1 VL, VH and FBC39 scFv sequences.

D. FY1/39 BiS3 100/44

The FY1/39 BiS3 100/44 construct, containing FY1/39 Bis3 100/44 Light Chain (SEQ ID NO:115) and FY1/39 Bis3 100/44 Heavy Chain (SEQ ID NO:116) was constructed in a similar manner.

The following primers were used to amplify FBC39 scFv (SEQ ID NO:112) from FBC39 scFv-FY1 VH DNA (SEQ ID NO:111) which was synthesized by Geneart.

```
Forward primer:
                                        (SEQ ID NO: 78)
AAAGGCGGAGGGGGATCCGGCGGAGGGGGCTCTGACATCCAGATGACCCA

GTCTC

Reverse primer:
                                        (SEQ ID NO: 79)
TCAATGAATTCGCGGCCGCTCATGAGGAGACGGTGACCGTGGTC
```

Amplification of the FBC scFv DNA was verified and gel purified.

FY1/FBC39 BiS4 100/44 was digested with BssHII/SalI to obtain FY1 LC/VH. FY1 LC/VH band was gel purified and ligated with a vector containing LC, HC and scFv sequences (BiS3 vector), which had also been digested with BssHII/SalI, to form the FY1 BiS3 vector.

The FY1 BiS3 vector was then digested with BamHI and gel purified. The purified FY1 BiS3 vector was infused with FBC39 scFv (SEQ ID NO:112) PCR products using the In-Fusion (Clontech®) system to form the FY1/39 BiS3 100/44 construct. Stellar competent cells were transformed with the FY1/39 BiS3 100/44 construct and colonies were sequenced for correct FY1 VL, VH and FBC39 scFv sequences.

E. FY1/94 BiS2 100/44

FY1/94 BiS2 100/44, which contains FY1/94 Bis2 100/44 Light Chain (SEQ ID NO: 117) and FY1/94 Bis2 100/44 Heavy Chain (SEQ ID NO: 118) was constructed as follows.

FBD94 scFv DNA (SEQ ID NO: 119) was synthesized by Eurofin and amplified for insertion into the BiS2 vector using the following primers:

```
Forward primer:
                                        (SEQ ID NO: 80)
TTCTCTCCACAGGTGTACACTCCGAAATTGTGTTGACACAGTCTC Reverse primer:
                                        (SEQ ID NO: 81)
CCCCTCCGCCGGATCCCCCTCCGCCTGAGGAGACGGTGACCGTGGTC
```

FY1 VH (SEQ ID NO:6) was PCR amplified from FY1/39 BiS4 100/44 (SEQ ID NO:110) using the following primers:

```
Forward primer:
                                        (SEQ ID NO: 82)
AGGGGGATCCGGCGGAGGGGGCTCTCAGGTCCAGCTGCAGGAGAGC Reverse primer:
                                        (SEQ ID NO: 83)
GGATGGGCCCTTGGTCGACGCGCTTGACACGGTGACCATAGTC
```

Amplification of the PCR products, FBD94 scFv DNA (SEQ ID NO:119) and FY1 VH (SEQ ID NO:6), was verified and the PCR products were gel purified. BiS2-FY1-LC vector was linearized by digestion with BsrGI/SalI and infused with FBD94 scFv DNA (SEQ ID NO:119) and FY1 VH (SEQ ID NO:6) using the In-Fusion system (Clontech®). The orientation of the PCR products within the vector was controlled using primers containing overlap sequences with vector. Stellar competent cells were transformed with the FY1/94 BiS2 100/44 construct and colonies were sequenced for correct FY1 VL, VH and FBD94 scFv sequences.

F. FY1/94 BiS4 100/44

FY1/94 BiS4 100/44 was constructed as follows:

FBD94 scFv (SEQ ID NO:119) was synthesized by Eurofin and amplified for insertion into a vector containing light chain, VH, CH1, scFv, CH2 and CH3 sequences (BiS4 vector) using the following primers:

```
Forward primer:
                                        (SEQ ID NO: 84)
CTCTGGCGGAGGGGGATCCGAAATTGTGTTGACACAGTCTC (SEQ ID NO: 85)
Reverse primer:
GTGAGTTTTGTCGGATCCCCCTCCGCCAGAGCCACCTCCGCCTGAGGAGA
CGGTGACCGTGG
```

Amplification of the PCR product was verified and FBD94 was gel purified.

BiS4-FY1 vector (described above) was linearized using BamHI and was infused with FBD94 using the In-Fusion system (Clontech®). Stellar competent cells were transformed with the FY1/94 BiS4 100/44 construct and colonies were sequenced for correct FY1 VL, VH and FBD94 scFv sequences.

G. FY1/39 BiS4 43/105

FY1/39 BiS4 43/105, which contains FY1/39 Bis4 43/105 Light Chain (SEQ ID NO:120) and FY1/39 Bis4 43/105 Heavy Chain (SEQ ID NO: 121) was constructed as follows:

FBC39-43/105 scFv DNA was synthesized by Eurofin and was amplified for insertion into the BiS4 vector using the following primers:

```
Forward primer:
                                        (SEQ ID NO: 86)
CTCTGGCGGAGGGGGATCCGACATCCAGATGACCCAGTCTC Reverse primer:
                                        (SEQ ID NO: 87)
GTGAGTTTTGTCGGATCCCCCTCCGCCAGAGCCACCTCCGCCTGAGGAGA
CGGTGACCGTGG
```

Amplification of the PCR product was verified and was gel purified.

BiS4-FY1 vector was linearized with BamHI and infused with FBC39-43/105 scFv DNA (SEQ ID NO:124) obtained above using the In-Fusion system (Clontech®). Stellar competent cells were transformed with the FY1/39 BiS4 43/105 construct and colonies were sequenced for correct FY1 VL, VH and FBC39-43/105 scFv sequences.

H. GL20/39 BiS4 100/44

GL20/39 BiS4 100/44, which includes GL20/39 BiS4 100/44 heavy chain (SEQ ID NO: 66) and GL20/39 BiS4 100/44 light chain (SEQ ID NO:67) was constructed in a similar manner.

A vector containing FY-GL20 LC and HC (pOE-FY1-GL20) was digested with BssHII/SalI to obtain GL20 LC(VL-CL) and VH (SEQ ID NO:123), which was gel purified. FY1/39 BiS4 100/44 vector was digested with BssHII/SalI and ligated with GL20 LC/VH (SEQ ID NO:123). Colonies were sequenced for correct GL20 VL, VH and FBC39 scFv sequences.

I. GL20/39 BiS4 43/105

GL20/39 BiS4 43/105, which includes GL20/39 BiS4 43/105 heavy chain (SEQ ID NO:68) and GL20/39 BiS4 43/105 light chain (SEQ ID NO:69) was constructed in a similar manner. pOE-FY1-GL20 was digested with BssHII/SalI to obtain GL20 LC/VH (SEQ ID NO: 123), which was gel purified. FY1/39 BiS4 43/105 Light Chain (SEQ ID NO:120) was digested with BssHII/SalI and ligated with GL20 LC/VH (SEQ ID NO:123). Colonies were sequenced for correct GL20 VL, VH and FBC39-43/105 scFv sequences.

J. GL20/39FTL BiS4 100/44

GL20/39FTL BiS4 100/44 was constructed in a similar manner.

FBC39FTL scFv DNA (SEQ ID NO:124) was synthesized by Eurofin and amplified for insertion into the BiS4 vector using the following primers:

```
Forward primer:
                                        (SEQ ID NO: 88)
CTCTGGCGGAGGGGGATCCGACATCCAGATGACCCAGTCTC Reverse primer:
                                        (SEQ ID NO: 89)
GTGAGTTTTGTCGGATCCCCCTCCGCCAGAGCCACCTCCGCCTGAGGAGA
CGGTGACCGTGG
```

Amplification of the PCR product was verified and FBC39FTL scFv DNA (SEQ ID NO:124) was purified. GL20/39 BiS4 43/105 vector was linearized with BamHI and infused with FBC39FTL scFv DNA (SEQ ID NO:124) using the In-Fusion system (Clontech®). Colonies were sequenced for correct GL20 VL, VH and FBC39FTL scFv sequences.

K. GL20/39FTL BiS4 43/105

GL20/39FTL BiS4 43/105, which includes GL20/39FTL BiS4 43/105 Light Chain (SEQ ID NO:125) and GL20/39FTL BiS4 43/105 Heavy Chain (SEQ ID NO: 126) was constructed in a similar manner.

FBC39FTL43/105 scFv DNA (SEQ ID NO:127) was synthesized by Eurofin and amplified for insertion into the BiS4 vector using the following primers:

```
Forward primer:
                                        (SEQ ID NO: 90)
CTCTGGCGGAGGGGGATCCGACATCCAGATGACCCAGTCTC Reverse primer:
                                        (SEQ ID NO: 91)
GTGAGTTTTGTCGGATCCCCCTCCGCCAGAGCCACCTCCGCCTGAGGAGA
CGGTGACCGTGG
```

The amplified PCR product was purified and infused with linearized GL20/39 BiS4 43/105 vector (digested with BamHI) and colonies were sequenced for correct GL20 VL, VH and FBC39FTL-43/105 scFv sequences.

L. BiS5 GL20-FBC39
*FY1GL20VL*-Ckappa
(SEQ ID NO: 128)

*DIQMTQSPSSLSASVGDRVTITCRTSQSLSSYTHWYQQKPGKAPKLLIYAASSRGSGVPSRFSGS*

*GSGTDFTLTISSLQPEDFATYYCQQSRTFGQGTKVEIK*RTVAAPSVFIFPPSDEQLKSGTASV

VCLLNNFYPREAKVQWKVDNALQSGNSQESVTEQDSKDSTYSLSSTLTLSKADYEKHK

VYACEVTHQGLSSPVTKSFNRGEC

*FY1GL20VH* - Fc (CH3-) - Linker - FBC39 scFv - Linker - Fc (-CH3)
(SEQ ID NO: 129)

*QVQLQQSGPGLVKPSQTLSLTCAISGDSVSSYNAVWNWIRQSPSRGLEWLGRTYYRSGWYNDY*

*AESVKSRITINPDTSKNQFSLQLNSVTPEDTAVYYCARSGHITVFGVNVDAFDMWGQGTMVTV*

*SS*ASTKGPSVFPLAPSSKSTSGGTAALGCLVKDYFPEPVTVSWNSGALTSGVHTFPAVLQ

SSGLYSLSSVVTVPSSSLGTQTYTCNVNHKPSNTKVDKRVEPKSCDKTHTCPPCPAPELL

GGPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLPP

SREEMTKNQVSLTCLVKGFYPSDIAVEWESNGGGGSGGGGSDIQMTQSPSSVSASVGD

RVTITCRASQDISTWLAWYQQKPGKAPKLLIYAASSLQSGVPSRFSGSGSGTDFTLTISSL

QPEDFATYFCQQANSFPPTFGCGTKLEIKGGGGSGGGGSGGGGSGGGGSEVQLVVSGG

GLVKPGGSLRLSCAASGLSFLNAWMSWVRQAPGKCLEWVGRIKSNTDGGTTDYAAPV

KGRFSISRDDSKNMLFLHMSSLRTEDTAVYYCATDGPYSDDFRSGYAARYRYFGMDV

WGQGTTVTVSSGGGGSGGGGSGQPENNYKTTPPVLDSDGSFFLYSKLTVDKSRWQQG

NVFSCSVMHEALHNHYTQKSLSLSPGK

M. BiS5 GL20-FBC39-43-105
FY1GL20VL-Ckappa
(SEQ ID NO: 130)

DIQMTQSPSSLSASVGDRVTITCRTSQSLSSYTHWYQQKPGKAPKLLIYAASSRGSGVPS

RFSGSGSGTDFTLTISSLQPEDFATYYCQQSRTFGQGTKVEIKRTVAAPSVFIFPPSDEQLK

SGTASVVCLLNNFYPREAKVQWKVDNALQSGNSQESVTEQDSKDSTYSLSSTLTLSKA

DYEKHKVYACEVTHQGLSSPVTKSFNRGEC

*FY1GL20VH* - Fc (CH3-) - Linker - FBC39 (43-105) scFv - Linker - Fc (-CH3)
(SEQ ID NO: 131)

*QVQLQQSGPGLVKPSQTLSLTCAISGDSVSSYNAVWNWIRQSPSRGLEWLGRTYYRSGWYNDY*

*AESVKSRITINPDTSKNQFSLQLNSVTPEDTAVYYCARSGHITVFGVNVDAFDMWGQGTMVTV*

*SS*ASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKRVEPKSCDKTHTCPPCPAPELL

GGPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLPP

SREEMTKNQVSLTCLVKGFYPSDIAVEWESNGGGGSGGGGSDIQMTQSPSSVSASVGD

RVTITCRASQDISTWLAWYQQKPGKCPKLLIYAASSLQSGVPSRFSGSGSGTDFTLTISSL

QPEDFATYFCQQANSFPPTFGQGTKLEIKGGGGSGGGGSGGGGSGGGGSEVQLVVSGG

GLVKPGGSLRLSCAASGLSFLNAWMSWVRQAPGKGLEWVGRIKSNTDGGTTDYAAPV

KGRFSISRDDSKNMLFLHMSSLRTEDTAVYYCATDGPYSDDFRSGYAARYRYFGMDV

WGCGTTVTVSSGGGGSGGGGSGQPENNYKTTPPVLDSDGSFFLYSKLTVDKSRWQQG

NVFSCSVMHEALHNHYTQKSLSLSPGK

Example 2: BiS Construct Expression

Recombinant antibodies were produced by transient transfection of mammalian cell lines derived from 293F or CHO cells. Supernatants from transfected cells were collected after 7-10 days of culture. Purification was performed using a protein A column (HiTrap Protein A HP from GE Healthcare). Monomer content was determined by HPLC-SEC analysis and aggregates were removed by size-exclusion chromatography.

Example 3: BiS4 Construct Optimization

The FY1/39 BiS4 construct was used as a backbone to optimized the scFv to create a high monomer expressing construct that was still active. For these studies, the orientation of the scFv was changed from VL/VH to VH/VL, the scFv linker length was changed from 20 amino acids to 10, 15, or 25 amino acids, stabilizing disulfide bonds were removed or changed in the location from 100/44 to four different locations, and the framework regions of FBC39 were fully germlined. Table 7 provides specific information for the constructs.

night at 4° C. with 1 ug/ml of recombinant HA derived from influenza A strains, A/California/07/2009 H1N1 (A/CA/09) and A/Perth/2009 H3N2 (A/PTH/09), and influenza B strains B/Florida/4/2006 of the Yamagata lineage (B/FLA/06) and B/Brisbane/60/2008 of the Victoria lineage (B/BNE/08) in PBS. The plate was washed with PBS containing 0.1% v/v Tween-20 to remove uncoated protein and blocking solution containing 1% (w/v) casein (Thermo Scientific) was added for 1 hr at room temperature. The blocking solution was discarded and a 3-fold serial dilution of each of the anti-HA IgGs and BiS antibodies in PBS was added and incubated for 1 hr at room temperature. The plate was washed three times and bound IgG and BiS antibodies were detected using a peroxidase-conjugated goat anti-human IgG (H+L) antibody (KPL). The binding activity was calculated by measuring the color change at 450 nm after incubation with Tetramethylbenzidine (TMB) one component substrate (KPL) followed by the addition of 2N sulfuric acid to stop the reaction.

Table 8 shows the $EC_{50}$ values calculated from the binding curves. As expected the Flu A IgG mAbs (FY1 and GL20) bound to both influenza A HA proteins and the three

TABLE 7

| | BiS4 Components | | scfv Properties | | Construct Properties | |
|---|---|---|---|---|---|---|
| Clone Name | IgG | scfv | orientation | linker length | disulfide bond | Expression/ Agregation | Antiviral Activity |
| FY1/39 VH/VL | FY1 | FBC-39 | VH/VL | 20 | 44/100 | + | ++ |
| FY1/39 100/44 | FY1 | FBC-39 | VL/VH | 20 | 100/44 | + | ++ |
| FY1/39 43/105 | FY1 | FBC-39 | VL/VH | 20 | 43/105 | ++ | ++ |
| FY1/39 46/101 | FY1 | FBC-39 | VL/VH | 20 | 46/101 | ++ | + |
| FY1/39 50/100 | FY1 | FBC-39 | VL/VH | 20 | 50/100 | + | − |
| FY1/39 49/100 | FY1 | FBC-39 | VL/VH | 20 | 49/100 | ++ | − |
| FY1/39 no C | FY1 | FBC-39 | VL/VH | 20 | no | ++ | + |
| FY1/39 2 link | FY1 | FBC-39 | VL/VH | 10 | 100/44 | − | ++ |
| FY1/39 2 link no C | FY1 | FBC-39 | VL/VH | 10 | no | ++ | + |
| FY1/39 3 link | FY1 | FBC-39 | VL/VH | 15 | 100/44 | + | ++ |
| FY1/39 5 link | FY1 | FBC-39 | VL/VH | 25 | 100/44 | + | ++ |
| FY1/39GL | FY1 | FBC-39 GL | VL/VH | 20 | 100/44 | ++ | − |

Expression and activity of these optimized BiS4 constructs was not greatly affected by linker length. However, the position of the disulfide bond was important for both expression and activity. The best expression profile was observed in constructs containing no disulfide bonds, disulfide bond location changed to 43/105, 46/101 or 49/100, or the germlined FBC39 construct with disulfide bond 100/44. However, although expression was improved, many of these clones lost antiviral activity measured by HA binding and neutralization as described in Examples 4 and 5, TABLE 8-continued

| | Binding to rHA by ELISA (EC$_{50}$, nM) | | | |
|---|---|---|---|---|
| Clone Name | A/CA/09 (H1) | A/PTH/09 (H3) | B/FL/06 (yam) | B/BNE/08 (vic) |
| FY1/39 BiS3 100/44 | 1.52 | 5.86 | 1.22 | 37.75 |
| FY1/39 BiS4 100/44 | 1.19 | 4.44 | 0.36 | 15.39 |
| FY1/39 BiS4 43/105 | 0.78 | 3.69 | 0.31 | 12.34 |
| GL20/39 BiS4 100/44 | 0.95 | 0.67 | 0.28 | 7.42 |
| GL20/39 BiS4 43/105 | 0.78 | 0.60 | 0.21 | 7.21 |
| GL20/39FTL BiS4 100/44 | 0.99 | 0.96 | 0.44 | 15.04 |
| GL20/39FTL BiS4 43/105 | 0.86 | 1.27 | 0.50 | 11.34 |

— = no binding

To further characterize the kinetics of the binding interaction, affinity measurements were performed using a ForteBio Octet QK 384 Kinetic Analyzer (Menlo Park, California) using 384 slanted-well plates. All reagents were diluted in Octet Kinetics Buffer (ForteBio). His-tagged HA of different influenza viruses: influenza A subtype H1 (A/California/7/04 (H1N1)), influenza A subtype H3 (A/Perth/16/09 (H3N2)), influenza B lineage Victoria (B/Brisbane/60/2008 (Victoria)), and influenza B lineage Yamagata (B/Florida/4/2006 (Yamagata)) were immobilized onto anti-His Ni-NTA sensors at 8 µg/mL. Anti-HA mAb association/dissociation were then monitored in 2-fold dilutions from 100 nM, plus a zero mAb control. Association and dissociation raw data were corrected for any drift in the zero mAb controls, and then exported to GraphPad Prism (San Diego, California) for affinity curve fitting. Data were fitted using a global association/dissociation equation with an imposed limit of $>5 \times 10^{-6}$ sec$^{-1}$. As shown in Table 9, both BiS constructs showed high affinity binding to all four HA proteins belonging to influenza A and B strains.

TABLE 9

| | GL20/39 BiS4 100/44 | | | GL20/39 BiS4 43/105 | | |
|---|---|---|---|---|---|---|
| Viral HA Protein | K$_{on}$ (e$^3$ M$^{-1}$s$^{-1}$) | K$_{off}$ (e$^{-6}$ s$^{-1}$) | K$_D$ (nM) | K$_{on}$ (e$^3$ M$^{-1}$s$^{-1}$) | K$_{off}$ (e$^{-6}$ s$^{-1}$) | K$_D$ (nM) |
| A/CA/09 H1 | 3.11 | 9.03 | 4.39 | 9.62 | 5.00 | 0.57 |
| A/Perth/09 H3 | 1.31 | 5.00 | 3.89 | 3.44 | 5.00 | 1.50 |
| B/Fla/06 yam | 50.5 | 310.0 | 6.15 | 46.0 | 115.0 | 2.60 |
| B/Bne/08 vic | 11.0 | 86.0 | 7.65 | 8.40 | 88.5 | 10.0 |

Example 5. In Vitro Neutralizing Activity of Flu A+B BiS Constructs

A modified microneutralization assay was based on a previously described accelerated viral inhibition assay using neuraminidase activity (NA) as a read-out (Hassantoufighi, A. et al. 2010, Vaccine 28:790). Briefly, assays were performed on MDCK cells that were cultured in MEM medium (Invitrogen) supplemented with antibiotics, glutamine (complete MEM medium) and 10% (v/v) fetal bovine serum. 60 TCID$_{50}$ (50% tissue culture infectious doses) of virus was added to three-fold dilutions of antibody in a 384-well plate in MEM medium containing 0.75 ug/ml TPCK Trypsin (Worthington) in duplicate wells. After 30 minutes incubation at room temperature, $2 \times 10^4$ cells/well were added to the plate. After incubation at 33° C. in a 5% CO$_2$ incubator for approximately 40 hr, the NA activity was measured by adding a fluorescently-labelled substrate, methylumbelliferyl-N-acetyl neuraminic acid (MU-NANA) (Sigma) to each well and incubated at 37° C. for 1 hr. Virus replication represented by NA activity was quantified by reading fluorescence using an Envision Fluorometer (PerkinElmer) using the following settings: excitation 355 nm, emission 460 nm; 10 flashes per well. The neutralization titer (50% inhibitory concentration [IC$_{50}$]) was expressed as the final antibody concentration that reduced the fluorescence signal by 50% compared to cell control wells.

Influenza A and B virus strains used in Table 10 and 11 are as listed below.

In Table 10: A/WSN/33 (A/Wilson Smith N/33 (H1N1)); A/BJ/95 (A/Beijing/262/95 (H1N1)); A/SI/06 (A/Solomon Island/3/2006 (H1N1)); A/CA/09 (A/California/07/2009 (H1N1)); A/HK/68 (A/Hong Kong/8/68 (H3N2)); A/VIC/75 (A/Victoria/3/75 (H3N2)); A/SD/93 (A/Shangdong/9/93 (H3N3)); A/Pan/99 (cold-adapted (ca) A/Panama//2007/99 (H3N2)); B/BJ/97 (ca B/Beijing/243/97 (Vic)); B/HK/01 (B/Hong Kong/330/2001 (Vic)); B/MY/04 (B/Malaysia/2506/2004 (Vic)); B/OH/05 (B/Ohio/1/2005 (Vic)); B/YI/98 (B/Yamanashi/166/98 (Yam)); B/SIC/99 (B/Sichuan/379/99 (Yam)); and B/FLA/06 (B/Florida/4/2006 (Yam)).

In Table 11: A/WSN/33 H1 (A/Wilson Smith N/33 (H1N1)); A/PR/34 H1 (A/Puerto Rico/8/34 (H1N1)); A/FM/47 H1 (A/Fort Monmouth/1/47 (H1N1)); A/BJ/95 H1 (ca A/Beijing/262/95 (H1N1)); A/SZ/95 H1 (A/Shenzhen/227/95 (H1N1)); A/NC/99 H1 (ca A/New Caledonia/20/99 (H1N1)); A/SI/06 H1 (A/Solomon Island/3/2006 (H1N1)); A/SD/07 H1 (ca A/South Dakota/6/2007 (H1N1)); A/CA/09 H1 (ca A/California/7/2009 (H1N1)); A/BS/10 H1 (A/Brisbane/10/2010 (H1N1)); A/HK/10 H1 (A/Hong Kong/2212/2010 (H1N1)); A/NH/10 H1 (A/New Hampshire/04/2010 (H1N1)); A/WS/12 H1 (A/Washington/24/2012 (H1N1)); A/NY/12 H1 (A/New York/36/2012 (H1N1)); A/BO/13 H1 (A/Bolivia/559/2013 (H1N1)); A/Jap/57 H2 (ca A/Japan/57 (H2N2)); A/VN/04 H5 (ca A/Vietnam/1203/04 (H5N1)); A/Alb/85 H6 (ca A/mallard/Alberta/89/85 (H6N2)); A/HK/97 H9 (ca A/chicken/Hong Kong/G9/97 (H9N2)); A/HK/68 H3 (A/Hong Kong/8/68 (H3N2)); A/Vic/75 H3 (A/Victoria/3/75 (H3N2)); A/SD/93 H3 (A/Shan dong/9/93 (H3N2)); A/WH/95 H3 (ca A/Wuhan/359/95 (H3N2)); A/SY/97 H3 (ca A/Sydney/5/97 (H3N2)); APA/99 H3 (ca A/Panama/2007/99 (H3N2)); A/CA/04 H3 (A/California/7/2004 (H3N2)); A/WS/05 H3 (A/Wisconsin/67/2005 (H3N2)); A/Perth/09 H3 (ca A/Perth/16/2009 (H3N2)), A/VC/11 H3 (A/Victoria/361/2011 (H3N2)); A/BR/11 H3 (A/Berlin/93/2011 (H3N2)); A/NY/12 H3 A/New York/39/2012 (H3N2)); A/X/12 H3 (A/Texas/50/2012 (H3N2)); A/AS/13 H3 (A/AmericanSomoa/4786/2013 (H3N2)); A/SW/13 H3 (A/Switzerland/9715293/2013 (H3N2)); A/PU/14 H3 (A/Palau/6759/2014 (H3N2)); A/NC/14 H3 (A/New Caledonia/71/2014 (H3N2)); A/IN/11 H3v (A/Indiana/10/2011 (H3N2v)); A/MN/10 H3v (A/Minnesota/11/2010 (H3N2v)); A/BC/04 H7 (ca A/Brit. Columbia/CN-6/04 (H7N3-LP)); B/Lee/40 (B/Lee/40); B/AA/66 (ca B/Ann Arbor/1/66); B/HK/72 (B/Hong Kong/5/72); B/BJ/97 (ca B/Beijing/243/97 (victoria)), B/HK/01 (B/Hong Kong/330/2001 (victoria)); B/MY/04 (B/Malaysia/2506/2004 (victoria)); B/OH/05 (B/Ohio/1/2005 (victoria)); B/BNE/08 (ca B/Brisbane/60/2008 (victoria)); B/NV/11 (B/Nevada/3/2011 (victoria)); B/NJ/12 (B/New Jersey/01/2012 (victoria)); B/TX/13 (B/Texas/2/2013 (victoria)); B/Wis/13 (B/Wisconsin/5/2013 (victoria)); B/Yam/88 (B/Yamagata/16/88 (yamagata)); B/AA/94 (ca B/Ann Arbor/2/94 (yamagata)); B/geo/98 (ca B/Georgia/02/98 (yamagata)); B/YSI/98 (ca B/Yamanashi/166/98 (yamagata)); B/Joh/99 (ca B/Johannesburg/5/99 (yamagata)); B/Sic/99 (B/Sichuan/379/99 (yamagata)); B/Vic/00 (ca B/Victoria/504/2000 (yamagata)); B/Shg/02 (B/Shanghai/361/02 (yamagata)); and B/FL/06 (B/Florida/4/2006 (yamagata)); B/WS/10 (B/Wisconsin/1/2010 (yamagata)); B/Mass/12 (B/Massachusetts/2/2012 (yamagata)); B/AZ/13 (B/Arizona/8/2013 (yamagata)); B/PH/13 (B/Phuket/3073/2013 (yamagata)).

| | Neutralization of infectious viruses (IC50 nM) | | | | | | | |
|---|---|---|---|---|---|---|---|---|
| | Influenza A (H1N1) | | | | Influenza A (H3N2) | | | |
| Clone Name | A/WSN/33 | A/BJ/95 | A/SI/06 | A/CA/09 | A/HK/68 | A/VIC/75 | A/SD/93 | A/PAN/99 |
| FY1 IgG | 8.8 | 21.0 | 3.1 | 10.4 | 10.6 | 12.0 | 34.6 | 103.7 |
| GL20 IgG | 13.0 | 8.3 | 4.4 | 18.6 | 7.0 | 12.9 | 19.2 | 46.9 |
| FBD94 IgG | >1000 | >1000 | >1000 | >1000 | >1000 | >1000 | >1000 | >1000 |
| FBC39 IgG | >1000 | >1000 | >1000 | >1000 | >1000 | >1000 | >1000 | >1000 |
| FBC39FTL IgG | >1000 | >1000 | >1000 | >1000 | >1000 | >1000 | >1000 | >1000 |
| FY1/94 BiS2 100/44 | 19.9 | 42.0 | 4.1 | 23.1 | 17.2 | 15.8 | 207.9 | 484.2 |
| FY1/94 BiS4 100/44 | 7.3 | 13.1 | 2.5 | 6.2 | 9.1 | 7.2 | 37.9 | 38.2 |
| FY1/39 BiS1 100/44 | 28.2 | 62.2 | 14.7 | 32.5 | 31.4 | 336.8 | >1000 | >1000 |
| FY1/39 BiS2 100/44 | 17.7 | 61.3 | 9.9 | 18.7 | 10.2 | >1000 | 72.1 | >1000 |
| FY1/39 BiS3 100/44 | 10.6 | 20.2 | 2.5 | 9.9 | 5.8 | 45.2 | 7.8 | 149.4 |
| FY1/39 BiS4 100/44 | 10.6 | 20.2 | 3.9 | 8.2 | 10.6 | 26.4 | 12.8 | 151.5 |
| FY1/39 BiS4 43/105 | 4.3 | 10.9 | 2.6 | 7.1 | 4.0 | 6.5 | 20.4 | 52.7 |
| GL20/39 BiS4 100/44 | 16.3 | 11.9 | 4.7 | 20.6 | 6.0 | 15.9 | 30.3 | 37.3 |
| GL20/39 BiS4 43/105 | 12.9 | 12.3 | 3.5 | 18.5 | 6.6 | 11.4 | 15.6 | 40.6 |
| GL20/39FTL BiS4 100/44 | 13.7 | 16.4 | 4.4 | 25.4 | 10.8 | 13.3 | 21.9 | 34.1 |
| GL20/39FTL BiS4 43/105 | 9.6 | 11.8 | 3.8 | 20.8 | 6.3 | 14.9 | 22.2 | 35.5 |

| | Neutralization of infectious viruses (IC50 nM) | | | | | | |
|---|---|---|---|---|---|---|---|
| | Influenza B (Victoria) | | | | Influenza B (Yamagata) | | |
| Clone Name | B/BJ/97 | B/HK/01 | B/MY/04 | B/OH/05 | B/YI/98 | B/SIC/99 | B/FLA/06 |
| FY1 IgG | >1000 | >1000 | >1000 | >1000 | >1000 | >1000 | >1000 |
| GL20 IgG | >1000 | >1000 | >1000 | >1000 | >1000 | >1000 | >1000 |
| FBD94 IgG | 0.1 | 0.1 | 0.1 | 0.0 | 0.1 | 0.2 | 0.1 |
| FBC39 IgG | 0.4 | 1.0 | 1.0 | 0.6 | 0.0 | 0.2 | 0.4 |
| FBC39FTL IgG | 0.8 | 2.1 | 1.4 | 0.7 | 0.0 | 0.3 | 0.3 |
| FY1/94 BiS2 100/44 | 1.1 | 2.1 | 0.8 | 1.3 | 0.5 | 1.7 | 0.6 |
| FY1/94 BiS4 100/44 | 1.8 | 4.0 | 1.8 | 3.0 | 2.3 | 5.2 | 1.8 |
| FY1/39 BiS1 100/44 | 3.6 | 5.3 | 4.1 | 2.6 | 0.1 | 1.5 | 1.1 |
| FY1/39 BiS2 100/44 | 6.1 | 7.0 | 5.6 | 2.8 | 0.4 | 2.1 | 1.7 |
| FY1/39 BiS3 100/44 | 21.5 | 112.2 | 43.7 | 8.1 | 0.7 | 12.3 | 5.9 |
| FY1/39 BiS4 100/44 | 5.8 | 69.3 | 27.6 | 5.6 | 0.9 | 8.2 | 3.6 |
| FY1/39 BiS4 43/105 | 2.6 | 19.1 | 12.6 | 5.4 | 0.6 | 3.5 | 1.6 |
| GL20/39 BiS4 100/44 | 44.3 | 75.8 | 25.8 | 16.5 | 1.2 | 7.8 | 3.6 |
| GL20/39 BiS4 43/105 | 25.0 | 47.3 | 17.1 | 10.8 | 1.0 | 6.1 | 4.8 |
| GL20/39FTL BiS4 100/44 | 96.2 | 105.8 | 42.8 | 20.9 | 1.4 | 9.8 | 7.3 |
| GL20/39FTL BiS4 43/105 | 23.5 | 163.5 | 16.2 | 17.5 | 1.1 | 8.7 | 4.2 |

Table 10 shows the average $IC_{50}$ value from two independent experiments. The parental IgGs FY1 and GL20 neutralized all the influenza A strains and showed no cross reactivity with the influenza B strains tested. As expected, the FBD94, FBC39 and FBC39 LTL IgGs neutralized all the influenza B strains with no activity against the influenza A strains tested. However, similar to the binding experiments, the BiS4 constructs showed the best overall neutralization profile with neutralizing activity against all of the influenza A and all B strains tested. The BiS4 construct generated with the optimized antibody clones, GL20/39 BiS4 100/44 and GL20/39 BiS4 43/105, showed improved overall neutralization against all strains tested over the parental BiS4. The GL20/39 BiS4 43/105 resulted in $IC_{50}$ values <50 nM for all 15 Flu A and B viruses tested.

To confirm that the breadth of coverage was maintained for the optimized BiS4 constructs, a larger panel of 39 influenza A and 25 influenza B viruses were tested for neutralization. Table 11 shows the average $IC_{50}$ values from two independent experiments. GL20/39 BiS4 100/44 and GL20/39 BiS4 43/105 demonstrated neutralizing activity against all viruses tested. The mean $IC_{50}$ (nM) for the influenza A viruses was 8.2, 8.0, and 7.5 for GL20 IgG, GL20/39 BiS4100/44, and GL20/39 BiS4 43/105, respectively, showing that the BiS constructs maintained the overall neutralization activity of the parental IgG. The mean $IC_{50}$ for the influenza B viruses was 0.4, 13.9, and 9.0 for the FBC39 IgG, GL20/39 BiS4100/44, and GL20/39 BiS4 43/105 respectively. The BiS constructs exhibited >10-fold reduced activity against the B viruses compared to the parental IgG mAb, however, the overall neutralization activity was maintained at levels similar to that against the influenza A viruses. Although both BiS constructs, GL20/39 BiS4100/44, and GL20/39 BiS4 43/105, showed similar profiles, GL20/39 BiS4 43/105 exhibited a better overall neutralization profile with $IC_{50}$ values <50 nM for all viruses. As described previously, like influenza A mAb GL20, the FBC39 mAb was able to neutralize influenza A/HK/97 H9 strain in addition to the influenza B strains. When constructed into BiS4 format, the BiS4 antibodies showed enhanced neutralization activity against A/HK/97 H9 compared to either parental mAb, with $IC_{50}$ values (nM) of 1.6 and 1.1 for the GL20/39 BiS4 100/44 and GL/20/39 BiS4 43/105 and 3.0 and 13.3 for the GL20 and FBC39 respectively.

TABLE 11

| | Neutralization of infectious viruses (IC50 nM) | | | |
|---|---|---|---|---|
| Virus | GL20 | FBC39 | GL20/39 BiS4 100/44 | GL20/39 BiS4 43/105 |
| A/WSN/33 H1 | 7.6 | — | 9.5 | 7.3 |
| A/PR/34 H1 | 10.0 | — | 18.6 | 11.6 |
| A/FM/47 H1 | 6.1 | — | 5.2 | 6.1 |
| A/BJ/95 H1 | 10.8 | — | 10.6 | 12.6 |
| A/SZ/95 H1 | 9.3 | — | 7.9 | 8.1 |
| A/NC/99 H1 | 4.2 | — | 6.2 | 5.9 |
| A/SI/06 H1 | 4.3 | — | 4.4 | 3.9 |
| A/SD/07 H1 | 10.8 | — | 6.8 | 6.2 |
| A/CA/09 H1 | 10.2 | — | 10.9 | 10.8 |
| A/BS/10 H1 | 10.5 | — | 9.8 | 12.3 |
| A/HK/10 H1 | 0.6 | — | 0.4 | 0.1 |
| A/NH/10 H1 | 0.4 | — | 0.4 | 0.1 |
| A/WS/12 H1 | 1.4 | — | 2.1 | 1.1 |
| A/NY/12 H1 | 0.6 | — | 0.7 | 0.4 |
| A/BO/13 H1 | 0.9 | — | 0.9 | 0.6 |
| A/Jap/57 H2 | 5.0 | — | 5.3 | 2.8 |
| A/Vit/04 H5 | 5.6 | — | 10.2 | 7.6 |
| A/Alb/85 H6 | 4.8 | — | 6.5 | 5.4 |
| A/HK/97 H9 | 3.0 | 13.3 | 1.6 | 1.1 |
| A/HK/68 H3 | 3.0 | — | 3.3 | 2.3 |
| A/Vic/75 H3 | 3.0 | — | 5.2 | 4.5 |
| A/SD/93 H3 | 21.8 | — | 18.3 | 18.9 |
| A/WH/95 H3 | 16.3 | — | 16.7 | 15.7 |
| A/SY/97 H3 | 32.1 | — | 22.6 | 24.2 |
| A/PA/99 H3 | 44.2 | — | 28.5 | 33.3 |
| A/CA/04 H3 | 14.2 | — | 10.5 | 11.8 |
| A/WS/05 H3 | 10.7 | — | 10.3 | 11.8 |
| A/Perth/09 H3 | 4.2 | — | 4.0 | 5.5 |
| A/Vic/11 H3 | 5.7 | — | 5.2 | 6.3 |
| A/BR/11 H3 | 1.1 | — | 1.1 | 0.5 |
| A/NY/12 H3 | 0.7 | — | 0.5 | 0.2 |
| A/TX/12 H3 | 4.8 | — | 3.1 | 1.9 |
| A/AS/13 H3 | 0.9 | — | 0.8 | 0.4 |
| A/SW/13 H3 | 0.3 | — | 0.9 | 0.3 |
| A/PU/14 H3 | 6.8 | — | 4.6 | 2.2 |
| A/NC/14 H3 | 1.0 | — | 0.8 | 0.4 |
| A/IN/11 (H3v) | 26.0 | — | 23.5 | 23.9 |
| A/MN/10 (H3v) | 11.1 | — | 17.1 | 10.5 |
| A/BC/04 H7 | 7.4 | — | 18.3 | 14.8 |
| B/Lee/40 (un) | — | 0.1 | 1.0 | 0.4 |
| B/AA/66 (un) | — | 0.6 | 12.8 | 4.7 |
| B/HK/72 (un) | — | 0.4 | 5.7 | 3.6 |
| B/BJ/97 (vic) | — | 0.9 | 25.9 | 11.0 |
| B/HK/01 (vic) | — | 1.8 | 66.9 | 37.7 |
| B/Mal/04 (vic) | — | 1.2 | 33.0 | 23.7 |
| B/OH/05 (vic) | — | 0.5 | 18.7 | 9.5 |
| B/Bne/08 (vic) | — | 1.5 | 51.8 | 41.6 |
| B/NV/11 (vic) | — | 1.2 | 38.2 | 25.2 |
| B/NJ/12 (vic) | — | 0.7 | 23.0 | 29.1 |
| B/TX/13 (vic) | — | 0.4 | 13.8 | 12.6 |
| B/Wis/13 (vic) | — | 0.5 | 14.5 | 5.0 |
| B/Yam/88 (yam) | — | 0.1 | 1.3 | 0.8 |
| B/AA/94 (yam) | — | 0.0 | 0.7 | 0.8 |
| B/Geo/98 (yam) | — | 0.1 | 1.0 | 0.8 |
| B/Ysh/98 (yam) | — | 0.0 | 0.3 | 0.5 |
| B/Joh/99 (yam) | — | 0.0 | 0.6 | 0.4 |
| B/Sic/99 (yam) | — | 0.3 | 12.1 | 5.6 |
| B/Vic/00 (yam) | — | 0.2 | 1.3 | 1.2 |
| B/Shg/02 (yam) | — | 0.0 | 0.6 | 0.3 |
| B/Fla/06 (yam) | — | 0.2 | 1.4 | 1.0 |
| B/WS/10 (yam) | — | 0.1 | 4.4 | 2.3 |
| B/Mass/12 (yam) | — | 0.0 | 0.7 | 0.4 |
| B/AZ/13 (yam) | — | 0.1 | 2.2 | 2.0 |
| B/PH/13 (yam) | — | 0.2 | 15.4 | 5.8 |

Example 6. Hemaglutination Inhibition Activity

The influenza B mAb portion of the BiS constructs binds to the globular head of the HA protein and inhibits viral entry into the host cell. To determine whether this same mechanism of action important for the influenza B functionality of the BiS construct, we preformed hemagglutination inhibition (HAI) assays using a diverse group of influenza B virus strains. The HAI assay detects antibodies that block the viral receptor engagement of the cellular surface expressed sialic acid by measuring the inhibition of virus-mediated agglutination of erythrocytes. Influenza B viruses (abbreviations as described in Example 5) were adjusted to 4 HA units determined by incubation with 0.05% turkey red blood cells (Lampire Biological Laboratories) in the absence of antibody. In a 96-well U-bottom plate, GL20/39 BiS4 100/44, GL20/39 BiS4 43/105, and FBC39 IgG were serially diluted in two-fold increments and diluted virus was added to the wells. After 30 to 60 min incubation, 50 ul of 0.05% turkey red blood cells was added. Plates were incubated an additional 30 to 60 min and observed for agglutination. The HAI titer was determined to be the minimum effective concentration (nM) of antibody that completely inhibited agglutination. Table 12 shows that both GL20/39 BiS4 constructs had HAI activity against all influenza B strains tested, providing evidence that the BiS constructs bind to the globular head of the influenza B HA. The overall potency of the HAI activity varied between the two constructs, with the GL20/39 BiS4 43/105 resulting in more potent inhibition than the GL20/39 BiS4 100/44, with similar activity as the FBC39 parental mAb on many of the viruses tested.

TABLE 12

| | Hemagglutination Inhibition Titer (nM) | | |
|---|---|---|---|
| Viral Strain | FBC39 | GL20/39 Bis4 100/44 | GL20/39 Bis4 43/105 |
| B/Lee/40 (un) | 5 | 61 | 15 |
| B/AA/66 (un) | 6 | 244 | 38 |
| B/HK/72(Un) | 8 | 244 | 15 |
| B/BJ/97 (Vic) | 14 | 91 | 15 |
| B/HK/01 (Vic) | 16 | 244 | 122 |
| B/Mal/04 (Vic) | 20 | 244 | 122 |
| B/OH/05 (Vic) | 24 | 244 | 61 |
| B/Bne/08 (Vic) | 20 | 244 | 61 |
| B/Yam/88 (Yam) | 11 | 122 | 15 |
| B/AA/94 (Yam) | 6 | 61 | 15 |
| B/Geo/98 (Yam) | 16 | 122 | 15 |
| B/Ysh/98 (Yam) | 13 | 122 | 15 |
| B/Joh/99 (Yam) | 18 | 122 | 30 |
| B/Sic/99 (Yam) | 10 | 122 | 8 |
| B/Vic/2000 (Yam) | 16 | 61 | 15 |
| B/Shg/02 (Yam) | 16 | 91 | 15 |
| B/Fla/4/06 (Yam) | 7 | 61 | 8 |

Example 7. In Vitro Fc-Effector Function of Flu A+B BiS Constructs

Influenza HA monoclonal antibodies have the potential to clear virus infected cells through Fc-effector function such as antibody dependent cellular cytotoxicity (ADCC), antibody dependent cellular phagocytosis (ADCP), and complement dependent killing (CDC). To confirm that the BiS constructs exhibited similar levels of these effector functions to their parental IgG mAbs, we tested them in three different in vitro assays to determine ADCC, ADCP and CDC activity. The ADCC assay measures the ability of primary human NK cells to kill influenza infected cells when activated by antibody. A549 cells were infected with A/California/07/2009 H1N1 at a multiplicity of infection (MOI) of 10, A/Hong Kong/8/68 H3N2 at a MOI of 10, B/Malaysia/2506/2004 victoria lineage at a MOI of 20 and B/Sichuan/379/99 yamagata lineage at a MOI of 10 and incubated at 37° C. for 15 hours. Infected cells were incubated with a dilution series of GL20, FBC39, or GL20/39 BiS4 43/105, and then incubated with purified NK cells positively selected from human peripheral blood mononucleated cell (PBMC) (Miltenyi), at an effector to target ratio of 6:1. The infected cells, antibody, and NK cells were incubated for 4 hours, and cell killing was measured by LDH release (Roche). FIG. 2 shows that the GL20/39 BiS4 43/105 exhibited an approximate 3-fold reduced dose dependent killing of influenza A infected A549 cells compared to GL20 with $IC_{50}$ values (nM) of 0.024 and 0.086 for the A/California/07/2009 H1N1 and 0.018 and 0.052 for the A/Hong Kong/8/68 H3N2 for GL20 and GL20/39 BiS4 43/105 respectively (A and B). The GL20/39 BiS4 43/105 exhibited the same dose-dependent response as the FBC39 IgG with a calculated $IC_{50}$ value (nM) of 1.45 and 1.50 for the B/Malaysia/2506/2004 victoria and 0.85 and 0.42 for the B/Sichuan/379/99 yamagata for the FBC39 and GL20/39 BiS4 43/105, respectively (C and D).

To measure the ability of the anti-HA BiS antibodies to mediate phagocytosis in an ADCP assay, we used MDCK cells stability transfected with the HA proteins derived from A/South Dakota/6/2007 H1N1 and A/Hong Kong/8/68 H3N2, respectively as target cells. Human monocytes were isolated from PBMCs, and cultured for 7 days in the presence of M-CSF to differentiate into macrophages. The human macrophages and HA-expressing target cells were fluorescently labelled violet and green, respectively (CellTrace Violet or CSFE, Invitrogen). Labelled effector and target cells were incubated at a 6:1 ratio in the presence of a dilution series of IgG or BiS antibodies for 2 hours, and then analysed by flow cytometry. The percent phagocytosis was measured as the percent of violet stained macrophages that also were positive for the green target cells (double positive). FIG. 3 shows that the GL20/39 BiS4 43/105 had similar ADCP activity as the GL20 IgG against H1 expressing cells and H3 expressing cells, as expected the FBC39 IgG showed no phagocytosis of influenza A expressing cells.

To measure anti-HA BiS antibody-mediated complement-dependent cell killing, we used influenza infected MDCK cells as targets. In this CDC assay, MDCK cells were infected with A/Puerto Rico/8/34 at an MOI of 2, incubated with a dilution series of GL20 IgG, GL20/39 BiS4 43/105, or irrelevant control mAb, in the presence of complement derived from a rabbit (Cedarlane) at an effector to target ratio of 1:18. Cell killing was measured by LDH release (Roche). FIG. 3 C shows that the GL20/39 BiS 43/105 exhibited similar level of cell killing capacities as the GL20 IgG.

Example 8. In Vivo Prophylactic Protection of Flu A+B BiS Constructs in Lethal Murine Models of Influenza A and Influenza B Infection To test prophylactic efficacy, six-to-eight week old BALB/c (Harlan Laboratories) mice were administered a single intraperitoneal injection (IP) of GL20 IgG at 3, 0.3, or 0.03 mg/kg or the equal molar equivalent of GL20/39 BiS4 43/105 in 100 μl volume. Four hours after dosing, mice were inoculated intranasally with 2.5 times the fifty percent mouse lethal dose (2.5 $MLD_{50}$) of A/Wilson Smith N/33 H1N1 (A/WSN/33) or 7 $MLD_{50}$ of the 7:1 A/Puerto Rico/8/34:A/Hong Kong/8/68 HA reassortant (rA/HK/68) in a 50 μl volume for the study in influenza A infection model; or 7 $MLD_{50}$ of B/Florida/4/2006 yamagata lineage (B/FLA/06) or 10 $MLD_{50}$ of the B/Malaysia//2506/2004 victoria lineage (B/MAL/04) in a 50 μl volume in the study using influenza B infection model. Groups of 8-10 mice were weighed on the day of virus challenge and monitored daily for weight loss and survival for 14 days (mice with body weight loss 25% were euthanized). In addition, lungs were collected from 4 additional animals on Day 5 post-infection for viral titration. Lungs were homogenized using Teen Lysing Matrix A in a 10% w/v solution and a Fastprep24 homogenizer. TCID50 quantitation was performed on the serially diluted lung homogenate in a 384-well black walled tissue culture plate in quadruplicate. Trypsinized MDCK cells were then added to the homogenate at $2.0\times10^4$ cells/well and plates were incubated at 33° C. with 5% $CO_2$ for approximately 40 hours. Viral replication was measured by the addition of 40 pM MU-NANA as described above. Infectious virus titers were calculated using the Karber method (Karber et al, 1931 Arch. Exp. Pathol. Pharmak. 162:480-3)

and positive samples defined as those showing greater than 10 standard deviations above the mean value of the cells alone.

Prophylactic Activity Against Influenza A Infection

Both GL20/39 BiS4 43/105 and the parental IgG GL20 provided protection to mice from lethal challenge with influenza A in a similar dose-dependent manner. Like GL20, IP injection of 3 mg/kg equivalent of the BiS molecule protected 100% of the animals challenged with the A/WSN/33 H1 virus and IP injection of 3 and 0.3 mg/kg equivalent prevented lethality in 100% of the animals challenged with the rA/HK/68 H3 virus (FIGS. 4 A and C). When viral titer was assessed in the lungs harvested at Day 5 post infection, both antibody molecules reduced viral lung titers with more pronounced reduction at the 3 mg/kg equivalent dose. Comparing the BiS with the IgG, we see similar viral titer reductions in the two groups with the GL20 treated animals having slightly lower viral titers in the H1 model, whereas the BiS showed lower viral titers in the H3 model (FIGS. 4 B and D). Overall these data show that the GL20/39 BiS4 43/105 can prevent lethality and reduce lung viral replication to a similar extent as the GL20 IgG.

Prophylactic Activity Against Influenza B Infection

Figure 5B:
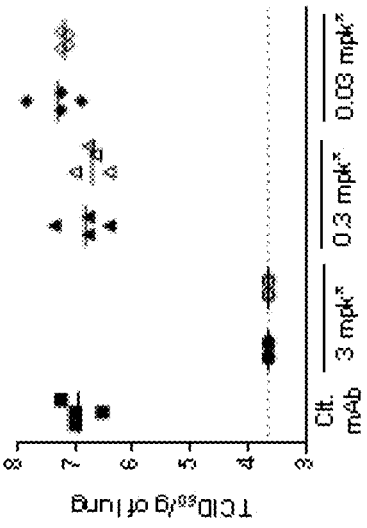
FIGS. 5A-D show the survival rate (A and C) and lung viral titers at day 5 post-infection (B and D) in each group of a study when different concentrations of GL20/39 BiS4 43/105 (Flu BiS), FBC39, and a non-relevant control antibody (Ctl. mAb) were administered to mice 4 hours before infection with a lethal dose of (A and B) B/Florida/4/2006 yamagata lineage and (C and D) B/Malaysia/2506/2004 victoria lineage influenza virus.
Figure 5D:
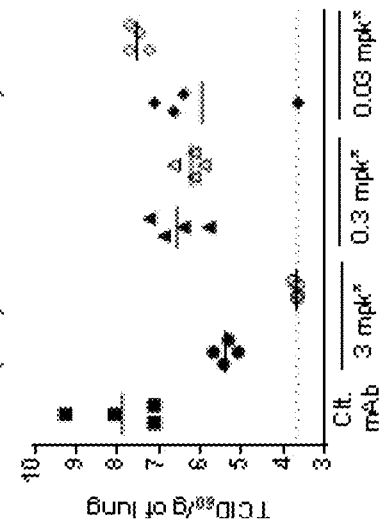
Figure 5A:
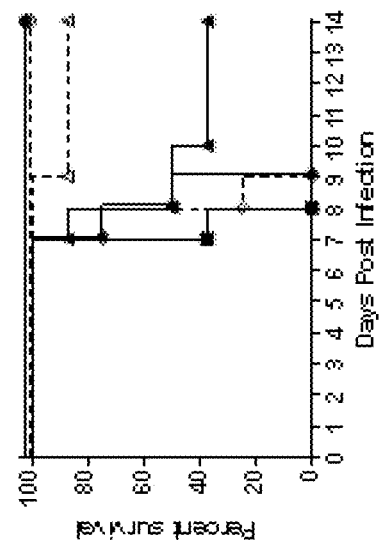
Figure 5C:
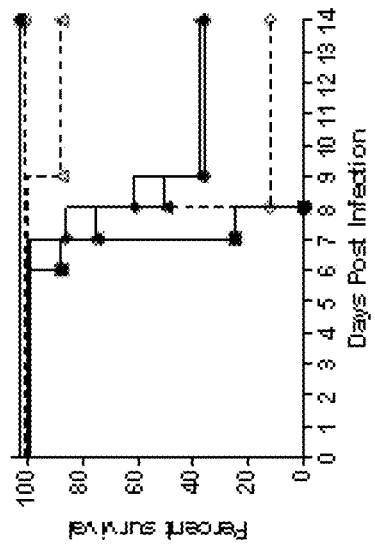

Both GL20/39 BiS4 43/105 and the parental FBC39 IgG conferred protection against lethal influenza B infection in a dose-dependent manner. IP injection of 3 mg/kg equivalent of the BiS molecule protected 100% of the animals challenged with the B/FLA/06 yamagata lineage and the B/MAL/04 victoria lineage viruses (FIGS. 5A and C solid lines). Although the BiS and FBC39 at 3 mg/kg dose provided complete protection with 100% survival rate, the FBC39 showed better protection than FBC39 at the 0.3 mg/kg dose level in both influenza B infection models. When viral titer in the lungs was assessed at Day 5 post infection, both antibody molecules reduced viral lung titers, which was most apparent at the 3 mg/kg equivalent dose. Comparing the BiS with the IgG, we see similar viral titer reductions in the B/FLA/06 yamagata infection model, however, the BiS was less effective than FBC39 in reducing viral lung titer in in mice infected with the B/Mal/04 victoria strain (FIGS. 5 B and D) Taken together, these data in FIGS. 4 and 5 show that GL20/39 BiS4 43/105 can effectively prevent lethality and reduce lung viral replication in both influenza A and B lethal infection models.

Example 9. In Vivo Therapeutic Protection of Flu A+B BiS Constructs Compared to Oseltamivir in a Lethal Murine Model of Influenza A and Influenza B Infection To directly compare the therapeutic efficacy of the BiS molecule to the small molecule NA inhibitor, oseltamivir, we used the influenza murine model of influenza A and B infection.

Therapeutic Comparison of GL20/39 BiS4 43/105 and Oseltamivir (FIG. 5)

Mice were inoculated with 2.5 $MLD_{50}$ of A/WSN/33 H1 virus or 7 $MLD_{50}$ of the B/FLA/06 yamagata lineage virus, and then treated with a single IV does at 10 mg/kg equivalent (14.1 mg/kg) of GL20/39 BiS4 43/105 or 25 mg/kg BID, orally for 5 days of oseltamivir initiated either at Day 1, Day 2, Day 3, or Day 4 post infection. 10 animals per group were monitored for body weight loss and survival, and 4 animals were sacrificed to measure lung viral titer as described above. In addition, as a non-invasive readout of lung function, blood oxygen saturation level was measured using pulse oximetry (mouse ox) on day 6 post infection for 4 animals per group.

Treatment with the BiS molecule protected 100% of mice from lethal infection with A/WSN/33 or B/FLA/06 when administered on Day 2 post infection (FIGS. 6A and B). Even when treatment was delayed until Day 3 post-infection, the BiS molecule still prevented lethality in 50% of the animals infected with either influenza A or B virus. In the influenza A infection model, oseltamivir showed no protection when treatment was given on Day 1 or later, however, it provided good protection with 90-100% survival rates when administration was initiated on Day 1 or Day 2 post influenza B infection. Although the oseltamivir protected well in the influenza B model, the BiS showed a trend for better protection with higher survival rates than oseltamivir when administered on Day 2, Day 3, and Day 4 post infection (FIGS. 6A and B).

FIG. 6 (C and D) showed the lung viral titer in the BiS or oseltamivir treated mice 5 days post infection. Treatment with the BiS molecule at different times post infection with the A/WSN/33 H1N1 virus inhibited lung viral replication in a time dependent fashion from greater than 3 logs of viral reduction when treatment was initiated on Day 1 post infection, to 1 log viral titer reduction when treatment was initiated on Day 4 post infection (FIG. 6 C). As compared to oseltamivir, the BiS molecule showed 1-2 logs greater reduction when treatment was initiated on Day 2, Day 3, or Day 4 post infection.

To assess the effect of different treatments on lung function, oxygen saturation level was measured by pulse oximetry (FIGS. 6 E and F). Infected animals treated with only irrelevant control mAb showed a reduction in the percent oxygen saturation to 80% for the A/WSN/33 and 78% on Day 6 post infection compared to the 98% for the naive animals. Treatment with the GL20/39 BiS4 43/105 prevented oxygen saturation levels from dropping below 90% even when treatment was delayed until Day 4 post infection, whereas the oseltamivir treated animals showed reduced oxygen saturation at similar levels as those treated with an irrelevant control mAb (FIG. 6 E). When mice were infected with B/FLA/06 and then treated with the BiS or oseltamivir, both agents protected lung function with BiS-treated animals having slightly higher oxygen saturation level when treatment was initiated on Day 1 post infection (FIG. 6 F). When treatment was initiated on Day 2 post infection, the BiS treated animals showed significantly improved lung function in 3 out 4 treated animals than the oseltamivir treated animals (avg. 92% vs 86%). Overall these two studies show that GL20/39 BiS4 43/105 can prevent lethality, reduce viral titers, and protect lung function in animals infected with lethal dose of influenza A and B when treatment is initiated up to Day 3 post infection.

INCORPORATION BY REFERENCE

All references cited herein, including patents, patent applications, papers, text books and the like, and the references cited therein, to the extent that they are not already, are hereby incorporated herein by reference in their entirety.

| Sequences |
|---|

SEQ ID NO: 1 (FY1 VL nucleic acid sequence)
GACATCCAGATGACCCAGTCGCCATCCTCCCTGTCTGCATCTGTAGGAGACAGAG
TAACCATCACTTGCCGGACAAGTCAGAGCCTTAGTAGCTATTTACATTGGTATCAG
CAGAAACCAGGGAAAGCCCCTAAGCTCCTGATCTATGCTGCATCCAGTTTGCAAAG
TGGGGTCCCATCAAGGTTCAGTGGCAGTGGATCTGGGACAGATTTCACTCTCACC
ATCAGTAGTCTGCAACCTGAAGATTTTGCAACTTACTACTGTCAACAGAGTCGGAC
GTTCGGCCAAGGGACCAAGGTGGAAATCAAA SEQ ID NO: 2 (FY1 VL amino acid sequence)
DIQMTQSPSSLSASVGDRVTITCRTSQSLSSYLHWYQQKPGKAPKLLIYAASSLQSGV
PSRFSGSGSGTDFTLTISSLQPEDFATYYCQQSRTFGQGTKVEIK

SEQ ID NO: 3 LCDR1 RTSQSLSSYLH

SEQ ID NO: 4 LCDR2 AASSLQS

SEQ ID NO: 5 LCDR3 QQSRT

SEQ ID NO: 6 (FY1 VH nucleic acid sequence)
CAGGTACAGCTGCAGGAGTCGGGTCCAGGACTGGTGAAGCCCTCGCAGACCCTC
TCACTCACCTGTGCCATCTCCGGGGACAGTGTCTCTAGCAACAATGCTGTTTGGAA
CTGGATCAGGCAGTCCCCATCGAGAGGCCTTGAGTGGCTGGGAAGGACATACTAC
AGGTCCAAGTGGTATAATGATTATGCAGAATCTGTGAAAAGTCGAATAACCGTCAA
TCCAGACACATCCAAGAACCAGTTCTCCCTGCACCTGAAGTCTGTGACTCCCGAA
GACACGGCTGTGTTTTACTGTGTACGATCTGGCCACATTACGGTTTTTGGAGTGAA
TGTTGACGCTTTTGATATGTGGGGCCAAGGGACAATGGTCACCGTCTCTTCAG SEQ ID NO: 7 (FY1 VH amino acid sequence)
QVQLQESGPGLVKPSQTLSLTCAISGDSVSSNNAVWNWIRQSPSRGLEWLGRTYYRS
KWYNDYAESVKSRITVNPDTSKNQFSLHLKSVTPEDTAVFYCVRSGHITVFGVNVDAF
DMWGQGTMVTVSS

SEQ ID NO: 8 HCDR1 SNNAVWN

SEQ ID NO: 9 HCDR2 RTYYRSKWYNDYAESVKS

SEQ ID NO: 10 HCDR3 SGHITVFGVNVDAFDM

SEQ ID NO: 11 (GL20 VL nucleic acid sequence)
GATATTCAGATGACCCAGAGCCCTTCCAGCCTGTCCGCTTCAGTGGGGGATCGAG
TGACCATTACCTGCCGAACCAGCCAGAGCCTGAGCTCCTACACGCACTGGTATCA
GCAGAAGCCCGGCAAAGCCCCTAAGCTGCTGATCTACGCCGCTTCTAGTCGGGG
GTCCGGAGTGCCAAGCCGGTTCTCCGGATCTGGGAGTGGAACCGACTTTACCCTG
ACAATTTCAAGCCTGCAGCCCGAGGATTTCGCTACATACTACTGTCAGCAGAGCAG
AACTTTCGGGCAGGGCACTAAGGTGGAGATCAAA SEQ ID NO: 12 (GL20 VL amino acid sequence)
DIQMTQSPSSLSASVGDRVTITCRTSQSLSSYTHWYQQKPGKAPKLLIYAASSRGSGV
PSRFSGSGSGTDFTLTISSLQPEDFATYYCQQSRTFGQGTKVEIK

SEQID NO: 13 LCDR1 RTSQSLSSYTH

SEQID NO: 14 LCDR2 AASSRGS

SEQID NO: 15 LCDR3 QQSRT

SEQ ID NO: 16 (GL20 VH nucleic acid sequence)
CAGGTCCAGCTGCAGCAGAGCGGCCCCGGACTGGTCAAGCCCTTCACAGACACTG
AGCCTGACATGCGCCATTAGCGGAGATAGCGTGAGCTCCTACAATGCCGTGTGGA
ACTGGATCAGGCAGTCTCCAAGTCGAGGACTGGAGTGGCTGGGACGAACATACTA
TAGATCCGGTGGTACAATGACTATGCTGAATCAGTGAAAAGCCGAATTACTATCA
ACCCCGATACCTCCAAGAATCAGTTCTCTCTGCAGCTGAACAGTGTGACCCCTGAG
GACACAGCCGTGTACTACTGCGCCAGAAGCGGCCATATCACCGTCTTTGGCGTCA
ATGTGGATGCTTTCGATATGTGGGGGCAGGGGACTATGGTCACCGTGTCAAGC SEQ ID NO: 17 (GL20 VH amino acid sequence)
QVQLQQSGPGLVKPSQTLSLTCAISGDSVSSYNAVWNWIRQSPSRGLEWLGRTYYRS
GWYNDYAESVKSRITINPDTSKNQFSLQLNSVTPEDTAVYYCARSGHITVFGVNVDAF
DMWGQGTMVTVSS

SEQ ID NO: 18 HCDR1 SYNAVWN

SEQ ID NO: 19 HCDR2 RTYYRSGWYNDYAESVKS

SEQ ID NO: 20 HCDR3 SGHITVFGVNVDAFDM

SEQ ID NO: 21 (FBC39 VL DNA)
GACATCCAGATGACCCAGTCTCCATCTTCCGTGTCTGCATCTGTGGGAGACAGAGT
CACCATCACTTGTCGGGCGAGTCAGGATATTAGCACCTGGTTAGCCTGGTATCAG

| Sequences |
|---|
| CAGAAACCAGGGAAAGCCCCTAAGCTCCTGATCTATGCTGCATCCAGTTTGCAAAG<br>TGGGGTCCCATCAAGATTCAGCGGCAGTGGATCTGGGACAGATTTCACTCTCACC<br>ATCAGCAGCCTGCAGCCTGAAGATTTTGCAACTTACTTTTGTCAGCAGGCTAACAG<br>TTTCCCTCCGACTTTTGGCCAGGGGACCAAGCTGGAGATCAAAC<br><br>SEQ ID NO: 22 (FBC39 VL protein)<br>DIQMTQSPSSVSASVGDRVTITCRASQDISTWLAWYQQKPGKAPKLLIYAASSLQSGV<br>PSRFSGSGSGTDFTLTISSLQPEDFATYFCQQANSFPPTFGQGTKLEIK<br><br>SEQ ID NO: 23 (FBC39 LCDR-1 - Kabat): RASQDISTWLA<br><br>SEQ ID NO: 24 (FBC39 LCDR-2 - Kabat): AASSLQS<br><br>SEQ ID NO: 25 (FBC39 LCDR-3 - Kabat): QQANSFPPT<br><br>SEQ ID NO: 26 (FBC39 VH DNA)<br>GAGGTGCAGCTGGTGGTGTCTGGGGGAGGCTTGGTAAAGCCTGGGGGGTCCCTT<br>AGACTCTCCTGTGCAGCCTCTGGACTCAGTTTCCTTAACGCCTGGATGAGCTGGGT<br>CCGCCAGGCTCCAGGGAAGGGGCTGGAGTGGGTTGGCCGTATTAAAAGTAATACT<br>GATGGTGGGACAACAGACTACGCCGCACCCGTGAAAGGCAGATTCAGCATCTCAA<br>GAGACGATTCAAAGAACATGCTGTTTCTGCATATGAGCAGCCTGAGAACCGAGGA<br>CACAGCCGTCTATTACTGCGCCACAGATGGACCTTACTCTGACGATTTTAGAAGTG<br>GTTATGCCGCACGCTACCGTTATTTCGGAATGGACGTCTGGGGCCAAGGGACCAC<br>GGTCACCGTCTCCTCAG<br><br>SEQ ID NO: 27 (FBC39 VH protein)<br>EVQLVVSGGGLVKPGGSLRLSCAASGLSFLNAWMSWVRQAPGKGLEWVGRIKSNTD<br>GGTTDYAAPVKGRFSISRDDSKNMLFLHMSSLRTEDTAVYYCATDGPYSDDFRSGYA<br>ARYRYFGMDVWGQGTTVTVSS<br><br>SEQ ID NO: 28 (FBC39 HCDR-1 - Kabat): NAWMS<br><br>SEQ ID NO: 29 (FBC39 HCDR-2 - Kabat): RIKSNTDGGTTDYAAPVKG<br><br>SEQ ID NO: 30 (FBC39 HCDR-3 - Kabat): DGPYSDDFRSGYAARYRYFGMDV<br><br>SEQ ID NO: 31 (FBC39 scFv amino acid sequence):<br>DIQMTQSPSSVSASVGDRVTITCRASQDISTWLAWYQQKPGKAPKLLIYAASSLQSGV<br>PSRFSGSGSGTDFTLTISSLQPEDFATYFCQQANSFPPTFGCGTKLEIKGGGGSGGGG<br>GSGGGGSGGGGSEVQLVVSGGGLVKPGGSLRLSCAASGLSFLNAWMSWVRQAPGK<br>CLEWVGRIKSNTDGGTTDYAAPVKGRFSISRDDSKNMLFLHMSSLRTEDTAVYYCATD<br>GPYSDDFRSGYAARYRYFGMDVWGQGTTVTVSS<br><br>SEQ ID NO: 32 (FBC39 VL protein - scFv)<br>DIQMTQSPSSVSASVGDRVTITCRASQDISTWLAWYQQKPGKAPKLLIYAASSLQSGV<br>PSRFSGSGSGTDFTLTISSLQPEDFATYFCQQANSFPPTFGCGTKLEIK<br><br>SEQ ID NO: 33 (FBC39 VH protein - scFv)<br>EVQLVVSGGGLVKPGGSLRLSCAASGLSFLNAWMSWVRQAPGKCLEWVGRIKSNTD<br>GGTTDYAAPVKGRFSISRDDSKNMLFLHMSSLRTEDTAVYYCATDGPYSDDFRSGYA<br>ARYRYFGMDVWGQGTTVTVSS<br><br>SEQ ID NO: 34 (FBC39-43/105 scFv amino acid sequence):<br>DIQMTQSPSSVSASVGDRVTITCRASQDISTWLAWYQQKPGKCPKLLIYAASSLQSGV<br>PSRFSGSGSGTDFTLTISSLQPEDFATYFCQQANSFPPTFGCGTKLEIKGGGGSGGGG<br>GSGGGGSGGGGSEVQLVVSGGGLVKPGGSLRLSCAASGLSFLNAWMSWVRQAPGK<br>GLEWVGRIKSNTDGGTTDYAAPVKGRFSISRDDSKNMLFLHMSSLRTEDTAVYYCATD<br>GPYSDDFRSGYAARYRYFGMDVWGCGTTVTVSS<br><br>SEQ ID NO: 35 (FBC39 VL protein - scFv 43/105)<br>DIQMTQSPSSVSASVGDRVTITCRASQDISTWLAWYQQKPGKCPKLLIYAASSLQSGV<br>PSRFSGSGSGTDFTLTISSLQPEDFATYFCQQANSFPPTFGQGTKLEIK<br><br>SEQ ID NO: 36 (FBC39 VH protein - scFv 43/105)<br>EVQLVVSGGGLVKPGGSLRLSCAASGLSFLNAWMSWVRQAPGKGLEWVGRIKSNTD<br>GGTTDYAAPVKGRFSISRDDSKNMLFLHMSSLRTEDTAVYYCATDGPYSDDFRSGYA<br>ARYRYFGMDVWGCGTTVTVSS<br><br>SEQ ID NO: 37 (FBC39 FTL VL DNA)<br>GACATCCAGATGACCCAGTCTCCATCTTCCGTGTCTGCATCTGTGGGAGACAGAGT<br>CACCATCACTTGTCGGGCGAGTCAGGATATTAGCACCTGGTTAGCCTGGTATCAG<br>CAGAAACCAGGGAAAGCCCCTAAGCTCCTGATCTATGCTGCATCCAGTTTGCAAAG<br>TGGGGTCCCATCAAGATTCAGCGGCAGTGGATCTGGGACAGATTTCACTCTCACC<br>ATCAGCAGCCTGCAGCCTGAAGATTTTGCAACTTACTATTGTCAGCAGGCTAACAG<br>TTTCCCTCCGACTTTTGGCCAGGGGACCAAGCTGGAGATCAAAC |

| Sequences |
| --- |
| SEQ ID NO: 38 (FBC39 FTL VL protein)<br>DIQMTQSPSSVSASVGDRVTITCRASQDISTWLAWYQQKPGKAPKLLIYAASSLQSGV<br>PSRFSGSGSGTDFTLTISSLQPEDFATYYCQQANSFPPTFGQGTKLEIK<br><br>SEQ ID NO: 39 (FBC39 FTL LCDR-1 - Kabat): RASQDISTWLA<br><br>SEQ ID NO: 40 (FBC39 FTL LCDR-2 - Kabat): AASSLQS<br><br>SEQ ID NO: 41 (FBC39 FTL LCDR-3 - Kabat): QQANSFPPT<br><br>SEQ ID NO: 42 (FBC39 FTL VH DNA)<br>GAGGTGCAGCTGGTGGAGTCTGGGGGAGGCTTGGTAAAGCCTGGGGGGTCCCTT<br>AGACTCTCCTGTGCAGCCTCTGGATTCACTTTCCTTAACGCCTGGATGAGCTGGGT<br>CCGCCAGGCTCCAGGGAAGGGCCTGGAGTGGGTTGGCCGTATTAAAAGTAATACT<br>GATGGTGGGACAACAGACTACGCCGCACCCGTGAAAGGCAGATTCACCATCTCAA<br>GAGACGATTCAAAGAACACGCTGTATCTGCAAATGAGCAGCCTGAAAACCGAGGA<br>CACAGCCGTCTATTACTGCACCACAGAIGGACCTTACTCTGACGATTTTAGAAGTG<br>GTTATGCCGCACGCTACCGTTATTTCGGAATGGACGTCTGGGGCCAAGGGACCAC<br>GGTCACCGTCTCCTCA<br><br>SEQ ID NO: 43 (FBC39 FTL VH protein)<br>EVQLVESGGGLVKPGGSLRLSCAASGFTFLNAWMSWVRQAPGKGLEWVGRIKSNTD<br>GGTTDYAAPVKGRFTISRDDSKNTLYLQMSSLKTEDTAVYYCTTDGPYSDDFRSGYAA<br>RYRYFGMDVWGQGTTVTVSS<br><br>SEQ ID NO: 44 (FBC39 FTL HCDR-1 - Kabat): NAWMS<br><br>SEQ ID NO: 45 (FBC39 FTL HCDR-2 - Kabat): RIKSNTDGGTTDYAAPVKG<br><br>SEQ ID NO: 46 (FBC39 FTL HCDR-3 - Kabat): DGPYSDDFRSGYAARYRYFGMDV<br><br>SEQ ID NO: 47 (FBC39FTL scFv amino acid sequence):<br>DIQMTQSPSSVSASVGDRVTITCRASQDISTWLAWYQQKPGKAPKLLIYAASSLQSGV<br>PSRFSGSGSGTDFTLTISSLQPEDFATYYCQQANSFPPTFGCGTKLEIKGGGGSGGG<br>GSGGGGSGGGGSEVQLVESGGGLVKPGGSLRLSCAASGFTFLNAWMSWVRQAPGK<br>CLEWVGRIKSNTDGGTTDYAAPVKGRFTISRDDSKNTLYLQMSSLKTEDTAVYYCTTD<br>GPYSDDFRSGYAARYRYFGMDVWGQGTTVTVSS<br><br>SEQ ID NO: 48 (FBC39 FTL VL protein - scFv)<br>DIQMTQSPSSVSASVGDRVTITCRASQDISTWLAWYQQKPGKAPKLLIYAASSLQSGV<br>PSRFSGSGSGTDFTLTISSLQPEDFATYYCQQANSFPPTFGCGTKLEIK<br><br>SEQ ID NO: 49 (FBC39 FTL VH protein - scFv)<br>EVQLVESGGGLVKPGGSLRLSCAASGFTFLNAWMSWVRQAPGKCLEWVGRIKSNTD<br>GGTTDYAAPVKGRFTISRDDSKNTLYLQMSSLKTEDTAVYYCTTDGPYSDDFRSGYAA<br>RYRYFGMDVWGQGTTVTVSS<br><br>SEQ ID NO: 50: (FBC39FTL-43/105 scFv amino acid sequence):<br>DIQMTQSPSSVSASVGDRVTITCRASQDISTWLAWYQQKPGKCPKLLIYAASSLQSGV<br>PSRFSGSGSGTDFTLTISSLQPEDFATYYCQQANSFPPTFGQGTKLEIKGGGGSGGG<br>GSGGGGSGGGGSEVQLVESGGGLVKPGGSLRLSCAASGFTFLNAWMSWVRQAPGK<br>GLEWVGRIKSNTDGGTTDYAAPVKGRFTISRDDSKNTLYLQMSSLKTEDTAVYYCTTD<br>GPYSDDFRSGYAARYRYFGMDVWGCGTTVTVSS<br><br>SEQ ID NO: 51 (FBC39 FTL VL protein - scFv 43/105)<br>DIQMTQSPSSVSASVGDRVTITCRASQDISTWLAWYQQKPGKCPKLLIYAASSLQSGV<br>PSRFSGSGSGTDFTLTISSLQPEDFATYYCQQANSFPPTFGQGTKLEIK<br><br>SEQ ID NO: 52 (FBC39 FTL VH protein - scFv 43/105)<br>EVQLVESGGGLVKPGGSLRLSCAASGFTFLNAWMSWVRQAPGKGLEWVGRIKSNTD<br>GGTTDYAAPVKGRFTISRDDSKNTLYLQMSSLKTEDTAVYYCTTDGPYSDDFRSGYAA<br>RYRYFGMDVWGCGTTVTVSS<br><br>SEQ ID NO: 53 (FBD94 VL DNA)<br>GAAATTGTGTTGACACAGTCTCCAGCCACTCTGTCTTTGTCTCCAGGGGAAAGAGC<br>CACCCTCTCCTGCAGGGCCAGTCGGAGTATTACCACCTTCTTAGCCTGGTACCAAC<br>AAAAACCTGGCCAGGCTCCCAGGCTCCTCATCTACGATGCATCCAACAGGGCCAC<br>TGGCGTCCCAGCCAGGTTCAGTGGCAGTGGGTCTGGGACAGACTTCACTCTCACC<br>ATCAACAGCCTAGAGCCTGACGATTTTGCAATTTATTACTGTCAGCAGCGTGACCA<br>CTGGCCTCCGATCTTCGGCCAAGGGACACGACTGGAGATTAAAC<br><br>SEQ ID NO: 54 (FBD94 VL protein)<br>EIVLTQSPATLSLSPGERATLSCRASRSITTFLAWYQQKPGQAPRLLIYDASNRATGVP<br>ARFSGSGSGTDFTLTINSLEPDDFAIYYCQQRDHWPPIFGQGTRLEIK |

| Sequences |
| --- |

SEQ ID NO: 55 (FBD94 LCDR-1 - Kabat): RASRSITTFLA

SEQ ID NO: 56 (FBD94 LCDR-2 - Kabat): DASNRAT

SEQ ID NO: 57 (FBD94 LCDR-3 - Kabat): QQRDHWPPI

SEQ ID NO: 58 (FBD94 VH DNA)
GAAGTGCAGCTGGTGGAGTCTGGGGGAGGCTTGGTGCAACCTGGCAGGTCCCTG
AGACTCTCCTGTGCAGTTTCTGGATTCATCTTTGAAGATTATGCCATAAACTGGGTC
CGGCAAGCTCCAGGGAAGGGCCTGGAGTGGGTCTCAATTATTAGTTGGGACAGTG
GTAGGATAGGCTACGCGGACTCTGTGAGGGGCCGATTCACCATCTCCAGAGACAA
CGCCAAGAACTCCTCGTTTCTGCAAATGAACAGTCTGAGACCCGAAGACACGGCC
GTGTATTATTGTGTAAAAGATATGTTGGCGTATTATTATGATGGTAGCGGCATCAGG
TACAACCTCTACGGTATGGACGTCTGGGGCCAAGGGACCACGGTCACCGTCTCCT
CAG

SEQ ID NO: 59 (FBD94 VH protein)
EVQLVESGGGLVQPGRSLRLSCAVSGFIFEDYAINWVRQAPGKGLEWVSIISWDSGRI
GYADSVRGRFTISRDNAKNSSFLQMNSLRPEDTAVYYCVKDMLAYYYDGSGIRYNLY
GMDVWGQGTTVTVSS SEQ ID NO: 60 (FBD94 HCDR-1 - Kabat): DYAIN SEQ ID NO: 61 (FBD94 HCDR-2 - Kabat): IISWDSGRIGYADSVRG SEQ ID NO: 62 (FBD94 HCDR-3 - Kabat): DMLAYYYDGSGIRYNLYGMDV SEQ ID NO: 63 (FBD94 scFv amino acid sequence):
EIVLTQSPATLSLSPGERATLSCRASRSITTFLAWYQQKPGQAPRLLIYDASNRATGVP
ARFSGSGSGTDFTLTINSLEPDDFAIYYCQQRDHWPPIFGCGTRLEIKGGGGSGGGGS
GGGGSGGGGSEVQLVESGGGLVQPGRSLRLSCAVSGFIFEDYAINWVRQAPGKCLE
WVSIISWDSGRIGYADSVRGRFTISRDNAKNSSFLQMNSLRPEDTAVYYCVKDMLAYY
YDGSGIRYNLYGMDVWGQGTTVTVSS SEQ ID NO: 64 (FBD94 VL protein -scFv)
EIVLTQSPATLSLSPGERATLSCRASRSITTFLAWYQQKPGQAPRLLIYDASNRATGVP
ARFSGSGSGTDFTLTINSLEPDDFAIYYCQQRDHWPPIFGCGTRLEIK SEQ ID NO: 65 (FBD94 VH protein - scFv)
EVQLVESGGGLVQPGRSLRLSCAVSGFIFEDYAINWVRQAPGKCLEWVSIISWDSGRI
GYADSVRGRFTISRDNAKNSSFLQMNSLRPEDTAVYYCVKDMLAYYYDGSGIRYNLY
GMDVWGQGTTVTVSS SEQ ID NO: 66 (GL20/39 BiS4 100/44 Light chain):
DIQMTQSPSSLSASVGDRVTITCRTSQSLSSYTHWYQQKPGKAPKLLIYAASSRGSGV
PSRFSGSGSGTDFTLTISSLQPEDFATYYCQQSRTFGQGTKVEIKRTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO: 67 (GL20/39 BiS4 100/44 Heavy chain):
QVQLQQSGPGLVKPSQTLSLTCAISGDSVSSYNAVWNWIRQSPSRGLEWLGRTYYRS
GWYNDYAESVKSRITINPDTSKNQFSLQLNSVTPEDTAVYYCARSGHITVFGVNVDAF
DMWGQGTMVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPK
SCGGGGSGGGGSDIQMTQSPSSVSASVGDRVTITCRASQDISTWLAWYQQKPGKAP
KLLIYAASSLQSGVPSRFSGSGSGTDFTLTISSLQPEDFATYFCQQANSFPPTFGCGTK
LEIKGGGGSGGGGSGGGGSGGGGSEVQLVVSGGGLVKPGGSLRLSCAASGLSFLNA
WMSWVRQAPGKCLEWVGRIKSNTDGGTTDYAAPVKGRFSISRDDSKNMLFLHMSSL
RTEDTAVYYCATDGPYSDDFRSGYAARYRYFGMDVWGQGTTVTVSSGGGGSGGGG
SDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK SEQ ID NO: 68 (GL20/39 BiS4 43/105 Light chain):
DIQMTQSPSSLSASVGDRVTITCRTSQSLSSYTHWYQQKPGKAPKLLIYAASSRGSGV
PSRFSGSGSGTDFTLTISSLQPEDFATYYCQQSRTFGQGTKVEIKRTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO: 69 (GL20/39 BiS4 43/105 Heavy chain):
QVQLQQSGPGLVKPSQTLSLTCAISGDSVSSYNAVWNWIRQSPSRGLEWLGRTYYRS
GWYNDYAESVKSRITINPDTSKNQFSLQLNSVTPEDTAVYYCARSGHITVFGVNVDAF
DMWGQGTMVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPK
SCGGGGSGGGGSDIQMTQSPSSVSASVGDRVTITCRASQDISTWLAWYQQKPGKCP
KLLIYAASSLQSGVPSRFSGSGSGTDFTLTISSLQPEDFATYFCQQANSFPPTFGQGTK

| Sequences |
|---|
| LEIKGGGGSGGGGSGGGGSGGGGSEVQLVVSGGGLVKPGGSLRLSCAASGLSFLNA<br>WMSWVRQAPGKGLEWVGRIKSNTDGGTTDYAAPVKGRFSISRDDSKNMLFLHMSSL<br>RTEDTAVYYCATDGPYSDDFRSGYAARYRYFGMDVWGCGTTVTVSSGGGGSGGGG<br>SDKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEKT<br>ISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK<br><br>SEQ ID NO: 70 (FBC39 scFv-FY1 VH DNA for FY1/39 BiS2 100/44 forward primer)<br>TTCTCTCCACAGGTGTACACTCCGACATCCAGATGACCCAGTCTC<br><br>SEQ ID NO: 71 (FBC39 scFv-FY1 VH DNA for FY1/39 BiS2 100/44 reverse primer)<br>GGATGGGCCCTTGGTCGACGCGCTTGACACGGTGACCATAGTC<br><br>SEQ ID NO: 72 (FBC39 scFv FY1/39 BiS4 100/44 forward primer)<br>CTCTGGCGGAGGGggatccGACATCCAGATGACCCAGTCTC<br><br>SEQ ID NO: 73 (FBC39 scFv FY1/39 BiS4 100/44 reverse primer)<br>GTGAGTTTTGTCggatccCCCTCCGCCAGAGCCACCTCCGCCTGAGGAGACGGTGA<br>CCGTGG<br><br>SEQ ID NO: 74 (BiS1 FBC39 forward primer):<br>CTGGCTCCCCGGGGCGCGCTGTGACATCCAGATGACCCAGTCTCC<br><br>SEQ ID NO: 75 (BiS1 FBC39 reverse primer):<br>CCCCTCCGCCGGATCCCCCTCCGCCTGAGGAGACGGTGACCGTGGTC<br><br>SEQ ID NO: 76 (BiD1 FY1-VL forward primer):<br>AGGGGGATCCGGCGGAGGGGGCTCTGATATTCAGATGACCCAGAGCCC<br><br>SEQ ID NO: 77 (BiS1 FY1-VL reverse primer):<br>TGGTGCAGCCACCGTACGTTTGATCTCCACCTTAGTGCCC<br><br>SEQ ID NO: 78 (FY1/39 BiS3 100/44 - FBC39 scFv forward primer):<br>AAAGGCGGAGGGGGATCCGGCGGAGGGGGCTCTGACATCCAGATGACCCAGTCT<br>C<br><br>SEQ ID NO: 79 (FY1/39 BiS3 100/44 - FBC39 scFv reverse primer):<br>TCAATGAATTCGCGGCCGCTCATGAGGAGACGGTGACCGTGGTC<br><br>SEQ ID NO: 80 (FY1/94 BiS2 100/44 - FBD94 scFv forward primer):<br>TTCTCTCCACAGGTGTACACTCCGAAATTGTGTTGACACAGTCTC<br><br>SEQ ID NO: 81 (FY1/94 BiS2 100/44 - FBD94 scFv reverse primer):<br>CCCCTCCGCCGGATCCCCCTCCGCCTGAGGAGACGGTGACCGTGGTC<br><br>SEQ ID NO: 82 (FY1/94 BiS2 100/44 - FY1 VH forward primer):<br>AGGGGGATCCGGCGGAGGGGGCTCTCAGGTCCAGCTGCAGGAGAGC<br><br>SEQ ID NO: 83 (FY1/94 BiS2 100/44 - FY1 VH reverse primer):<br>GGATGGGCCCTTGGTCGACGCGCTTGACACGGTGACCATAGTC<br><br>SEQ ID NO: 84 (FY1/94 BiS4 100/44 - FBD94 scFv forward primer):<br>CTCTGGCGGAGGGGGATCCGAAATTGTGTTGACACAGTCTC<br><br>SEQ ID NO: 85 (FY1/94 BiS4 100/44 - FBD94 scFv reverse primer):<br>GTGAGTTTTGTCGGATCCCCCTCCGCCAGAGCCACCTCCGCCTGAGGAGACGGTG<br>ACCGTGG<br><br>SEQ ID NO: 86 (FY1/39 BiS4 43/105 - FBC39-43/105 scFv forward primer):<br>CTCTGGCGGAGGGggatccGACATCCAGATGACCCAGTCTC<br><br>SEQ ID NO: 87 (FY1/39 BiS4 43/105 - FBC39-43/105 scFv reverse primer):<br>GTGAGTTTTGTCggatccCCCTCCGCCAGAGCCACCTCCGCCTGAGGAGACGGTGA<br>CCGTGG<br><br>SEQ ID NO: 88 (GL20/39FTL BiS4 100/44 - FBC39FTL scFv forward primer):<br>CTCTGGCGGAGGGGGATCCGACATCCAGATGACCCAGTCTC<br><br>SEQ ID NO: 89 (GL20/39FTL BiS4 100/44 - FBC39FTL scFv reverse primer):<br>GTGAGTTTTGTCGGATCCCCCTCCGCCAGAGCCACCTCCGCCTGAGGAGACGGTG<br>ACCGTGG<br><br>SEQ ID NO: 90 (GL20/39FTL BiS4 43/105 - FBC39FTL43/105 scFv forward primer):<br>CTCTGGCGGAGGGggatccGACATCCAGATGACCCAGTCTC |

| Sequences |
| --- |

SEQ ID NO: 91 (GL20/39FTL BiS4 43/105 - FBC39FTL43/105 scFv reverse primer):
GTGAGTTTTGTCggatccCCCTCCGCCAGAGCCACCTCCGCCTGAGGAGACGGTGA
CCGTGG SEQ ID NO: 92 (Gly/ser linker)
GGGGSGGGGSGGGGSGGGGS SEQ ID NO: 93 (Gly/ser linker)
[GGGGS]n, wherein n is 0, 1, 2, 3, 4, or 5

SEQ ID NO: 94 (FBC-39 LCDR-1 -TMGT): QDISTW

SEQ ID NO: 95 (FBC-39 LCDR-2 -TMGT): AAS

SEQ ID NO: 96 (FBC-39 LCDR-3 -TMGT): QQANSFPPT

SEQ ID NO: 97 (FBC-39 HCDR-1 -TMGT): GLSFLNAW

SEQ ID NO: 98 (FBC-39 HCDR-2 -TMGT): IKSNTDGGTT

SEQ ID NO: 99 (FBC-39 HCDR-3 -TMGT): TDGPYSDDFRSGYAARYRYFGMDVW

SEQ ID NO: 100 (FBC-39 FTL LCDR-1 -TMGT): QDISTW

SEQ ID NO: 101 (FBC-39 FTL LCDR-2 -TMGT): AAS

SEQ ID NO: 102 (FBC-39 FTL LCDR-3 -TMGT): QQANSFPPT

SEQ ID NO: 103 (FBC-39 FTL HCDR-1 -TMGT): GFTFLNAW

SEQ ID NO: 104 (FBC-39 FTL HCDR-2 -TMGT): IKSNTDGGTT

SEQ ID NO: 105 (FBC-39 FTL HCDR-3 -TMGT):
TTDGPYSDDFRSGYAARYRYFGMDV

SEQ ID NO: 106 (Gly/ser linker)
[GGGG]n, wherein n is 0, 1, 2, 3, 4, or 5

SEQ ID NO: 107 (FY1/39 Bis2 100/44 Light Chain)
DIQMTQSPSSLSASVGDRVTITCRTSQSLSSYLHWYQQKPGKAPKLLIYAASSLQSGV
PSRFSGSGSGTDFTLTISSLQPEDFATYYCQQSRTFGQGTKVEIKRTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO: 108 (FY1/39 Bis2 100/44 Heavy Chain)
DIQMTQSPSSVSASVGDRVTITCRASQDISTWLAWYQQKPGKAPKLLIYAASSLQSGV
PSRFSGSGSGTDFTLTISSLQPEDFATYFCQQANSFPPTFGCGTKLEIKGGGGSGGGG
GSGGGGSGGGGSEVQLVVSGGGLVKPGGSLRLSCAASGLSFLNAWMSWVRQAPGK
CLEWVGRIKSNTDGGTTDYAAPVKGRFSISRDDSKNMLFLHMSSLRTEDTAVYYCATD
GPYSDDFRSGYAARYRYFGMDVWGQGTTVTVSSGGGGSGGGGSQVQLQESGPGL
VKPSQTLSLTCAISGDSVSSNNAVWNWIRQSPSRGLEWLGRTYYRSKWYNDYAESVK
SRITVNPDTSKNQFSLHLKSVTPEDTAVFYCVRSGHITVFGVNVDAFDMWGQGTMVT
VSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSCDKTHTCPPCP
APELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 109 (FY1/39 Bis4 100/44 Light Chain)
DIQMTQSPSSLSASVGDRVTITCRTSQSLSSYLHWYQQKPGKAPKLLIYAASSLQSGV
PSRFSGSGSGTDFTLTISSLQPEDFATYYCQQSRTFGQGTKVEIKRTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO: 110 (FY1/39 Bis4 100/44 Heavy Chain)
QVQLQESGPGLVKPSQTLSLTCAISGDSVSSNNAVWNWIRQSPSRGLEWLGRTYYRS
KWYNDYAESVKSRITVNPDTSKNQFSLHLKSVTPEDTAVFYCVRSGHITVFGVNVDAF
DMWGQGTMVTVSSASTKGPSVFPLAPSSKSTSGGTAALGCLVKDYFPEPVTVSWNS
GALTSGVHTFPAVLQSSGLYSLSSVVTVPSSSLGTQTYTCNVNHKPSNTKVDKRVEPK
SCGGGGSGGGGSDIQMTQSPSSVSASVGDRVTITCRASQDISTWLAWYQQKPGKAP
KLLIYAASSLQSGVPSRFSGSGSGTDFTLTISSLQPEDFATYFCQQANSFPPTFGCGTK
LEIKGGGGSGGGGSGGGGSGGGGSEVQLVVSGGGLVKPGGSLRLSCAASGLSFLNA
WMSWVRQAPGKCLEWVGRIKSNTDGGTTDYAAPVKGRFSISRDDSKNMLFLHMSSL
RTEDTAVYYCATDGPYSDDFRSGYAARYRYFGMDVWGQGTTVTVSSGGGGSGGGG
SDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKT ISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK SEQ ID NO: 111 (FBC39 scFv-FY1 VH DNA):
GACATCCAGATGACCCAGTCTCCATCTTCCGTGTCTGCATCTGTGGGAGACAGAGT
CACCATCACTTGTCGGGCGAGTCAGGATATTAGCACCTGGTTAGCCTGGTATCAG
CAGAAACCAGGGAAAGCCCCTAAGCTCCTGATCTATGCTGCATCCAGTTTGCAAAG
TGGGGTCCCATCAAGATTCAGCGGCAGTGGATCTGGGACAGATTTCACTCTCACC
ATCAGCAGCCTGCAGCCTGAAGATTTTGCAACTTACTTTTGTCAGCAGGCTAACAG
TTTCCCTCCGACTTTTGGCTGCGGGACCAAGCTGGAGATCAAAGGCGGAGGGGG
CTCTGGGGAGGGGCAGCGGCGGCGGAGGATCTGGGGGAGGGGGCAGCGAG
GTGCAGCTGGTGGTGTCTGGGGGAGGCTTGGTAAAGCCTGGGGGGTCCCTTAGA
CTCTCCTGTGCAGCCTCTGGACTCAGTTTCCTTAACGCCTGGATGAGCTGGGTCC
GCCAGGCTCCAGGGAAGTGCCTGGAGTGGGTTGGCCGTATTAAAAGTAATACTGA
TGGTGGGACAACAGACTACGCCGCACCCGTGAAAGGCAGATTCAGCATCTCAAGA
GACGATTCAAAGAACACATGCTGTTTCTGCATATGAGCAGCCTGAGAACCGAGGACA
CAGCCGTCTATTACTGCGCCACAGATGGACCTTACTCTGACGATTTTAGAAGTGGT
TATGCCGCACGCTACCGTTATTTCGGAATGGACGTCTGGGGCCAAGGGACCACGG
TCACCGTCTCCTCAGGCGGAGGGGGATCCGGCGGAGGGGGCTCTCAGGTCCAGC
TGCAGGAGAGCGGCCCCGGACTGGTCAAGCCTTCACAGACACTGAGCCTGACAT
GCGCCATTAGCGGAGATAGCGTGAGCTCCAACAATGCCGTGTGGAACTGGATCAG
GCAGTCTCCAAGTCGAGGACTGGAGTGGCTGGGACGAACATACTATAGATCCAAG
TGGTACAATGACTATGCTGAATCAGTGAAAAGCCGAATTACTGTCAACCCCGATAC
CTCCAAGAATCAGTTCTCTCTGCACCTGAAAAGTGTGACCCCTGAGGACACAGCC
GTGTTCTACTGCGTCAGAAGCGGCCATATCACCGTCTTTGGCGTCAATGTGGATGC
TTTCGATATGTGGGGGCAGGGGACTATGGTCACCGTGTCAAGC SEQ ID NO: 112 (FBC39 scFv DNA):
GACATCCAGATGACCCAGTCTCCATCTTCCGTGTCTGCATCTGTGGGAGACAGAGT
CACCATCACTTGTCGGGCGAGTCAGGATATTAGCACCTGGTTAGCCTGGTATCAG
CAGAAACCAGGGAAAGCCCCTAAGCTCCTGATCTATGCTGCATCCAGTTTGCAAAG
TGGGGTCCCATCAAGATTCAGCGGCAGTGGATCTGGGACAGATTTCACTCTCACC
ATCAGCAGCCTGCAGCCTGAAGATTTTGCAACTTACTTTTGTCAGCAGGCTAACAG
TTTCCCTCCGACTTTTGGCTGCGGGACCAAGCTGGAGATCAAAGGCGGAGGGGG
CTCTGGGGAGGGGCAGCGGCGGCGGAGGATCTGGGGGAGGGGGCAGCGAG
GTGCAGCTGGTGGTGTCTGGGGGAGGCTTGGTAAAGCCTGGGGGGTCCCTTAGA
CTCTCCTGTGCAGCCTCTGGACTCAGTTTCCTTAACGCCTGGATGAGCTGGGTCC
GCCAGGCTCCAGGGAAGTGCCTGGAGTGGGTTGGCCGTATTAAAAGTAATACTGA
TGGTGGGACAACAGACTACGCCGCACCCGTGAAAGGCAGATTCAGCATCTCAAGA
GACGATTCAAAGAACATGCTGTTTCTGCATATGAGCAGCCTGAGAACCGAGGACA
CAGCCGTCTATTACTGCGCCACAGATGGACCTTACTCTGACGATTTTAGAAGTGGT
TATGCCGCACGCTACCGTTATTTCGGAATGGACGTCTGGGGCCAAGGGACCACGG
TCACCGTCTCCTCA SEQ ID NO: 113 (FY1/39 Bis1 100/44 Light Chain)
DIQMTQSPSSVSASVGDRVTITCRASQDISTWLAWYQQKPGKAPKLLIYAASSLQSGV
PSRFSGSGSGTDFTLTISSLQPEDFATYFCQQANSFPPTFGCGTKLEIKGGGSGGG
GSGGGGSGGGGSEVQLVVSGGGLVKPGGSLRLSCAASGLSFLNAWMSWVRQAPGK
CLEWVGRIKSNTDGGTTDYAAPVKGRFSISRDDSKNMLFLHMSSLRTEDTAVYYCATD
GPYSDDFRSGYAARYRYFGMDVWGQGTTVTVSSGGGGSGGGGSDIQMTQSPSSLS
ASVGDRVTITCRTSQSLSSYLHWYQQKPGKAPKLLIYAASSLQSGVPSRFSGSGSGTD
FTLTISSLQPEDFATYYCQQSRTFGQGTKVEIKRTVAAPSVFIFPPSDEQLKSGTASVV
CLLNNFYPREAKVQWKVDNALQSGNSQESVTEQDSKDSTYSLSSTLTLSKADYEKHK
VYACEVTHQGLSSPVTKSFNRGEC SEQ ID NO: 114 (FY1/39 Bis1 100/44 Heavy Chain)
QVQLQESGPGLVKPSQTLSLTCAISGDSVSSNNAVWNWIRQSPSRGLEWLGRTYYRS
KWYNDYAESVKSRITVNPDTSKNQFSLHLKSVTPEDTAVFYCVRSGHITVFGVNVDAF
DMWGQGTMVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK SEQ ID NO: 115 (FY1/39 Bis3 100/44 Light Chain)
DIQMTQSPSSLSASVGDRVTITCRTSQSLSSYLHWYQQKPGKAPKLLIYAASSLQSGV
PSRFSGSGSGTDFTLTISSLQPEDFATYYCQQSRTFGQGTKVEIKRTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO: 116 (FY1/39 Bis3 100/44 Heavy Chain)
QVQLQESGPGLVKPSQTLSLTCAISGDSVSSNNAVWNWIRQSPSRGLEWLGRTYYRS
KWYNDYAESVKSRITVNPDTSKNQFSLHLKSVTPEDTAVFYCVRSGHITVFGVNVDAF
DMWGQGTMVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPEVKFN

| Sequences |
|---|
| WYVDGVEVHNAKTKPREEQYNSTYRVVSVLTVLHQDWLNGKEYKCKVSNKALPAPIE<br>KTISKAKGQPREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKSLSLSPGKG<br>GGGSGGGGSDIQMTQSPSSVSASVGDRVTITCRASQDISTWLAWYQQKPGKAPKLLI<br>YAASSLQSGVPSRFSGSGSGTDFTLTISSLQPEDFATYFCQQANSFPPTFGCGTKLEIK<br>GGGGSGGGGSGGGGSGGGGSEVQLVVSGGGLVKPGGSLRLSCAASGLSFLNAWM<br>SVWRQAPGKCLEWVGRIKSNTDGGTTDYAAPVKGRFSISRDDSKNMLFLHMSSLRTE<br>DTAVYYCATDGPYSDDFRSGYAARYRYFGMDVWGQGTTVTVSS<br><br>SEQ ID NO: 117 (FY1/94 Bis2 100/44 Light Chain)<br>DIQMTQSPSSLSASVGDRVTITCRTSQSLSSYLHWYQQKPGKAPKLLIYAASSLQSGV<br>PSRFSGSGSGTDFTLTISSLQPEDFATYYCQQSRTFGQGTKVEIKRTVAAPSVFIFPPS<br>DEQLKSGTASVVCLLNNFYPREAKVQWKVDNALQSGNSQESVTEQDSKDSTYSLSST<br>LTLSKADYEKHKVYACEVTHQGLSSPVTKSFNRGEC<br><br>SEQ ID NO: 118 (FY1/94 Bis2 100/44 Heavy Chain)<br>EIVLTQSPATLSLSPGERATLSCRASRSITTFLAWYQQKPGQAPRLLIYDASNRATGVP<br>ARFSGSGSGTDFTLTINSLEPDDFAIYYCQQRDHWPPIFGCGTRLEIKGGGGSGGGGS<br>GGGGSGGGGSEVQLVESGGGLVQPGRSLRLSCAVSGFIFEDYAINWVRQAPGKCLE<br>WVSIISWDSGRIGYADSVRGRFTISRDNAKNSSFLQMNSLRPEDTAVYYCVKDMLAYY<br>YDGSGIRYNLYGMDVWGQGTTVTVSSGGGGSGGGGSQVQLQESGPGLVKPSQTLS<br>LTCAISGDSVSSNNAVWNWIRQSPSRGLEWLGRTYYRSKWYNDYAESVKSRITVNPD<br>TSKNQFSLHLKSVTPEDTAVFYCVRSGHITVFGVNVDAFDMWGQGTMVTVSSASTKG<br>PSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKRVEPKSCDKTHTCPPCPAPELLGGP<br>SVFLFPPKPKDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFFLYSKLTV<br>DKSRWQQGNVFSCSVMHEALHNHYTQKSLSLSPGK<br><br>SEQ ID NO: 119 (FBD94 scFv DNA):<br>GAAATTGTGTTGACACAGTCTCCAGCCACTCTGTCTTTGTCTCCAGGGGAAAGAGC<br>CACCCTCTCCTGCAGGGCCAGTCGGAGTATTACCACCTTCTTAGCCTGGTACCAAC<br>AAAAACCTGGCCAGGCTCCCAGGCTCCTCATCTACGATGCATCCAACAGGGCCAC<br>TGGCGTCCCAGCCAGGTTCAGTGGCAGTGGGTCTGGGACAGACTTCACTCTCACC<br>ATCAACAGCCTAGAGCCTGACGATTTTGCAATTTATTACTGTCAGCAGCGTGACCA<br>CTGGCCTCCGATCTTCGGCTGTGGGACACGACTGGAGATTAAAGGAGGCGGAGG<br>ATCTGGTGGTGGTGGATCTGGCGGCGGAGGAAGTGGTGGCGGAGGCTCTGAAGT<br>GCAGCTGGTGGAGTCTGGGGGAGGCTTGGTGCAACCTGGCAGGTCCCTGAGACT<br>CTCCTGTGCAGTTTCTGGATTCATCTTTGAAGATTATGCCATAAACTGGGTCCGGC<br>AAGCTCCAGGGAAGTGCCTGGAGTGGGTCTCAATTATTAGTTGGGACAGTGGTAG<br>GATAGGCTACGCGGACTCTGTGAGGGGCCGATTCACCATCTCCAGAGACAACGCC<br>AAGAACTCCTCGTTTCTGCAAATGAACAGTCTGAGACCCGAAGCACCGCCGTGTA<br>TTATTGTGTAAAAGATATGTTGGCGTATTATTATGATGGTAGCGGCATCAGGTACAA<br>CCTCTACGGTATGGACGTCTGGGGCCAAGGGACCACGGTCACCGTCTCCTCA<br><br>SEQ ID NO: 120 (FY1/39 Bis4 43/105 Light Chain)<br>DIQMTQSPSSLSASVGDRVTITCRTSQSLSSYLHWYQQKPGKAPKLLIYAASSLQSGV<br>PSRFSGSGSGTDFTLTISSLQPEDFATYYCQQSRTFGQGTKVEIKRTVAAPSVFIFPPS<br>DEQLKSGTASVVCLLNNFYPREAKVQWKVDNALQSGNSQESVTEQDSKDSTYSLSST<br>LTLSKADYEKHKVYACEVTHQGLSSPVTKSFNRGEC<br><br>SEQ ID NO: 121 (FY1/39 Bis4 43/105 Heavy Chain)<br>QVQLQESGPGLVKPSQTLSLTCAISGDSVSSNNAVWNWIRQSPSRGLEWLGRTYYRS<br>KWYNDYAESVKSRITVNPDTSKNQFSLHLKSVTPEDTAVFYCVRSGHITVFGVNVDAF<br>DMWGQGTMVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKRVEPK<br>SCGGGGSGGGGSDIQMTQSPSVSASVGDRVTITCRASQDISTWLAWYQQKPGKCP<br>KLLIYAASSLQSGVPSRFSGSGSGTDFTLTISSLQPEDFATYFCQQANSFPPTFGQGTK<br>LEIKGGGGSGGGGSGGGGSGGGGSEVQLVVSGGGLVKPGGSLRLSCAASGLSFLNA<br>WMSWVRQAPGKGLEWVGRIKSNTDGGTTDYAAPVKGRFSISRDDSKNMLFLHMSSL<br>RTEDTAVYYCATDGPYSDDFRSGYAARYRYFGMDVWGCGTTVTVSSGGGGSGGGG<br>SDKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEKT<br>ISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK<br><br>SEQ ID NO: 122 (FBC39-43/105 scFv DNA):<br>GACATCCAGATGACCCAGTCTCCATCTTCCGTGTCTGCATCTGTGGGAGACAGAGT<br>CACCATCACTTGTCGGGCGAGTCAGGATATTAGCACCTGGTTAGCCTGGTATCAG<br>CAGAAACCAGGGAAATGCCCTAAGCTCCTGATCTATGCTGCATCCAGTTTGCAAAG<br>TGGGGTCCCATCAAGATTCAGCGGCAGTGGATCTGGGACAGATTTCACTCTCACC<br>ATCAGCAGCCTGCAGCCTGAAGATTTTGCAACTTACTTTTGTCAGCAGGCTAACAG<br>TTTCCCTCCGACTTTTGGCCAGGGGACCAAGCTGGAGATCAAAGGAGGCGGAGGA<br>TCTGGTGGTGGTGGATCTGGCGGCGGAGGAAGTGGTGGCGGAGGCTCTGAGGTG<br>CAGCTGGTGGTGTCTGGGGGAGGCTTGGTAAAGCCTGGGGGGTCCCTTAGACTC<br>TCCTGTGCAGCCTCTGGACTCAGTTTCCTTAACGCCTGGATGAGCTGGGTCCGCC |

| Sequences |
|---|
| AGGCTCCAGGGAAGGGGCTGGAGTGGGTTGGCCGTATTAAAAGTAATACTGATGG<br>TGGGACAACAGACTACGCCGCACCCGTGAAAGGCAGATTCAGCATCTCAAGAGAC<br>GATTCAAAGAACATGCTGTTTCTGCATATGAGCAGCCTGAGAACCGAGGACACAG<br>CCGTCTATTACTGCGCCACAGATGGACCTTACTCTGACGATTTTAGAAGTGGTTAT<br>GCCGCACGCTACCGTTATTTCGGAATGGACGTCTGGGGCTGCGGGACCACGGTC<br>ACCGTCTCCTCA<br><br>SEQ ID NO: 123 (GL20 LC/VH)<br>GATATTCAGATGACCCAGAGCCCTTCCAGCCTGTCCGCTTCAGTGGGGGATCGAG<br>TGACCATTACCTGCCGAACCAGCCAGAGCCTGAGCTCCTACACGCACTGGTATCA<br>GCAGAAGCCCGGCAAAGCCCCTAAGCTGCTGATCTACGCCGCTTCTAGTCGGGG<br>GTCCGGAGTGCCAAGCCGGTTCTCCGGATCTGGGAGTGGAACCGACTTTACCCTG<br>ACAATTTCAAGCCTGCAGCCCGAGGATTTCGCTACATACTACTGTCAGCAGAGCAG<br>AACTTTCGGGCAGGGCACTAAGGTGGAGATCAAACGTACGGTGGCTGCACCATCT<br>GTCTTCATCTTCCCGCCATCTGATGAGCAGTTGAAATCTGGAACTGCCTCTGTTGT<br>GTGCCTGCTGAATAACTTCTATCCCAGAGAGGCCAAAGTACAGTGGAAGGTGGAT<br>AACGCCCTCCAATCGGGTAACTCCCAGGAGAGTGTCACAGAGCAGGACAGCAAG<br>GACAGCACCTACAGCCTCAGCAGCACCCTGACGCTGAGCAAAGCAGACTACGAGA<br>AACACAAAGTCTACGCCTGCGAAGTCACCCATCAGGGCCTGAGCTCGCCCGTCAC<br>AAAGAGCTTCAACAGGGGAGAGTGTTAGTGAGCTAGCGATGATAATCAGCCATAC<br>CACATTTGTAGAGGTTTTACTTGCTTTAAAAAACCTCCCACACCTCCCCCTGAACCT<br>GAAACATAAAATGAATGCAATTGTTGTTGTTAACTTGTTTATTGCAGCTTATAATGGT<br>TACAAATAAAGCAATAGCATCACAAATTTCACAAATAAAGCATTTTTTTCACTGCATT<br>CTAGTTGTGGTTTGTCCAAACTCATCAATGTATCTTATCATGTCTGGATGGGCCCGT<br>TTAAACCCGCTGATCAGCCTCGACTGTGCCTTCTAGTTGCCAGCCATCTGTTGTTT<br>GCCCCTCCCCCGTGCCTTCCTTGACCCTGGAAGGTGCCACTCCCACTGTCCTTTC<br>CTAATAAAATGAGGAAATTGCATCGCATTGTCTGAGTAGGTGTCATTCTATTCTGGG<br>GGGTGGGGTGGGGCAGGACAGCAAGGGGGAGGATTGGGAAGACAATAGCAGGC<br>ATGCTGGGGATGCGGTGGGCTCTATGGCTTCTGAGGCGGAAAGAACCAGCTGGG<br>GCTCTAGCTAGTTATTAATAGTAATCAATTACGGGGTCATTAGTTCATAGCCCATAT<br>ATGGAGTTCCGCGTTACATAACTTACGGTAAATGGCCCGCCTGGCTGACCGCCCA<br>ACGACCCCCGCCCATTGACGTCAATAATGACGTATGTTCCCATAGTAACGCCAATA<br>GGGACTTTCCATTGACGTCAATGGGTGGAGTATTTACGGTAAACTGCCCACTTGGC<br>AGTACATCAAGTGTATCATATGCCAAGTACGCCCCCTATTGACGTCAATGACGGTA<br>AATGGCCCGCCTGGCATTATGCCCAGTACATGACCTTATGGGACTTTCCTACTTGG<br>CAGTACATCTACGTATTAGTCATCGCTATTACCATGGTGATGCGGTTTTGGCAGTA<br>CATCAATGGGCGTGGATAGCGGTTTGACTCACGGGGATTTCCAAGTCTCCACCCC<br>ATTGACGTCAATGGGAGTTTGTTTTGGCACCAAAATCAACGGGACTTTCCAAAATG<br>TCGTAACAACTCCGCCCCATTGACGCAAATGGGCGGTAGGCGTGTACGGTGGGA<br>GGTCTATATAAGCAGAGCTCGTTTAGTGAACCGTCAGATCGCCTGGAGACGCCAT<br>CCACGCTGTTTTGACCTCCATAGAAGACACCGGGACCGATCCAGCCTCCGCGGCC<br>GGGAACGGTGCATTGGAACGCGGATTCCCCGTGCCAAGAGTGACGTAAGTACCG<br>CCTATAGACTCTATAGGCACACCCCTTTGGCTCTTATGCATGAATTAATACGACTCA<br>CTATAGGGAGACAGACTGTTCCTTTCCTGGGTCTTTTCTGCAGGCACCGTCGCCG<br>CCACCATGGGATGGAGCTGTATCATCCTCTTCTTGGTAGCAACAGCTACAGGTAAG<br>GGGCTCACAGTAGCAGGCTTGAGGTCTAGACATATATATGGGTGACAATGACATC<br>CACTTTGCCTTTCTCTCCACAGGTGTACACTCCCAGGTCCAGCTGCAGCAGAGCG<br>GCCCCGGACTGGTCAAGCCTTCACAGACACTGAGCCTGACATGCGCCATTAGCGG<br>AGATAGCGTGAGCTCCTACAATGCCGTGTGGAACTGGATCAGGCAGTCTCCAAGT<br>CGAGGACTGGAGTGGCTGGGACGAACATACTATAGATCCGGGTGGTACAATGACT<br>ATGCTGAATCAGTGAAAAGCCGAATTACTATCAACCCCGATACCTCCAAGAATCAG<br>TTCTCTCTGCAGCTGAACAGTGTGACCCCTGAGGACACAGCCGTGTACTACTGCG<br>CCAGAAGCGGCCATATCACCGTCTTTGGCGTCAATGTGGATGCTTTCGATATGTGG<br>GGGCAGGGGACTATGGTCACCGTGTCAAGC<br><br>SEQ ID NO: 124 (FBC39FTL scFv DNA):<br>GACATCCAGATGACCCAGTCTCCATCTTCCGTGTCTGCATCTGTGGGAGACAGAGT<br>CACCATCACTTGTCGGGCGAGTCAGGATATTAGCACCTGGTTAGCCTGGTATCAG<br>CAGAAACCAGGGAAAGCCCCTAAGCTCCTGATCTATGCTGCATCCAGTTTGCAAAG<br>TGGGGTCCCATCAAGATTCAGCGGCAGTGGATCTGGGACAGATTTCACTCTCACC<br>ATCAGCAGCCTGCAGCCTGAAGATTTTGCAACTTACTATTGTCAGCAGGCTAACAG<br>TTTCCCTCCGACTTTTGGCTGCGGGACCAAGCTGGAGATCAAAGGAGGCGGAGGA<br>TCTGGTGGTGGTGGATCTGGCGGCGGAGGAAGTGGTGGCGGAGGCTCTGAGGTG<br>CAGCTGGTGGAGTCTGGGGGAGGCTTGGTAAAGCCTGGGGGGTCCCTTAGACTC<br>TCCTGTGCAGCCTCTGGATTCACTTTCCTTAACGCCTGGATGAGCTGGGTCCGCCA<br>GGCTCCAGGGAAGTGCCTGGAGTGGGTTGGCCGTATTAAAAGTAATACTGATGGT<br>GGGACAACAGACTACGCCGCACCCGTGAAAGGCAGATTCACCATCTCAAGAGACG<br>ATTCAAAGAACACGCTGTATCTGCAAATGAGCAGCCTGAAACCGAGGACACAGC<br>CGTCTATTACTGCACCACAGATGGACCTTACTCTGACGATTTTAGAAGTGGTTATG<br>CCGCACGCTACCGTTATTTCGGAATGGACGTCTGGGGCCAAGGGACCACGGTCAC<br>CGTCTCCTCA<br><br>SEQ ID NO: 125 (GL20/39FTL Bis4 43/105 Light Chain)<br>DIQMTQSPSSLSASVGDRVTITCRTSQSLSSYTHWYQQKPGKAPKLLIYAASSRGSGV<br>PSRFSGSGSGTDFTLTISSLQPEDFATYYCQQSRTFGQGTKVEIKRTVAAPSVFIFPPS<br>DEQLKSGTASVVCLLNNFYPREAKVQWKVDNALQSGNSQESVTEQDSKDSTYSLSST<br>LTLSKADYEKHKVYACEVTHQGLSSPVTKSFNRGEC |

| Sequences |
|---|
| SEQ ID NO: 126 (GL20/39FTL Bis4 43/105 Heavy Chain)<br>QVQLQQSGPGLVKPSQTLSLTCAISGDSVSSYNAVWNWIRQSPSRGLEWLGRTYYRS<br>GWYNDYAESVKSRITINPDTSKNQFSLQLNSVTPEDTAVYYCARSGHITVFGVNVDAF<br>DMWGQGTMVTVSSASTKGPSVFPLAPSSKSTSGGTAALGCLVKDYFPEPVTVSWNS<br>GALTSGVHTFPAVLQSSGLYSLSSVVTVPSSLGTQTYICNVNHKPSNTKVDKRVEPK<br>SCGGGGSGGGGSDIQMTQSPSSVSASVGDRVTITCRASQDISTWLAWYQQKPGKCP<br>KLLIYAASSLQSGVPSRFSGSGSTDFTLTISSLQPEDFATYYCQQANSFPPTFGQGTK<br>LEIKGGGGSGGGGSGGGGSGGGGSEVQLVESGGGLVKPGGSLRLSCAASGFTFLNA<br>WMSWVRQAPGKGLEVWGRIKSNTDGGTTDYAAPVKGRFTISRDDSKNTLYLQMSSL<br>KTEDTAVYYCTTDGPYSDDFRSGYAARYRYFGMDVWGCGTTVTVSSGGGGSGGGG<br>SDKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEKT<br>ISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK<br><br>SEQ ID NO: 127 (FBC39FTL43/105 scFv DNA):<br>GACATCCAGATGACCCAGTCTCCATCTTCCGTGTCTGCATCTGTGGGAGACAGAGT<br>CACCATCACTTGTCGGGCGAGTCAGGATATTAGCACCTGGTTAGCCTGGTATCAG<br>CAGAAACCAGGGAAATGCCCTAAGCTCCTGATCTATGCTGCATCCAGTTTGCAAAG<br>TGGGGTCCCATCAAGATTCAGCGGCAGTGGATCTGGGACAGATTTCACTCTCACC<br>ATCAGCAGCCTGCAGCCTGAAGATTTTGCAACTTACTATTGTCAGCAGGCTAACAG<br>TTTTCCCTCCGACTTTTGGCCAGGGGACCAAGCTGGAGATCAAAGGAGGCGGAGGA<br>TCTGGTGGTGGTGGATCTGGCGGCGGAGGAAGTGGTGGCGGAGGCTCTGAGGTG<br>CAGCTGGTGGAGTCTGGGGGAGGCTTGGTAAAGCCTGGGGGGTCCCTTAGACTC<br>TCCTGTGCAGCCTCTGGATTCACTTTCCTTAACGCCTGGATGAGCTGGGTCCGCCA<br>GGCTCCAGGGAAGGGGCTGGAGTGGGTTGGCCGTATTAAAAGTAATACTGATGGT<br>GGGACAACAGATTACGCCGCACCCGTGAAAGGCAGATTCACCATCTCAAGAGACG<br>ATTCAAAGAACACGCTGTATCTGCAAATGAGCAGCCTGAAAACCGAGGACACAGC<br>CGTCTATTACTGCACCACAGATGGACCTTACTCTGACGATTTTAGAAGTGGITATG<br>CCGCACGCTACCGTTATTTCGGAATGGACGTCTGGGGCTGCGGGACCACGGTCAC<br>CGTCTCCTCA<br><br>SEQ ID NO: 128 (GL20/39FTL Bis5 43/105 Light Chain)<br>DIQMTQSPSSLSASVGDRVTITCRTSQSLSSYTHWYQQKPGKAPKLLIYAASSRGSGV<br>PSRFSGSGSGTDFTLTISSLQPEDFATYYCQQSRTFGQGTKVEIKRTVAAPSVFIFPPS<br>DEQLKSGTASVVCLLNNFYPREAKVQWKVDNALQSGNSQESVTEQDSKDSTYSLSST<br>LTLSKADYEKHKVYACEVTHQGLSSPVTKSFNRGEC<br><br>SEQ ID NO: 129 (GL20-FBC39 BiS5 - GL20VH - Fc (CH3-) - Linker - FBC39 scFv - Linker-Fc(-CH3))<br>QVQLQQSGPGLVKPSQTLSLTCAISGDSVSSYNAVWNWIRQSPSRGLEWLGRTYYRS<br>GWYNDYAESVKSRITINPDTSKNQFSLQLNSVTPEDTAVYYCARSGHITVFGVNVDAF<br>DMWGQGTMVTVSSASTKGPSVFPLAPSSKSTSGGTAALGCLVKDYFPEPVTVSWNS<br>GALTSGVHTFPAVLQSSGLYSLSSVVTVPSSLGTQTYICNVNHKPSNTKVDKRVEPK<br>SCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIE<br>KTISKAKGQPREPQVYTLPPSREEMTKNQVSLTCLVKGFYPSDIAVEWESNGGGSG<br>GGGSDIQMTQSPSSVSASVGDRVTITCRASQDISTWLAWYQQKPGKAPKLLIYAASSL<br>QSGVPSRFSGSGSTDFTLTISSLQPEDFATYFCQQANSFPPTFGCGTKLEIKGGGGS<br>GGGGSGGGGSGGGGSEVQLVVSGGGLVKPGGSLRLSCAASGLSFLNAWMSWVRQ<br>APGKCLEWVGRIKSNTDGGTTDYAAPVKGRFSISRDDSKNMLFLHMSSLRTEDTAVYY<br>CATDGPYSDDFRSGYAARYRYFGMDVWGQGTTVTVSSGGGGSGGGGSGQPENNY<br>KTTPPVLDSDGSFFLYSKLTVDKSRWQQGNVFSCSVMHEALHNHYTQKSLSLSPGK<br><br>SEQ ID NO: 130 (GL20/39FTL Bis5 43/105 Light Chain)<br>DIQMTQSPSSLSASVGDRVTITCRTSQSLSSYTHWYQQKPGKAPKLLIYAASSRGSGV<br>PSRFSGSGSGTDFTLTISSLQPEDFATYYCQQSRTFGQGTKVEIKRTVAAPSVFIFPPS<br>DEQLKSGTASVVCLLNNFYPREAKVQWKVDNALQSGNSQESVTEQDSKDSTYSLSST<br>LTLSKADYEKHKVYACEVTHQGLSSPVTKSFNRGEC<br><br>SEQ ID NO: 131 (GL20VH BiS5 - Fc (CH3-) - Linker - FBC39 (43-105) scFv - Linker - Fc (-CH3))<br>QVQLQQSGPGLVKPSQTLSLTCAISGDSVSSYNAVWNWIRQSPSRGLEWLGRTYYRS<br>GWYNDYAESVKSRITINPDTSKNQFSLQLNSVTPEDTAVYYCARSGHITVFGVNVDAF<br>DMWGQGTMVTVSSASTKGPSVFPLAPSSKSTSGGTAALGCLVKDYFPEPVTVSWNS<br>GALTSGVHTFPAVLQSSGLYSLSSVVTVPSSLGTQTYICNVNHKPSNTKVDKRVEPK<br>SCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIE<br>KTISKAKGQPREPQVYTLPPSREEMTKNQVSLTCLVKGFYPSDIAVEWESNGGGSG<br>GGGSDIQMTQSPSSVSASVGDRVTITCRASQDISTWLAWYQQKPGKCPKLLIYAASSL<br>QSGVPSRFSGSGSTDFTLTISSLQPEDFATYFCQQANSFPPTFGQGTKLEIKGGGGS<br>GGGGSGGGGSGGGGSEVQLVVSGGGLVKPGGSLRLSCAASGLSFLNAWMSWVRQ<br>APGKGLEWVGRIKSNTDGGTTDYAAPVKGRFSISRDDSKNMLFLHMSSLRTEDTAVY<br>YCATDGPYSDDFRSGYAARYRYFGMDVWGCGTTVTVSSGGGGSGGGGSGQPENN<br>YKTTPPVLDSDGSFFLYSKLTVDKSRWQQGNVFSCSVMHEALHNHYTQKSLSLSPGK |

What is claimed is:

1. An isolated binding molecule which specifically binds to influenza A virus and influenza B virus, comprising:
   (a) a first binding domain comprising an Fv domain of a first antibody that is capable of binding to influenza A virus hemagglutinin (HA) and neutralizing at least one group 1 subtype and at least 1 group 2 subtype of influenza A virus, wherein the first antibody comprises a VH and a VL selected from:
   (i) a VH at least 95% identical to SEQ ID NO.: 7 and a VL at least 95% identical to SEQ ID NO.: 2; and
   (ii) a VH at least 95% identical to SEQ ID NO.: 17 and a VL at least 95% identical to SEQ ID NO.: 12; and
   (b) a second binding domain comprising an scFv of a second antibody that is capable of binding to influenza B virus hemagglutinin (HA) and neutralizing influenza B virus in at least two phylogenetically distinct lineages, wherein the second antibody comprises a VH and a VL selected from:
   (i) a VH at least 95% identical to SEQ ID NO.: 27 and a VL at least 95% identical to SEQ ID NO.: 22;
   (iv) a VH at least 95% identical to SEQ ID NO.: 43 and a VL at least 95% identical to SEQ ID NO.: 38; and
   (vii) a VH at least 95% identical to SEQ ID NO.: 59 and a VL at least 95% identical to SEQ ID NO.: 54.

2. The isolated binding molecule according to claim 1, wherein the first binding domain is capable of neutralizing one or more influenza A virus group 1 subtypes selected from: H1, H2, H5, H6, H8, H9, H11, H12, H13, H16, H17, and H18 and one or more influenza A virus group 2 subtypes selected from: H3, H4, H7, H10, H14 and H15.

3. The isolated binding molecule according to claim 1, wherein the second binding domain is capable of neutralizing influenza B virus in both Yamagata and Victoria lineages.

4. The isolated binding molecule according to claim 1, wherein the binding molecule is a bispecific antibody.

5. The isolated binding molecule according to claim 1, wherein the Fv domain of the first binding domain comprises a heavy chain (HC) comprising a polypeptide chain having an amino terminus and a carboxy terminus and a light chain (LC) comprising a polypeptide chain having an amino terminus and a carboxy terminus, and
   (a) the second binding domain is covalently linked to the carboxy-terminus of the HC of the first binding domain;
   (b) the second binding domain is covalently linked to the amino-terminus of the HC of the first binding domain;
   (c) the second binding domain is covalently linked to the amino-terminus of the LC of the first binding domain; or
   (d) the second binding domain is covalently intercalated in the polypeptide chain of the HC of the first binding domain.

6. The isolated binding molecule according to claim 1, wherein the isolated binding molecule comprises an antibody Fc region.

7. The isolated binding molecule according to claim 6, wherein the isolated binding molecule has an enhanced serum half-life relative to a native Fc antibody.

8. An isolated polynucleotide comprising a nucleic acid which encodes the isolated binding molecule according to claim 1.

9. A vector comprising the polynucleotide of claim 8.

10. A host cell comprising the polynucleotide of claim 8.

11. A composition comprising the isolated binding molecule according to claim 1 and a pharmaceutically acceptable carrier.

12. A method for manufacturing an isolated binding molecule according to claim 1, comprising culturing a host cell under conditions suitable for expression of the binding molecule.

13. A method for prophylaxis or treatment of influenza A infection, influenza B infection, or a combination thereof in a subject comprising administering an effective amount of an isolated binding molecule according to claim 1 to the subject.

* * * * *